US005985935A

United States Patent [19]

Kharazmi et al.

[11] Patent Number: 5,985,935

[45] Date of Patent: Nov. 16, 1999

[54] TREATMENT AND PROPHYLAXIS OF DISEASES CAUSED BY PARASITES, OR BACTERIA

[75] Inventors: Arsalan Kharazmi, Charlottenlund; Søren Brøgger Christensen, Nivå; Chen Ming, Copenhagen Ø; Thor Grundtvig Theander, Holte, all of Denmark

[73] Assignee: Statens Seruminstitut, Copenhagen, Denmark

[21] Appl. No.: 08/302,726

[22] PCT Filed: Mar. 8, 1993

[86] PCT No.: PCT/DK93/00088

§ 371 Date: Nov. 1, 1994

§ 102(e) Date: Nov. 1, 1994

[87] PCT Pub. No.: WO93/17671

PCT Pub. Date: Sep. 16, 1993

[30] Foreign Application Priority Data

| | | | |
|---|---|---|---|
| Mar. 6, 1992 | [DK] | Denmark | 0312/92 |
| Sep. 30, 1992 | [DK] | Denmark | 1208/92 |

[51] Int. Cl.$^6$ .......... A61K 31/12

[52] U.S. Cl. .......... 514/679

[58] Field of Search .......... 514/679

[56] References Cited

U.S. PATENT DOCUMENTS

| | | | |
|---|---|---|---|
| 4,279,930 | 7/1981 | Hall et al. | 424/331 |
| 4,867,964 | 9/1989 | Forestier et al. | 424/47 |

FOREIGN PATENT DOCUMENTS

| | | | |
|---|---|---|---|
| 635156 | 3/1993 | Australia | A61K 31/12 |
| 0 013 960 A1 | 8/1980 | European Pat. Off. . | |
| 0 328 669 A1 | 8/1989 | European Pat. Off. . | |
| 62-181202 | 8/1987 | Japan . | |

OTHER PUBLICATIONS

N.B. Pappano et al., STN International, File Biosis, STN Accession No. 87:186434, 1977.

I.H. Hall et al., STN International, File Medline, Medline Accession No. 77143880,1977.

M. Szajda et al., *Pharmazie*, 44:190–191 (1989).

*Chemical Abstracts*, 115(5):41976j (1991).

J. Berenguer et al., *Annals of Internal Medicine*, 111(2):129–131 (1989).

J. Berman et al., *Infection and Immunity*, 26:375–379 (1979).

P. Flegg et al., *AIDS*, 4(4):366–367 (1990).

T. Hatano et al., *Chem. Pharm. Bull.*, 36:2090–2097 (1988).

B. Inoue et al., *The Journal of Toxicological Sciences*, 7:245–254 (1982).

K. Okada et al., *Chem. Pharm. Bull.*, 37(9):2528–2530 (1989).

S. Khan et al., *Indian Journal of Chemistry*, 22B:276–277 (1983).

Y. Kimura et al., *Phytotherapy Research*, 2(3):140–145 (1988).

C. Lambros et al., *J. Parasitol.*, 65(3):418–420 (1979).

R. Pearson et al., *Antimicrobial Agents and Chemotherapy*, 25(5):571–574 (1984).

R. Jun et al., *Journal of Traditional Chinese Medicine*, 8(4):307–309 (1988).

S. Demizu et al., *Chem. Pharm. Bull.*,36(9):3474–3479 (1988).

T. Saitoh et al., *Tetrahedron Letters*, No. 50, pp. 4461–4462 (1975).

D. Salmon et al., *Antimicrobial Agents and Chemotherapy*, 34(12):2327–2330 (1990).

W. Trager et al., *Science*, 193:673–675 (1976).

S. Wattanasin et al., *Synthesis: Communications*, (1980).

J. Sallai et al., *Acta Pharmaceutica Hungarica*, 46:49–56 (1976).

X. Ren–Sheng et al., *Acta Chimica Sinica*, 37(4):289–297 (1979).

R. Mentlein et al., *Liebigs Ann. Chem.*, pp. 401–406 (1984).

R. Mentlein et al., *Org. Mass. Spectrom.*, 19:330–333 (1984).

Takagaki et al. 114CA:88634R, 1991.

Lord et al. 69:CA:76943e, 1968.

*Primary Examiner*—Russell Travers
*Attorney, Agent, or Firm*—David G. Conlin; Peter F. Corless

[57] ABSTRACT

Aromatic compounds, or prodrugs thereof, which contain an alkylating site and which are capable of alkylating the thiol group in N-acetyl-L-cysteine, in particular bis-aromatic α,β-unsaturated ketones, are used for the preparation of pharmaceutical compositions or medicated feed, food or drinking water for the treatment or prophylaxis of diseases caused by microorganisms or parasites, in particular protozoa such as Leishmannia, Trypanosoma, Toxoplasma, Plasmodium, Pneumocystis, Babesia and Theileria, intestinal protozoa such as Trichormionas and Ciardia; Coccidia such as Eimeria, Isospora, Cryptosporidium; Cappilaria, Microsporidium, Sarcocystis. Trichlodina, Trichoditella, Dacihylogurus, Pseudodacthylogurus, Acantocephalus, Ichthylophtherius, Botrecephalus; and intracellular bacteria, in particular Mycobacterium, Legionella species, Listeria and Salmonella. Preferred compounds have the formula (II): $X_m$—Ph—C(O)—CH═CH—Ph—$Y_n$, wherein each phenyl group (Ph) may be mono- or polysubstituted; X and Y designate $AR_H$ or AZ, wherein A is O, S, NH or N($C_{1-6}$alkyl), $R_H$ designates aliphatic hydrocarbyl, and Z is H or a masking group which is decomposed to liberate AH; m is 0, 1 or 2, and n is 0, 1, 2 or 3, whereby, when m is 2, then the two X are the same or different, and when n is 2 or 3, then the two or three Y are the same or different, with the proviso that n and m are not both 0. As examples of such compounds, chalcones, e.g. licochalcone A (obtainable i.a. from batches of Chinese licorice root of Glycyrrhiza species, e.g. *G. uralensis* or *G. inflata*) as well as hydroxy, alk(en)yl, and/or alk(en)yloxy analogues thereof are active in vitro and/or in vivo against i.a. *L. major* and *P. falciparum*.

47 Claims, 15 Drawing Sheets

TREATMENT AND PROPHYLAXIS OF DISEASES CAUSED BY PARASITES, OR BACTERIA

The present invention relates to the use of a particular class of aromatic compounds, in particular bis-aromatic α,β-unsaturated ketones, most of which are novel compounds, for the treatment or prophylaxis of a number of serious conditions caused by microorganisms or parasites, in particular protozoa such as Leishmania, Plasmodia, and Coccidia such as Eimeria, and intracellular bacteria, including Legionella and Mycobacteria. The invention also relates to the novel bis-aromatic α,β-unsaturated ketones and methods of preparing them, as well as to pharmaceutical and antiparasitic compositions. Furthermore, the invention also relates to a method for treatment or prophylaxis of diseases caused by microorganisms or parasites.

Parasitic diseases, among these malaria and leishmaniasis, are, on a world basis, among the most important diseases. The most effective known drugs against the diseases have many side effects for which reason it is not possible to maintain the treatment or prophylaxis of specific diseases for years.

Recently, the development of resistance against the available drugs against particularly malaria and leishmania parasites has been reported.

Especially malaria and leishmaniasis remain serious diseases despite the efforts to control the diseases and reduce their prevalence by vector eradication and drug treatment.

More than 12 million people in the world are inflicted by leishmaniasis. There are more than 400,000 new cases and 100,000 deaths each year but as many as 350 million people are at risk of infection (WHO,1990). The annual incidence of clinical leishmaniasis is estimated to exceed 2,000,000 cases in some 80 countries. It is one of the 7 important tropical diseases included in the TDR program.

Leishmaniasis are characterized by a broad spectrum of clinical manifestations depending on the strain of the parasite and the host immune response. The parasites infect macrophages and multiply inside these cells. The first step in the Leishmania/macrophage interactions is the binding of the parasite to the macrophage followed by uptake of the parasite. Integrity and fluidity of the host cell membrane is essential for this interaction. Certain parasite surface antigens such as membrane glycoprotein (Gp63) and lipophosphoglycan (LPG) as well as a number of macrophage surface receptors are also important in binding and uptake of the parasite by macrophages.

Various species of the protozoan parasite Leishmania cause a broad spectrum of diseases ranlpg from the cutaneous healing skin lesions caused by *L. major* to a fatal visceral form of the disease called kala azar caused by *L. donovani* (Manson-Bahr, 1987). Leishmaniases are widespread in many parts of the world with highest prevalence in Africa, Asia, and Latin America (WHO, 1989). Recently an increasing number of AIDS patients are becoming infected with Leishmania (Brenguer, 1989; Flegg 1990).

Therapy of patients with leishmaaniasis still poses a serious problem. Most of the available antileishmanial drugs exhibit considerable toxicity and there are reports of large scale clinical resistance to the conventional antimonial drugs. No effective, safe, and nontoxic antileishmanial drug is available at present.

There are also reports of large scale clinical drug resistance in visceral leishmaniasis. (TDR News No. 34,1990)

Malaria, another parasitic disease, is also a serious health problem. Human malaria is caused by four species of the protozoan genus, Plasmodium. The species *Plasmodium falciparum* is the most dangerous, causing acute severe infections that are often fatal, especially in young children and immigrants entering endemic areas. The life cycle of *P. falciparum* includes different stages; in the first stage, the sporozoite stage, the parasite is brought into the blood stream by the Anopheles mosquito. The sporozoites are carried in the blood stream to the liver where they invade the hepatocytes and develop into merozoites in the course of 5–7 days. Merozoites released from infected cells start a new cycle by invading the erythrocytes. It is the invasion of the erythrocyte which gives rise to the clinical disease. In the erythrocyte, the parasite shows an asexual multiplication which involve a maturation of the parasite through different parasite stages, the ring, the trophozoite and the schizont stage (the stage that undergoes nuclear division). When the schizont-infected erythrocyte bursts, new merozoites are released. Some merozoites, however, differentiate into gametocytes (microgametocytes and macrogametocytes), the sexual form of the parasite. Contrary to the asexual infected erythrocytes, these sexual parasite stages are able to continue the life cycle when the infected cells, the erythrocytes, are ingested by mosquitoes during a blood meal. By fertilitation in the mosquito gut, the gametocytes develop into a mobile ookinete stage. The ookinete pass through the epithet and matures into a oocyst. In the oocyst, the new sporozoites develop. These sporozoites are released and move to the salivary gland, and are then ready to be injected into a new host. The parasites are haploid in most of the life cycle as they perform a meiotic cell division shortly after fertilization. The Anopheles mosquito is the primary vector of malaria, but the disease can be seen after blood transfusion, i.v. injection of medicaments and after transfer from an infected mother to the newborn child through the placenta.

Each year, several hundreds of millions of human beings are affected by the parasitic disease malaria. The treatment and prophylaxis of malaria has been difficult because the available drugs exhibit severe side effects, and furthermore, the Plasmodia are showing increasing resistance towards the drugs (Ann (WHO) 1990).

Coccidial protozoa such as *Eimeria tenella* are some of the most important parasites causing disease in poultry resulting in significant economic loss. There are problems with resistance development against some of the available anticoccidial drugs used in prophylaxis and treatment of these diseases, for which reason there is a need for development of new anticoccidial drugs.

Also, Babesia species cause devastating damage to cattle in many parts of the world, and there is a need for the development of safe, effective and inexpensive drugs to control these diseases.

Thus, there is a great need for effective drugs against parasitic diseases, especially for drugs exhibiting none or only less severe side effects.

According to the present invention, it has been found that a class of aromatic compounds, said class comprising compounds containing an alkylating site, show a remarkable capability of effectively suppressing the growth of parasitic protozoa and intracellular bacteria, which compounds at the same time can be so chosen that they are tolerable to animal cells such as human cells. This valuable selective activity of such alkylating aromatic compounds seems to be based on their capability of interfering with oxygen metabolism in the parasites by destroving their mitochondria, at concentrations at which the compounds, while thus being harmful to the microorganisms, do not affect the mitochondria of the animal cells.

Without being limited to any particular theory, it is believed that the capability of the compounds to alkylate nudeophilic groups in biomolecules, as evidenced by their capability of alkylating the thiol group of N-acetyl-L-cysteine, is of importance for the antimicrobial effect.

In accordance with this, the present invention, in its broadest aspect, relates to the use of an aromatic compound which contains an alkylating site, and which is capable of alkylating the thiol group in N-acetyl-L-cysteine at physiological pH, for the preparation of a pharmaceutical composition or a medicated feed, food or drinking water for the treatment or prophylaxis of a disease caused by a microorganism or a parasite in an animal, including a vertebrate, such as a bird, a fish or a mammal, including a human, the microoganism or parasite being selected from parasitic protozoa, in particular tissue and blood protozoa such as Leishmania, Trypanosoma, Toxoplasma, Plasmodium, Pneumocystis, Babesia and Theileria; intestinal protozoan flagellates such as Trichomonas and Giardia; intestinal protozoan Coccidia such as Eimeria, Isospora, Cryptosporidium; Cappilaria, Microsporidium, Sarcacystis, Trichodina, Trichodinella, Dacthylogurus, Pseudodactylogurus, Acantocephalus, Ichthyophtherius, Botrecephalus; and intracellular bacteria, in particular Mycobacterium, Legionella species, Listeria, and Salmonella.

As it will appear from the following, the aromatic compound may in many cases advantageously be used in the form of a prodrug of the aromatic compound, and it will be understood that the present broadest aspect of the invention encompasses the use of such prodrugs. Expressed in another manner, the broadest aspect of the invention relates to a method for the treatment or prophylaxis of a disease caused by a microorganism or a parasite selected from the protozoa and bacteria stated above, the method comprising administering, to an animal in need thereof, an effective amount of an aromatic compound which contains an alkylating site, and which is capable of alkylating the thiol group in N-acetyl-L-cysteine at physiological pH, or a prodrug thereof.

From the description which follows, it will be seen that a large number of aromatic compounds which show the above-mentioned selective effect are compounds which have one or several electron-donating groups such as hydroxy or derivatives thereof substituted on an aromatic ring. It is believed that the above-described selectivity is obtained through such adequate substitution which modifies the alkylating potency. It will also appear from data described herein that important representatives of the compounds in question are compounds which contain an aromatic ring attached to the alkylating site.

As appears from the following, convenient and reproducible in vitro tests have been devised to test the selectivity of aromatic N-acetyl-L-cysteine-thiol-alkylating compounds, and based on a large number of tested compounds, it has been found that the above-mentioned aromatic N-acetyl-L-cysteine-thiol-alkylating compounds in which one or several electron-donating groups such as hydroxy or derivatives thereof is/are present on an aromatic ring, are almost consistently capable of showing a useful selectivity, resulting in effective suppression of the growth of pathogenic microorganisms or parasites in concentrations which are well tolerated by animal cells.

The in vitro tests involve establishing the inhibition of the multiplication of the protozoa or bacteria on the one hand and the animal cells on the other hand by determining the inhibition of the uptake of radiolabelled precursors as an indication of the inhibitiof of the growth of the parasite or the animal cells in the presence of the test compound in the concentration in question (see Example 14 herein and the examples to which it refers).

The tests involve a particularly suitable assay for assessing the tolerability of the aromatic alkylating compounds to animal cells, that is, an assay based on the assessment of the reduction caused by the compound on the thymidine uptake by lymphocytes of the animal in the Lymphocyte Proliferation Assay (LPA) which is the assay described in greater detail in Example 13.

It has also been found that compounds which are found to be promising in the in vitro model also cure animals infected with leishmania and malaria parasites, respectively, such as was shown in a suitable model involving intraperitoneal administration of the compounds to mice or hamsters (see Examples 8, 9 and 16).

Furthermore, it has been found that compounds with antileishmanial and antimalarial activity exhibit inhibitory effect on the growth of intracellular bacteria such as Mycobacteria which causes tuberculosis in humans, and Legionelia which causes legionnaires disease in humans (see Examples 17 and 19).

The fact that these compounds exhibit strong antiparasitic activity against several species of two important human protozoan parasites, Plasmodium and Leishmania, and against *Eimeria tenella*, the most important parasite in poultry (see Example 28) makes it justified to presume that these compounds will also be strongly active against important veterinarian protozoan parasites such as Babesia in cattle, which is intraerythrocytic similar to the malaria parasite, other Coccidia in poultry, and Pseudodactylogurus or Trichodina in fish.

Furthermore, based on the broad spectrum antimicrobial activity of the compounds (see Examples, 17, 18 and 19), it can be assumed that these compounds have similar activity against other microorganisms such as Salmonella, and Trichinella, and quite generally against a broad range of microorganisms as defined below, in particular aerobic microorganisms and, among those, in particular microorganisms which are found in tissues and host cells of an infected animal.

While it has been established that the alkylating site may be a carbon-carbon double bond conjugated with a carbonyl group, it is contemplated, based on general chemical considerations, that it mav also be a carbon-carbon triple bond conjugated with a carbonyl group, or an epoxy group. It is preferred that the alkylating site is a double or triple bond (from the point of view of availability of the compound preferably a double bond) conjugated with a carbonyl group. The carbonyl group may be the carbonyl group of an aldehyde or a ketone, or it may be the C═O group of a carboxylic acid group or a derivative thereof such as an ester.

In a preferred class of compounds, the carbonyl group is a ketonic carbonyl group which is further conjugated with an aromatic ring, such as a phenyl group. In this case, the phenyl group may carry electron-donating groups, confer what is discussed above, in particular one or several hydroxy groups or derivatives thereof. In the case of hydroxy groups, these may be masked in order to prevent metabolism, confer the detailed discussion further below. The masking groups are preferably chosen from groups from which the free phenol may be released in the body, either enzymatically or non-enzymatically.

Considering that human lymphocytes are representatives of sensitive animal cells, it is, as a general rule, it is preferred according to the present invention that the aromatic alkylating compound is one which, in a concentration in which it causes less than 50% reduction, preferably less than 40% reduction, and more preferably less than 20% reduction, of the thymidine uptake by human lymphocytes in the Lymphocyte Proliferation Assay using phytohemagglutinin (PHA), meets at least one of the following criteria:

a) the aromatic compound is capable of inhibiting in vitro the growth or multiplication of *Leishmania major* promastigotes by at least 80%, as determined by uptake of tritiated thymidine, b) the aromatic compound is capable of inhibiting in vitro the growth or multiplication of *Plasmodium falciparum* by at least 80%, as determined by uptake of tritiated hypoxanthine, c) the aromatic compound is capable of inhibiting in vitro the growth or multiplication of *Eimeria tenella* in chicken fibroblast cell cultures by at least 70%, as determined by counting the parasites, d) the aromatic compound is capable of inhibiting in vitro the growth or multiplication of *Mycobacterium tuberculosis* or *Legionella pneumophila* by at least 50%, as determined by colony counts.

However, it will be understood that the most important consideration is that the compound is tolerable to the animal in concentrations in which it will control the protozoa or the intracellular bacteria. In particular, preferred compounds to be used according to the invention are compounds which meets all of the criteria a) to d), because this is an indication of a broad spectred activity and selectivity.

According to an embodiment of the use according to the present invention, the pharmaceutical composition prepared is a composition for the treatment or prophylaxis of diseases caused by Leishmania in humans or dogs, and the aromatic compound used is capable of inhibiting in vitro the growth of *Leishmania major* promastigotes by at least 80%, as determined by uptake of tritiated thymidine, in a concentration of the compound in which it causes less than 50% reduction, preferably less than 40% reduction, more preferably less than 20% reduction, of the thymidine uptake by human lymphocytes in the Lymphocyte Proliferation Assay using PHA.

In the following, reasonable selection criteria based upon the behaviour of the compounds in representative tests are stated for compounds to be used for treatment or prophylaxis of a number of diseases, confer the corresponding claims 10–24:

As determined by a representative in vivo test, the pharmaceutical composition for the treatment or prophylaxis of diseases caused by Leishmania in humans or dogs, is preferably one in which the aromatic compound, or the prodrug, when administered intraperitoneally in the in vivo test described in Example 8 herein in a dose of up to 20 mg per kg body weight, especially in a dose of up to 10 mg er kg body weight, once daily for 40 days to female BALB/c mice which have been infected with *L. major* ($10^7$/mouse), the administration being initiated one week after infection, is capable of preventing increase in lesion size by at least 60%, preferably at least 80%, more preferably at least 90%.

In another embodiment, the pharmaceutical composition is a composition for the treatment or prophylaxis of diseases caused by Leishmania in humans or dogs, and the aromatic compound, or the prodrug, when administered intraperitoneally in the in vivo test described in Example 9 herein in a dose of up to 20 mg per kg body weight, preferably in a dose of up to 10 mg per kg body weight, two times daily for 7 days to male Syrian golden hamsters which have been infected with *L. donovani* promastigotes ($2\times10^7$/hamster), the administration being initiated one day after infection, is capable of reducing the parasite load in the liver of the hamsters by at least 60%, preferably by at least 80%, and more preferably by at least 90%.

In yet another embodiment, the pharmaceutical composition is a composition for the treatment or prophylaxis of malaria caused by Plasmodium spp. in humans, and the aromatic compound is capable of inhibiting in vitro the growth of *Plasmodium faiciparum* by at least 80%, as measured by uptake of tritiated hypoxanthine, in a concentration of the compound in which it causes less than 50% reduction, preferably 40% reduction, more preferably 20% reduction, of the thymidine uptake by human lymphocytes, as measured by the Lymphocyte Proliferation Assay using PHA.

In yet a further embodiment, the pharmaceutical composition is a composition for the treatment or prophylaxis of diseases caused by Plasmodium spp. in humans, and the aromatic compound, when administered intraperitoneally in the in vivo test described in Example 16 herein in a dose of up to 20 mg per kg body weight two times daily for 6 days to female BALB/c mice which have been infected with malaria *P. yoelii* ($2\times10^5$/mouse), the administration being initiated one day after infection, is able to prevent increase in the parasitemia during the administration period. In particular, the aromatic compound, or the prodrug, when administered intraperitoneally in the in vivo test described in Example 16 herein in a dose of up to 20 mg per kg body weight two times daily for 10 days to 8 weeks old female BALB/c mice which have been infected with malaria *P. yoelii* ($2\times10^5$/mouse), the administration being initiated one day after infection, is capable of clearing the parasite from the mice within at the most 23 days.

Especially, the aromatic compound, or the prodrug, when administered intraperitoneally in the in vivo test described in Example 16 herein in a dose of up to 20 mg per kg body weight two times daily for 8 days to 8 weeks old female BALB/c mice which have been infected with malaria *P. yoelii* strain YM ($1\times10^6$/mouse), the administration being initiated one day after infection, is capable of clearing the parasite from the mice within at the most 21 days, preferably within at the most 17 days.

It is also preferred that the aromatic compound, or the prodrug, when administered intraperitoneally in the in Vivo test described in Example 16 herein in a dose of 5 mg per kg body weight two times daily for 10 days to 8 weeks old female BALB/c mice which have been infected with malaria *P. yoelii* ($2\times10^5$/mouse), the administration being initiated one day after infection, is capable of clearing the parasite from the mice within at the most 23 days. In particular, the aromatic compound, or the prodrug, when administered intraperitoneally in the in vivo test described in Example 16 herein in a dose of 5 mg per kg body weight two times daily for 8 days to 8 weeks old female BALB/c mice which have been infected with malaria *P. yoelii* strain YM ($1\times10^6$/mouse), the administration being initiated one day after infection, is capable of clearing the parasite from the mice within at the most 21 days, preferably within at the most 17 days.

In a further embodiment of the invention, use is made of an aromatic compound, or a prodrug thereof, which aromatic compound contains an alkylating site and which aromatic compound is capable of alkylating the thiol group in N-acetyl-L-cysteine at physiological pH, for the preparation of a pharmaceutical composition or a medicated feed or drinking water for the treatment or propylaxis of diseases caused by Coccidia in poultry such as chickens or turkeys, wherein the aromatic compound, or the prodrug, when administered to chickens with the feed in a concentration of up to 400 ppm for at most 28 days in the in vivo test described in Example 28 herein, is capable of controlling infection by *Eimeria tenella* in at least 60% of the chickens and preventing pathological alterations in at least 50% of the chickens, the aromatic compound preferably being one which in a concentration of up to 120 ppm for at most 28 days in the in vivo test described in Example 28 herein, is capable of controlling infection by *Eimeria tenella* in at least 60% of the chickens and preventing pathological alterations in at least 65% of the chickens.

In a further embodiment, the pharmaceutical composition is a composition for the treatment or prophylaxis of diseases caused by intracellular bacteria such as Mycobacteria in humans or animals such as cattle, and the aromatic compound is one which is capable of inhibiting the growth and multiplication of *Mycobacteria tuberculosis* or *Legionella pneumophila* in vitro in the test described in Example 17 herein at a mean MIC of 10 $\mu$g per ml, and, in the same concentration, causes less than 50% reduction of the thymidine uptake of human lymphocytes as measured by The Lympocyte Proliferation Assay.

The aromatic compound is preferably one which contains an aromatic ring attached to the alkylating site. As indicated above, the compound in particular one which has electron-donating groups attached to an aromatic ring.

In the aromatic compound, the alkylating site is typically a double or triple bond conjugated with a carbonyl group which carbonyl group optionally is further conjugated with an aromatic ring such as a phenyl group, the aromatic ring attached to the alkylating site preferably containing at least one electron-donating group such as an oxygen, nitrogen or sulphur function such as hydroxy, alkoxy (e.g. methoxy), amino, alkylamino, dialkylamino, mercapto, or alkylthio. It is preferred that the electron-donating group(s) is/are attached to the aromatic ring in a position next to and/or most remote relative to the position through which the aromatic ring is attached to the alkylating site.

Particularly important diseases to be treated or prevented by means of the composition prepared according to the invention are human leishmaniasis caused by *Leishmania donovani, L. infantum, L. aethiopica, L. major, L. tropical L. mexicana* complex, or *L. braziliensis* complex or human malaria caused by *Plasmodium falciparum, P. ovale, P. vivax*, or *P. malariae*, as well as parasitic diseases in livestock, such as Babesia in cattle, or a parasitic disease in birds, such as a disease caused by Coccidia such as *Eimeria tenella* in poultry such as chicken or turkey, or a parasitic disease in fish, such as Pseudodactylogurus or Trichodina.

The important human malaria parasites with which hundreds of millions of humans are infected, are *Plasmodium falciparum, P. ovale, P. vivax*, and *P. malariae*. In particular, *Plasmodium falciparum* is the most important human parasite and the number one parasite killer-of mankind. The malaria parasites show widespread resistance against almost all available antimalarial drugs. For this reason, the fact that a new class of antimalarial drugs, chemically unrelated to the known antimalarial drugs has been provided, is a feature of the invention which is of great importance. Another important aspect of the invention is that malaria parasites resistant against Chloroquine, the most commonly used antimalarial drug, show very high degree susceptibility to the compounds described herein (Example 15).

Another important aspect of the invention is the antileishmanial activity of the compounds defined above. Visceral leishmaniasis, caused by *Leishmania donovani* or *L. infantum*, inflicts several million people in the world, and this disease recently appears to be a major problem for AIDS patients coming in contact with Leishmania parasites, combined with large scale clinical resistance in endemic areas such as India (which is announced "alarming" by the World Health Organization). Other major diseases are diseases caused by other species of Leishmania, such as *L. aethiopica, L. major, L. tropica, L. mexicana* complex, and *L. braziliensis* complex. Some of these species cause severe disfiguring and morbidity in millions of humans in Central and South America and many parts of Africa.

In one preferred aspect, the invention relates to the use of an aromatic compound which is a bis-aromatic α,β-unsaturated ketone of the general formula I $$X_m—Ar^1—CO—W—Ar^2—Y_n \qquad I$$

wherein

W is either —CR═CR— or —C≡C—, wherein each R independently of the other R designates hydrogen, $C_{1-3}$ alkyl, or halogen, $Ar^1$ and $Ar^2$ are the same or different and each designate an aromate selected from phenyl and 5- or 6-membered unsaturated heterocyclic rings containing one, two or three heteroatoms selected from oxygern, sulfur, and nitrogen, such as furanvl, thiophenyl, pyrrolyl, imidazolyl, isoxazolyl, oxazolyl, thiazolyl, pyrazolyl, pyridinyl, or pyrimidinyl, which aromate may be substituted with one or more substituents selected from halogen; nitro; nitroso; and $C_{1-2}$, preferably $C_{1-6}$, straight or branched aliphatic hydrocarbyl which may be saturated or may contain one or more unsaturated bonds selected from double bonds and triple bonds, which hydrocarbyl may be substituted with one or more substituents selected from hydroxy, halogen, amino, and amino which is optionally alkylated with one or two $C_{1-6}$ alkyl groups;

Y and X are the same or different and each designate a group $AR_H$ or a group AZ, wherein A is —O—, —S—, —NH—, or —N($C_{1-6}$ alkyl)-, $R_H$ designates $C_{1-6}$ straight or branched aliphatic hydrocarbyl which may be saturated or may contain one or more unsaturated bonds selected from double bonds and triple bonds, and Z designates H or (when the compound is a prodrug) a masking group which is readily decomposed under conditions prevailing in the animal body to liberate a group AH, in which A is as defined above; m designates 0, 1 or 2, and n designates 0, 1, 2 or 3, whereby, when m is 2, then the two groups X are the same or different, and when n is 2 or 3, then the two or three groups Y are the same or different, with the proviso that not both of n and m are 0.

When Z designates a masking group, it may typically be selected from the below groups (A)–(E)

$$—CO—R' \qquad (A)$$

$$—CON(CH_3)_2 \qquad (B)$$

$$—CR^*R^{**}—O—R'' \qquad (C)$$

-continued (D)

$$—CR^{*}R^{**}—O—CO—R'''$$

(E)

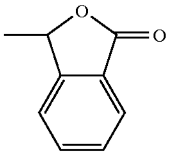

wherein R* and R** each independently designate hydrogen or $C_{1-3}$ alkyl, R', R" and R''' each designate $C_{1-6}$ alkyl or is an aromate $Ar^1$ or $Ar^2$ as defined above.

Preferred compounds of the general formula I are those, wherein $Ar^1$ or $Ar^2$ independently are phenyl or an aromatic 5- or 6-menbered heterocyclic ring containing one, two or three heteroatoms selected from oxygen, nitrogen or sulphur, n is 0, 1, 2, or 3, m is 0, 1 or 2, at least one of the groups X is in a position in $Ar^1$ most remote relative to and or next to the position through which $Ar^1$ is bound to the carbonyl group, and at least one of the groups Y is in a position in $Ar^2$ most remote relative to and/or next to the position through which $Ar^2$ is bound to W.

It is further preferred that A designates O, and Z designates pivaloyl, pivaloyloxymethyl or N,N-dimethylcarbamoyl.

In particular, the bis-aromatic α,β-unsaturated ketones act by selectively destroying the cells of the microorganisms or cells of multicellular parasites; as will appear from the below discussion and the examples herein, the bis-aromatic α,β-unsaturated ketones in appropriate concentration ranges will selectively kill the microorganisms or the multicellular parasites by destroying the cells of the microorganisms or cells of the multicellular parasites while showing a high degree of tolerance for the host cells which are subjected to exposure to the compounds.

As indicated above, it is contemplated (as described in detail in the following description of mechanism) that the mechanism of action is via interference of the $O_2$-metabolism of the microorganism or parasite in question in that the bis-aromatic α,β-unsaturated ketone inhibits or interferes with the $O_2$-metabolism of the mitochondria (where applicable) of the microorganism such as the parasite or the $O_2$-metabolism of the bacteria itself. At the same time, the mitochondria of humans have been found to be able to tolerate the compounds in question in the same concentrations which will inhibit or kill the microorganism or the multicellular parasite. It is this remarkable selectivity of certain classes of bis-aromatic α,β-unsaturated ketones which constitutes the basis of this aspect of the present invention.

Many of the bis-aromatic α,β-unsaturated ketones of the general formula I are novel, and the invention also relates to all such novel bis-aromatic α,β-unsaturated ketones. In the following, some preferred classes of the novel bis-aromatic α,β-unsaturated ketones are defined, and preferred individual compounds among these are discussed specifically.

Because the bis-aromatic α,β-unsaturated ketones used according to the invention have been found to be well tolerated by animal cells, including human cells, such as will be explained in detail in the following, and because these properties are contemplated to be possessed by the broader range of aromatic compounds defined above, the invention opens up the possibility of controlling parasitic diseases not only by administration to the animals, including humans, as therapy or prophylaxis, but also by killing the parasite in its vector by spraving or otherwise applying an aromatic compound of the type defined above, such as a bis-aromatic α,β-unsaturated ketone, in the infected areas so that the vector will take up the compound, whereby the parasite will be subjects to the compound. Thus, one aspect of the invention relates to a method for controlling transmission of parasitic diseases caused by parasites which have part of their life cycles in a vector, comprising applying an aromatic compound as defined above, such as a bis-aromatic α,β-ketone of the general formula I, to a locus which is a habitat of the vector so as to eradicate the parasites. The parasites will, in this case, in particular be Leishmania, Plasmodium, or Trypanosoma, and the eradication of the parasite will, depending on the vector's tolerance to the compound, take place with or without concomitant eradication of the vector.

When W in the general formula I is —CR═CR—, it may be either cis or trans configured. It is preferred that it is trans configured. It is often preferred that both groups R are hydrogen, but it is contemplated that also bis-aromatic α,β-unsaturated ketones in which one of or both groups R is/are e.g. methyl or ethyl are of great value with respect to the relevant activity and selectivity/tolerability.

With respect to the position of X and/or Y in its/their respective aromate(s), it is highly preferred, and indeed, in number of cases seems to be a condition for a high biological or therapeutic activity against the microorganism in question combined with a high tolerability by animal cells, that at least one of X and Y which is different from hydrogen is positioned in the aromate in a position most remote relative to and/or next to the position through which the aromate is bound to the α,β-unsaturated ketone group. Examples of preferred combinations in this regard are the cases where $Ar^1$ is phenyl or an aromatic heterocyclic ring containing one, two or three heteroatoms, m is 0, 1 or 2, and X is in a position in $Ar^1$ most remote relative to and/or next to the position through which $Ar^1$ is bound to the carbonyl group;

$Ar^2$ is phenyl or an aromatic heterocyclic ring containing one, two or three heteroatoms, n is 1, 2 or 3, and each Y is in the a position in $Ar^2$ most remote relative to and/or next to the position through which $Ar^2$ is bound to W; or $Ar^1$ and $Ar^2$ are selected from phenyl and an aromatic heterocyclic ring containing one, two or three heteroatoms, m and n are each 1, 2 or 3, each X is in an position most remote relative to and/or next to the position through which $Ar^1$ is bound to the carbonyl group, and each Y is in a position most remote relative to and/or next to W.

The aromate is suitably phenyl such as illustrated in most of the examples herein, but it is reasonable to contemplate that anv of the aromate types mentioned above can be the $Ar^1$ or; $Ar^2$ of the bis-aromatic α,β-unsaturated ketone, considering that such aromatic rings will affect the electron density in the unsaturated ketone similarly to the two phenyl rings, and that such aromates will also give possibilities for charge transfer complexes and lipophilic interactions with the target molecule, such as do the two phenyl rings.

Apart from the important substitution with X and/or Y as explained herein, the aromate may carry other substituents which either will not to any substantial extent detract from the useful effect and selectivity of the bis-aromatic α,β-unsaturated ketones, or will enhance these properties or relevant properties related to the use and utility of the bis-aromatic α,β-unsaturated ketones, e.g., their solubility (such as when the bis-aromatic α,β-unsaturated ketones carry a nitrogen-containing basic group or a carboxyl group which can form water-soluble salts with pharmaceutically acceptable counter ions).

Among the bis-aromatic α,β-unsaturated ketones of the general formula I, the preferred ones are generally those in which A is O, mainly because of their excellent properties with respect to activity and selectivity/tolerability, such as will appear from the results reported herein. However, it is well known that the oxygen atom in the form of oxy in many biologically active compounds may, with greater or lesser retention of, and indeed in certain cases with enhancement of, the biological activity, be replaced with bioisosteric groups, such as —S—, —NH—, and —N($C_{1-6}$alkyl)- as mentioned above.

As appears from the discussion herein and the results reported herein, the presence of a particular substituent X or Y or of particular substituents X and Y, preferably in specific positions in the aromate, in particular in the position in the aromate which is remote relative to and/or next to the position of attachment of the aromate, seems to be important to the effect and selectivity of the bis-aromatic α,β-unsaturated ketones. Based upon the above-mentioned general preference for substituents X and Y which contain —O— (but taking into consideration that the oxygen atom could be replaced with the a bioisosteric group), this substituent could be called "an oxy-functional substituent". While it is presumed that the activity of the oxy-functional substituent is related to the substituent in the "free" form, that is, to hydroxy when A is —O—, to thiolo when A is —S—, and to amino or monoalkylamino when A is —NH— or —N($C_{1-6}$- alkyl)-, very interesting results obtained with bis-aromatic α,β-unsaturated ketones of the formula I where X or Y is alkenyloxy raise the intriguing question whether the active form in theses cases is the alkenyloxy-substituted form, or whether the alkenyloxy group is converted to a hydroxy group, maybe even by the microorganism or parasite itself, before the bis-aromatic α,β-unsaturated ketone exerts it action. As will be understood, this possibility is covered by the definition $R_H$ above, while the definition of Z, when Z is not hydrogen, is adapted to represent "prodrug" forms which, in accordance with well known principles used in the construction of suitable administration embodiments of chemical compounds containing, e.g., free hydro groups as substituents on aromatic rings, will be decomposed in the animal body to result in the corresponding compound in which Z is hydrogen.

In a preferred embodiment, the bis-aromatic α,β-unsaturated ketone has the general formula II $$X_m—Ph—C(O)—CH{=}CH—Ph—Y_n \qquad II$$

wherein Ph designates phenyl, and $X_m$ and $Y_n$ are as defined above, and each phenyl group may be substituted with one or more substituents selected from halogen; nitro; nitroso; and $C_{1-12}$, preferably $C_{1-6}$, straight or branched aliphatic hydrocarbyl which may be saturated or may contain one or more unsaturated bonds selected from double bonds and triple bonds, which hydrocarbyl may be substituted with one or more substituents selected from hydroxy, halogen, amino, and amino which is optionally alkylated with one or two $C_{1-6}$ alkyl groups.

In these compounds, it is preferred that X and/or Y designates OH or a group $OR_H$, in which $R_H$ is as defined above, or OZ*, in which Z* is a masking group which is readily decomposed under conditions prevailing in the animal body to liberate the group OH, in particular one of the groups (A)–(E) as defined above, preferably pivaloyl, pivaloyloxymethyl or N,N-dimethylcarbonyl.

The substituent or substituents on the phenyl group(s) is/are preferably selected from $C_{1-12}$, preferably $C_{1-6}$, straight or branched aliphatic hydrocarbyl which may be saturated or may contain one or more unsaturated bonds selected from double bonds and triple bonds, which hydrocarbyl may be substituted with one or more substituents selected from hydroxy, halogen, amino, and amino which is optionally alkylated with one and two $C_{1-6}$ alkyl groups.

In especially preferred embodiments, the substituent or substituents on the phenyl groups is/are selected from methyl, ethyl, propyl, isopropyl, tert.-butyl, prop-2-enyl, 1,1-dimethylpropyl, 1,1-dimethylprop-2-enyl, 3-methylbutyl, and 3-methylbut-2-enyl.

The host animals to be treated, either to obtain a therapeutic effect, or to obtain a prophylaxis or protection against infection, are primarily vertebrates such as birds, fish and mammals, including humans. It is evident that with respect to some of the microorganisms and multicellular parasites mentioned above, the host to be treated is defined once the microorganism or multicellular parasite is given. Thus, for example, when the microorganism is Leishmania, the hosts to be treated are humans or dogs; when the microorganism is Theileria, the animals to be treated are cattle, sheep and goats; when the microorganism is Eimeria, the animals to be treated are chickens and turkeys.

Based upon findings as explained in the examples below, it is presumed that the mechanism of action of the bis-aromatic α,β-unsaturated ketones of the general formulae I and II above, and prodrugs thereof, is as follows:

The bis-aromatic α,β-unsaturated ketones severely damage the mitochondria of the parasites. Mitochondria are oval-shaped organelles, typically about 2 μm in length and 0.5 μm in diameter, located intracellularv in all organisms except bacteria. Mitochondria have two membrane systems, an outer membrane and an extensive, highly folded inner membrane, hence there are two compartments in mitochondria: the intermembrane space between the inner membrane and the outer membrane, and the matrix, which is bounded by the inner membrane.

Mitochondria are the organelles involved in the $O_2$-metabolism of the cell. Oxidative phosphorylation is the process in which ATP is formed as electrons are transferred from NADH or $FADH_2$ to $O_2$ by a series of electron carriers. This is the major source of ATP in aerobic organisms. Oxidative phosphorylation is carried out by respiratory assemblies located as an integral part of the inner mitochondrial membrane. The outer membrane is quite permeable to most small molecules and ions.

From B. Inoue, K. Inaba, T. Mori, F. Izushi, K. Eto, R. Sakai, M. Ogata and K. Utsumi, *J. Toxicol. Sci.* 7 (1982), 245–254 it is known that echinastin, 4-hydroxychalcone, chalcone, and 3,4'-dihydroxychalcone cause deterioration of respiratory control and oxidative phosphorylation of isolated rat liver mitochondria. The present inventors have found that bis-aromatic α,β-unsaturated ketones and derivatives thereof of the general formula I or II cause deterioration of respiratory control and oxidative phosphorylation of mitochondria of parasites in concentrations that are so small that the mitochondria of the animal cell are not affected.

Due to the interference with the $O_2$-metabolism of the mitochondria the mitochondria are destroyed and as a consequence the cell to which the mitochondria belong is destroyed.

Thus, the compound known as licochalcone A does not appear to exhibit anv toxicity in animal cells even at fairly high concentrations, cf. the data given in Example 14 herein. Thus, licochalcone A is an important potential antiparasitic, in particular, antimalarial and antileishmanial drug. However, as appears from the experiments reported in the examples herein, the surprising effect and selectivity found is not limited to licochalcone A, but is characteristic of the class of bis-aromatic α,β-unsaturated ketones discussed herein and, for the reasons given above, is believed to apply more broadly to the aromatic compounds defined above.

Leishmania parasites are transferred through bites from sandflies belonging to the genera Phlebotomus and Lutzomyia. In the gastrointestinal canal of the flies the parasite is transformed from the amastigote phase to the promastigote phase and is propagated. Thereupon the promastigotes migrate to the mouth, especially the salivary glands of the flies and are transferred with the next bite from the fly.

The promastigotes are bound to the macrophage of the infected organism followed by uptake of the parasite into the macrophage where it is transformed to the amastigote phase and multiply inside these cells.

bis-Aromatic α,β-unsaturated ketones as defined herein have been found to have effect on the Leishmania parasite in the amastigote phase as well as in the promastigote phase. This means that the compounds in question are both useful in the prophylaxis of leishmaniasis, because of the effect against the promastigotes, and in the treatment of the disease, because of the effect against the amastigqtes. Again, this is believed to apply more broadly to the aromatic compounds defined above.

In cultures, promastigotes multiply with exponential rate the first three days, called the log-phase, and for the following three days the promastigotes are still alive but not multiplying any longer (this phase is called the stationary phase), unless they are transported to another medium. In case the promastigotes are transferred to another medium the log-phase will continue for another three days, and then the promastigotes will enter the stationary phase.

If promastigotes are bound to macrophages in the log-phase, the promastigotes will be killed by the macrophage. On the other hand, if the promastigotes are bound to macrophages in the stationary phase, then the promastigotes are able to infect the cells and multiply inside them.

The stationary phase of the promastigotes, the infective form of the parasite, is generally more sensitive to the bis-aromatic α,β-unsaturated ketones than the log phase of the promastigote, which means that the bis-aromatic α,β-unsaturated ketones are able to prevent infection with the Leishmania parasite; in accordance with the explanation given above, this is believed to apply more broadly to the aromatic compounds defined above.

Bacteria possess a cell wall and a cytoplasmic membrane, but lack mitochondria. Instead, the electron transport and the oxidative phosphorylation, and the latter only in the aerobic bacteria, takes place in the cytoplasmic membrane which then serves the mitochondria-like function in the bacteria.

It is contemplated that the aromatic compounds, such as the bis-aromatic α,β-unsaturated ketones defined herein interfere with the $O_2$-metabolism of the cytoplasmic membrane corresponding to the interference with the $O_2$-metabolism of the mitochondria of higher developed organisms, thereby destroying the bacteria.

As mentioned above, important findings on which the present invention is based are not only the remarkable efficiency of the bis-aromatic α,β-unsaturated ketones with respect to destroying the pathogenic microorganisms, but also the high degree of selectivity which they show with respect to the pathogenic microorganisms as contrasted to animal cells, including human cells. Thus, as will appear from the data given in the examples below, bis-aromatic α,β-unsaturated ketones have been found to be substantially harmless to human cells in concentrations at which they effectively control the parasites. This selectivity was surprising. Moreover, as appears from the examples, a still much higher activity against the microorganisms is found when the microorganisms are present in tissue, such as in cells, such as will be the case in the actual therapeutic use. In many cases, a further increase by a factor 10 in the selectivity is seen.

Preliminary experiments (Example 25) involving oral administration of licochalcone A to mice and rats and injection of licochalcone A to mice indicate that in animals such as mammals, the bis-aromatic α,β-unsaturated ketones which possess a free phenolic hydroxy group will be eliminated from the blood stream already after the first passage to through the liver. This is in accordance with what is known about the metabolism of other phenolic compounds. For this reason, an important aspect of the invention is constituted by compounds in which the phenolic hydroxy group or groups or bioisosteric other group or groups AZ are masked, in other words, the so-called prodrugs, that is, compounds which are readily decomposed under conditions prevailing in the animal body to liberate the free groups which are associated with the active forms of the drugs.

The prodrugs used according to the invention are, e.g., compounds of the general formula I or II in which Z is a group which is readily decomposed under conditions prevailing in the animal body to liberate the group AH. As an important example, when A is O such as is the case in important compounds used according to the invention, it is preferred that Z is a group which is readily decomposed under conditions prevailing in the animal body to liberate the group OH.

The establishment of prodrug forms suitable in connection with particular substituents in drugs is based upon the fact that certain types of groups will tend to be decomposed in the animal body in accordance with various decomposition pathways. Thus, among the above-mentioned specific prodrug groups (A)–(E), the groups (A), (D), and (E) are groups which will be decomposed by esterases to result in the corresponding free group such as the hydroxy group. The group (B) will be subjected to removal of one of the methyl groups in the liver, and the group thus formed will be relatively readily decomposable in plasma. The oxy-containing groups (C) are groups which are relatively labile under acidic conditions and, as thus, are adapated to be decoposed, e.g., under the conditions under which Leishmania amastigotes exist in the human body, that is, in macrophages. Quite generally, the prodrup group Z will be one which prevents the active molecule from being converted, in the liver, to a form which, from a practical point of view, will be inactive and quickly will be eliminated from the animal body, such as the forms where free phenolic OH groups are sulfated in the liver or are coupled to glucomic acid in the liver.

In preferred embodiments, Z is a group selected from the groups (A)–(E) as defined above. Examples of particularly preferred groups Z are pivaloyl, pivaloyloxymethyl and N,N-dimethylcarbamoyl.

The above considerations concerning prodrug derivatives of hydroxy groups in the compounds of the general formula I or II also apply to ther hydroxy group-containing aromatic alkylating compounds as defomed above.

In the following, valuable and interesting subclasses of the bis-aromatic α,β-unsaturated ketones used according to the invetion will be discussed.

Based upon their generally very interesting selective propertiees, an interesting class of compounds used according to the invention is constituted by compounds of the general formula III

III

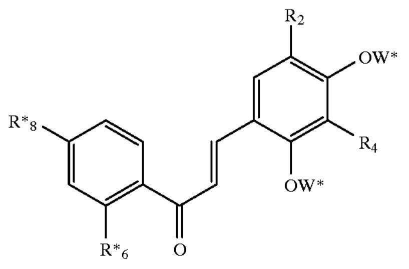

wherein $R_2$ and $R_4$ designate $R_H$ as defined above, or H, one of $R^*_6$ and $R^*_8$ designate OW* and the other is H, or both $R^*_6$ and $R^*_8$ designate H, and W* designates H, $R_H$ or a group (A)–(E) as defined above, wherein both R* and R** designate H.

Other interesting bis-aromatic α,β-unsaturated ketones used according to the invention have the general formula IV

IV

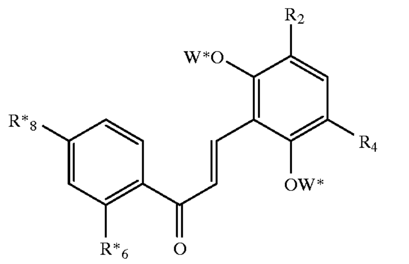

wherein $R_2$, $R_4$, $R^*_6$, $R^*_8$ and OW* are as defined above.

Because of the very interesting properties possessed by licochalcone A, confer the examples which follow, very interesting compounds used according to the invention are bis-aromatic α,β-unsaturated ketones in which the two hydroxy groups in licochalcone are replaced with a group OW*, in which each W* independently designates H, $R_H$ or a group (A)–(E) as defined above, wherein both R* and R** designated H, such as compounds which have the general formula V or VI

V

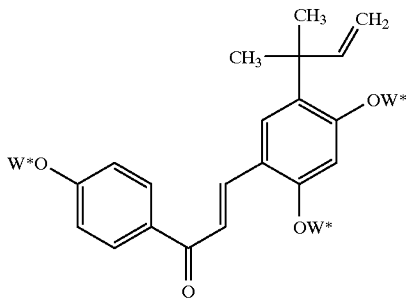

-continued

VI

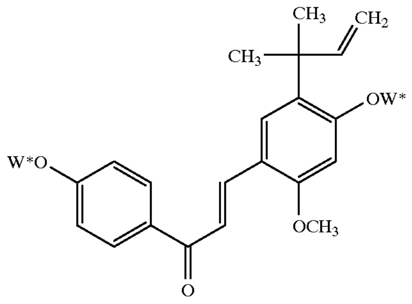

Also, bis-aromatic α,β-unsaturated ketones of the general formula VII

VII

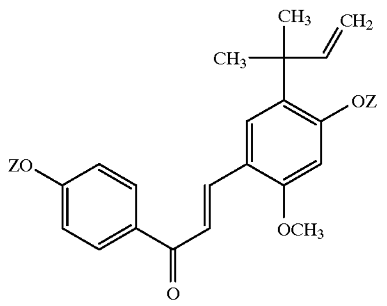

wherein Z is as defined above, are evidently very interesting compounds. In those compounds, it is preferred that Z designates pivaloyl, pivaloyloxymethyl or N,N-dimethylcarbonyl.

Another interesting class of bis-aromatic α,β-unsaturated ketones has the general formula VIII

VIII

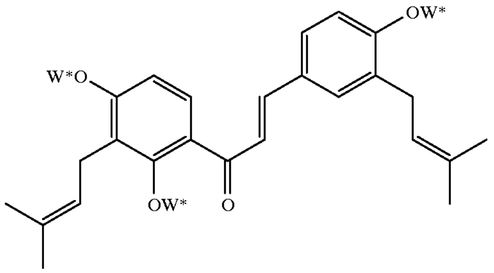

wherein W is as defined above.

Many of the bis-aromatic α,β-unsaturated ketones of the general formula I are novel compounds, and the invention also relates to all such novel compounds per se.

Among the novel compounds of the invention are the bis-aromatic α,β-unsaturated ketones of the general formula IX

IX

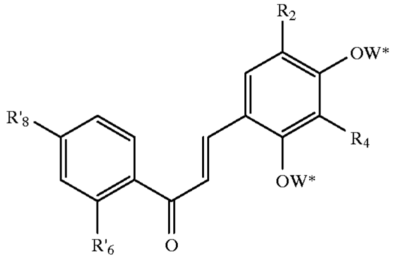

wherein one of $R'_6$ and $R'_8$ designate A(W*), and the other designates H, or both designate H, A designates S, N or O, whereby, when A designates S or O, then p designates 1, and when A designates N, then p designates 2, with the proviso that when $R_2$ and $R_4$ both are H, then at least one W* designates a masking group Z as defined above, andwith the exception of the known compounds licochalcone A, licochalcone C, 3-[4-hydroxy-5-(1,1-dimethylprop-2-enyl)-2-methoxyphenyl]-1-[4-(methoxymethoxy)phenyl]-2-propen-1-one, 3-[4-acetyloxy-5-(1,1-dimethylprop-2-enyl)-2-methoxyphenyl]-1-[4-(methoxymethoxy)phenyl]-2-propen-1-one, 3-[5-(1,1-dimethylprop-2-enyl)-2, 4dimethoxyphenyl]-1-[4-(methoxy)phenyl]-2-propen-1-one, 3-[4acetyloxy-5-(1,1-dimethylprop-2-enyl)-2-methoxyphenyl]-1-(4-acetyloxyphenyl)2-prop-1-one, 3-[2-hydroxy-4-methoxy-3-(3-methylbut-2-enyl)phenyl]-1-[4-[(3,7,11-trimethyl-2,6-dodecatri-10-enyl)oxy]phenyl]-2-prop-1one, and 2,4-dihydroxy-3-methylchalcone.

Among such novel compounds of the formula IX, very interesting compound are of the general formula X

X

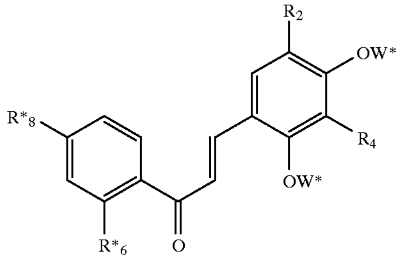

wherein $R_2$ and $R_4$ are as defined in claim 41, one of $R^*_8$ and $R^*_6$ designates OW*, and the other designates H, or both designate H, and W* is as defined above.

Particularly interesting compounds have the general formula XI

XI

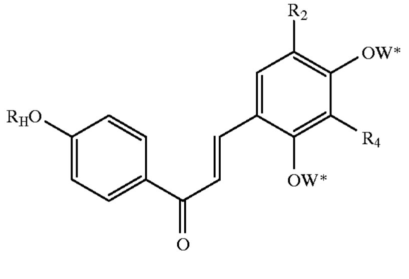

wherein $R_2$, $R_4$ and W* are as defined above. The compounds in which $R_2$ and/or $R_4$ designates methyl, ethyl, propyl, isopropyl, tert.-butyl, prop-2-enyl, 1,1-dimethylpropyl, 1,1-dimethylprop-2-enyl, 3-methylbutyl, or 3-methylbut-2-enyl are especially preferred compounds.

Important novel compounds according to the invention are of the general formula XII

XII

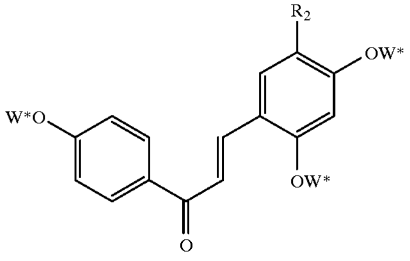

wherein $R_2$ and W* are as defined above.

Also, the bis-aromatic α,β-unsaturated ketones of the general formula XIII

XIII

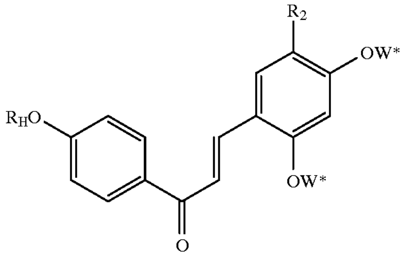

wherein $R_H$, $R_2$ and W* are as defined above are interesting novel compounds. Among these, very interesting compounds are those in which $R_2$ designates methyl, ethyl, propyl, isopropyl, tert.-butyl, prop-2-enyl, 1,1-dimethylpropyl, 1,1imethylprop-2-enyl, 3-methylbutyl, or 3methylbut-2-enyl.

Particularly interesting novel bis-aromatic α,β-unsaturated ketones are prodrugs of Licochalcone A of the general formula XIV

XIV

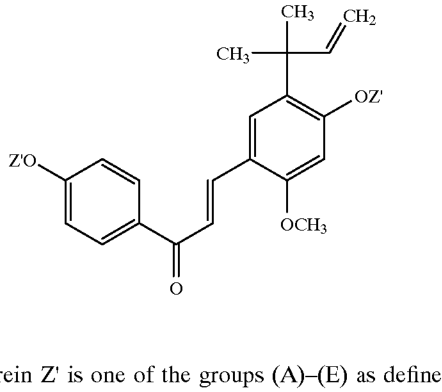

wherein Z' is one of the groups (A)–(E) as defined above.

Novel bis-aromatic α,β-unsaturated ketones of the general formula XV

XV

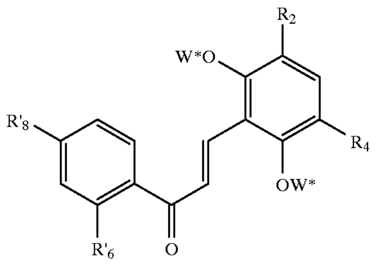

wherein one of $R'_6$ and $R'_8$ designates $A(W^*)_p$ and the other designates H, or both designate H, W* is as defined above, A designate S, N or O, whereby when A designates S or O then p designates 1, and when A designates N then p designates 2, with the exception of 2,6-methoxychalcone and 2-hydroxy-6-methoxychalcone, form a further interesting class of compounds. Of these compounds, an interesting subclass of bis-aromatic α,β-unsaturated ketones have the general formula XVI

XVI

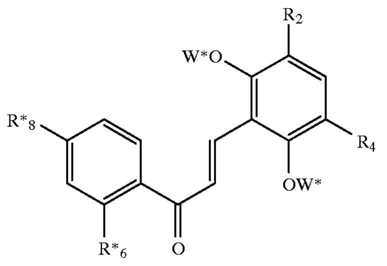

wherein $R_2$, $R_4$, $R^*_8$, $R^*_6$ and W* are as defined above.

Among these, interesting novel bis-aromatic α,β-unsaturated ketones have the general formula XVII

XVII

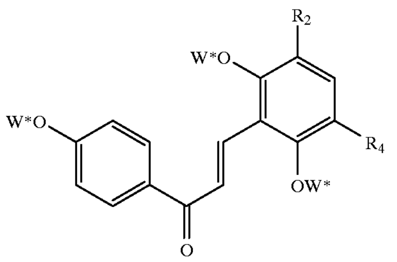

wherein $R_2$, $R_4$ and W* are as defined above, in particular the compounds of the general formula XVIII

XVIII

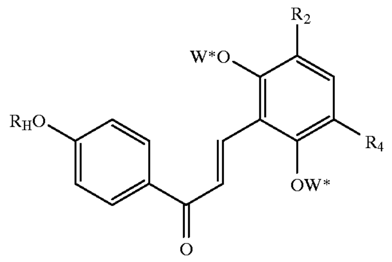

wherein $R_H$, $R_2$, $R_4$ and W* are as defined above. Those compound in which $R_2$ and/or $R_4$ designates methyl, ethyl, propyl, isopropyl, tert.-butyl, prop-2-enyl, 1,1-dimethylpropyl, 1,1-dimethylprop-2-enyl, 3-methylbutyl, or 3-methylbut-2-enyl are especially interesting.

Other novel bis-aromatic α,β-unsaturated ketones have the general formula XIX

XIX

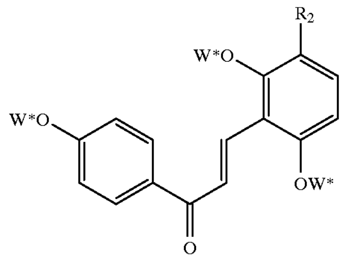

wherein $R_2$ and W* are as defined above. Among these, the compounds in which $R_2$ designates propyl, prop-2-enyl, 1,1-dimethylpropyl, or 1,1dimethylprop-2enyl are especially interesting.

Another interesting class of novel bis-aromatic α,β-unsaturated ketones have the general formula XX

XX

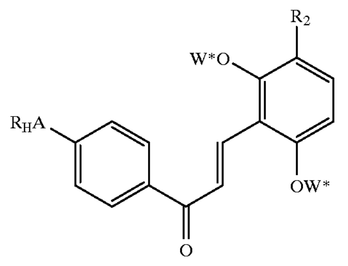

wherein A, $R_H$, and $R_2$ is as defined above. Among these, the ones in which $R_2$ designates propyl, prop-2-enyl, 1,1-dimethylpropyl, 1,1-dimethylprop-2-enyl, 3-methylbutyl, or 3-methylbut-2-enyl are especially interesting.

Also, the bis-aromatic α,β-unsaturated ketones of the general formula XXI

XXI

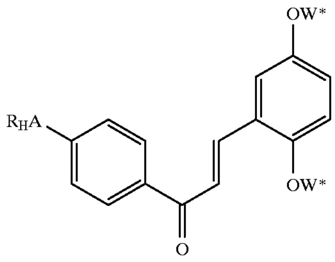

wherein A, $R_H$, and W* are as defined above, are interesting novel compounds.

Specific examples of these novel bis-aromatic α,β-unsaturated ketones are the ones selected from
2,4-dimethoxy-4'-hydroxy-chalcone,
2,4-diethoxy-4'-hydroxy-chalcone,
2,4-di-n-propoxy-4'-hydroxy-chalcone,
2,4-diisopropoxy-4'-hydroxy-chalcone,
2,4-di-n-butoxy-4'-hydroxy-chalcone,
2,4-di-t-butoxy-4'-hydroxy-chalcone,
2,4-dimethoxy-4'-thiolo-chalcone,
2,4-diethoxy-4'-thiolocalcone,
2,4-di-n-propoxy-4'-thiolo-chalcone,
2,4-diisopropoxy-4'-thiolo-chalcone,
2,4-di-n-butoxy-4'-thiolo-chalcone,
2,4-di-t-butoxy-4'-thiolo-chalcone,
2,4-dimethoxy-4'-amino-chalcone,
2,4-diethoxy-4'-amino-chalcone,
2,4-di-n-propoxy-4'-amino-chalcone,
2,4-diisopropoxy-4'-amino-chalcone,
2,4-di-n-butoxy-4'-amino-chalcone,
2,4-di-t-butoxy-4'-amino-chalcone,
2,4-dimethoxy-4'-methylamino-chalcone,
2,4-diethoxy-4'-methylamino-chalcone,
2,4-di-n-propoxy-4'-methylamino-chalcone,
2,4-diisopropoxy-4'-methylamino-chalcone,
2,4-di-n-butoxy-4'-methylarmino-chalcone,
2,4-di-t-butoxy-4'-methylamino-chalcone,
2,4-dimethoxy-5-methyl-4'-hydroxy-chalcone,
2,4-diethoxy-5-methyl-4'-hydroxy-chalcone,
2,4-di-n-propoxy-5-methyl-4'-hydroxy-chalcone,
2,4-diisopropoxy-5-methyl-4'-hydroxy-chalcone,
2,4-di-n-butoxy-5-methyl-4'-hydroxy-chalcone,
2,4-di-t-butoxy-5-methyl-4'-hydroxy-chalcone,
2,4-dimethoxy-5-methyl-4'-thiolo-chalcone,
2,4-diethoxy-5-methyl-4'-thiolo-chalcone,
2,4-di-n-propoxy-5-methyl-4'-thiolochalcone,
2,4-diisopropoxy-5-methyl-4'-thiolo-halcone,
2,4-di-n-butoxy-5-methyl-4'-thiolo-chalcone,
2,4-di-t-butoxy-5-methyl-4'-thiolo-chalcone,
2,4-dimethoxy-5-methyl-4'-amino-chalcone,
2,4-diethoxy-5-methyl-4'-amino-chalcone,
2,4-di-n-propoxy-5-methyl-4'-amino-chalcone,
2,4-diisopropoxy-5-methyl-4'-amino-chaicone,
2,4-di-n-butoxy-5-methyl-4'-armino-chalcone,
2,4-di-t-butoxy-5-methyl-4'-amino-chalcone,
2,4-dimethoxy-5-methyl-4'-methylamino-chalcone,
2,4-diethoxy-5-methyl-4'-methylamino-chalcone,
2,4-di-n-propoxy-5-methyl-4'-methylamino-chalcone,
2,4-diisopropoxy-5-methyl-4'-methylamino-chalcone,
2,4-di-n-butoxy-5-methyl-4'-methylarmino-chalcone,
2,4-di-t-butoxy-5-methyl-4'-methylaminochalcone,
2,4-dimethoxy-5-prop-2-enyl-4'-hydroxy-chalcone,
2,4-diethoxy-5prop-2-enyl-4'-hydroxy-chalcone,
2,4-di-n-propoxy-5prop-2-enyl-4'-hydroxy-chalcone,
2,4-diisopropoxy-5-prop-2-enyl-4'-hydroxy-chalcone,
2,4-di-n-butoxy-5-prop-2-enyl-4'-hydroxy-chalcone,
2,4-di-t-butoxy-5-prop-2-enyl-4'-hydroxy-chalcone,
2,4-dimethoxy-5-prop-2-enyl-4'-thiolo-chalcone,
2,4-diethoxy-5-prop-2-enyl-4'-thiolo-chalcone,
2,4-di-n-propoxy-5-prop-2-enyl-4'-thiolo-chalcone,
2,4-diisopropoxy-5-prop-2-enyl-4'-thiolo-chalcone,
2,4-di-n-butoxy-5-prop-2-enyl-4'-thiolo-chalcone,
2,4-di-t-butoxy-5-prop-2-enyl-4'-thiolo-chalcone,
2,4-dimethoxy-5-prop-2-enyl-4'-amino-chalcone,
2,4-diethoxy-5-prop-2-enyl-4'-amino-chalcone,
2,4-di-n-propoxy-5-prop-2-enyl-4'-amino-chalcone,
2,4-diisopropoxy-5-prop-2-enyl-4'-amino-chalcone,
2,4-di-n-butoxy-5-prop-2-enyl-4'-amino-chalcone,
2,4-di-t-butoxy-5-prop-2-enyl-4'-amino-chalcone,
2,4-dimethoxy-5-prop-2-enyl-4'-methylarmino-chalcone,
2.4-diethoxy-5-prop-2-enyl-4'-methylamino-chalcone,
2,4-di-n-propoxy-5-prop-2-enyl-4'-methylamino-chalcone,
2,4-diisopropoxy-5-prop-2-enyl-4'-methylamino-chalcone,
2,4-di-n-butoxy-5-prop-2-enyl-4'-methylamino-chalcone,
2,4-di-t-butoxy-5-prop-2-enyl-4'-methylamino-chalone,
2,4-dimethoxy-5-propyl-4'-hydroxy-chalcone,
2,4-diethoxy-5-propyl-4'-hydroxy-chalcone,
2,4-di-n-propoxy-5-propyl-4'-hydroxyvchalcone,
2,4-diisopropoxy-5-propyl-4'-hydroxy-chalcone,
2,4-di-n-butoxy-5-propyl-4'-hydroxy-chalcone,
2,4-di-t-butoxy-5-propyl-4'-hydroxy-chalcone,
2,4-dimethoxy-5-propyl-4'-thiolo-chalcone,
2,4-diethoxy-5-propyl-4'-thiolo-chalcone,
2,4-di-n-propoxy-5-propyl-4'-thiolo-chalcone,
2,4-diisopropoxy-5-propyl-4'-thiolo-chalcone,
2,4-di-n-butoxy-5-propyl-4'-thiolo-chalcone,
2,4-di-t-butoxy-5-propyl-4'-thiolo-chalcone,
2,4-dimethoxy-5-propyl-4'-amino-chalcone,
2,4-diethoxy-5-propyl-4'-amnino-chalcone,
2,4-di-n-propoxy-5-propyl-4'-amino-chalcone,
2,4-diisopropoxy-5-propyl-4'-amino-chalcone,
2,4-di-n-butoxy-5-propyl-4'-amino-chalcone,
2,4-di-t-butoxy-5-propyl-4'-amino-chalcone,
2,4-dimethoxy-5-propyl-4'-methylamino-chalcone,
2,4-diethoxy-5-propyl-4'-methylamino-chalcone,
2,4-di-n-propoxy-5-propyl-4'-methylamino-chalcone,
2,4-diisopropoxy-5-propyl-4'-methylamino-chalcone,
2,4-di-n-butoxy-5-propyl-4'-methylamino-chalcone,
2,4-di-t-butoxy-5-propyl-4'-methylamino-chalcone,
2,4-dimethoxy-5-(1,1-dimethylethyv)-4'-hydroxy-chalcone,
2,4-diethoxy-5-(1,1-dimethylethyl)-4'-hydroxy-chalcone,
2,4-di-n-propoxy-5-(1,1-dimethylethyl)-4'-hydroxy-chalcone,
2,4-diisopropoxy-5-(1,1-dimethylethyl)-4'-hydroxy-chalcone,
2,4-di-n-butoxy-5-(1,1-dimethylethyl)-4'-hydroxy-chalcone,
2,4-di-t-butoxy-5-(1,1-dimethylethyl)-4'-hydroxy-chalcone,
2,4-dimethoxy-5-(1,1-dimethylethyl)-4'-thiolo-chalcone,
2,4-diethoxy-5-(1,1-dimethylethyl)-4'-thiolo-chalcone,
2,4-di-n-propoxy-5-(1,1-dimethylethyl)-4'-thiolo-chalcone,
2,4-diisopropoxy-5-(1,1-dimethylethyl)-4'-thiolo-chalcone,
2,4-di-n-butoxy-5-(1,1-dimethylethyl)-4'-thiolo-chalcone,
2,4-di-t-butoxy-5-(1,1-dimethylethyl)-4'-thiolo-chalcone,
2,4-dimethoxy-5-(1,1-dimethylethyl)-4'-armino-chalcone,
2,4-diethoxy-5-(1,1-dimethylethyl)-4'-amino-chalcone,
2,4-di-n-propoxy-5-(1,1-dixnethylethyl)-4'-amino-chalcone,
2,4-diisopropoxy-5-(1,1-dimethylethyl)-4'-amino-chalcone,
2,4-di-n-butoxy-5-(1,1-dimethylethyl)-4'-amino-chalcone, 2,4-di-t-butoxy-5-(1,1-dimethylethyl)-4'-amino-chalcone,
2,4-dimethoxy-5-(1,1-dimethylethyl)-4'-methylamino-chalcone,
2,4-diethoxy-5-(1,1-dimethylethyl)-4'-methylamino-chalcone,
2,4-di-n-propoxy-5-(1,1-dimethylethyl)-4'-methylamino-chalcone,
2,4-diisopropoxy-5-(1,1-dimethylethyl)-4'-methylamino-chalcone,
2,4-di-n-butoxy-5-(1,1-dimethylethyl)-4'-methylamino-chalcone,
2,4-di-t-butoxy-5-(1,1-dimethylethyl)-4'-methylamino-chalcone,
2,4-dimethoxy-5-(1,1-dimethylprop-2-enyl)-4'-hydroxy-chalcone,
2,4-diethoxy-5-(1,1-dimethylprop-2-enyl)-4'-hydroxy-chalcone,
2,4-di-n-propoxy-5-(1,1-dimethylprop-2-enyl)-4'-hydroxy-chalcone,
2,4-diisopropoxy-5-(1,1-dimethylprop-2-enyl)-4'-hydroxy-chalcone,
2,4-di-n-butoxy-5-(1,1-dimethylprop-2-enyl)-4'-hydroxy-chalcone,
2,4-di-t-butoxy-5-(1,1-dimethylprop-2-enyl)-4'-hydroxy-chalcone,
2,4-dimethoxy-5-(1,1-dimethylprop-2enyl)-4'-thiolo-halcone,
2,4-diethoxy-5-(1,1-dimethylprop-2-enyl)-4'-thiolo-chalcone,
2,4-di-n-propoxy-5-(1,1-dimethylprop-2-enyl)-4'-thiolo-chalcone,
2,4-diisopropoxy-5-(1,1-dimethylprop-2-enyi)-4'-thiolo-chalcone,
2,4-di-n-butoxy-5-(1,1-dimethylprop-2-enyl)-4'-thiolo-chalcone,
2,4-di-t-butoxy-5-(1,1-dimethy1prop-2-enyl)-4'-thiolo-chacone,
2,4-dimethoxy-5-(1,1-dimethyvprop-2-enyl)-4'-amino-chalcone,
2,4-diethoxy-5-(1,1-dimethylprop-2-enyl)-4'-amino-chalcone,
2,4-di-n-pfopoxy-5-(1,1-dimethylprop-2-enyl)-4'-amino-halcone,
2,4-diisopfpoxy-5-(1,1-dimethylprop-2-enyl)-4'-amino-chalcone,
2,4-di-n-butoxy-5-(1,1-dimethylprop-2-enyl)-4'-amino-chalcone,
2,4-di-t-butoxy-5-(1,1-dimethylprop-2-enyl)-4'-amino-chalcone,
2,4-dimethoxy-5-(1,1-dimethylprop-2-enyl)-4'-methylamino-chalcone,
2,4-diethoxy-5-(1,1-dimethylprop-2-enyl)-4'-methylamino-chalcone,
2,4-di-n-propoxy-5-(1,1-dimethylprop-2-enyl)-4'-methylammo-chalcone,
2,4-diisopropoxy-5-(1,1-dimethylprop-2-enyl)-4'-methylamino-chalcone,
2,4-di-n-butoxy-5-(1,1-dimethylprop-2-enyl)-4'-methylamino-chalcone,
2,4-di-t-butoxy-5-(1,1-dimethylprop-2-enyl)-4'-methylamino-halcone, and the corresponding ketones in which Z is one of the groups (A)–(E) defined above in particular pivaolyloxymethyl or N,N-dimethylcarbamoyl, such as 2,4-dimethoxy-4'-pivaloyloxy-chalcone,
2,4-diethoxy-4'-pivaloyloxy-chalcone,
2,4-di-n-propoxy-4'-pivaloyloxy-chalcone,
2,4-diisopropoxy-4'-pivaloyloxy-chalcone,
2,4-di-n-butoxy-4'-pivaloyloxy-chalone,
2,4-di-t-butoxy-4'-pivaloyloxy-chalcone,
2,4-dimethoxy-5-methyl-4'-pivaloyloxy-chalcone,
2,4-diethoxy-5-methyl-4'-pivaloyloxy-chalcone,
2,4-di-n-propoxy-5-methyl-4'-pivaloyloxy-chalcone,
2,4-diisopropoxy-5-methyl-4'-pivaloyloxy-chalcone,
2,4-di-n-butoxy-5-methyl-4'-pivaloyloxy-chalcone,
2,4-di-t-butoxy-5-methyl-4'-pivaloyloxy-chalcone,
2,4-dimethoxy-5-prop-2-enyl-4'-pivaloyloxy-chalcone,
2,4-dethoxy-5-prop-2-enyl-4'-pivaloyloxy-chalcone,
2,4-di-n-propoxy-5-prop-2-enyl-4'-pivaloyloxy-chalcone,
2,4-diisopropoxy-5-prop-2-enyl-4'-pivaloyloxy-chalcone,
2,4-di-n-butoxy-5-prop-2-enyl-4'-pivaloyloxy-chalcone,
2,4-di-t-butoxy-5-prop-2-enyl-4'-pivaloyloxy-chalcone,
2,4-dimethoxy-5-propyl-4'-pivaloyloxy-chalcone,
2,4-diethoxy-5-propyl-4'-pivaloyloxy-chalcone,
2,4-di-n-propoxy-5-propyl-4'-pivaloyloxy-chalcone,
2,4-diisopropoxy-5-propyl-4'-pivaloyloxy-chalcone,
2,4-di-n-butoxy-5-propyl-4'-pivaloyloxy-chalcone,
2,4-di-t-butoxy-5-propyl-4'-pivaloyloxyvchalcone,
2,4-dimethoxy-5-(1,1-dimethylethyl)-4'-pivaloyloxy-chalcone,
2,4-diethox-(1,1-dimethylethyl)-4'-pivaloyloxy-chalcone,
2,4-di-n-propoxy-5-(1,1-dimethylethyl)-4'-pivaloyloxy-chaicone,
2,4-diisopropoxy-5-(1,1-dimethylethyl)-4'-pivaloyloxy-chalcone,
2,4-di-n-butoxy-5-(1,1-dimethylethyl)-4'-pivaloyloxy-chalcone,
2,4-di-t-butoxy-5-(1,1-dimethylethyl)-4'-pivaloyloxy-chalcone,
2,4-dimethoxy-5-(1,1-dimethylethyl)-4'-pivaloyloxy-chalcone,
2,4-diethoxy-5-(1,1-dimethylethyl)-4'-pivaloyloxy-chalcone,
2,4-di-n-propoxy-5-(1,1-dimethylethyl)-4'-pivaloyloxy-chalcone,
2,4-diisopropoxy-5-(1,1-dimethylethyl)-4'-pivaloyloxy-chalcone,
2,4-di-n-butoxy-5-(1,1-dimethylethyl)-pivaloyloxy-chalcone,
2,4-di-t-butoxy-5-(1,1-dimethylethyl)-4'-pivaloyloxy-chalcone,
2,4-dimethoxy4'-pivaloyloxymethoxy-chalcone,
2,4-diethoxy4'-pivaloyloxyrnethoxy-chalcone,
2,4-di-n-propoxy4'-pivaloyloxymethoxy-chalcone,
2,4-diisopropoxy-4'-pivaloyloxymethoxy-chalcone,
2,4-di-n-butoxy4'-pivaloyloxymethoxy-chalcone,
2,4-di-t-butoxy-4'-pivaloyloxymethoxy-chalcone,
2,4-dimethoxy-5-methyl-4'-pivaloyloxymethoxy-chalcone,
2,4-diethoxy-5-methyl-4'-pivaloyloxymethoxy-chaicone,
2,4-di-n-propoxy-5-methyl-4'-pivaloyloxymethoxy-chalcone,
2,4-diisopropoxy-5-methyl-4'-pivaloyloxymethoxy-chalcone,
2,4-di-n-butoxy-5-methyl-4'-pivaloyloxymethoxy-chalcone,
2,4-di-t-butoxy-5-methyl-4'-pivaloyloxymethoxy-chalcone,
2,4-dimethoxy-5-prop-2-enyl-4'-pivaloyloxymethoxy-chalcone,
2,4-diethoxy-5-prop-2-enyl-4'-pivaloyloxymethoxy-chalcone,
2,4-di-n-propoxy-5-prop-2-enyl-4'-pivaloyloxymethoxy-chalcone,
2,4-diisopropoxy-5-prop-2-enyl-4'-pivaloyloxymethoxy-chalcone, 2,4-di-n-butoxy-5-prop-2-enyl-4'-pivaloyloxymethoxy-chalcone,
2,4-di-t-butoxy-5-prop-2-enyl-4'-pivaloyloxymethoxy-chalcone,
2,4-dimethoxy-5-propyl-4'-pivaloyloxymethoxy-chalcone,
2,4-diethoxy-5-propyl-4'-pivaloyloxymethoxy-chalcone,
2,4-di-n-propoxy-5-propy-4'-pivaloyloxymethoxy-chalcone,
2,4-diisopropoxy-5-propyl-4'-pivaloyloxymethoxy-chalcone,
2,4-di-n-butoxy-5-propyl-4'-pivaloyloxymethoxy-chalcone,
2,4-di-t-butoxy-5-propyl4'-pivaloyloxymethoxy-chalcone,
2,4-dimethoxy-5-(1,1-dimethylethyl)-4'-pivaloyloxymethoxy-chalcone,
2,4-diethoxy-5-(1,1-dimethylethyl)-4'-pivaloyloxymethoxy-chalcone,
2,4-di-n-propoxy-5-(1,1-dimethylethyl)-4'-pivaloyloxymethoxy-chalcone,
2,4-diisopropoxy-5-(1,1-dimethylethyl)-4'-pivaloyloxymethoxy-chalcone,
2,4-di-n-butoxy-5-(1,1-dimethylethyl)-4'-pivaloyloxymethoxy-chalcone,
2,4-di-t-butoxy-5-(1,1-dimethylethyl)-4'-pivaloyloxymethoxy-chalcone,
2,4-dimethoxy-5-(1,1-dimethylethyl)-4'-pivaloyloxymethoxy-chalcone,
2,4-diethoxy-5-(1,1-dimethylethyl)-4'-pivaloyloxymethoxy-chalcone,
2,4-di-n-propoxy-5-(1,1-dimethylethyl)-4'-pivaloyloxymethoxy-chalcone,
2,4-diisopropoxy-5-(1,1-dimethylethyl)-4'-pivaloyloxymethoxy-chalcone,
2,4-di-n-butoxy-5-(1,1-dimethylethyl)-4'-pivaloyloxymethoxy-chalcone,
2,4-di-t-butoxy-5-(1,1-dimethylethyl)-4'-pivaloyloxymethoxy-chalcone,
2,4-dimethoxy-4'-(N,N-dimethylcarbamoyl)-chalcone,
2,4-diethoxy-4'-(N,N-dimethylcarbamoyl)-chalcone,
2,4-di-n-propoxy-4'-(N,N-dimethylcarbamoyl)-chalcone,
2,4-diisopropoxy-4'-(N,N-dimethylcarbamoyl)-chalcone,
2,4-di-n-butoxy-4'-(N,N-dimethylcarbamoyl)-chalcone,
2,4-di-t-butoxy-4'-(N,N-dimethylcarbamoyl)-halcone,
2,4-dimethoxy-5-methyl-4'-(N,N-dimethylcarbamoyl)-chalcone,
2,4-diethoxy-5-methyl-4'-(N,N-dimethylcarbamoyl)-chaicone,
2,4-di-n-propoxy-5-methyl-4'-(N,N-dimethylcarbamoyl)-chalcone,
2,4-diisopropoxy-5-methyl4'-(N,N-dimethylcarbamoyl)-chalcone,
2,4-di-n-butoxy-5-methyl-4'-(N,N-dimethylcarbamoyl)-chalcone,
2,4-di-t-butoxy-5-methyl-4'-(N,N-dimethylcarbamoyl)-chalcone,
2,4-dimethoxy-5-prop-2-enyl-4'-(N,N-dimethylcarbamoyl)-chalcone,
2,4-diethoxy-5-prop-2-enyl-4'-(N,N-dimethylcarbamoyl)-chacone,
2,4-di-n-propoxy-5-prop-2-enyl-4'-(N,N-dimethylcarbamoyl)-chalcone,
2,4-diisopropoxy-5-prop-2-enyl-4'-(N,N-dimethylcarbamoyl)-chalcone,
2,4-di-n-butoxy-5-prop-2-enyl-4'-(N,N-dimethylcarbamoyl)-chalcone,
2,4-di-t-butoxy-5-prop-2-enyl-4'-(N,N-dimethylcarbamoyl)-chalcone,
2,4-dinethoxy-5-propyl-4'-(N,N-dimethylcarbamoyl)-chalcone,
2,4-diethoxy-5-propyl-4'-(N,N-dimethylcarbamoyl)-chalcone,
2,4-di-n-propoxy-5-propyl-4'-(N,N-dimethylcarbamoyl)-chalcone,
2,4-diisopropoxy-5-propyl-4'-(N,N-dimethylcarbamoyl)-chalcone,
2,4-di-n-butoxy-5-propyl-4'-(N,N-dimethylcarbamoyl) chalcone,
2,4-di-t-butoxy-5-propyl-4'-(N,N-dimethylcarbamoyl)-chalcone,
2,4-dimethoxy-5-(1,1-dimethylethyl)-4'-(N,N-dimethylcarbamoyl)-chalcone,
2,4-diethoxy-5-(1,1-dimethylethyl)-4'-(N,N-dimethylcarbamoyl)-chalcone,
2,4-di-n-propoxy-5-(1,1-dimethylethyl)-4'-(N,N-dimethylcarbamoyl)-chalcone,
2,4-diisopropoxy-5-(1,1-dimethylethyl)-4'-(N,N-dimethylcarbamoyl)-chalcone,
2,4-di-n-butoxy-5-(1,1-dimethylethyl)4'-(N,N-dimethylcarbamoyl)-chalcone,
2,4-di-t-butoxy-5-(1,1-dimethylethyl)-4'-(N,N-dimethylcarbamoyl)-chalcone,
2,4-dimethoxy-5-(1,1-dimethylethyl)-4'-(N,N-dimethylcarbamoyl)-chalcone,
2,4-diethoxy-5-(1,1-dimethylethyl)-4'-(N,N-dimethylcarbamoyl)-chalcone,
2,4-di-n-propoxy-5-(1,1-dimethylethyl)-4'-(N,N-dimethylcarbamoyl)-chalcone,
2,4-diisopreoxy-5-(1,1-dimethylethyl)-4'-(N,N-dimethylcarbamoyl)-chalcone,
2,4-di-n-butoxy-5-(1,1-dimethylethyl)-4'-(N,N-dimethylcarbamoyl)-chalcone,
2,4-di-t-butoxy-5-(1,1-dimethylethyl)-4'-(N,N-dimethylcarbamoyl)-chalcone.

Specific examples of bis-aromatic $\alpha,\beta$-unsaturated ketones are:

2-methoxy-4,4'-di-pivaloyloxy-5-methyl-chalcone,
2-methoxy-4,4'-di-pivaloyloxy-5-ethyl-chalcone,
2-methoxy-4,4'-di-pivaloyloxy-5-propyl-chalcone,
2-methoxy-4,4'-di-pivaloyloxy-5-prop-2-enyl-chalcone,
2-methoxy-4,4'-di-pivaloyloxy-5-(1,1-dimethylprop-2-enyl)-chalcone,
2-methoxy-4,4'-di-pivaloyloxy-5-(1,1-dimethylethyl)-halcone,
2-methoxy-4,4'-di-pivaloyloxymethoxy-5-methyl-chalcone,
2-methoxy-4,4'-di-pivaloyloxymethoxy-5-ethyl-chalcone,
2-methoxy-4,4'-di-pivaloyloxymethoxy-5-propyl-chalone,
2-methoxy-4,4'-di-pivaloyloxymethoxy-5-propenyl-chalcone,
2-methoxy-4,4'-di-pivaloyloxymethoxy-5-(1,1-dimethylprop-2-enyl)-chalcone,
2-methoxy-4,4'-di-pivaloyloxymethoxy-5-(1,1-dimethylethyl)-chalcone,
2-methoxy-4,4'-di-(N,N-dimethylcarbamoyl)-5-methyl-chalcone,
2-methoxy-4,4'-di-(N,N-dimethylcarbamoyl)-5-ethyl-chalcone,
2-methoxy-4,4'-di-(N,N-dimethylcarbamoyl)-5-propyl-chalcone,
2-methoxy-4,4'-di-(N,N-dimethylcarbamoyl)-5-propenyl-chalcone,
2-methoxy-4,4'-di-(N,N-dimethykarbamoyl)-5-(1,1-dimethylprop-2-enyl)-chalcone,
2-methoxy-4,4'-di-(N,N-dimethylcarbamoyl)-5-(1,1-dimethylethyl)-chalcone,
2-methoxy-4,4'-di-methoxymethoxy-5-methy-chalcone,
2-methoxy-4,4'-di-methoxymethoxy-5-ethyl-chalcone, 2-methoxy-4,4'-di-methoxymethoxy-5-propyl-chalcone,
2-methoxy-4,4'-di-methoxymethoxy-5-prop-2-enyl-chalcone,
2-methoxy-4,4'-di-methoxymethoxy-5-(1,1-dimethylpropenyl)-chalcone,
2-methoxy-4,4'-di-methoxymethoxy-5-(1,1-dimethylethyl)-chalcone,
2-methoxy-4,4'-di-propenoxy-5-methyl-chalcone,
2-methoxy-4,4'-di-propenoxy-5-ethyl-chalcone,
2-methoxy-4,4'-di-propenoxy-5-propyl-chalcone,
2-methoxy-4,4'-di-propenoxy-5-prop-2-enyl-chalcone,
2-methoxy-4,4'-di-propenoxy-5-(1,1-dimethylpropenyl)-chalcone, and
2-methoxy-4,4'-di-propenoxy-5-(1,1-dimethylethyl)-chalcone.
2,4-dimethoxy-4'-(2-prop-2-enyloxy)-chalcone,
2,4-diethoxy-4'-(2-prop-2-enyloxy)chalcone,
2,4-di-n-propoxy-4'-(2-prop-2-enyioxy)-chalcone,
2,4-diisopropoxy-4'-(2-prop-2-enyioxy)-chalcone,
2,4-di-n-butoxy-4'-(2-prop-2-enyloxy)-chalcone,
2,4-di-t-butoxy-4'-(2-prop-2-enyloxy)-chalcone,
2,4-dimhethoxy-5-methyl-4'-(2-prop-2-enyloxy)-chalcone,
2,4-diethoxy-5-methyl-4'-(2-prop-2-enyloxy)-chalcone,
2,4-di-n-propoxy-5-methyl-4'-(2-prop-2-enyloxy)-chalcone,
2,4-diisopropoxy-5-methyl-4'-(2-prop-2-enyloxy)-chalcone,
2,4-di-n-butoxy-5-methyl-4'-(2-prop-2-enyloxy)-chalcone,
2,4-di-t-butoxy-5-methyl-4'-(2-prop-2-enyloxy)-chalcone,
2,4-dimethoxy-5-prop-2-enyl-4'-(2-prop-2-enyloxy)-chalcone,
2,4-diethoxy-5-prop-2-enyl-4'-(2-prop-2-enyloxy)-chalcone,
2,4-di-n-propoxy-5-prop-2-enyl-4'-(2-prop-2-enyloxy)-chalcone,
2,4-diisopropoxy-5-prop-2-enyl-4'-(2-prop-2-enyloxy)-chalcone,
2,4-di-n-butoxy-5-prop-2-enyl-4'-(2-prop-2-enyloxy)-chalcone,
2,4-di-t-butoxy-5-prop-2-enyl-4'-(2-prop-2-enyloxy)-chalcone,
2,4-dimethoxy-5-propyl-4'-(2-prop-2-enyloxy)-chalcone,
2,4-diethoxy-5-propyl-4'-(2-prop-2-enyloxy)-chalcone,
2,4-di-n-propoxy-5-propyl-4'-(2-prop-2-enyloxy)-chalcone,
2,4-diisopropoxy-5-propyl-4'-(2-prop-2-enyloxy)-chalcone,
2,4-di-n-butoxy-5-propyl-4'-(2-prop-2-enyloxy)-chalcone,
2,4-di-t-butoxy-5propyl4'-(2-prop-2enyloxy)-chalcone,
2,4-dimethoxy-5-(1,1-dimethylethyl)-4'-(2-prop-2-enyloxy)-chalone,
2,4-dethoxy-5-(1,1-dimethylethyl)-4'-(2-prop-2-enyloxy)-halcone,
2,4-di-n-propoxy-5-(1,1-dimethylethyl)4'-(2-prop-2-enyloxy)-chalcone,
2,4-diisopropoxy-5-(1,1-dimethylethyl)-4'-(2-prop-2-enyloxy)-chalcone,
2,4-di-n-butoxy-5-(1,1-dimethylethyl)-4'-(2-prop-2-enyloxy)-chalcone,
2,4-di-t-butoxy-5-(1,1-dimethylethyl)-4'-(2-prop-2-enyloxy)-chalcone,
2,4-dimethoxy-5-(1,1-dimethylethyl)-4'-(2-prop-2-enyloxy)-chalcone,
2,4-diethoxy-5-(1,1-dimethylethyl)-4'-(2-prop-2-enyloxy)-chalcone,
2,4-di-n-propoxy-5-(1,1-dimethylethyl)-4'-(2-prop-2-enyloxy)-chalcone,
2,4-diisopropoxy-5-(1,1-dimethylethyl)4'-(2-prop-2-enyloxy)-chalcone,
2,4-di-n-butoxy-5-(1,1-dimethylethyl)-4'-(2-prop-2-enyloxy)-chalcone,
2,4-di-t-butoxy-5-(1,1-dimethylethyl)4'-(2-prop-2-enyloxy)-chalcone.
2,6-dimethoxy-4'-hydroxy-chalcone,
2,6-diethoxy-4'-hydroxychalcone,
2,6-di-n-propoxy-4'-hydroxy-chalcone,
2,6-diisopropoxy-4'-hydroxy-chalcone,
2,6-di-n-butoxy-4'-hydroxy-halcone,
2,6-di-t-butoxy-4'-hydroxy-chalcone,
2,6-dimethoxy-4'-thiolo-chalcone,
2,6-diethoxy-4'-thiolo-chalcone,
2,6-di-n-propoxyl-4'-thiolo-chalcone,
2,6-diisopropoxy-4'-thiolo-chalcone,
2,6-di-n-butoxy-4'-thiolo-chalcone,
2,6-di-t-butoxy-4'-thiolo-chalcone,
2,6-dimethoxy-4'-amino-chalcone,
2,6-diethoxy-4'-anino-chalcone,
2,6-di-n-propoxy-4'-amino-halcone,
2,6-diisopropoxy-4'-amino-chalcone,
2,6-di-n-butoxy-4'-amino-chalcone,
2,6-di-t-butoxy-4'-amino-chalcone,
2,6-dimethoxy-4'-methylamino-chalcone,
2,6-diethoxy-4'-methylaamino-chalcone,
2,6-di-n-propoxy-4'-methylamino-chalcone,
2,6-diisopropoxy-4'-methylamino-chalcone,
2,6-di-n-butoxy-4'-methylamino-chalcone,
2,6-di-t-butoxy-4'-methylamino-chalcone,
2,6-dimethoxy-5-methyl-4'-hydroxy-chalcone,
2,6-diethoxy-5-methyl-4'-hydroxy-chalcone,
2,6-di-n-propoxy-5-methyl-4'-hydroxy-chalcone,
2,6-diisopropoxy-5-methyl4'-hydroxy&chalcone,
2,6-di-n-butoxy-5-methy-4'-hydroxy-chalcone,
2,6-di-t-butoxy-5-methyl-4'-hydroxy-chalcone,
2,6-dimethoxy-5-methyl-4'-thiolo-chalcone,
2,6-diethoxy-5-methyl-4'-thiolo-chalcone,
2,6-di-n-propoxy-5-methyl-4'-thiolo-chalcone,
2,6-diisopropoxy-5-methyl-4'-thiolo-chalcone,
2,6-di-n-butoxy-5-methy-4'-thiolo-chalcone,
2,6-di-t-butoxy-5-methyl-4'-thiolo-chalcone,
2,6-dimethoxy-5-methyl-4'-amino-chalcone,
2,6-diethoxy-5-methyl-4'-amino-chalcone,
2,6-di-n-propoxy-5-methyl-4'-amino-chalcone,
2,6-diisopropoxy-5-methyl4'-amino-chalcone,
2,6-di-n-butoxy-5-methyl-4'-amino-chalcone,
2,6-di-t-butoxy-5-methyl-4'-amino-chalcone,
2,6-dimethoxy-5-methyl-4'-methylamino-chalcone,
2,6-diethoxy-5-methyl4'-methylamino-chalcone,
2,6-di-n-propoxy-5-methyl-4'-methylamino-chalcone,
2,6-diisopropoxy-5-methyl-4'-methylamino-chalcone,
2,6-di-n-butoxy-5-methyl-4'-methylamino-chalcone,
2,6-di-t-butoxy-5-methyl-4'-methylamino-chalcone,
2,6-dimethoxy-5-prop-2-enyl-4'-hydroxychalcone,
2,6-diethoxy-5-prop-2-enyl-4'-hydroxy-chalcone,
2,6-di-n-propoxy-5-prop-2-enyl-4'-hydroxy-halcone,
2,6-diisopropoxy-5-prop-2-enyl-4'-hydroxy-chalcone,
2,6-di-n-butoxy-5-prop-2-enyl-4'-hydroxy-chalcone,
2,6-di-t-butoxy-5-prop-2-eyyl-4'-hydroxy-chalcone,
2,6-dimethoxy-5-prop-2-enyl-4'-thiolo-chalcone,
2,6-diethoxy-5-prop-2-enyl-4'-thiolo-chalcone,
2,6-di-n-propoxy-5-prop-2-enyl-4'-thiolo-chalcone,
2,6-diisopropoxy-5-prop-2-enyl-4'-thiolo-chalcone,
2,6-di-n-butoxy-5-prop-2-enyl-4'-thiolo-chalcone,
2,6-di-t-butoxy-5-prop-2-enyl-4'-thiolo-chalcone,
2,6-dimethoxy-5-prop-2-enyl-4'-amino-chalcone,
2,6-diethoxy-5-prop-2-enyl-4'-amino-chalcone,
2,6-di-n-propoxy-5-prop-2-enyl-4'-amino-chalcone,
2,6-diisopropoxy-5-prop-2-enyl-4'-amino-chalcone,
2,6-di-n-butoxy-5-prop-2enyl-4'-amino-chalcone, 2,6-di-t-butoxy-5-prop-2enyl-4'-aminoe-chalcone,
2,6-dimethoxy-5-prop-2-enyl-4'-methylamino-chalcone,
2,6-diethoxy-5-prop-2-enyl-4'-methylamino-chalcone,
2,6-di-n-propoxy-5-prop-2-enyl-4'-methylamino-chalcone,
2,6-diisopropoxy-5-prop-2-enyl-4'-methylamino-chalcone,
2,6-di-n-butoxy-5-prop-2-enyl-4'-methylamino-chalcone,
2,6-di-t-butoxy-5-prop-2enyl-4'-methylaminol-chacone,
2,6-dimethoxy-5-propyl-4'-hydroxy-chalcone,
2,6-diethoxy-5-propyl-4'-hydroxy-chalcone,
2,6-di-n-propoxy-5-propyl-4'-hydroxy-chalcone,
2,6-diisopropoxy-5-propyl-4'-hydroxy-chalcone,
2,6-di-n-butoxy-5-propyl-4'-hydroxy-chalcone,
2,6-ditbutoxy-5-propyl-4'-hydroxy-chalcone,
2,6-dimethoxy-5-propyl-4'-thiolo-chalcone,
2,6-diethoxy-5-propyl-4'-thiolo-chalcone,
2,6-di-n-propoxy-5-propyl-4'-thiolo-chalcone,
2,6-diisopropoxy-5-propyl-4'-thiolo-chalcone,
2,6-di-n-butoxy-5-propyl-4'-thiolo-chalcone,
2,6-di-t-butoxy-5-propyl-4'-thiono-chalcone,
2,6-dimethoxy-5-propyl-4'-amino-chalcone,
2,6-diethoxy-proppyl4'-amino-chalcone,
2.6-di-ispropoxy-5-propyl-4'-amino-chalcone,
2,6-diisopropoxy-5-propyl-4'-amino-chalcone,
2,6-di-n-butoxy-5-propyl-4'-amino-chalone,
2.6-di-t-butoxy-5-propyl-4'-amino-chalcone,
2,6-dimethoxy-5-propyl-4'-methylamino-chalcone,
2,6-diethoxy-5-propyl-4'-methylamino-chalcone,
2,6-di-n-propoxy-5-propyl-4'-methylamino-chalcone,
2,6-diisopropoxy-5-propyl-4'-methylarmino-chalcone,
2,6-di-n-butoxy-5-propyl-4'-methylarmino-chalcone,
2,6-di-t-butoxy-5-propyl-4'-methylamino-chalcone,
2,6-dimethoxy-5-(1,1-dimethylethyl)-4'-hydroxy-chalcone,
2,6-diethoxy-5-(1,1-dimethylethyl)-4'-hydroxy-alcone,
2,6-di-n-propoxy-5-(1,1-dimethylethyl)-4'-hydroxy-chalcone,
2,6-diisopropoxy-5-(1,1-dimethylethyl)-4'-hydroxy-chalcone,
2,6-di-n-butoxy-5-(1,1-dimethylethyl)-4'-hydroxy-chalcone,
2,6-di-t-butoxy-5-(1,1-dimethylethyl)-4'-hydroxy-chalcone,
2,6-dimethoxy-5-(1,1-dimethylethyl)-4'-thiolo-chalcone,
2,6-diethoxy-5-(1,1-dimethylethyl)-4'-thiolo-chalcone,
2,6-di-n-propoxy-5-(1,1-dimethylethyl)4'-thiolo-chalcone,
2,6-diisopropoxy-5-(1,1-dimethylethyl)-4'-thiolo-chalcone,
2,6-di-n-butoxy-5-(1,1-dimethylethyl)-4'-thiolo-chalcone,
2,6-di-t-butoxy-5-(1,1-dimethylethyl)-4'-thiolo-chalcone,
2,6-dimethoxy-5-(1,1-dimethylethyl)-4'-amino-chalcone,
2,6-diethoxy-5-(1,1-dimethylethyl)-4'-amino-chalcone,
2,6-di-n-propoxy-5-(1,1-dimethylethyl)-4'-amino-chalcone,
2,6-diisopropoxy-5-(1,1-dimethylethyl)-4'-amino-chalcone,
2,6-di-n-butoxy-5-(1,1-dimethylethyl)-4'-amino-chalcone,
2,6-di-t-butoxy-5-(1,1-dimethylethyl)-4'-aminochalcone,
2,6-dimethoxy-5-(1,1-dimethylethyl)-4'-methylamino-chalcone,
2,6-diethoxy-5-(1,1-dimethylethyl)-4'-methylamino-chalcone,
2,6-di-n-propoxy-5-(1,1-diinethyvethyl)-4'-methylamino-chalcone,
2,6-diisopropoxy-5-(1,1-dimethylethyl)-4'-methylamino-chalcone,
2,6-di-n-butoxy-5-(1,1-dimethylethyl)-4'-methylarmino-chalcone,
2,6-di-t-butoxy-5-(1,1-dimethylethyl)-4'-methylamino-chalcone,
2,6-dimethoxy-5-(1,1-dimethylprop-2-enyl)-4'-hydroxy-chalcone,
2,6-diethoxy-5-(1,1-dimethylprop-2-enyl)-4'-hydroxy-chalcone,
2,6-di-n-propoxy-5-(1,1-dimethylprop-2-enyl)-4'-hydroxy-chalcone,
2,6-diisopropoxy-5-(1,1dimethylprop-2-enyl)-4'-hydroxy-chalcone,
2,6-di-n-butoxy-5(1,1-dimethylprop-2enyl)-4'-hydroxy-chalcone,
2,6-di-t-butoxy-5-(1,1-dimethylprop-2-enyl)-4'-hydroxy-chalcone,
2,6-dimethoxy-5-(1,1-dimethylprop-2-enyl)-4'-thiolo-chalcone,
2,6-diethoxy-5-(1,1-dimethylprop-2enyl)-4'-thiolo-chalcone,
2,6-di-n-propoxy-5-(1,1-dimethylprop-2-enyl)-4'-thiolo-chalcone,
2,6-diisopropoxy-5-(1,1-dimethyvprop-2enyl)-4'-thiolo-chalcone,
2,6-di-n-butoxy-5-(1,1-dimethy prop-2enyl)-4'-thiolo-chalcone,
2,6-di-t-butoxy-5-(1,1-dimethyvprop-2enyl)-4'-thioio-chalcone,
2,6dimethoxy-5-(1,1-dimethylprop-2-enyl)-4'-amino-chalcone,
2,6-diethgxy-5-(1,1-dimethylprop-2-enyl)-4'-amino-chalcone,
2,6-di-n-propoxy-5-(1,1-dimethylprop-2-enyl)-4'-amino-chalcone,
2,6-diisopropoxy-5-(1,1-dimethylprop-2-enyl)-4'-amino-chalcone,
2,6-di-n-butoxy-5-(1,1-dimethylprop-2-enyl)-4'-amino-chalcone,
2,6-di-t-butoxy-5-(1,1-dimethylprop-2-enyl)-4'-amino-chalcone,
2,6-dimethoxy-5-(1,1-dimethylprop-2-enyl)-4'-methylamino-chalcone,
2,6-diethoxy-5-(1,1-dimethylprop-2-enyl)-4'-methylamino-chalcone,
2,6-di-n-propoxy-5-(1,1-dimethylprop-2-enyl)-4'-methylamino-chalcone,
2,6-diisopropoxy-5-(1,1-dimethylprop-2-enyl)-4'-methylamino-chalcone,
2,6-di-n-butoxy-5-(1,1-dimethylprop-2-enyl)-4'-methylamino-chalcone,
2,6-di-t-butoxy-5-(1,1-dimethylprop-2-enyl)-4'-methylamino-chalcone, and the corresponding ketones in which Z is one of the groups (A)–(E) defined above, in particular pivaolyloxymethyl or N,N-dimethylcarbamoyl, such as 2,6-dimethoxy-4'-pivaloyloxy-chalcone,
2,6-diethoxy-4'-pivaloyloxy-chalcone,
2,6-di-n-propoxy-4'-pivaloyloxy-chalcone,
2,6-diisopropoxy-4'-pivaloyloxy-chalcone,
2,6-di-n-butoxy-4'-pivaloyloxy-chalcone,
2,6-di-t-butoxy-4'-pivaloyloxy-chalcone,
2,6-dimethoxy-5-methyl-4'-pivaloyloxy-chalcone,
2,6-diethoxy-5-methyl-4'-pivaloyloxy-chalcone,
2,6-di-n-propoxy-5-methyl-4'-pivaloyloxy-chalcone,
2,6-diisopropoxy-5-methyl-4'-pivaloyloxy-chalcone,
2,6-di-n-butoxy-5-methyl-4'-pivaloyloxy-chalcone,
2,6-di-t-butoxy-5-methyl-4'-pivaloyloxy-chalcone,
2,6-dimetoxy-5-prop-2-enyl-4'-pivaloyloxy-chalcone,
2,6-diethoxy-5-prop-2-enyl-4'-pivaloyloxy-chalcone,
2,6-di-n-propoxy-5-prop-2-enyl-4'-pivaloyloxy-chalcone,
2,6-diisopropoxy-5-prop-2-enyl-4'-pivaloyloxy-chalcone,
2,6-di-n-butoxy-5-prop-2-enyl-4'-pivaloyloxy-chalcone,
2,6-di-t-butoxy-5prop-2enyl-4'-pivaloyloxy-chalcone,
2,6-dimethoxy-5-propyl-4'-pivaloyloxy-chalcone,
2,6-diethoxy-5-propyl-4'-pivaloyloxy-chalcone, 2,6-di-n-propoxy-5-propyl-4'-pivaloyloxy-chalcone,
2,6-diisopropoxy-5-propyl-4'-pivaloyloxy-chalcone,
2,6-di-n-butoxy-5-propyl-4'-pivaloyloxy-chalcone,
2,6-di-t-butoxy-5-propyl-4'-pivaloyloxy-chalcone,
2,6-dimethoxy-5-(1,1-dimethylethyl)-4'-pivaloyloxy-chalcone,
2,6-diethoxy-5-(1,1-dimethylethyl)-4'-pivaloyloxy-chalcone,
2,6-di-n-propoxy-5-(1,1-dimethylethyl)-4'-pivaloyloxy-chalcone,
2,6-diisopropoxy-5-(1,1-dimethylethyl)-4'-pivaloyloxy-chalcone,
2,6-di-n-butoxy-5-(1,1-dimethylethyl)-4'-pivaloyloxy-chalcone,
2,6-di-t-butoxy-5-(1,1-dimethylethyl)-4'-pivaiovioxychalcone,
2,6-dimethoxy-5-(1,1-dimethylethyl)-4'-pivaloyloxy-chalcone,
2,6-diethoxy-5-(1,1-dimethylethyl)-4'-pivaloyloxy-chalcone,
2,6-di-n-propoxy-5-(1,1-dimethylethyl)-4'-pivaloyloxy-chalcone,
2,6-diisopropoxy-5-(1,1-dimethylethyl)-4'-pivaloyloxy-chalcone,
2,6-di-n-butoxy-5-(1,1-dimethylethyl)-4'-pivaloyloxy-chalcone,
2,6-di-t-butoxy-5-(1,1-dimethylethyl)-4'-pivaloyloxy-chalcone,
2,6-dimethoxy-4'-pivaloyloxymethoxy-chalcone,
2,6-diethoxy-4'-pivaloyloxymethoxy-chalcone,
2,6-di-n-propoxy-4'-pivaloyloxymethoxy-chalcone,
2,6-diisopropoxy-4'-pivaloyloxymethoxy-chalcone,
2,6-di-n-butoxy-4'-pivaloyloxrvmethoxy-chalcone,
2,6-di-t-butoxy-4'-pivaloyloxyvnethoxy-chalcone,
2,6-dimethoxy-5-methyl-4'-pivaloyloxymethoxy-chalcone,
2,6-diethoxy-5-methyl-4'-pivaloyloxymethoxy-chalcone,
2,6-di-n-propoxy-5-methyl-4'-pivaloyloxymethoxy-chalcone,
2,6-diisopropoxy-5-methyl-4'-pivaloyloxymethoxy-chalcone,
2,6-di-n-butoxy-5-methyl-4'-pivaloyloxymethoxy-chalcone,
2,6-di-t-butoxy-5-methyl-4'-pivaloyloxymethoxy-chalcone,
2,6-dimethoxy-5-prop-2-enyl-4'-pivaloyloxymethoxy-chalcone,
2,6-diethoxy-5-prop-2-enyl-4'-pivaloyloxymethoxy-chalcone,
2,6-di-n-propoxy-5-prop-2-enyl-4'-pivaloyloxymethoxy-chalcone,
2,6-diisopropoxy-5-prop-2enyl-4'-pivaloyloxymethoxy-chalcone,
2,6-di-n-butoxy-5-prop-2-enyl-4'-pivaloytoxyrcthoxy-chalcone,
2,6-di-t-butoxy-5-prop-2-enyl-4'-pivaloyloxyrnethoxy-chalcone,
2,6-dimethoxy-5-propyl-4'-pivaloyloxymethoxy-chalcone,
2,6-diethoxy-5-propyl-4'-pivaloyloxymethoxy-chalcone,
2,6-di-n-propoxy-5-propyl-4'-pivaloyloxymethoxy-chalcone,
2,6-diisopropoxy-5-propyl-4'-pivaloyloxymethoxy-chalcone,
2,6-di-n-butoxy-5-propyl-4'-pivaloyloxymethoxy-chalcone,
2,6-di-t-butoxy-5-propyl-4'-pivaloyloxymethoxy-chalcone,
2,6-dimethoxy-5-(1,1-dimethylethyl)-4'-pivaloyloxymethoxy-chalcone,
2,6-diethoxy-5-(1,1-dimethylethyl)-4'-pivaloyloxymethoxy-chalcone,
2,6-di-n-propoxy-5-(1,1-dimethylethyl)-4'-pivaloyloxymethoxy-chalcone,
2,6-diisopropoxy-5-(1,1-dinethyiethyl)-4'-pivaloyloxymethoxy-chalcone,
2,6-di-n-butoxy-5(1,1-dimethylethyl)-4'-pivaloyloxymethoxy-chalcone,
2,6-di-t-butoxy-5-(1,1-dimethylethyl)-4'-pivaloyloxymethoxy-chalcone,
2,6-dimethoxy-5-(1,1-dimethylethyl)-4'-pivaloyloxymethoxy-chalcone,
2,6-diethoxy-5-(1,1-dimethylethyl)-4'-pivaloyloxymethoxy-chalcone,
2,6-di-n-propoxy-5-(1,1-dimethylethyl)-4'-pivaloyloxymethoxy-chalcone,
2,6-diisopropoxy-5-(1,1-dimethylethyl)-4'-pivaloyloxymethoxy-chalcone,
2,6-di-n-butoxy-5-(1,1-dimethylethyl)-4'-pivaloyloxymethoxy-chalcone,
2,6-di-t-butoxy-5-(1,1-dimethylethyl)-4'-pivaloyloxymethoxy-chalcone,
2,6-dimethoxy-4'-(N,N-dimethylcarbamoyl)-chalcone,
2,6-diethoxy-4'-(N,N-dimethylcarbamoyl)-chalcone,
2,6-di-n-propoxy-4'-(N,N-dimethylcarbamoyl)-chalcone,
2,6-diisopropoxy-4'-(N,N-dimethylcarbamoyl)-chalcone,
2,6-di-n-butoxy-4'-(N,N-dimethylcarbamoyl)-chalcone,
2,6-di-t-butoxy-4'-(N,N-dimethylcarbamoyi)-chalcone,
2,6-dimethoxy-5-methyl-4'-(N,N-dimethylcarbamoyl)-chalcone,
2,6-diethoxy-5-methyl-4'-(N,N-dimethylcarbamoyl)-chalcone,
2,6-di-n-propoxy-5-methyl-4'-(N,N-dimethylcarbamoyl)-chalcone,
2,6-diisopropoxy-5-methyl-4'-(N,N-dimethylcarbamoyl)-chalcone,
2,6-di-n-butoxy-5-methyl-4'-(N,N-dimethylcarbamoyl)-chalcone,
2,6-di-t-butoxy-5-methyl-4'-(N,N-dimethylcarbamoyl)-chalcone,
2,6-dimethoxy-5-prop-2-enyl-4'-(N,N-dimethylcarbamoyl)-chalcone,
2,6-diethoxy-5-prop-2-enyl-4'-(N,N-dimethylcarbamoyl)-chalcone,
2,6-di-n-propoxy-5-prop-2-enyl-4'-(N,N-dimethylcarbamoyl)-chalcone,
2,6-diisopropoxy-5-prop-2-enyl-4'-(N,N-dimethylcarbamoyl)-chalcone,
2,6-di-n-butoxy-5-prop-2-enyl-4'-(N,N-dimethylcarbamoyl)-chalcone,
2,6-di-t-butoxy-5-prop-2-enyl-4'-(N,N-dimethylcarbamoyl)-chalcone,
2,6-dimethoxy-5-propyl-4'-(N,N-dimethylcarbamoyl)-chalcone,
2,6-diethoxy-5-propyl-4'-(N,N-dimethylcarbamoyl)-chalcone,
2,6-di-n-propoxy-5-propyl-4'-(N,N dimethylcarbamoyl)-chalcone,
2,6-diisopropoxy-5-propyl-4'-(N,N-dimethylcarbamoyl)-chalcone,
2,6-di-n-butoxy-5-propyl-4'-(N,N-dimethylcarbamoyl)-chalcone,
2,6-di-t-butoxy-5-propyl-4'-(N,N-dimethylcarbamoyl)-chalcone,
2,6-dimethoxy-5-(1,1-dimethylethyl)-4'-(N,N-dimethylcarbamoyl)-chalcone,
2,6-diethoxy-5-(1,1-dimethylethyl)-4'-(N,N-dimethylcarbamoyl)-chalcone,
2,6-di-n-propoxy-5-(1,1-dimethylethyl)-4'-(N,N-dimethylcarbamoyl)-chalcone, 2,6-diisopropoxy-5-(1,1-dimethylethyl)-4-(N, Ndimethylcarbamoyl)-chalcone,
2,6-di-n-butoxy-5-(1,1-dimethylethyl)-4'-(N,N-dimethylcarbamoyl)-chalcone,
2,6-di-t-butoxy-5-(1,1-dimethylethyl)-4'-(N,N-dimethylcarbamoyl)-chalcone,
2,6-dimethoxy-5-(1,1-dimethylethyl)-4'-(N,N-dimethylcarbamoyl)-chalcone,
2,6-diethoxy-5-(1,1-dimethylethyl)-4'-(N,N-dimethylcarbamoyl)-chalcone,
2,6-di-n-propoxy-5-(1,1-dimethylethyl)-4'-(N,N-dimethylcarbamoyl)-chalcone,
2,6-diisopropoxy-5-(1,1-dimethylethyl)-4'-(N,N-dimethylcarbamoyl)-chalcone,
2,6-di-n-butoxy-5-(1,1-dimethylethyl)-4'-(N,N-dimethylcarbamoyl)-chalcone,
2,6-di-t-butoxy-5-(1,1-dimethylethyl)-4'-(N,N-dimethylcarbamoyl)-chalcone,
2,6-dimethoxy-4'-di-pivaloyloxy-3-methyl-chalcone,
2,6-dimethoxy-4'-di-pivaloyloxy-3-ethyl-chalcone,
2,6-dimethoxy-4'-di-pivaloyloxy-3-propyl-chalcone,
2,6-dimethoxy-4'-di-pivaloyloxy-3-prop-2-enyl-chalcone,
2,6-dimethoxy-4'-di-pivaloyloxy-3-(1,1-dimethylprop-2-enyl)-chalcone,
2,6-dimethoxy-4'-di-pivaloyloxy-3-(1,1-dimethy ethyl)-chalcone,
2,6-dimethoxy-4'-di-pivaloyloxymethoxy-3-methyl-chalcone,
2,6-dimethoxy-4'-di-pivaloyloxymethoxy-3-ethyl-chalcone,
2,6-dimethoxy-4'-di-pivaloyloxymethoxy-3-propyl-chalcone,
2,6-dimethoxy-4'-di-pivaloyloxymethoxy-3-propenyl-chalcone,
2,6-dimethoxy-4'-di-pivaloyloxymethoxy-3-(1,1-dimethylprop-2-enyl)-chalcone,
2,6-dimethoxy-4'-di-pivaloyloxymethoxy3)-1,1-dimethylethyl)-chalcone,
2,6-dimethoxy-4'-di-(N,N-dimethylcarbamoyl)-3-methyl-chalcone,
2,6-dimethoxy-4'-di-(N,N-dimethylcarbamoyl)-3ethyl-chalcone,
2,6-dimethoxy-4'-di-(N,N-dimethylcarbamoyl)-3-propyl-chalcone,
2,6-dimethoxy-4'-di-(N,N-dimethylcarbamoyl)-3-propenyl-chalcone,
2,6-dimethoxy-4'-di-(N,N-dimethylcarbamoyl)-3-(1,1-dimethylprop-2-enyl)-chalcone,
2,6-dimethoxy-4'-di-(N,N-dimethylcarbamoyl)-3-(1,1-dimethylethyl)-chalcone,
2,6-dimethoxy-4'-di-methoxymethoxy-3-methyl-chalcone,
2,6-dimethoxy-4'-di-methoxymethoxy-3-ethyl-chalcone,
2,6-dimethoxy-4'-di-methoxymethoxy-3-propyl-chalcone,
2,6-dimethoxy-4'-di-methoxymethoxy-3-prop-2-enyl-chalcone,
2,6-dimethoxy-4'-di-methoxymethoxy-3-(1,1-dimethylprop-2-enyl)-chalcone,
2,6-dimethoxy-4'-di-methoxymethoxy-3-(1,1-dimethylethyl)-chalcone,
2,6-dimethoxy-4'-di-propenoxy-3-methyl-chalcone,
2,6-dimethoxy-4'-di-propenoxy-3-ethyl-chalcone,
2,6-dimethoxy-4'-di-propenoxy-3propyl-chalcone,
2,6-dimethoxy-4'-di-propenoxy-3-prop-2-enyl-chalcone,
2,6-dimethoxy-4'-di-propenoxy-3-(1,1-dimethylprop-2-enyl)-chalcone, and
2,6-dimethoxy-4'-di-propenoxy-3-(1,1-dimethylethyl)-chalcone.

Specific examples of bis-aromatic $\alpha,\beta$-unsaturated ketones are 2,6-dimethoxy-4'-(2-prop-2-enyloxy)-chalcone,
2,6-diethoxy-4'-(2-prop-2-enyloxy)-chalcone,
2,6-di-n-propoxy-4'-(2-prop-2-enyloxy)-chalcone,
2,6-diisopropoxy-4'-(2-prop-2-enyloxy)-chalcone,
2,6-di-n-butoxy-4'-(2-prop-2enyloxy)-chalcone,
2,6-di-t-butoxy-4'-(2-prop-2enyioxy)-chalcone,
2,6-dimethoxy-5-methyl-4'-(2-prop-2-enyloxy)-chalcone,
2,6-diethoxy-5-methyl-4'-(2-prop-2enyloxy)-chalcone,
2,6-di-n-propoxy-5-methyl-4'-(2-prop-2-enyloxy)-chalcone,
2,6-diisopropoxy-5-methyl-4'-(2-prop-2-enyioxy)-chalcone,
2,6-di-n-butoxy-5-methyl-4'-(2-prop-2-enyloxy)-chalcone,
2,6-di-t-butoxy-5-methyl-4'-(2-prop-2-enyloxy)-chalcone,
2,6-dimethoxy-5-prop-2-enyl-4'-(2-prop-2-enyloxy)-chalcone,
2,6-diethoxy-5-prop-2-enyl-4'-(2-prop-2-enyloxy)-chalcone,
2,6-di-n-propoxy-5-prop-2-enyl-4'-(2-prop-2-enyloxy)-chalcone,
2,6-diisopropoxy-5-prop-2-enyl-4'-(2-prop-2-enyloxy)-chalcone,
2,6-di-n-butoxy-5-prop-2-enyl-4'-(2-prop-2-enyloxy)-chalcone,
2,6-di-t-butoxy-5-prop-2-enyl-4'-(2-prop-2enyloxy)-chalcone,
2,6-dimethoxy-5-propyl-4'-(2-prop-2-enyloxy)-chalcone,
2,6-diethoxy-5-propyl-4'-(2-prop-2-enyloxy)-chalcone,
2,6-di-n-propoxy-5-propyl-4'-(2-prop-2-enyloxy)-chalcone,
2,6-diisopropoxy-5-propyl-4'-(2-prop-2-enyloxy)-chalcone,
2,6-di-n-butoxy-5-propyl-4'-(2-prop-2-enyloxy)-chalcone,
2,6-di-t-butoxy-5-propyl-4'-(2-prop2-enyloxy)-chalcone,
2,6-dimethoxy-5-(1,1-dimethylethyl)-4'-(2-prop-2-enyvoxy)-chalcone,
2,6-diethoxy-5-(1,1-dimethylethyl)-4'-(2-prop-2enyloxy)-chalcone,
2,6-di-n-propoxy-5-(1,1-dimethylethyl)-4'-(2-prop-2-enyloxy)-chalcone,
2,6-diisopropoxy-5-(1,1-dimethylethyl)-4'-(2-prop-2-enyloxy)-chalcone,
2,6-di-n-butoxy-5-(1,1-dimethylethyl)-4'-(2-prop-2enyloxy)-chalcone,
2,6-di-t-butoxy-5-(1,1-dimethylethyl)-4'-(2-prop-2enyloxy)-chalcone,
2,6-dimethoxy-5-(1,1-dimethylethyl)-4'-(2-prop-2-enyloxy)-chalcone,
2,6-diethoxy-5-(1,1-dimethylethyl)-4'-(2-prop-2-enyloxy)-chalcone,
2,6-di-n-propoxy-5-(1,1-dimethylethyl)-4'-(2-prop-2enyloxy)-chalcone,
2,6-diisopropoxy-5-(1,1-dimethylethyl)-4'-(2-prop-2-enyloxy)-chalcone,
2,6-di-n-butoxy-5-(1,1-dimethylethyl)-4'-(2-prop-2enyvoxy)-chalcone,
2,6-di-t-butoxy-5-(1,1-dimethylethyl)-4'-(2-prop-2enyloxy)-chalcone.
2,5-dimethoxy-4'-methoxychalcone,
2,5-diethoxy-4'-methoxychalcone,
2,5-di-n-propoxy-4'-methoxychalcone,
2,5-diisopropoxy-4'-methoxychalcone,
2,5-di-n-butoxy-4'-methoxychalcone,
2,5-di-t-butoxy-4'-methoxychalcone,
2,5-dimethoxy-4'-ethoxychalcone
2,5-diethoxy-4'-ethoxychalcone,
2,5-di-n-propoxy-4'-ethoxychalcone,
2,5-diisopropoxy-4'-ethoxychalcone,
2,5-di-n-butoxy-4'-ethoxychalcone,
2,5-di-t-butoxy-4'-ethoxychalcone, 2,5-dimethoxy-4'-(2-prop-2-enyloxy)-chalcone,
2,5-diethoxy-4'-(2-prop-2-enyloxy)-chalcone,
2,5-di-n-propoxy-4'-(2-prop-2-enyloxy)-chalcone,
2,5-diisopropoxy-4'-(2-prop-2-enyloxy)-chalcone,
2,5-di-n-butoxy-4'-(2-prop-2-enyloxy)-chalcone,
2,5-di-t-butoxy-4'-(2-prop-2-enyloxy)-chalcone.
2-methoxy-4,4'-dihydroxy-5-methylchalcone
2-methoxy-4,4'-dihydroxy-5-ethylchalcone
2-methoxy-4,4'-dihydroxy-5-propylchalcone
2-methoxy-4,4'-dihydroxy-5-isopropylchalcone
2-methoxy-4,4'-dihydroxy-5-t-butyichalcone
2-methoxy-4,4'-dihydroxy-5-(1,1-dimethylpropyl)chalcone
2-methoxy-4,4'-dihydroxy-5-prop-2-enylchalcone
2-methoxy-4,4'-dihydroxy-5-but-2-enylchalcone
2-ethoxy-4,4'-dihydroxy-5-methylchalcone
2-ethoxy-4,4'-dihydroxy-5-ethylchalcone
2-ethoxy-4,4'-dihydroxy-5-propylchalcone
2-ethoxy-4,4'-dihydroxy-5-isopropylchalcone
2-ethoxy-4,4'-dihydroxy-5-t-butychalcone
2-ethoxy-4,4'-dihydroxy-5-(1,1-methylpropyl)chalcone
2-ethoxy-4,4'-dihydroxy-5-prop-2-enylchalcone
2-ethoxy-4,4'-dihydroxy-5-but-2-enylchalcone
2-ethoxy-4,4'-dihydroxy-5-(1,1-dimethylprop-2-enyl) chalcone
2-propoxy-4,4'-dihydroxy-5-methylchalcone
2-propoxy-4,4'-dihydroxy-5-ethylchalcone
2-propoxy-4,4'-dihydroxy-5-propylchalcone
2-propoxy-4,4'-dihydroxy-5-isopropylchalcone
2-propoxy-4,4'-dihydroxy-5-t-butylchalcone
2-propoxy-4,4'-dihydroxy-5-(1,1-dimethylpropyl)chalcone
2-propoxy-4,4'-dihydroxy-5-prop-2-enylchalcone
2-propoxy-4,4'-dihydroxy-5-but-2-enylchalcone
2-propoxy-4,4'-dihydroxy-5-(1,1-dimethylprop-2-enyl) chalcone
2-isopropoxy-4,4'-dihydroxy-5-methylchalcone
2-isopropoxy-4,4'-dihydroxy-5-ethylchalcone
2-isopropoxy-4,4'-dihydroxy-5-propylchalcone
2-isopropog-4,4'-dihydroxy-5-isopropylchalcone
2-isopropoxy-4,4'-dihydroxy-5-t-butylchalcone
2-isopropoxy-4,4'-dihydroxy-5-(1,1-dimethylpropyl) chalcone
2-isopropoxy-4,4'-dihydroxy-5-prop-2-enylchalcone
2-isopropoxy-4,4'-dihydroxy-5-but-2-enylchalcone
2-isopropoxy-4,4'-dihydroxy-5-(1,1-dimethylprop-2-enyl) chalcone
2-methoxy-4-hydroxy-4'-amino-5-methylchalcone
2-methoxy-4-hydroxy-4'-amino-5-ethylchalcone
2-methoxy-4-hydroxy-4'-amino-5-propylchalcone
2-methoxy-4-hydroxy-4'-amino-5-isopropylchalcone
2-methoxy-4-hydroxy-4'-amino-5-t-butylchalcone
2-methoxy-4-hydroxy-4'-amino-5-(1,1-dimethylpropyl) chalcone
2-methoxy-4-hydroxy-4'-amino-5-prop-2-enylchalcone
2-methoxy-4-hydroxy-4'-amino-5-but-2-enylchalcone
2-ethoxy-4-hydroxy-4'-amino-5-methylchalone
2-ethoxy-4-hydroxy-4'-amino-5-ethylchalcone
2-ethoxy-4-hydroxy-4'-amino-5-propylchalcone
2-ethoxy-4-hydroxy-4'-amino-5-isopropylchalcone
2-ethoxy-4-hydroxy-4'-amino-5-t-butyichalcone
2-ethoxy-4-hydroxy-4'-amino-5-(1,1-dimethylpropyl) chalcone
2-ethoxy-4-hydroxy-4'-amino-5-prop-2-enylchalcone
2-ethoxy-4-hydroxy-4'-amino-5-but-2-enylchalcone
2-ethoxy-4-hydroxy-4'-amino-5-(1,1-dimethylprop-2-enyl) chalcone
2-propoxy-4-hydroxy-4'-amino-5-methylchalcone
2-propoxy-4-hydroxy-4'-amino-5-ethylchalcone
2-propoxy-4-hydroxy-4'-amino-5-propylchalcone
2-propoxy-4-hydroxy-4'-amino-5-isopropylchalcone
2-propoxy-4-hydroxy-4'-amino-5-t-butylchalcone
2-propoxy-4-hydroxy-4'-amino-5-(1,1-dimethylpropyl) chalcone
2-propoxy-4-hydroxy-4'-amino-5-prop-2-enylchalcone
2-propoxy-4-hydroxy-4'-amino-5-but-2-enylchalcone
2-propoxy-4-hydroxy-4'-amino-5-(1,1-dimethylprop-2-enyl)chalcone
2-isopropoxy-4-hydroxy-4'-amino-5-methylchalcone
2-isopropoxy-4-hydroxy-4'-amino-5-ethylchalcone
2-isopropoxy-4-hydroxy-4'-amino-5-propylchalcone
2-isopropoxyy-4-hydroxy-4'-amino-5-isopropylchalcone
2-isopropoxy-4-hydroxy-4'-amino-5-t-butylchalcone
2-isopropoxy-4-hydroxy-4'-amino-5-(1,1dimethylpropyl) chalcone
2-isopropoxy-4hydroxy-4'-amino-5-prop-2-enylchalcone
2-isopropoxy-4-hydroxy-4'-amino-5-but-2-enylchalcone
2-isopropoxy-4-hydroxy-4'-amino-5-(1,1-dimethylprop-2-enyl)chalcone
2-methoxy-4-hydroxy-4'-methylamino-5-methylchalcone
2-methoxy-4-hydroxy-4'-methylamino-5-ethylchalcone
2-methoxy-4-hydroxy-4'-methylamino-5-propylchalcone
2-methoxy-4-hydroxy-4'-methylamino-5-isopropylchalcone
2-methoxy-4-hydroxy-4'-methylarrino-5-t-butylchalcone
2-methoxy-4hydroxy-4'-methylamino-5-(1,1-dimethylpropyl)chalcone
2-methoxy-4-hydroxy-4'-methylamino-5-prop-2-enylchalcone
2-methoxy-4-hydroxy-4'-methylamino-5-but-2-enylchalcone
2-ethoxy-4-hydroxy-4'-methylamino-5-methylchalcone
2-ethoxy-4-hydroxy-4'-methylamino-5-ethylchalcone
2-ethoxy-4-hydroxy-4'-methylamino-5-propylchalcone
2-ethoxy-4-hydroxy-4'-methylamino-5-isopropylchalcone
2-ethoxy-4-hydroxy-4'-methylamino-5-t-butylchalcone
2-ethoxy-4-hydroxy-4'-methylamino-5-(1,1-dimethylpropyl)chalcone
2-ethoxy-4-hydroxy-4'-methylamino-5-prop-2enylchalcone
2-ethoxy-4-hydroxy-4'-methylamino-5-but-2-enylchalcone
2-ethoxy-4-hydroxy-4'-methylamino-5-(1,1-dimethylprop-2-enyl)chalcone
2-propoxy-4-hydroxy-4'-methylamino-5-methylchalcone
2-propoxy-4-hydroxy-4'-methylamino-5-ethylchalcone
2-propoxy-4-hydroxy-4'-methylamino-5-propylchalcone
2-propoxy-4-hydroxy-4'-methylamino-5-isopropylchalcone
2-propoxy-4-hydroxy-4'-methylamino-5-t-butylchalcone
2-propoxy-4-hydroxy-4'-methylamino-5-(1,1-dimethylpropyl)chalcone
2-propoxy-4-hydroxy-4'-methylamino-5-prop-2-enylchalcone
2-propoxy-4-hydroxy-4'-methylamino-5-but-2-enylchalcone
2-propoxythydroxy-4'-methylamino-5-(1,1-dimethylprop-2-enyl)chalcone
2-isopropoxy-4-hydroxy-4'-methylamino-5-methylchalcone
2-isopropoxy-4-hydroxy-4'-methylamino-5-ethylchalcone
2-isopropoxy-4-hydroxy-4'-methylamino-5-propylchalcone
2-isopropoxy-4-hydroxy-4'-methylamino-5-isopropylchalcone
2-isopropoxy-4-hydroxy-4'-methylarmino-5-t-butylchalcone
2-isopropoxy-4-hydroxy-4'-methylamino-5-(1,1-dimethylpropyl)chalcone
2-isopropoxy-4-hydroxy-4'-methylamino-5-prop-2-enylchalcone
2-isopropoxyvhydroxy-4'-methylamino-5-but-2-enylchalcone 2-isopropoxy-4-hydroxy-4'-methylamino-5-(1,1-dimethylprop-2-enyl)chalcone and the corresponding ketones in which Z is selected from the groups (A)–(E) as defined above 2-methoxy-4,4'-dipivaloyloxy-5-methylchalcone
2-methoxy-4,4'-dipivaloyloxy-5-ethylchalcone
2-methoxy-4,4'-dipivaloyloxy-5-propylchalcone
2-methoxy-4,4'-dipivaloyloxy-5-isopropylchalcone
2-methoxy-4,4'-dipivaloyloxy-5-t-butylchalcone
2-methoxy-4,4'-dipivaloyloxy-5-(1,1-dimethylpropyl)chalcone
2-methoxy-4,4'-dipivaloyloxy-5-prop-2-enylchalcone
2-methoxy-4,4'-dipivaloyloxy-5-but-2-enylchalcone
2-ethoxy-4,4'-dipivaloyloxy-5-methylchalcone
2-ethoxy-4,4'-dipivaloyloxy-5-ethylchalcone
2-ethoxy-4,4'-dipivaloyloxy-5-propylchalcone
2-ethoxy-4,4'-dipivaloyloxy-5-isopropylchalcone
2-ethoxy-4,4'-dipivaloyloxy-5-t-butylchalcone
2-ethoxy-4,4'-dipivaloyloxy-5-(1,1-dimethylpropyl)chalcone
2-ethoxy-4,4'-dipivaloyloxy-5-prop-2-enylchalcone
2-ethoxy-4,4'-dipivaloyloxy-5-but-2-enylchalcone
2-ethoxy-4,4'-dipivaloyloxy-5-(1,1-dimethylprop-2-enyl)chalcone
2-propoxy-4,4'-dipivaloyloxy-5-methylchalcone
2-propoxy-4,4'-dipivaloyloxy-5-ethylchalcone
2-propoxy-4,4'-dipivaloyloxy-5-propyldialcone
2-propoxy-4,4'-ipivaloyloxy-5-isopropylchalcone
2-propoxy-4,4'-dipivaloyloxy-5-t-butylchalcone
2-propoxy-4,4'-dipivaloyloxy-5-(1,1-dimethylpropyl)chalcone
2-propoxy-4,4'-dipivaloyloxy-5-prop-2-enylchalcone
2-propoxy-4,4'-dipivaloyloxy-5-but-2-enylchalcone
2-propoxy-4,4'-dipivaloyloxy-5-(1,1-dimethylprop-2-enyl)chalcone
2-isopropoxy-4,4'-dipivaloyloxy-5-methylchalcone
2-isopropoxy-4,4'-dipivaloyloxy-5-ethylchalcone
2-isopropoxy-4,4'-dipivaloyloxy-5-propylchalcone
2-isopropoxy-4,4'-dipivaloyloxy-5-isopropylchalcone
2-isopropoxy-4,4'-dipivaloyloxy-5-t-butylchalcone
2-isopropoxy-4,4'-dipivaloyloxy-5-(1,1dimethylpropyl)chalcone
2-isopropoxy-4,4'-dipivaloyloxy-5-prop-2enylchalcone
2-isopropoxy-4,4'-dipivaloyloxy-5-but-2-enylchalone
2-isopropoxy-4,4'-dipivaloyloxy-5-(1,1-dimethylprop-2-enyl)chalcone
2-methoxy-4,4'-dipivaloyloxymethoxy-5-methylchalcone
2-methoxy-4,4'-dipivaloyloxymethoxy-5-ethylchalcone
2-methoxy-4,4'-dipivaloyloxymethoxy-5-propylchalcone
2-methoxy-4,4'-dipivaloyloxymethoxy-5-isopropylchalcone
2-methoxy-4,4'-dipivaloyloxymethoxy-5-t-butylchalcone
2-methoxy-4,4'-dipivaloyloxymethoxy-5-(1,1-dimethylpropyl)chalcone
2-methoxy-4,4'-dipivaloyloxymethoxy-5-prop-2-enylchalcone
2-methoxy-4,4 '-dipivaloyloxymethoxy-5-but-2-enylchalcone
2-ethoxy-4,4'-dipivaloyloxymethoxy-5-methylchalcone
2-ethoxy-4,4'-dipivaloyloxymethoxy-5-ethylchalcone
2-ethoxy-4,4'-dipivaloyloxymethoxy-5-propylchalcone
2-ethoxy-4,4'-dipivaloyloxymethoxy-5-isopropylchalcone
2-ethoxy-4,4'-dipivaloyloxymethoxy-5-t-butylchalcone
2-ethoxy-4,4'-dipivaloyloxymethoxy-5-(1,1-dimethylpropyl)chalcone
2-ethoxy-4,4'-dipivaloyloxymethoxy-5-prop-2-enylchalcone
2-ethoxy-4,4'-dipivaloyloxymethoxy-5-but-2-enylchalcone
2-ethoxy-4,4'-dipivaloyloxymethoxy-5-(1,1-dimethylprop-2-enyl)chalcone
2-propoxy-4,4'-dipivaloyloxymethoxy-5-methylchalcone
2-propoxy-4,4'-dipivaloyloxymethoxy-5-ethylchalcone
2-propoxy-4,4'-dipivaloyloxymethoxy-5-propylchalcone
2-propoxy-4,4'-dipivaloyloxyrnethoxy-5-isopropylchalcone
2-propoxy-4,4'-dipivaloyloxymethoxy-5-t-butylchalcone
2-propoxy-4,4'-dipivaloyloxymethoxy-5-(1,1-dimethylpropyl)chalcone
2-propoxy-4,4'-dipivaloyloxymethoxy-5-prop-2-enylchalcone
2-propoxy-4,4'-dipivaloyloxymethoxy-5-but-2-enylchalone
2-propoxy-4,4'-dipivaloyloxymethoxy-5-(1,1-dimethylprop-2-enyl)chalcone
2-isopropoxy-4,4'-dipivaloyloxymethoxy-5-methylchalcone
2-isopropoxy-4,4'-dipivaloyloxymethoxy-5-ethylchalcone
2-isopropoxy-4,4'-dipivaloyloxymethoxy-5-propylchalcone
2-isopropoxy-4,4'-dipivaloyloxyvmethoxy-5-isopropylchalcone
2-isopropoxy-4,4'-dipivaloyloxymethoxy-5-t-butylchalcone
2-isopropoxy-4,4'-dipivaloyloxymethoxy-5-(1,1-dimethylpropyl)chalcone
2-isopropoxy-4,4'-dipivaloyloxymethoxy-5-prop-2-enylchalcone
2-isopropoxy-4,4'-dipivaloyloxymethoxy-5-but-2-enylchalcone
2-isopropoxy-4,4'-dipivaloyloxymethoxy-5-(1,1-dimethylprop-2-enyl)chalcone
2-methoxy-4,4'-(N,N-dimethylcarbamoyl)-5-methylchalcone
2-methoxy-4,4'-(N,N-dimethylcarbamoyl)-5-ethylchalcone
2-methoxy-4,4'-(N,N-dimethylcarbamoyl)-5-propylchalcone
2-methoxy-4,4'-(N,N-dimethylcarbamoyl)-5-isopropylchalcone
2-methoxy-4,4'-(N,N-dimethylcarbamoyl)-5-t-butylchalcone
2-methoxy-4,4'-(N,N-dimethylcarbamoyl)-5-(1,1-dimethylpropyl)chalcone
2-methoxy-4,4'-(N,N-dimethylcarbamoyl)-5-prop-2-enylchalcone
2-methoxy-4,4'-(N,N-dimethylcarbamoyl)-5-but-2-enylchalcone
2-ethoxy-4,4'-(N,N-dimethylcarbamoyl)-5-methylchalcone
2-ethoxy-4,4'-(N,N-dimethylcarbamoyl)-3-ethylchalcone
2-ethoxy-4,4'-(N,N-dimethylcarbamoyl)-5-propylchalcone
2-ethoxy-4,4'-(N,N-dimethylcarbamoyl)-5-isopropylchalcone
2-ethoxy-4,4'-(N,N-dimethylcarbamoyl)-5-t-butylchalcone
2-ethoxy-4,4'-(N,N-dimethylcarbamoyl)-5-(1,1-dimethylpropyl)chalcone
2-ethoxy-4,4-(N,N-dimethylcarbamoyl)-5-prop-2-enylchalcone
2-ethoxy-4,4'-(N,N-dimethylcarbamoyl)-5-but-2-enylchalcone
2-ethoxy-4,4'-(N,N-dimethylcarbamoyl)-5-(1,1-dimethylprop-2-enyl)chalcone
2-propoxy-4,4'-(N,N-dimethylcarbamoyl)-5-methylchalcone
2-propoxy-4,4'-(N,N-dimethylcarbamoyl)-5-ethylchalcone
2-propoxy-4,4'-(N,N-dimethylcarbamoyl)-5-propylchalcone
2-propoxy-4,4'-(N,N-dimethylcarbamoyl)-5-isopropylchalcone
2-propoxy-4,4'-(N,N-dimethylcarbamoyl)-5-t-butylchalcone
2-propoxy-4,4'-(NN-dimethylcarbamoyl)-5-(1,1dimethylpropyl)chalcone 2-propoxy-4,4'-(N,N-dimethylcarbamoyl)-5-prop-2-enylchalcone
2-propoxy-4,4'-(N,N-dimethylcarbamoyl)-5-but-2-enylchalcone
2-propoxy-4,4'-(N,N-dimethylcarbamoyl)-5(1,1-dimethylprop-2-enyl)chalcone
2-isopropoxy-4,4'-(N,N-dimethylcarbamoyl)-5-methylchalcone
2-isopropoxy-4,4'-(N,N-dimethylcarbamoyl)-5-ethylchalcone
2-isopropoxy-4,4'-(N,N-dimethylcarbamoyl)-5-propylchalcone
2-isopropoxy-4,4'-(N,N-dimethylcarbamoyl)-5-isopropylchalcone
2-isopropoxy-4,4'-(N,N-dimethylcarbamoyl)-5-t-butylchalcone
2-isopropoxy-4,4'-(N,N-dimethylcarbamoyl)-5-(1,1dimethylpropyl)chalcone
2-isopropoxy-4,4'-(N,Ndethylcarbamoyl)-5-prop-2-enylchalcone
2-isopropoxy-4,4'-(N,N-dimethylcarbamoyl)-5-but-2-enylchalcone
2-isopropoxy-4,4'-(N,N-dimethylcarbamoyl)-5-(1,1-dimethylprop-2-enylchalcone Specific examples of bis-aromatic α,β-unsaturated ketones are 2-methoxy-4,4'-dihydroxy-5-methylchalcone
2-methoxy-4,4'-dihydroxy-3,5-diethylchalcone
2-methoxy-4,4'-dihydroxy-3,5-dipropylchalcone
2-methoxy-4,4'-dihydroxy-3,5-diisopropylchalcone
2-methoxy-4,4'-dihydroxy-3,5-di-t-butylchalcone
2-methoxy-4,4'-dihydroxy-3,5-di-(1,1-dimethylpropyl)chalcone
2-methoxy-4,4'-dihydroxy-3,5-diprop-2-enylchalcone
2-methoxy-4,4'-dihydroxy-3,5-dibut-2-enylchalcone
2-ethoxy-4,4'-dihydroxy-3,5-dimethylchalcone
2-ethoxy-4,4'-dihydroxy-3,5-diethylchalcone
2-ethoxy-4,4'-dihydroxy-3,5-dipropylchalcone
2-ethoxy-4,4'-dihydroxy-3,5-diisopropylchalcone
2-ethoxy-4,4'-dihydroxy-3,5-di-t-butylchalcone
2-ethoxy-4,4'-dihydroxy-3,5di-(1,1-dimethylpropyl)chalcone
2-ethoxy-4,4'-dihydroxy-3,5-diprop-2-enylchalcone
2-ethoxy-4,4'-dihydroxy-3,5dibut-2-enylchalcone
2-ethoxy-4,4-dihydroxy-3,5-di-(1,1-dimethylprop-2enyl)chalcone
2-propoxy-4,4'-dihydroxy-3,5-dimethylchalcone
2-propoxy-4,4'-dihydroxy-3,5-diethylchalcone
2-propoxy-4,4'-dihydroxy-3,5-dipropylchalcone
2-propoxy-4,4'-dihydroxy-3,5-diisopropylchalcone
2-propoxy-4,4'-dihydroxy-3,5-di-t-butyichalcone
2-propoxy-4,4'-dihydroxy-3,5-di-(1,1-dimethylpropyl)chalcone
2-propoxy-4,4'-dihydroxy-3,5-diprop-2-enylchalcone
2-propoxy-4,4'-dihydroxy-3,5-dibut-2-enylchalcone
2-propoxy-4,4'-diydroxy-3,5-di-(1,1-dimethylprop-2-enyl)chalcone
2-isopropoxy-4,4'-dihydroxy-3,5-dimethylchalcone
2-isopropoxy-4,4'-dihydroxy-3,5-diethylchalcone
2-isopropoxy-4,4'-dihydroxy-3,5-dipropylchalcone
2-isopropoxy-4,4'-dihydroxy-3,5-diisopropylchalcone
2-isopropoxy-4,4'-dihydroxy-3,5-di-t-butyichalcone
2-isopropoxy-4,4'-dihydroxy-3,5-di-(1,1-dimethylpropyl)chalcone
2-isopropoxy-4,4'-dihydroxy-3,5-diprop-2-enylchalcone
2-isopropoxy-4,4'-dihydroxy-3,5-dibut-2-enylchalcone
2-isopropoxy-4,4'-dihydroxy-3,5-di-(1,1-dimethylprop-2-enyl)chalcone
2-methoxy-4hydroxy-4'-armino-3,5-dimethylchalcone
2-methoxy-4-hydroxy-4'-amino-3,5-diethylchalcone
2-methoxy-4hydroxy-4'-amino-3,5-dipropylchalcone
2-methoxy-4-hydroxy-4'-amino-3,5-diisopropylchalcone
2-methoxy-4hydroxy-4'-amino-3,5-di-t-butylchalcone
2-methoxy-4-hydroxy-4'-amino-3,5-di-(1,1-dimethylpropyl)chalcone
2-methoxy-4-hydroxy-4'-amino-3,5-diprop-2-enylchalcone
2-methoxy-4-hydroxy-4'-amino-3,5-dibut-2-enylchalcone
2-ethoxy-4-hydroxy-4'-amino-3,5-dimethylchalcone
2-ethoxy-4-hydroxy-4'-amino-3,5-diethylchalcone
2-ethoxy-4-hydroxy-4'-amino-3,5-dipropylchalcone
2-ethoxy-4-hydroxy-4'-amino-3,5-diisopropylchalcone
2-ethoxy-4-hydroxy-4'-amino-3,5-di-t-butylchalcone
2-ethoxy-4-hydroxy-4'-amino-3,5-di-(1,1-dimethylpropyl)chalcone
2-ethoxy-4-hydroxy-4'-amino-3,5-diprop-2-enylchalcone
2-ethoxy-4-hydroxy-4'-amino-3,5-dibut-2-enylchalcone
2-ethoxy-4-hydroxy-4'-amino-3,5-di-(1,1-dimethylprop-2-enyl)chalcone
2-propoxy-4-hydroxy-4'-amino-3,5-dimethylchalcone
2-propoxy-4-hydroxy-4'-amino-3,5-diethylchalcone
2-propoxy-4-hydroxy-4'-amino-3,5-dipropylchalcone
2-propoxy-4-hydroxy-4'-amino-3,5-diisopropylchalcone
2-propoxy-4-hydroxy-4'-amino-3,5di-t-butychalone
2-propoxy-4-hydroxy-4'-amino-3,5-di-(1,1-dimethylpropyl)chalcone
2-propoxy-4-hydroxy-4'-amino-3,5-diprop-2-enylchalcone
2-propoxy-4-hydroxy-4'-amino-3,5-dibut-2-enylchalcone
2-propoxy-4-hydroxy-4'-amino-3,5-di-(1,1-dimethylprop-2-enyl)chalcone
2-isopropoxy-4-hydroxy-4'-amino-3,5-dimethylchalcone
2-isopropoxy-4-hydroxy-4'-amino-3,5-diethylchalcone
2-isopropoxy-4-hydroxy-4'-amino-3,5-dipropylchalcone
2-isopropoxy-4-hydroxy-4'-amino-3,5-diisopropylchalcone
2-isopropoxy-4-hydroxy-4'-amino-3,5-di-t-butylchalcone
2-isopropoxy-4-hydroxy-4'-amino-3,5-di-(1,1-dimethylpropyl)chalcone
2-isopropoxy-4-hydroxy-4'-amino-3,5-diprop-2-enylchalcone
2-isopropoxy-4-hydroxy-4'-amino-3,5-dibut-2-enylchalcone
2-isopropoxy-4-hydroxy-4'-amino-5-(1,1-dimethylprop-2-enyl)chalcone
2-methoxy-4-hydroxy-4'-methylamino-3,5-dimethylchalcone
2-methoxy-4-hydroxy-4'-methylamino-3,5-diethylchalcone
2-methoxy-4-hydroxy-4'-methylamino-3,5-dipropylchalcone
2-methoxy-4-hydroxy-4'-methylamino-3,5-diisopropylchalcone
2-methoxy-4-hydroxy-4'-methylamino-3,5-di-t-butylchalcone
2-methoxy-4-hydroxy-4'-methylamino-3,5-di-(1,1-dimethylpropyl)chalcone
2-methoxy-4-hydroxy-4'-methylamino-3,5-diprop-2-enylchalcone
2-methoxy-4-hydroxy-4'-methylamino-3,5-dibut-2-enylchalcone
2-ethoxy-4-hydroxy-4'-methylamino-3,5-dimethylchalcone
2-ethoxy-4-hydroxy-4'-methylamino-3,5-diethylchalcone
2-ethoxy-4-hydroxy-4'-methylamino-3,5-dipropylchalcone
2-ethoxy-4-hydroxy-4'-methylamino-3,5-diisopropylchalcone
2-ethoxy-4hydroxy-4'-methylamino-3,5-di-t-butylchalcone
2-ethoxy-4-hydroxy-4'-methylamino-3,5-di-(1,1-dimethylpropyl)chalcone 2-ethoxy-4-hydroxy-4'-methylamino-3,5-diprop-2-enylchalcone
2-ethoxy-4-hydroxy-4'-methylamino-3,5-dibut-2-enylchalcone
2-ethoxy-4-hydroxy-4'-methylamino-5-(1,1-dimethylprop-2-enyl)chalcone
2-propoxy-4-hydroxxy-4'-methylamino-3,5-dimethylchalcone
2-propoxy-4-hydroxy-4'-methylamino-3,5-diethylchalcone
2-propoxy-4-hydroxy-4'-methylamino-3,5-dipropylchalcone
2-propoxy-4-hydroxy-4'-methylamino-3,5-diisopropylchalcone
2-propoxy-4-hydroxy-4'-methylamino-3,5-di-t-butylchalcone
2-propoxy-4-hydroxy-4'-methylamino-3,5-di-(1,1-dimethylpropyl)chalcone
2-propoxy-4-hydroxy-4'-methylamino-3,5-diprop-2-enylchalcone
2-propoxy-4hydroxy-4'-methylamino-3,5-dibut-2-enylchalcone
2-propoxy-4-hydroxy-4'-methylamino-5-(1,1-dimethylprop-2-enyl)chalcone
2-isopropoxy-4-hydroxy-4'-methylamino-3,5-dimethylchalcone
2-isopropoxy-4-hydroxy-4'-methylamino-3,5-diethylchalcone
2-isopropoxy-4-hydroxy-4'-methylamino-3,5-dipropylchalcone
2-isopropoxy-4-hydroxy-4'-methylamino-3,5-diisopropylchalcone
2-isopropoxy-4-hydroxy-4'-methylamino-3,5-di-t-butylchalcone
2-isopropoxy-4-hydroxy-4'-methylamino-3,5-di-(1,1-dimethylpropyl)chalcone
2-isopropoxy-4-hydroxy-4'-methylamino-3,5-diprop-2-enylchalcone
2-isopropoxy-4-hydroxy-4'-methylamino-3,5-dibut-2-enylchalcone
2-isopropoxythydroxy-4'-methylamino-5-(1,1-dimethylprop-2-enyl)chalcone and the corresponding ketones in which Z is selected form the groups (A)–(E) as defined above 2-methoxy-4,4'-dipivaloyloxy-3,5-dimethylchalcone
2-methoxy-4,4'-dipivaloyloxy-3,5-diethylchalcone
2-methoxy-4,4'-dipivaloyloxy-3,5-dipropylchalcone
2-methoxy-4,4'-dipivaloyloxy-3,5-diisopropylchalcone
2-methoxy-4,4'-dipivaloyloxy-3,5-di-t-butylchalcone
2-methoxy-4,4'-dipivaloyloxy-3,5-di-(1,1-dimethylpropyl)chalcone
2-methoxy-4,4'-dipivaloyloxy-3,5-diprop-2-enylchalcone
2-methoxy-4,4'-dipivaloyloxy-3,5-dibut-2enylchalcone
2-ethoxy-4,4'-dipivaloyloxy-3,5-dimethylchalcone
2-ethoxy-4,4'-dipivaloyloxy-3,5-diethylchalcone
2-ethoxy-4,4'-dipivaloyloxy-3,5-dipropylchalcone
2-ethoxy-4,4'-dipivaloyloxy-3,5-diisopropylchalcone
2-ethoxy-4,4'-dipivaloyloxy-3,5-di-t-butylchalcone
2-ethoxy-4,4'-dipivaloyloxy-3,5-di-(1,1-dimethylpropyl)chalcone
2-ethoxy-4,4'-dipivaloyloxy-3,5-diprop-2-enylchalcone
2-ethoxy-4,4'-dipivaloyloxy-3,5-dibut-2-enylchalcone
2-ethoxy-4,4'-dipivaloyloxy-3,5-di-(1,1-dimethylprop-2-enyl)chalcone
2-propoxy-4,4'-dipivaloyloxy-3,5-dimethylchalcone
2-propoxy-4,4'-dipivaloyloxy-3,5-diethylchalcone
2-propoxy-4,4'-dipivaloyloxy-3,5-dipropylchalcone
2-propoxy-4,4'-dipivaloyloxy-3,5-diisopropylchalcone
2-propoxy-4,4'-dipivaloyloxy-3,5-di-t-butylchalcone
2-propoxy-4,4'-dipivaloyloxy-3,5-di-(1,1-dimethylpropyl)chalcone
2-propoxy-4,4'-dipivaloyloxy-3,5-diprop-2-enylchalcone
2-propoxy-4,4'-dipivaloyloxy-3,5-dibut-2-enylchalcone
2-propoxy-4,4'-dipivaloyloxy-3,5-di-(1,1-dimethylprop-2-enyl)chalcone
2-isopropoxy-4,4'-dipivaloyloxy-3,5-dimethylchalcone
2-isopropoxy-4,4'-dipivaloyloxy-3,5-dimethylchalcone
2-isopropoxy-4,4'-dipivaloyloxy-3,5-dipropylchalcone
2-isopropoxy-4,4'-dipivaloyloxy-3,5-diisopropylchalcone
2-isopropoxy-4,4'-dipivaloyloxy-3,5-di-t-butychalcone
2-isopropoxy-4,4'-dipivaloyloxy-3,5-di-(1,1-dimethylpropyl)chalcone
2-isopropoxy-4,4'-dipivaloyloxy-3,5-diprop-2-enylchalcone
2-isopropoxy-4,4'-dipivaloyloxy-3,5-dibut-2-enylchalcone
2-isopropoxy 4,4'-dipivaloyloxy-3,5-di-(1,1-dimethylprop-2-enyl)chalcone
2-methoxy-4,4'-dipivaloyloxymethoxy-3,5-dimethylchalcone
2-methoxy-4,4'-dipivaloyloxymethoxy-3,5-diethylchalcone
2-methoxy-4,4'-dipivaloyloxymethoxy-3,5-dipropylchalcone
2-methoxy-4,4'-dipivaloyloxymethoxy-3,5-diisopropylchalcone
2-methoxy-4,4'-dipivaloyloxymethoxy-3,5-di-t-butylchalcone
2-methoxy-4,4'-dipivaloyloxymethoxy-3,5-di-(1,1-dimethylpropyl)chalcone
2-methoxy-4,4'-dipivaloyloxymethoxy-3,5-diprop-2-enylchalcone
2-methoxy-4,4'-dipivaloyloxymethoxy-3,5-dibut-2-enylchalcone
2-ethoxy-4,4'-dipivaloyloxymethoxy-3,5-dimethylchalcone
2-ethoxy-4,4'-dipivaloyloxymethoxy-3,5-diethylchalcone
2-ethoxy-4,4'-dipivaloyloxyrnethoxy-3,5-dipropylchalcone
2-ethoxy-4,4'-dipivaloyloxymethoxy-3,5-diisopropylchalcone
2-ethoxy-4,4'-dipivaloyloxymethoxy-3,5-di-t-butylchalcone
2-ethoxy-4,4'-dipivaloyloxymethoxy-3,5-di-(1,1-dimethylpropyl)chalcone
2-ethoxy-4,4'-dipivaloyloxymethoxy-3,5-diprop-2-enylchalcone
2-ethoxy-4,4'-dipivaloyloxymethoxy-3,5-dibut-2-enylchalcone
2-ethoxy-4,4'-dipivaloyloxymethoxy-5-(1,1-dimethylprop-2-enyl)chalcone
2-propoxy-4,4'-dipivaloyloxymethoxy-3,5-dimethylchalcone
2-propoxy-4,4'-dipivaloyloxymethoxy-3,5-diethylchalcone
2-propoxy-4,4'-dipivaloyloxymethoxy-3,5-dipropylchalcone
2-propoxy-4,4'-dipivaloyloxymethoxy-3,5-diisopropylchalcone
2-propoxy-4,4'-dipivaloyloxymethoxy-3,5-di-t-butylchalcone
2-propoxy-4,4'-dipivaloyloxymethoxy-3,5-di-(1,1-dimethylpropyl)chalcone
2-propoxy-4,4'-dipivaloyloxymethoxy-3,5-diprop-2-enylchalcone
2-propoxy-4,4'-dipivaloyloxymethoxy-3,5-dibut-2-enylchalcone
2-propoxy-4,4'-dipivaloyloxymethoxy-5-(1,1-dimethylprop-2-enyl)chalcone
2-isopropoxy-4,4'-dipivaloyloxymethoxy-3,5-dimethylchalcone
2-isopropoxy-4,4'-dipivaloyloxymethoxy-3,5-diethylchalcone 2-isopropoxy-4,4'-dipivaloyloxymethoxy-3,5-dipropylchalcone
2-isopropoxy-4,4'-dipivaloyloxymethoxy-3,5-diisopropylchalcone
2-isopropoxy-4,4'-dipivaloyloxymethoxy-3,5-di-t-butylchalcone
2-isopropoxy-4,4'-dipivaloyloxymethoxy-3,5-di-(1,1-dimethylpropyl)chalcone
2-isopropoxy-4,4'-dipivaloyloxymethoxy-3,5-diprop-2-enylchalcone
2-isopropoxy-4,4'-dipivaloyloxymethoxy-3,5-dibut-2-enylchalcone
2-isopropoxy-4,4'-dipivaloyloxymethoxy-5(1,1-dimethylprop-2enyl)chalcone
2-methoxy-4,4'-(N,N-dimethylcarbamoyl)-3,5-dimethylchalcone
2-methoxy-4,4'-(N,N-dimethylcarbamoyl)-3,5-diethylchalcone
2-methoxy-4,4'-(N,N-dimethylcarbamoyl)-3,5-dipropylchalcone
2-methoxy-4,4'-(N,N-dimethylcarbamoyl)-3,5-diisopropylchalcone
2-methoxy-4,4'-(N,N-dimethylcarbamoyl)-3,5-di-t-butyichalcone
2-methoxy-4,4'-(N,N-dimethylcarbamoyl)-5-(1,1-dimethylpropyl)chalcone
2-methoxy-4,4'-(N,N-dimethylcarbamoyl)-3,5-diprop-2-enylchalcone
2-methoxy-4,4'-(N,N-dimethylcarbamoyl)-3,5-dibut-2-enylchalcone
2-ethoxy-4,4'-(N,N-dimethylcarbamoyl)-3,5-dimethylchalcone
2-ethoxy-4,4'-(N,N-dimethylcarbamoyl)-3,5-diethylchalcone
2-ethoxy-4,4'-(N,N-dimethylcarbamoyl)-3,5-dipropylchalcone
2-ethoxy-4,4'-(N,N-dimethylcarbamoyl)-3,5-diisopropylchalcone
2-ethoxy-4,4'-(N,N-dimethylcarbamoyl)-3,5-di-t-butylchalcone
2-ethoxy-4,4'-(N,N-dimethylcarbamoyl)-5-(1,1-dimethylpropyl)chalcone
2-ethoxy-4,4'-(N,N-dimethylcarbamoyl)-3,5-diprop-2-enylchalcone
2-ethoxy-4,4'-(N,N-dimethylcarbamoyl)-3,5-dibut-2-enylchalcone
2-ethoxy-4,4'-(N,N-dimethylcarbamoyl)-5-(1,1-dimethylprop-2-enyl)chalcone
2-propoxy-4,4'-(N,N-dimethylcarbamoyl)-3,5-dimethylchalcone
2-propoxy-4,4'-(N,N-dimethylcarbamoyl)-3,5-diethylchalcone
2-propoxy-4,4'-(N,N-dimethylcarbamoyl)-3,5-dipropylchalcone
2-propoxy-4,4'-(N,N-dimethylcarbamoyl)-3,5-diisopropylchalcone
2-propoxy-4,4'-(N,N-dimethylcarbamoyl)-3,5-di-t-butylchalcone
2-propoxy-4,4'-(N,N-dimethylcarbamoyl)-5-(1,1-dimethylpropyl)chalcone
2-propoxy-4,4'-(N,N-dimethylcarbamoyl)-3,5-diprop-2-enylchalcone
2-propoxy-4,4'-(N,N-dimethylcarbamoyi)-3,5-dibut-2-enylchalcone
2-propoxy-4,4'-(N,N-dimethylcarbamoyl)-5-(1,1-dimethylprop-2-enyl)chalcone
2-isopropoxy-4,4'-(N,N-dimethylcarbamoyl)-3,5-dimethylchalcone
2-isopropoxy-4,4'-(N,N-dimethylcarbamoyl)-3,5-diethylchalcone
2-isopropoxy-4,4'-(N,N-dimethylcarbamoyl)-3,5-dipropylchalcone
2-isopropoxy-4,4'-(N,N-dimethylcarbamoyl)-3,5-diisopropylchalcone
2-isopropoxy-4,4'-(N,N-dimethykarbamoyl)-3,5-di-t-butylchalcone
2-isopropoxy-4,4'-(N,N-dimethylcarbamoyl)-5-(1,1-dimethylpropyl)chalcone
2-isopropoxy-4,4'-(N,N-dimethylcarbamoyl)-3,5-diprop-2-enylchalcone
2-isopropoxy-4,4'-(N,N-dimethylcarbamoyl)-3,5-dibut-2-enylchalcone
2-isopropoxy-4,4'-(N,N-dimethylcarbamoyl)-5-(1,1-dimethylprop-2-enyl)chalcone Specific examples of bis-aromatic α,β-unsaturated ketones are
2-methoxy-6,4'-dihydroxy-5-methylchalcone
2-methoxy-6,4'-dihydroxy-3,5-diethylchalcone
2-methoxy-6,4'-dihydroxy-3,5-dipropylchalcone
2-methoxy-6,4'-dihydroxy-3,5-diisopropylchalcone
2-methoxy-6,4'-dihydroxy-3,5-di-t-butylchalcone
2-methoxy-6,4'-dihydroxy-3,5-di-(1,1-dimethylpropyl)chalcone
2-methoxy-6,4'-dihydroxy-3,5-diprop-2-enylchalcone
2-methoxy-6,4'-dihydroxy-3,5-dibut-2-enylchalcone
2-ethoxy-6,4'-dihydroxy-3,5-dimethylchalcone
2-ethoxy-6,4'-dihydroxy-3,5-diethylchalcone
2-ethoxy-6,4 '-dihydroxy-3,5-dipropylchalcone
2-ethoxy-6,4'-dihydroxy-3,5-diisopropylchalcone
2-ethoxy-6,4'-dihydroxy-3,5-di-t-butylchalcone
2-ethoxy-6,4'-dihydroxy-3,5-di-(1,1-dimethylpropyl)chalcone
2-ethoxy-6,4'-dihydroxy-3,5-diprop-2-enylchalcone
2-ethoxy-6,4'-dihydroxy-3,5-dibut-2-enylchalcone
2-ethoxy-6,4'-dihydroxy-3,5-di-(1,1-dimethylprop-2-enyl)chalcone
2-propoxy-6,4'-dihydroxy-3,5-dimethylchalcone
2-propoxy-6,4'-dihydroxy-3,5-diethylchalcone
2-propoxy-6,4'-dihydroxy-3,5-dipropylchalcone
2-propoxy-6,4'-dihydroxy-3,5-diisopropylchalcone
2-propoxy-6,4'-dihydroxy-3,5-di-t-butylchalcone
2-propoxy-6,4'-dihydroxy-3,5-di-(1,1-methylpropyl)chalcone
2-propoxy-6,4'-dihydroxy-3,5-diprop-2-enylchalcone
2-propoxy-6,4'-dihydroxy-3,5-dibut-2-enylchalcone
2-propoxy-4'-dihydroxy-3,5-di-(1,1-dimethylprop-2-enyl)chalcone
2-isopropoxy-6,4'-dihydroxy-3,5-dimethylchalcone
2-isopropoxy-6,4'-dihydroxy-3,5-diethylchalcone
2-isopropoxy-6,4'-dihydroxy-3,5-dipropylchalcone
2-isopropoxy-6,4'-dihydroxy-3,5-diisopropylchalcone
2-isopropoxy-6,4'-dihydroxy-3,5-di-t-butylchalcone
2-isopropoxy-6,4'-dihydroxy-3,5-di-(1,1-dimethylpropyl)chalcone
2-isopropoxy-6,4'-dihydroxy-3,5-diprop-2-enylchalcone
2-isopropoxy-6,4'-dihydroxy-3,5-dibut-2-enylchalcone
2-isopropoxy-6,4'-dihydroxy-3,5-di-(1,1-methylprop-2-enyl)chalcone
2-methoxy-6-hydroxy-4'-amino-3,5-dimethylchalcone
2-methoxythydroxy-4'-amino-3,5-diethylchalcone
2-methoxy-6-hydroxy-4'-amino-3,5-dipropylchalcone
2-methoxy-6-hydroxy-4'-amino-3,5-diisopropylchalcone
2-methoxy-6-hydroxy-4'-amino-3,5-di-t-butylchalcone
2-methoxy-6-hydroxy-4'-amino-3,5-di-(1,1-dimethylpropyl)chalcone 2-methoxy-6-hydroxy-4'-amino-3,5-diprop-2-enylchalcone
2-methoxy-6-hydroxy-4'-amino-3,5-dibut-2-enylchalcone
2-ethoxy-6-hydroxy-4'-amino-3,5-dimethylchalcone
2-ethoxy-6-hydroxy-4'-amino-3,5-diethylchalcone
2-ethoxy-6-hydroxy-4'-amino-3,5-dipropylchalcone
2-ethoxy-6-hydroxy-4'-amino-3,5-diisopropylchalcone
2-ethoxy-6-hydroxy-4'-amino-3,5-di-t-butylchaylclone
2-ethoxy-6-hydroxy-4'-amino-3,5-di-(1,1-dimethylpropyl) chalcone
2-ethoxy-6-hydroxy-4'-amino-3,5-diprop-2-enylchalcone
2-ethoxy-6-hydroxy-4'-amino-3,5-dibut-2-enylchalcone
2-ethoxy-6-hydroxy-4'-amino-3,5-di-(1,1-dimethylprop-2enyl)chalcone
2-propoxy-6-hydroxy-4'-amino-3,5-dimethylchalcone
2-propoxy-6-hydroxy-4'-amino-3,5-diethylchalcone
2-propoxy-6-hydroxy-4'-amino-3,5-dipropylchalcone
2-propoxy-6-hydroxy-4'-amino-3,5-diisopropylchalcone
2-propoxy-6-hydroxy-4'-amino-3,5-di-t-butylchalcone
2-propoxy-6-hydroxy-4'-amino-3,5-di-(1,1-direthylpropyl) chalcone
2-propoxy-6-hydroxy-4'-amino-3,5-diprop-2-enylchalcone
2-propoxy-6-hydroxy-4'-amino-3,5-dibut-2-enylchalcone
2-propoxy-6-hydroxy-4'-amino-3,5-di-(1,1-dimethylprop-2-enyl)chalcone
2-isopropoxy-6-hydroxy-4'-amino-3,5-dimethylchalcone
2-isopropoxy-6-hydroxy-4'-amino-3,5-diethylchalone
2-isopropoxy-6-hydroxy-4'-amino-3,5-dipropylchalcone
2-isopropoxy-6-hydroxy-4'-amino-3,5-disopropylchalcone
2-isopropoxy-6-hydroxy-4'-amino-3,5-di-t-butylchalcone
2-isopropoxy-6-hydroxy-4'-amino-3,5-di-(1,1-dimethylpropyl)chalcone
2-isopropoxy-6-hydroxy-4'-amino-3,5-diprop-2-enylchalcone
2-isopropoxy-6-hydroxy-4'-amino-3,5-dibut-2-enylchalone
2-isopropoxy-6-hydroxy-4'-amino-5-(1,1-dimethylprop-2-enyl)chalcone
2-methoxy-6-hydroxy-4'-methylamino-3,5-dimethylchalcone
2-methoxy-6-hydroxy-4'-methylamino-3,5-diethylchalcone
2-methoxy-6-hydroxy-4'-methylamino-3,5-dipropylchalcone
2-methoxy-6-hydroxy-4'-methylamino-3,5-diisopropylchalcone
2-methoxy-6-hydroxy-4'-methylamino-3,5-di-t-butylchalcone
2-methoxy-6-hydroxy-4'-methylamino-3,5-di-(1,1-dimethylpropyl)chalcone
2-methoxy-6-hydroxy-4'-methylamino-3,5-diprop-2-enylchalcone
2-methoxy-6hydroxy-4'-methylamino-3,5-dibut-2-enylchalcone
2-ethoxy-6-hydroxy-4'-methylamino-3,5-dimethylchalcone
2-ethoxy-6-hydroxy-4'-methylamino-3,5-diethylchalcone
2-ethoxy-6-hydroxy-4'-methylamino-3,5-dipropylchalcone
2-ethoxy-6-hydroxy-4'-methylamino-3,5-diisopropylchalcone
2-ethoxy-6-hydroxy-4'-methylamino-3,5-di-t-butylchalcone
2-ethoxy-6-hydroxy-4'-methylamino-3,5-di-(1,1-dimethylpropyl)chalcone
2-ethoxy-6-hydroxy-4'-methylamino-3,5-diprop-2-enylchalcone
2-ethoxy-6-hydroxy-4'-methylramino-3,5-dibut-2-enylchalcone
2-ethoxy-6-hydroxy-4'-methylamino-5-(1,1-dimethylprop-2-enyl)chalcone
2-propoxy-6-hydroxy-4'-methylamino-3,5-dimethylchalcone
2-propoxy-6-hydroxy-4'-methylamino-3,5-diethylchalcone
2-propoxy-6-hydroxy-4'-methylamino-3,5-dipropylchalcone
2-propoxy-6-hydroxy-4'-methylamino-3,5-diisopropylchalcone
2-propoxy-6-hydroxy-4'-methylamino-3,5-di-t-butylchalcone
2-propoxy-6-hydroxy-4'-methylamino-3,5-di-(1,1-dimethylpropyl)chalcone
2-propoxy-6-hydroxy-4'-methylamino-3,5-diprop-2-enylchalcone
2-propoxy-6-hydroxy-4'-methylamino-3,5-dibut-2-enylchalcone
2-propoxy-6-hydroxy-4'-methylamino-5-(1,1-dimethylprop-2-enyl)chalcone
2-isopropoxy-6-hydroxy-4'-methylamino-3,5-dimethylchalcone
2-isopropoxy-6-hydroxy-4'-methylamino-3,5-diethylchalcone
2-isopropoxy-6-hydroxy-4'-methylamino-3,5-dipropylchalcone
2-isopropoxy-6-hydroxy-4'-methylamino-3,5-diisopropylchalcone
2-isopropoxy-6-hydroxy-4'-methylamino-3,5-di-t-butylchalcone
2-isopropoxy-6-hydroxy-4'-methylamino-3,5-di-(1,1-dimethylpropyl)chalcone
2-isopropoxy-6-hydroxy-4'-methylamino-3,5-diprop-2-enylchalcone
2-isopropoxy-6-hydroxy-4'-methylamino-3,5-dibut-2-enylchalcone
2-isopropoxy-6-hydroxy-4'-methylamino-5-(1,1-dimethylprop-2-enyl)chalcone and the corresponding ketones in which Z is selected from the groups (A)–(E) as defined above 2-methoxy-6,4'-dipivaloyloxy-3,5-dimethylchalcone
2-methoxy-6,4'-dipivaloyloxy-3,5-diethylchalcone
2-methoxy-6,4'-dipivaloyloxy-3,5-dipropylchalcone
2-methoxy-6,4'-dipivaloyloxy-3,5-diisopropylchalcone
2-methoxy-6,4'-dipivaloyloxy-3,5-di-t-butylchalcone
2-methoxy-6,4'-dipivaloyloxy-3,5-di-(1,1-dimethylpropyl) chalcone
2-methoxy-6,4'-dipivaloyloxy-3,5-diprop-2-enylchalcone
2-methoxy-6,4'-dipivaloyloxy-3,5-dibut-2-enylchalcone
2-ethoxy-6,4'-dipivaloyloxy-3,5-dimethylchalcone
2-ethoxy-6,4'-dipivaloyloxy-3,5-diethylchalcone
2-ethoxy-6,4'-dipivaloyloxy-3,5-dipropylchalcone
2-ethoxy-6,4'-dipivaloyloxy-3,5-diisopropylchalcone
2-ethoxy-6,4'-dipivaloyloxy-3,5-di-t-butylchalcone
2-ethoxy-6,4'-dipivaloyloxy-3,5-di-(1,1-dimethylpropyl) chalcone
2-ethoxy-6,4'-dipivaloyloxy-3,5-diprop-2-enylchalcone
2-ethoxy-6,4'-dipivaloyloxy-3,5-dibut-2-enylchalcone
2-ethoxy-6,4'-dipivaloyloxy-3,5-di-(1,1-dimethylprop-2-enyl)chalcone
2-propoxy-6,4'-dipivaloyloxy-3,5-dimethylchalcone
2-propoxy-6,4'-dipivaloyloxy-3,5-diethylchalcone
2-propoxy-6,4'-dipivaloyloxy-3,5-dipropylchalcone
2-propoxy-6,4'-dipivaloyloxy-3,5-diisopropylchalcone
2-propoxy-6,4'-dipivaloyloxy-3,5-di-t-butylchalcone
2-propoxy-6,4'-dipivaloyloxy-3,5-di-(1,1-dimethylpropyl) chalcone
2-propoxy-6,4'-dipivaloyloxy-3,5-diprop-2-enylchalcone
2-propoxy-6,4'-dipivaloyloxy-3,5-dibut-2-enylchalcone
2-propoxy-6,4'-dipivaloyloxy-3,5-di-(1,1-dimethylprop-2-enyl)chalcone
2-isopropoxy-6,4'-dipivaloyloxy-3,5-dimethylchalcone 2-isopropoxy-6,4'-dipivaloyloxy-3,5-diethylchalcone
2-isopropoxy-6,4'-dipivaloyloxy-3,5-dipropylchalcone
2-isopropoxy-6,4'-dipivaloyloxy-3,5-diisopropylchalcone
2-isopropoxy-6,4'-dipivaloyloxy-3,5-di-t-butylchalcone
2-isopropoxy-6,4'-dipivaloyloxy-3,5-di-(1,1-dimethylpropyl)chalcone
2-isopropoxy-6,4'-dipivaloyloxy-3,5-diprop-2-enylchalcone
2-isopropoxy-6,4'-dipivaloyloxy-3,5-dibut-2-enylchalcone
2-isopropoxy-6,4'-dipivaloyloxy-3,5-di-(1,1-dimethylprop-2-enyl)chalcone
2-methoxy-6,4'-dipivaloyloxymethoxy-3,5-dimethylchalcone
2-methoxy-6,4'-dipivaloyloxymethoxy-3,5-diethylchalcone
2-methoxy-6,4'-dipivaloyloxymethoxy-3,5-dipropylchalcone
2-methoxy-6,4'-dipivaloyloxymethoxy-3,5-diisopropylchalcone
2-methoxy-6,4'-dipivaloyloxymethoxy-3,5-di-t-butylchalcone
2-methoxy-6,4'-dipivaloyloxymethoxy-3,5-di-(1,1-dimethylpropyl)chalcone
2-methoxy-6,4'-dipivaloyloxymethoxy-3,5-diprop-2-enylchalcone
2-methoxy-6,4'-dipivaloyloxymethoxy-3,5-dibut-2-enylchalcone
2-ethoxy-6,4'-dipivaloyloxymethoxy-3,5-dimethylchalcone
2-ethoxy-6,4'-dipivaloyloxymethoxy-3,5-diethylchalcone
2-ethoxy-6,4'-dipivaloyloxymethoxy-3,5-dipropylchalcone
2-ethoxy-6,4'-dipivaloyloxymethoxy-3,5-diisopropylchalcone
2-ethoxy-6,4'-dipivaloyloxymethoxy-3,5-di-t-butylchalcone
2-ethoxy-6,4'-dipivaloyloxymethoxy-3,5-di-(1,1-dimethylpropyl)chalcone
2-ethoxy-6,4'-dipivaloyloxymethoxy-3,5-diprop-2-enylchalcone
2-ethoxy-6,4'-dipivaloyloxymethoxy-3,5-dibut-2-enylchalcone
2-ethoxy-6,4'-dipivaloyloxymethoxy-5-(1,1-dimethylprop-2-enyl)chalcone
2-propoxy-6,4'-dipivaloyloxymethoxy-3,5-dimethylchalcone
2-propoxy-6,4'-dipivaloyloxymethoxy-3,5-diethylchalcone
2-propoxy-6,4'-dipivaloyloxymethoxy-3,5-dipropylchalcone
2-propoxy-6,4'-dipivaloyloxymethoxy-3,5-diisopropylchalcone
2-propoxy-6,4'-dipivaloyloxymethoxy-3,5-di-t-butylchalcone
2-propoxy-6,4'-dipivaloyloxymethoxy-3,5-di-(1,1-dimethylpropyl)chalcone
2-propoxy-6,4'-dipivaloyloxymethoxy-3,5-diprop-2enylchalcone
2-propoxy-6,4'-dipivaloyloxymethoxy-3,5-dibut-2-enylchalcone
2-propoxy-6,4'-dipivaloyloxymethoxy-5-(1,1-dimethyvprop-2-enyl)chalcone
2-isopropoxy-6,4'-dipivaloyloxymethoxy-3,5-dimethylchalcone
2-isopropoxy-6,4'-dipivaloyloxymethoxy-3,5-diethylchalcone
2-isopropoxy-6,4'-dipivaloyloxymethoxy-3,5-dipropylchalcone
2-isopropoxy-6,4'-dipivaloyloxymethoxy-3,5-diisopropylchalcone
2-isopropoxy-6,4'-dipivaloyloxymethoxy-3,5-di-t-butylchalcone
2-isopropoxy-6,4'-dipivaloyloxymethoxy-3,5-di-(1,1-dimetylpropyl)chalcone
2-isopropoxy-6,4'-dipivaloyloxymethoxy-3,5-diprop-2-enylchalcone
2-isopropoxy-6,4'-dipivaloyloxymethoxy-3,5-dibut-2-enylchalcone
2-isopropoxy-6,4'-dipivaloyloxymethoxy-5-(1,1-dimethylprop-2-enyl)chalcone
2-methoxy-6,4'-(N,N-dimethylcarbamoyl)-3,5-dimethylchalcone
2-methoxy-6,4'-(N,N-dimethylcarbamoyl)-3,5-diethylchalcone
2-methoxy-6,4'-(N,N-dimethylcarbamoyl)-3,5-dipropylchalcone
2-methoxy-6,4'-(N,N-dimethylcarbamoyl)-3,5-diisopropylchalcone
2-methoxy-6,4'-(N,N-dimethylcarbamoyl)-3,5-di-t-butylchalcone
2-methoxy-6,4'-(N,N-dimethylcarbamoyl)-5-(1,1-dimethylpropyl)chalcone
2-methoxy-6,4'-(N,N -dimethylcarbamoyl)-3,5-diprop-2-enylchalcone
2-methoxy-6,4'-(N,N-dimnethylcarbamoyl)-3,5-dibut-2-enylchalcone
2-ethoxy-6,4'-(N,N-dimethylcarbamoyl)-3,5-dimethylchalcone
2-ethoxy-6,4'-(N,N-dimethylcarbamoyl)-3,5-diethychalcone
2-ethoxy-6,4'-(N,N-dimethylcarbamoyl)-3,5-dipropylchalcone
2-ethoxy-6,4'-(N,N-dimethylcarbamoyl)-3,5-diisopropylchalcone
2-ethoxy-6,4'-(N,N-dimethylcarbamoyl)-3,5-di-t-butylchalcone
2-ethoxy-6,4'-(N,N-dimethylcarbamoyl)-5-(1,1-dimethylpropyl)chalcone
2-ethoxy-6,4'-(N,N-dimethylcarbamoyl)-3,5-diprop-2-enylchalcone
2-ethoxy-6,4'-(N,N-dimethylcarbamoyl)-3,5-dibut-2-enylchalcone
2-ethoxy-6,4'-(N,N-dimethylcarbamoyl)-5-(1,1-dimethylprop-2-enyl)chalcone
2-propoxy-6,4'-(N,N-dimethylcarbamoyl)-3,5-dimethylchalcone
2-propoxy-6,4'-(N,N-dimethylcarbamoyl)-3,5-diethylchalcone
2-propoxy-6,4'-(N,N-dimethylcarbamoyl)-3,5-dipropylchalcone
2-propoxy-6,4'-(N,N-dimethylcarbamoyl)-3,5-diisopropylchalcone
2-propoxy-6,4'-(N,N-dimethylcarbamoyl)-3,5-di-t-butylchalcone
2-propoxy-6,4'-(N,N-dimethylcarbamoyl)-5-(1,1-dimethylpropyl)chalcone
2-propoxy-6,4'-(N,N-dimethylcarbamoyl)-3,5-diprop-2-enylchalcone
2-propoxy-6,4'-(N,N-dimethylcarbamoyl)-3,5-dibut-2-enylchalcone
2-propoxy-6,4'-(N,N-dimethylcarbamoyl)-5-(1,1-dimethylprop-2-enyl)chalcone
2-isopropoxy-6,4'-(N,N-dimethylcarbamoyl)-3,5-dimethylchalcone
2-isopropoxy-6,4'-(N,N-dimethylcarbamoyl)-3,5-diethylchalcone
2-isopropoxy-6,4'-(N,N-dimethylcarbamoyl)-3,5-dipropylchalcone
2-isopropoxy-6,4'-(N,N-dimethylcarbamoyl)-3,5-diisopropylchalcone
2-isopropoxy-6,4'-(N,N-dimethylcarbamoyl)-3,5-di-t-butylchalcone 2-isopropoxy-6,4'-(N,N-dimethylcarbamoyl)-5-(1,1-dimethylpropyl)chalcone
2-isopropoxy-6,4'-(N,N-dimethylcarbamoyl)-3,5-diprop-2-enylchalcone
2-isopropoxy-6,4'-(N,N-dimethylcarbamoyl)-3,5-dibut-2-enylchalcone
2-isopropoxy-6,4'-(N,N-dimethylcarbamoyl)-5-(1,1-dimethylprop-2-enyl)chalcone Specific examples of bis-aromatic α,β-unsaturated ketones are 2-methoxy-4,4'-dihydroxy-5-propylchalcone
2-methoxy-4,4'-dihydroxy-5-(1,1-dimethylpropyl)chalcone
2-methoxy-4,4'-dihydroxy-5-prop-2-enylchalcone
2-methoxy-4,4'-dihydroxy-5-but-2-enylchalcone
2-ethoxy-4,4'-dihydroxy-5-propylchalcone
2-ethoxy-4,4'-dihydroxy-5-(1,1-dimethylpropyl)chalcone
2-ethoxy-4,4'-dihydroxy-5-prop-2-enylchalcone
2-ethoxy-4,4'-dihydroxy-5-but-2-enylchalcone
2-ethoxy-4,4'-dihydroxy-5-(1,1-dimethylprop-2-enyl)chalcone
2-propoxy-4,4'-dihydroxy-5-propylchalcone
2-propoxy-4,4'-dihydroxy-5-(1,1-dimethylpropyl)chalcone
2-propoxy-4,4'-dihydroxy-5-prop-2-enylchalcone
2-propoxy-4,4'-dihydroxy-5-but-2-enylchalcone
2-propoxy-4,4'-dihydroxy-5-(1,1-dimethylprop-2-enyl)chalcone
2-isopropoxy-4,4'-dihydroxy-5-propylchalcone
2-isopropoxy-4,4'-dihydroxy-5-(1,1-dimethylpropyl)chalcone
2-isopropoxy-4,4'-dihydroxy-5-prop-2-enylchalcone
2-isopropoxy-4,4'-dihydroxy-5-but-2-enylchalcone
2-isopropoxy-4,4'-dihydroxy-5-(1,1-dimethylprop-2-enyl)chalcone
2-methoxythydroxy-4'-amino-5-propylchalcone
2-methoxyvhydroxy-4'-amino-5-(1,1-dimethylpropyl)chalcone
2-methoxy-4-hydroxy-4'-amino-5-prop-2-enylchalcone
2-methoxy-4-hydroxy-4'-amino-5-but-2-enylchalcone
2-ethoxy-4-hydroxy-4'-amino-5-propylchalcone
2-ethoxy-4hydroxy-4'-amino-5-(1,1-dimethylpropyl)chalone
2-ethoxy-4-hydroxy-4'-amino-5-prop-2-enylchalcone
2-ethoxy-4-hydroxy-4'-amino-5-but-2-enylchalcone
2-ethoxy-4-hydroxy-4'-amino-5-(1,1-dimethylprop-2-enyl)chalcone
2-propoxy-4-hydroxy-4'-amino-5-propylchalcone
2-propoxy-4-hydroxy-4'-amino-5-(1,1-dimethylpropyl)chalcone
2-propoxy-4hydroxy-4'-amino-5-prop-2-enylchalcone
2-propoxy-4-hydroxy-4'-amino-5-but-2-enylchalcone
2-propoxy-4-hydroxy-4'-amino-5-(1,1-dimethylprop-2-enyl)chalcone
2-isopropoxy-4-hydroxy-4'-amino-5-propylchalcone
2-isopropoxy-4-hydroxy-4'-amino-5-(1,1-dimethylpropyl)chalcone
2-isopropoxy-4-hydroxy-4'-amino-5-prop-2-enylchalcone
2-isopropoxy-4-hydroxy-4'-amino-5-but-2-enylchalcone
2-isopropoxy-4hydroxy-4'-amino-5-(1,1-dimethylprop-2-enyl)chalcone
2-methoxy-4-hydroxy-4'-methylamino-5-propylchalcone
2-methoxy-4-hydroxy-4'-methylamino-5-(1,1-dimethylpropyl)chalcone
2-methoxy-4-hydroxy-4'-methylamino-5-prop-2-enylchalcone
2-methoxy-4-hydroxy-4'-methylamino-5-but-2-enylchalcone
2-ethoxy-4-hydroxy-4'-methylamino-5-propylchalcone
2-ethoxy-4-hydroxy-4'-methylamino-5-(1,1-dimethylpropyl)chalcone
2-ethoxy-4-hydroxy-4'-methylamino-5-prop-2-enylchalcone
2-ethoxy-4-hydroxy-4'-methylamino-5-but-2-enylchalcone
2-ethoxy-4-hydroxy-4'-methylamino-5-(1,1-dimethylprop-2-enyl)chalcone
2-propoxy-4-hydroxy-4'-methylaamino-5-propylchalcone
2-propoxy-4-hydroxy-4'-methylamino-5-(1,1-dimethylpropyl)chalcone
2-propoxy-4-hydroxy-4'-methylamino-5-prop-2-enylchalcone
2-propoxy-4-hydroxy-4'-methylamino-5-but-2-enylchalcone
2-propoxy-4-hydroxy-4'-methylamino-5-(1,1-dimethylprop-2-enyl)chalcone
2-isopropoxy-4-hydroxy-4'-methylamino-5-propylchalcone
2-isopropoxy-4-hydroxy-4'-methylamino-5-(1,1-dimethylpropyl)chalcone
2-isopropoxy-4-hydroxy-4'-methylamino-5-prop-2-enylchalcone
2-isopropoxy-4-hydroxy-4'-methylamino-5-but-2-enylchalcone
2-isopropoxy-4-hydroxy-4'-methylamino-5-(1,1-dimethylprop-2-enyl)chalcone and the corresponding ketons in which Z is selected from the groups (A)–(E) as defined above 2-methoxy-4,4'-dipivaloyloxy-5-propylchalcone
2-methoxy-4,4'-dipivaloyloxy-5-(1,1-dimethylpropyl)chalcone
2-methoxy-4,4'-dipivaloyloxy-5-prop-2-enylchalcone
2-methoxy-4,4'-dipivaloyloxy-5-but-2-enylchalcone
2-ethoxy-4,4'-dipivaloyloxy-5-propylchalcone
2-ethoxy-4,4-dipivaloyloxy-5-(1,1-dimethylpropyl)chalcone
2-ethoxy-4,4'-dipivaloyloxy-5-prop-2-enylchalcone
2-ethoxy-4,4'-dipivaloyloxy-5-but-2-enylchalcone
2-ethoxy-4,4'-dipivaloyloxy-5-(1,1-dimethylprop-2-enyl)chalcone
2-propoxy-4,4'-dipivaloyloxy-5-propylchalcone
2-propoxy-4,4'-dipivaloyloxy-5-(1,1-dimethylpropyl)chalcone
2-propoxy-4,4'-dipivaloyloxy-5-prop-2-enylchalcone
2-propoxy-4,4'-dipivaloyloxy-5-but-2-enylchalcone
2-propoxy-4,4'-dipivaloyloxy-5-(1,1-dimethylprop-2-enyl)chalcone
2-isopropoxy-4,4'-dipivaloyloxy-5-propylchalcone
2-isopropoxy-4,4'-dipivaloyloxy-5-(1,1-dimethylpropyl)chalcone
2-isopropoxy-4,4'-dipivaloyloxy-5-prop-2-enylchalcone
2-isopropoxy-4,4'-dipivaloyloxy-5-but-2-enylchalcone
2-isopropoxy-4,4'-dipivaloyloxy-5-(1,1-dimethylprop-2-enyl)chalcone
2-methoxy-4,4'-dipivaloyloxymethoxy-5-propylchalcone
2-methoxy-4,4'-dipivaloyloxymethoxy-5-(1,1-dimethylpropyl)chalcone
2-methoxy-4,4'-dipivaloyloxymethoxy-5-prop-2-enylchalcone
2-methoxy-4,4'-dipivaloyloxymethoxy-5-but-2-enylchalcone
2-ethoxy-4,4'-dipivaloyloxymethoxy-5-propylchalcone
2-ethoxy-4,4'-dipivaloyloxymethoxy-5-(1,1-dimethylpropyl)chalcone
2-ethoxy-4,4'-dipivaloyloxymethoxy-5-prop-2-enylchalcone
2-ethoxy-4,4'-dipivaloyloxymethoxy-5-but-2-enylchalcone
2-ethoxy-4,4'-dipivaloyloxymethoxy-5-(1,1-dimethylprop-2-enyl)chalcone 2-propoxy-4,4'-dipivaloyloxymethoxy-5-propylchalcone
2-propoxy-4,4'-dipivaloyloxymethoxy-5-(1,1-dimethylpropyl)chalcone
2-propoxy-4,4'-dipivaloyloxymethoxy-5-prop-2-enylchalcone
2-propoxy-4,4'-dipivaloyloxymethoxy-5-but-2-enylchalcone
2-propoxy-4,4'-dipivaloyloxymethoxy-5-(1,1-dimethylprop-2-enyl)chalcone
2-isopropoxy-4,4'-dipivaloyloxymethoxy-5-propylchalcone
2-isopropoxy-4,4'-dipivaloyloxymethoxy-5-(1,1-dimethylpropyl)chalcone
2-isopropoxy-4,4'-dipivaloyloxymethoxy-5-prop-2-enylchalcone
2-isopropoxy-4,4'-dipivaloyloxymethoxy-5-but-2-enylchalcone
2-isopropoxy-4,4'-dipivaloyloxymethoxy-5-(1,1-dimethylprop-2-enyl)chalcone
2-methoxy-4,4'-(N,N-dimethylcarbamoyl)-5-propylchalcone
2-methoxy-4,4'-(N,N-dimethyycarbamoyl)-5-(1,1-dimethylpropyl)chalcone
2-methoxy-4,4'-(N,N-dimethylcarbamoyl)-5-prop-2-enylchalcone
2-methoxy-4,4'-(N,N-dimethylcarbamoyl)-5-but-2-enylchalcone
2-ethoxy-4,4'-(N,N-dimethylcarbamoyl)-5-propylchalcone
2-ethoxy-4,4'-(N,N-dimethylcarbamoyl)-5-(1,1-dimethylpropyl)chalcone
2-ethoxy-4,4'-(N,N-dimethylcarbamoyl)-5-prop-2-enylchalcone
2-ethoxy-4,4'-(N,N-dimethylcarbamoyl)-5-but-2enylchalcone
2-ethoxy-4,4'-(N,N-dimethylcarbamoyl)-5-(1,1-dimethylprop-2-enyl)chalcone
2-propoxy-4,4'-(N,N-dimethylcarbamoyl)-5-propylchalcone
2-propoxy-4,4'-(N,N-dimethylcarbamoyl)-5-(1,1-dimethylpropyl)chalcone
2-propoxy-4,4'-(N,N-dimethylcarbamoyl)-5-prop-2-enylchalcone
2-propoxy-4,4'-(N,N-dimethylcarbamoyl)-5-but-2-enylchalcone
2-propoxy-4,4'-(N,N-dimethylcarbamoyl)-5-(1,1-dimethylprop-2-enyl)chalcone
2-isopropoxy-4,4'-(N,N-dimethylcarbamoyl)-5-propylchalcone
2-isopropoxy-4,4'-(N,N-dimethylcarbamoyl)-5-(1,1-dimethylpropyl)chalcone
2-isopropoxy-4,4'-(N,N-dimethylcarbamoyl)-5-prop-2-enylchalcone
2-isopropoxy-4,4'-(N,N-dimethylcarbamoyl)-5-but-2enylchalcone
2-isopropoxy-4,4'-(N,N-dimethylcarbamoyl)-5-(1,1-dimethylprop-2-enyl)chalcone Formulation of pharmaceutical compositions The administration route of the aromatic compound as defined above, such as the bis-aromatic α,β-unsaturated ketones of the general formula I, may be of any-suitable route which leads to a concentration in the blood corresponding to a therapeutic concentration. Thus, e.g., the following administration routes may be applicable although the invention is not limited thereto: the oral route, the parenteral route, the cutaneous route, the nasal route, the rectal route, the vaginal route and the ocular route. It should be clear to a person skilled in the art that the administration route is dependant on the compound in question, particularly, the choice of administration route depends on the physico-chemical properties of the compound together with the age and weight of the patient and on the particular disease and the severity of the same.

The aromatic compounds as defined above, such as the bis-aromatic α,β-unsaturated ketones or derivatives thereof, may be contained in any appropriate amount in a pharmaceutical composition, and are generally contained in an amount of about 1–95% by weight of the total weight of the composition. The composition may be presented in a dosage form which is suitable for the oral, parenteral, rectal, cutaneous, nasal, vaginal and/or ocular administration route. Thus, the composition may be in form of, e.g., tablets, capsules, pills, powders, granulates, suspensions, emulsions, solutions, gels including hydrogels, pastes, ointments, creams, plasters, drenches, delivery devices, suppositories, enemas, injectables, implants, sprays, aerosols and in other suitable form.

The pharmaceutical compositions may be formulated according to conventional pharmaceutical practice, see, e.g., "Remington's Pharmaceutical Sciences" and "Encyclopedia of Pharmaceutical Technology", edited by Swarbrick, J. & J. C. Bovlan. Marcel Dekker, Inc., New York, 1988.

Pharmaceutical compositions according to the present invention may be formulated to release the active compound substantially immediately upon administration or at any substantially predetermined time or time period after administration. The latter type of compositions are generally known as controlled release formulations.

In the present context, the term "controlled release formulation" embraces i) formulations which create a substantially constant concentration of the drug within the body over an extended period of time, ii) formulations which after a predetermined lag time create a substantially constant concentration of the drug within the body over an extended period of time, iii) formulations which sustain drug action during a predetermined time period by maintaining a relatively, constant, effective drug level in the body with concomitant minimization of undesirable side effects associated with fluctuations in the plasma level of the active drug substance (sawtooth kinetic pattern), iv) formulations which attempt to localize drug action by, e.g., spatial placement of a controlled release composition adjacent to or in the diseased tissue or organ, v) formulations which attempt to target drug action by using carriers or chemical derivatives to deliver the drug to a particular target cell type.

Controlled release formulations may also be denoted "sustained release", "prolonged release", "programmed release", "time release", "rate-controlled" and /or "targeted release" formulations.

Controlled release pharmaceutical compositions may be presented in any suitable dosage forms, especially in dosage forms intended for oral, parenteral, cutaneous nasal, rectal, vaginal and/or ocular administration.

Administration of the aromatic compounds defined above, such as bis-aromatic α,β-unsaturated ketones in form of a controlled release formulation is especially preferred in such cases where the compound in question i) has a narrow therapeutic index [i.e. the difference between the plasma concentration leading to harmful side effects or toxic reactions and the plasma concentration leading to a therapeutic effect is small; in general, the therapeutive index, TI, is defined as the ratio of median lethal dose ($LD_{50}$) to median effective dose ($ED_{50}$)], ii) has a narrow absorption window in the gastro-intestinal tract. In such cases, it is important that the intact dose of the aromatic compound reaches the site of absorption in order to avoid a substantially uniform distribution of the compound administered in the whole gastrointestinal tract, iii) has a very short biological half-live so that frequent dosing during a day is required in order to sustain the plasma level at a therapeutic level, or iv) in cases where it is desirable to enable preparation of a pharmaceutical composition intended for use only once or twice daily or even less frequent with the purpose of reducing patient compliance problems, v) in cases where it is desirable to avoid peak concentrations in the plasma so that harmful side or toxic effects related to such high concentrations can be substantially reduced, vi) in cases where it is desirable to avoid fluctuations in plasma concentration of the compound administered (in order to even out any peak and valley concentration).

In general, two basically different strategies can be applied in order to obtain a controlled release formulation in which the rate of release outweighs the rate of metabolism of the compound in question.

In the first strategy, the principle aims at changing the properties of the active drug substance by converting the substance into a masked form. The compounds of the above formulae in which Z is one of the groups (A)–(E) are representatives of this strategy.

In the second strategy, controlled release is obtained by appropriate selection of various formulation parameters and ingredients, including, e.g. various types of controlled release compositions and coatings (formulation-method).

As mentioned above, the first strategy comprises use of the prodrug principle, i.e. converting the active drug substance into a per se inactive derivative which, upon administration to the organism, within the body of the organism by an enzymatic or non-enzymatic process releases the active drug substance so that the drug substance can exert its therapeutic effect. By proper choice of the prodrug it is possible to obtain a prodrug which releases the active drug substance with a controlled rate so that it thereby is possible to extend the effect of the drug in the body.

The other strategy comprises the use of the active drug substance per se and then formulate the active drug substance together with appropriate excipients into a pharmaceutical composition which upon administration of the composition to the organism releases the active substance in a controlled manner. Examples include single or multiple unit tablet or capsule compositions, oil solutions, suspensions, emulsions, microcapsules, microspheres, nanoparticles, liposomes, delivery devices such as those intended for oral, parenteral, cutaneous, nasal, vaginal or ocular use.

It will be appreciated that a combination of the above-mentioned two methods can be used in controlled release compositions, comprising the aromatic compounds defined above, such as bis-aromatic α,β-unsaturated ketones, according to the invention, e.g., by using a prodrug of the compound in question and then formulating according to the principles mentioned above.

In the present context every pharmaceutical composition is an actual drug delivery system, since upon administration it presents the active drug substance to the body of the organism.

Solid dosage forms for oral use

Formulations for oral use include tablets which contain the active ingredient in admixture with non-toxic pharmaceutically acceptable excipients. These excipients may be, for example, inert diluents or fillers, such as sucrose, sorbitol, sugar, mannitol, microcrystalline cellulose, starches including potato starch, calcium carbonate, sodium chloride, lactose, calcium phosphate, calcium sulfate or sodium phosphate;

granulating and disintegrating agents, for example, cellulose derivatives including microcrystalline cellulose, starches including potato starch, croscarmellose sodium, alginates or alginic acid;

binding agents, for example, sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone or polyethylene glycol; and lubricating agents, including glidants and antiadhesives, for example, magnesium stearate, zinc stearate, stearic acid, silicas, hydrogenated vegetable oils or talc.

Other pharmaceutically acceptable excipients can be colorants, flavouring agents, plasticizers, humectants, buffering agents etc.

The tablets may be uncoated or they may be coated by known techniques, optionally to delay disintegration and absorption in the gastrointestinal tract and thereby providing a sustained action over a longer period. The coating may be adapted to release the active drug substance in a predetermined pattern, e.g. in order to achieve a controlled release formulation (see below) or it may be adapted not to release the active drug substance until after passage of the stomach (enteric coating). The coating may be a sugar coating, a film coating (e.g. based on hydroxypropyl methylcellulose, methylcellulose, methyl hydroxyethylcellulose, hydroxypropylcellulose, carboxymethylcellulose, acrylate copolymers (Eudragit E®), polyethylene glycols and/or polyvinylpyrrolidone) or an enteric coating (e.g. based on methacrylic acid copolymer (Eudragit® L and S), cellulose acetate phthalate, hydroxypropyl methylcellulose phthalate, hydroxypropyl methylcellulose acetate succinate, polyvinyl acetate phthalate, shellac and/or ethylcellulose).

Furthermore, a time delay material such as, e.g., glyceryl monostearate or glyceryl distearate may be employed.

In addition, the solid tablet compositions as mentioned above may be provided with a coating adapted to protect the composition from unwanted chemical changes, e.g. chemical degradation, prior to the release of the active drug substance.

The coating may be applied on the solid dosage form in a similar manner as that described in "Aqueous film coating" by James A. Seitz in "Encyclopedia of Pharmaceutical Technology", Vol 1, pp. 337–349 edited by Swarbrick, J. & J. C. Boylan, Marcel Dekker, Inc., New York, 1988.

Formulations for oral use may also be presented as chewing tablets, or as hard gelatin capsules wherein the active ingredient is mixed with an inert solid diluent, for example, potato starch, lactose, microcrystalline cellulose, calcium carbonate, calcium phosphate or kaolin, or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus or a spray drying equipment.

Controlled release oral dosage forms

Controlled release compositions for oral use may, e.g., be constructed to release the active drug substance by controlling the dissolution and/or the diffusion of the active drug substance.

Dissolution or diffusion controlled release can be achieved by appropriate coating of a tablet, capsule, pellet or granulate formulation of the aromatic compounds defined above, such as the bis-aromatic α,β-unsaturated ketones, or by incorporating the compound in question in, e.g., an appropriate matrix.

A controlled release coating may comprise one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3butylene glycol, ethylene glycol methacrylate and/or polyethylene glycols.

In a controlled release matrix formulation of the aromatic compounds defined above, such as the bis-aromatic α,β-unsaturated ketones, the matrix material may comprise, e.g., hydrated metylcellulose, carnauba wax and stearyl alcohol, carbopol 934, silicone, glyceryl tristearate, methyl acrylate-methyl methacrylate, polyvinyl chloride, polyethylene and/or halogenated fluorocarbon.

A controlled release composition of the aromatic compound defined above, such as the bis-aromatic α,β-unsaturated ketones, may also be in the form of a buoyant tablet or capsule, i.e. a tablet or capsule which upon oral administration floats on top of the gastric content for a certain period of time. A buoyant tablet formulation of the compound in question can be prepared by granulating a mixture of the drug, excipients and 20–75% w/w of hydrocolloids, such as hydroxyethrlcellulose, hydroxypropylcellulose and hydroxypropylmethylcellulose. The obtained granules can then be compressed into tablets. On contact with the gastric juice, the tablet can form a substantially water-impermeable gel barrier around its surface. This gel barrier takes part in maintaining a density of less than one, thereby allowing the tablet to remain buoyant in the gastric juice.

Fluid/liquid compositions

Powders, dispersible powders or granules suitable for preparation of an aqueous suspension by addition of water are also convenient dosage forms. Formulation as a suspension provides the active ingredient in admixture with a dispersing or wetting agent, suspending agent and one or more preservatives.

Suitable dispersing or wetting agents are, for example, naturally-occurring phosphatides, as e.g. lecithin, or condensation products of ethylene oxide with e.g. a fatty acid, a long chain aliphatic alcohol or a partial ester derived from fatty acids and a hexitol or a hexitol anhydrides, for example, polyoxyethylene stearate, polyoxyethylene sorbitol monooleate, polyoxyethylene sorbitan monooleate etc.

Suitable suspending agents are, for example, sodium carboxymethylcellulose, methylcellulose, sodium alginate etc.

Parenteral compositions

The pharmaceutical composition may also be administered parenterally by injection, infusion or implantation (intravenous, intramuscular, intraarticular, subcutaneous or the like) in dosage forms, formulations or e.g. suitable delivery devices or implants containing conventional, non-toxic pharmaceutically acceptable carriers and adjuvants.

The formulation and preparation of such compositions is well-known to those skilled in the art of pharmaceutical formulation. Specific formulations can be found in the textbook entitled "Remington's Pharmaceutical Sciences".

Compositions for parenteral use may be presented in unit dosage forms, e.g. in ampoules, or in vials containing several doses and in which a suitable preservative may be added (see below). The composition may be in form of a solution, a suspension, an emulsion, an infusion device or a delivery device for implantation or it may be presented as a dry powder to be reconstituted with water or another suitable vehicle before use. Apart from the active drug substance, the compositions may comprise suitable parenterally acceptable carriers and/or excipients or the active drug substance may be incorporated into microspheres, microcapsules, nanoparticles, liposomes or the like for controlled release. Furthermore, the composition may, in addition, conveniently comprise suspending, solubilizing, stabilizing, pH-adjusting agents and/or dispersing agents.

As indicated above, the pharmaceutical compositions according to the invention may comprise the active drug substances in the form of a sterile injection. To prepare such a composition, the suitable active drug substances are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution and isotonic sodium chloride solution. The aqueous formulation may also contain one or more preservatives, for example, methyl, ethyl or n-propyl p-hydroxybenzoate. In cases where the aromatic compound defined above, such as the bis-aromatic α,β-unsaturated ketone, is only sparingly or slightly soluble in water, a dissolution enhancing or solubilizing agent can be added or the solvent may apart from water comprise 10–60% w/w of propylene glycol or the like.

Controlled release parenteral compositions

As mentioned above under the heading parenteral compositions, controlled release parenteral compositions may be in form of aqueous suspensions, microspheres, microcapsules, magnetic microspheres, oil solutions, oil suspensions, emulsions or the active drug substance may be incorporated in biocompatible carrier(s), liposomes, nanoparticles, implants or infusion devices.

Materials for use in the preparation of microspheres and/or microcapsules are, e.g., biodegradable/bioerodible polymers such as polyglactin, poly-(isobutyl cyanoacrylate), poly(2-hydroxyethyl-L-glutamnine) and poly(lactic acid).

Biocompatible carriers which may be used when formulating a controlled release parenteral formulation are, e.g., carbohydrates such as dextrans, proteins such as albumin, lipoproteins or antibodies.

Materials for use in implants are, e.g., non-biodegradable as, e.g., polydimethyl siloxane, or biodegradable such as, e.g., poly(caprolactone), poly(lactic acid), poly(glycolic acid) or poly(ortho esters).

Rectal compositions

For rectal application, suitable dosage forms for a composition include suppositories (emulsion or suspension type), and rectal gelatin capsules (solutions or suspensions). In a typical suppository formulation, the active drug compounds are combined with an appropriate pharmaceutically acceptable suppository base such as cocoa butter, esterified fatty acids, glycerinated gelatin, and various water-soluble or dispersible bases like polyethylene glycols and polvoxyethylene sorbitan fatty acid esters. Various additives like, e.g., enhancers or surfactants may be incorporated.

Nasal compositions

For nasal application, typical dosage forms include nasal sprays and aerosols for inhalation. In a typically nasal formulation, the active ingredients are dissolved or dispersed in a suitable vehicle. The pharmaceutically acceptable vehicles and excipients and optionally other pharmaceutically acceptable materials present in the composition such as diluents, enhancers, flavouring agents, preservatives etc. are all selected in accordance with conventional pharmaceutical practice in a manner understood by the persons skilled in the art of formulating pharmaceuticals.

Percutaneous and topical compositions

The pharmaceutical compositions may also be administered topically on the skin for percutaneous absorption in dosage forms or formulations containing conventionally non-toxic pharmaceutical acceptable carriers and excipients including microspheres and liposomes. The formulations include creams, ointments, lotions, liniments, gels, hydrogels, solutions, suspensions, sticks, sprays, pastes, plasters and other kinds of transdermal drug delivery systems. The pharmaceutically acceptable carriers or excipients may include emulsifying agents, antioxidants, buffering agents, preservatives, humectants, penetration enhancers, chelating agents, gelforming agents, ointment bases, perfumes and skin protective agents.

Examples of emulsifying agents are naturally occurring gums, e.g. gum acacia or gum tragacanth, naturally occurring phosphatides, e.g. soybean lecithin and sorbitan monooleate derivatives.

Examples of antioxidants are butylated hydroxy anisole (BHA), ascorbic acid and derivatives thereof, tocopherol and derivatives thereof, butylated hydroxy anisole and cysteine.

Examples of preservatives are parabens, such as methyl or propyl p-hydroxybenzoate and benzalkonium chloride.

Examples of humectants are glycerin, propylene glycol, sorbitol and urea.

Examples of penetration enhancers are propylene glycol, DMSO, triethanolamine, N,N-dimethylacetamide, N,N-dimethylformamide, 2-pyrrolidone and derivatives thereof, tetrahydrofurfuryl alcohol and Azone®.

Examples of chelating agents are sodium EDTA, citric acid and phosphoric acid.

Examples of gel forming agents are Carbopol, cellulose derivatives, bentonite, alginates, gelatin and polyvinylpyrrolidone.

Examples of ointment bases are beeswax, paraffin, cetyl palmitate, vegetable oils, sorbitan esters of fatty acids (Span), polyethylene glycols, and condensation products between sorbitan esters of fatty acids and ethylene oxide, e.g. polyoxyethylene sorbitan monooleate (Tween).

The pharmaceutical compositions mentioned above for topical administration on the skin may also be used in connection with topical administration onto or close to the infected parts of the body which is to be treated. The compositions may be any suitable medicated mass adapted for direct application or for introduction into relevant orifice(s) of the body, e.g. the rectal, urethral, vaginal or oral orifices. The compositions may simply be applied directly onto the infected part, e.g. the mucosa. In certain cases it might be applied by means of special drug delivery devices such as dressings or alternatively plasters, pads, sponges, strips or other forms of suitable flexible material.

Controlled release percutaneous and topical compositions

In general, four different approaches are applicable in order to provide rate control over the release and transdermal permeation of a drug compound. These approaches are: membrane-moderated systems, adhesive diffusion-controlled systems, matrix dispersion-type systems and microreservoir systems. It is appreciated that a controlled release percutaneous and/or topical composition may be obtained by using a suitable mixture of the above-mentioned approaches.

In a membrane-moderated system, the active drug substance is present in a reservoir which is totally encapsulated in a shallow compartment molded from a drug-impermeable laminate, such as a metallic plastic laminate, and a rate-controlling polymeric membrane such as a microporous or a non-porous polymeric membrane, e.g., ethylene-vinyl acetate copolymer. The active drug substance is only permitted to be released through the rate-controlling polymeric membrane. In the drug reservoir, the active drug substance may either be dispersed in a solid polymer matrix or suspended in an unleachable, viscous liquid medium such as silicone fluid. On the external surface of the polymeric membrane, a thin layer of an adhesive polymer is applied to achieve an intimate contact of the transdermal system with the skin surface. The adhesive polymer is preferably a polymer which is hypoallergenic and compatible with the active drug substance.

In an adhesive diffusion-controlled system, a reservoir of the active drug substance is formed by directly dispersing the active drug substance in an adhesive polymer and then—by, e.g., solvent casting—spreading the adhesive containing the active drug substance onto a flat sheet of substantially drug-impermeable metallic plastic backing to form a thin drug reservoir layer.

A matrix dispersion-type system is characterized in that a reservoir of the active drug substance is formed by substantially homogeneously dispersing the active drug substance in a hydrophilic or lipophilic polymer matrix and then, the drug-containing polymer is molded into disc with a substantially well-defined surface area and controlled thickness. The adhesive polymer is spread along the circumference to form a strip of adhesive around the disc.

A microreservoir system may be considered as a combination of the reservoir and matrix dispersion type systems. In this case, the reservoir of the active substance is formed by first suspending the drug solids in an aqueous solution of water-soluble polymer and then dispersing the drug suspension in a lipophilic polymer to form a multiplicity of unleachable, microscopic spheres of drug reservoirs.

Compositions for administration to the eye

Formulations for administration to the eye may be presented in the form of eye drops, lotions, ointments or delivery devices. Typically, the composition comprises the active drug substance in combination with pharmaceutically inert vehicles or the active drug substance is incorporated in a suitable carrier system. Pharmaceutically inert vehicles and/or excipients for the preparation of eye drops include, e.g., buffering agents such as boric acid or borates, pH adjusting agents to obtain optimal stability or solubility of the active drug substance, tonicity adjusting agents such as sodium chloride or borates, viscosity adjusting agents such as hydroxypropyl cellulose, methylcellulose, polyvinylpyrrolidone, polyvinyl alcohols or polyacrylamide, oily vehicle such as vehicles comprising arachis oil, castor oil and/or mineral oil. Emulsions and suspensions of the active drug substance may also be presented in form of eye drops. In these cases, the composition may furthermore comprise stabilizing, dispersing, wetting, emulsifying and/or suspending agents. Eye lotions and eye ointments may comprise pharmaceutically acceptable carriers and/or excipients such as those used in an eye drop composition or in other relevant topical composition such as, e.g., ointments, creams and lotions.

In general, an aqueous eye drop composition may be prepared by dissolving the active drug substance (or preferably a water-soluble salt or prodrug thereof) in sterile water in a specific concentration, optionally adjusting pH to a suitable pH by adding an appropriate amount of an appropriate buffer solution or hydrochloric acid or sodium hydroxide optionally adding a preservative such as phenethanol, optionally adding a viscosity increasing agent such as methylcellulose, and subject the resulting solution to filtration followed by sterilization e.g. by autoclaving or by membrane filtration.

The formulation and preparation of the above-mentioned compositions are well-known to those skilled in the art of pharmaceutical formulation. Specific formulations can be found in "Remington's Pharmaceutical Sciences".

Addition to animal feed and fish water

As mentioned above, the aromatic compounds defined above, such as the bis-aromatic α,β-unsaturated ketones or derivatives thereof, may be most valuable for controlling parasites in e.g. cattle, birds and fish. This may be carried out, e.g. by adding the compound in question to the feed or the drinking water of the animals, or when the animals to be treated are fish, the compound in question may also be added to the fish water.

Dosages

The dosage of an appropriate compound as defined herein or derivative thereof depends on the administration method, the disease to be treated and the severity of same, and whether the disease is to be treated or prevented, as well as the age and weight of the person or animal to be treated.

The bis-aromatic α,β-ketones are preferably administered in an amount of about 0.1–30 mg per kg body weight per day, such as about 0.5–15 mg per kg body weight per day. As mentioned above, the compound in question may be administered orally in the form of tablets, capsules, elixirs or syrups, or rectally in the form of suppositories. Parenteral administration of the aromatic compound defined above, such as the bis-aromatic α,β-unsaturated ketone, is suitably performed in the form of saline solutions of the ketones (or salts thereof) or with the compound incorporated into liposomes. In cases where the compound in itself is not sufficiently soluble to be dissolved, an acid addition salt of a basic compound of the formula I (that is, a compound of the formula I in which either an aromatic ring or a substituent contains a basic nitrogen atom) can be used, or a solubilizer such as ethanol can be applied.

Acid addition salts of basic compounds of the formula II, such as compounds containing basic substituents, e.g. dimethylamino, on the aromatic ring, or compounds containing an aromatic ring with basic properties, such as pyridine, are also interesting compounds and may be of special value in cases where a water-soluble compound is preferred, e.g. as sprays in transmission control, or in solutions for injection. The acid addition salts, may, e.g. be hydrochlorides, oxalates, malonates, fumarates citrates, acetates, propionates, formates, sulphates. The acid addition salts may be easily prepared from the corresponding basic compounds by addition of the appropriate acid.

Oral administration

For compositions adapted for oral administration for systemic use, the dosage is normally 1 mg to 1 g per dose administered 1–4 times daily for 1 week to 12 months depending on the disease to be treated.

The dosage for oral administration for the treatment of parasitic diseases is normally 1 mg to 1 g per dose administered 1–2 times daily for 1–4 weeks, in particular the treatment of malaria is to be continued for 1–2 weeks whereas the treatment of leishmaniasis will normally be carried out for 3–4 weeks.

The dosage for oral administration for the treatment of bacterial diseases is normally 1 mg to 1 g per dose administered 1–4 times daily for 1 week to 12 months; in particular, the treatment of tuberculosis will normally be carried out for 6–12 months.

The dosage for oral administration of the composition in order to prevent diseases, in particular, parasitic diseases, is normally 1 mg to 75 mg per kg body weight per day. The dosage may be administered once or twice daily for a period starting 1 week before the exposure to the disease until 4 weeks after the exposure.

Rectal administration

For compositions adapted for rectal use for preventing diseases, a somewhat higher amount of aromatic compounds, such as bis-aromatic α,β-unsaturated ketones or derivatives thereof is usually preferred, i.e. from approximately 1 mg to 100 mg per kg body weight per day.

Parenteral administration

For parenteral administration a dose of about 0.1 mg to about 50 mg per kg body weight per day is convenient.

For intravenous administration a dose of about 0.1 mg to about 20 mg per kg body weight per day administered for 1 day to 3 months is convenient.

For intraarticular administration a dose of about 0.1 mg to about 20 mg per kg body weight per day is usually preferable.

For parenteral administration in general, a solution in an aqueous medium of 0.5–2% or more of the active ingredients may be employed.

Percutaneous administration

For topical administration on the skin a dose of about 1 mg to about 5 g administered 1–10 times daily for 1 week to 12 months is usually preferable.

Transmission control

As mentioned above, the use of the aromatic compounds defined above, such as the bis-aromatic α,β-unsaturated ketones, or derivatives thereof in controlling parasites in their vectors is an interesting and promising aspect of the present invention. The principle is to destroy the parasites in their vectors, thereby preventing transmission of the disease.

The data presented herein demonstrate clearly that the promastigote stage, the same form of the parasite which is present in the sandfly vector, of the *L. major* and *L. donovani* parasite, is killed by the bis-aromatic α,β-unsaturated ketones or derivatives thereof.

For example, spraying endemic areas for malaria or leishmania or other protozoal diseases transmitted by their respective vectors will be of an attractive means of controlling such important parasitic diseases.

For the compounds mentioned above containing a double bond, the corresponding compounds in which the bond is a triple bond such as discussed in connection with the general formula I are also very interesting and should be considered correspondingly disclosed herein in connection with each and every structural formula shown herein and each and every compound named herein.

In many cases, it will be preferred to administer the compound defined herein together with another antiparasitic, antimycotic or antibiotic drug, thereby reducing the risk of development of resistance against the conventional drugs, and reducing the amount of each of the drugs to be administered, thus reducing the risk of side effects caused by the conventional drugs. Important aspects of this is the use of the compound against Leishmania, where the compound I is combined with another antileishmanial drug, or the antimalarial use of the compound I where the compound I is used together with another antimalarial drug.

As examples of other antileishmanial drugs to be combined with the compounds defined herein may be mentioned pentavalent antimonv-sodium gluconate and allopurinol.

As examples of other antimalarial drugs to be combined with the compounds defined herein may be mentioned chloroquine and derivatives thereof, quinine, proguanil, cycloguanil, mefloquine, pyrimethamine and artemisinin.

As an example of an additional antibiotic drug to be combined with the compounds defined herein may be mentioned an antituberculous drug such as isoniazide, ethambutol, pyrazinamide, and rifampicin.

As examples of additional antimycotic drugs to be combined with the compounds defined herein may be mentioned amphotericin B, muconarcidol, griseofulvin, and miconazol.

As examples of additional antibabesial drugs to be combined with the compounds defined herein may be mentioned quinuronium sulfate, pentamidine isethionate, imidocarb or diminazene.

As examples of additional anticoccidial drugs to be combined with the compounds defined herein may be mentioned fulfonamides, amprocid and coccidiostatic agents such as inomycins, in particular monensin and salinomycin.

As examples of additional drugs against fish parasites to be combined with the compounds defined herein may be mentioned benzimidazol and formaldehyde.

One general advantage of the compounds defined herein are their broad-spectered character, which makes it possible to use the compounds as sole medication in cases where the host to be treated is infected with, or suspected to be infected with, more than one of the bacteria and parasites discussed herein, or to use them as supplements to known antibacterial agents and antiparasitic agents in order to reduce the dose of the conventional antibiotics or antiparasitic agents, thus reducing the risk of side effects, in addition to the above-mentioned advantages with respect to reduction of drug resistance development.

In particular for prophylaxis, the broad-spectered character of the compounds of the general formula I is of great advantage, and may be further augmented by combination with more than one antibacterial or antiparasitic agent, such as combination with both another antileishmanial agent and another antimalarial agent. It is justified to presume that also the other aromatic compounds defined herein will show the same valuable broad-spectered character.

While the above-mentioned compounds of the general formula I are predominantly compounds in which W is —CR═CR—, it should be borne in mind that compounds which correspond to each of the compounds mentioned above, but in which W is —C≡C—, are also important compounds according to the invention.

As mentioned above, a number of the compounds of the general formula I are known, whereas many of the compounds of the general formula I are novel compounds. The known compounds may be isolated or synthesized in accordance with methods known from the literature or methods analogous thereto. The novel compounds may, likewise, be produced by methods known per se or methods which are analogous to such methods. A number of preferred and interesting methods for preparing the compounds of the general formula I are discussed in the following:

In a process a), compounds of the formula I in which W is —CH═CH— are prepared by reacting a ketone of the general formula I'

$$X—Ar^1—CO—CH_3 \qquad I'$$

with an aldehyde of the general formula I"

$$HCO—Ar^2—Y \qquad I''$$

This reaction, which is a condensation reaction, is suitably carried out under acid or base catalyzed conditions. A review of such processes may be found in Nielsen, A. T., Houlihahn, W. J., *Org. React.* 16,1968, p 1–444. In particular the method described by Wattanasin, S. and Murphy, S., Synthesis (1980) 647 has been found to be very successful.

The reaction may suitably be carried out in protic organic solvents, such as lower alcohols (e.g. methanol, ethanol, or tert.butanol), or lower carboxylic acids (formic, glacial acetic, or propionic acid), or in aprotic organic solvents such as ethers (e.g. tetrahydrofuran, dioxan, or diethyl ether), liquid amides (e.g. dimethylformamide or hexamethylphosphordiamide), dimethylsulfoxide, or hydrocarbons (e.g. toluene or benzene), or mixtures of such solvents.

When carrying out the reaction under base catalyzed conditions, the catalyst may be selected from sodium, lithium, potassium, barium, calcium, magnesium, aluminum, ammonium, or quaternary ammonium hydroxides, lower alkoxides (e.g. methoxides. ethoxides, tert.butoxides), carbonates, borates, oxides, hydrides, or amides of lower secondary amines (e.g. diisopropyl amides or methylphenyl amides). Primary aromatic arnines such as aniline, free secondary amines such as dimethyl amine, diethyl amine, piperidine, or pyrrolidine as well as basic ion exchange resins may also be used.

Acid catalysts may be selected from hydrogen chloride, hydrogen bromide, hydrogen iodide, sulfuric acid, sulfonic acids (such as paratoluenesulfonic or methanesulfonic acid), lower carboxylic acids (such as formic, acetic or propionic acid), lower halogenated carboxylic acids (such as trifluoroacetic acid), Lewis acids (such as $BP_3$, $POCl_3$, $PCl_5$, or $FeCl_3$), or acid ion exchange resins.

The reaction may be carried out at temperatures in the range of 0–100° C., typically at room temperature. Reaction times may be from 30 min to 24 hours.

In another process b), compounds of the formula I in which W is —C≡C— may be prepared by reacting an activated derivative of a carboxylic acid of the general formula $$X—Ar^1—COOH$$

wherein X and $Ar^1$ are as defined above, with an ethyne derivative of the formula II"

$$H-C≡C—Ar^2-Y \qquad II''$$

wherein $Ar^2$ and Y are as defined above. Reactions of this type are described by Tohda, Y., Sonogashihara, K., Haghara, N., *Synthesis* 1977, p777–778. It is contemplated that the activated derivative of the carboxylic acid IV may be an activated ester, an anhydride or, preferably, an acid halogenide, in particular the acid chloride. The reaction is normally carried out using the catalysts described by Tohda, Y. et al. cited above, namely copper(I)iodide/triphenylphosphine-palladium dichloride.

The reaction is suitably carried out in triethylamine, a mixture of triethylamine and pyridine or triethylamine and toluene under a dry inert atmosphere such as nitrogen or argon.

The reaction is generally carried out at reduced temperature such as in the range from −80° C. to room temperature, the reaction time typically being from 30 minutes to 6 hours.

In the above reactions, it may be preferred or necessary to protect various sensitive or reactive groups present in the starting compounds of formulas II, III, IV, or V so as to prevent said groups from interfering with the reactions. Such protection may be carried out in a well-known manner, e.g. as described in "Protective Groups in Organic Chemnistry" by Theodora Green. For example, in the reaction between the acid derivative IV and the acetylene derivative V, a hydroxy group on $Ar^1$ and/or $Ar^2$ may be protected in the form of the methoxymethyl ether, N,N-dimethylcarbamoyl ester, or allyl ether. The protecting group may be removed after the reaction in a manner known per se.

An alternative route for the preparation of the compounds of the general formula I goes via the 1,3-dipolar cycloaddition mechanism (Torssell, K. B. G., Nitrile oxides, Nitrones and nitronates in organic synthesis. Novel Strategies in Synthesis. VHC Verlagsgesellschaft, Weinheim 1988) known as the isoxazoline route.

Thus, by reaction of an aldehyde of the general formula A $X—Ar^1—CHOtm$ A wherein X and $Ar^1$ are as defined above, with hydroxylamnine (e.g. hydroxylamninehydrochloride) using water as a solvent, the corresponding oxime of the general formula B $X—Ar^1—CH{=}N—OH$ B is formed, and a chlorinating agent (e.g. NCS or t-butylhypochlorite) is added to chlorinate the oxime, which in contact with alkenes of the general formula C $CHR{=}CR—Ar^2—Y$ C in which $Ar^2$, Y and R are as defined above, will form the corresponding isoxazoline of the formula D

D

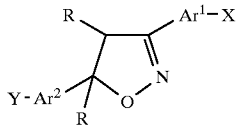

The chlorination and the formation of the isoxazoline ring can be performed by a one-pot method. Solvents like methylenechloride, chloroform are most commonoly used. By reducing the formed isoxazoline in an aqueous medium, the reduced product will be hydrolyzed to a β-hydroxyketone of the general formula E, $X—Ar^1—CO—CRH—C(OH)R—Ar^2—Y$ E wherein $Ar^1$, $Ar^2$, X and Y are as defined above. This reduction, including the hydrolysis, is a very efficient synthetic tool, and gives products in almost 100% yield. The reduction can be carried out by the use of Ra—Ni together with catalytic amounts of acid or by electrochemical reduction. Optionally, the hydroxy group is substituted with another leaving group such as halide, alkoxy, tosyloxy, or trifluoromethanesulfonoxy, such other leaving group being introduced in a manner known per se. When the hydroxy group is not substituted with such other leaving group, this β-hydroxy-ketone (E) is treated with acid (e.g. paratoluenesulfonic acid or a mixture of acetic acid and sodium acetate), whereby water is eliminated, giving the chalcone structure of the general formula (I).

Correspondingly, compounds in which W is —C≡C— can be made via a route where the oxime of the above general formula B is reacted with a halogenating agent and an acetylene of the general formula C1

$CH{\equiv}C—Ar^2—Y$ C1 wherein $Ar^2$ is as defined above, is added to form the corresponding isoxazole of the formula D1

D1

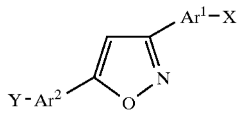

wherein $Ar^1$, $Ar^2$, X and Y are as defined above, which is then reduced, and the reduction product is hydrolysed to form a β-hydroxyketone of the general formula E1

$X—Ar^1—CO—CH{=}C(OH)—Ar^2—Y$ E1 wherein $Ar^1$, $Ar^2$, X and Y are as defined above, and optionally substituting the hydroxy group with another leaving group such as halide, alkoxy, tosyloxy, or trifluoromethanesulfonoxy, such other leaving group being introduced in a manner known per se. By elimination of the leaving group, the compound of the general formula I, wherein W is —C≡C—, is obtained.

Another route for the preparation of the compounds of the general formula I Is the Wittig reaction in which an aldehyde of the general formula F $Y—Ar^2—CHO$ F wherein $Ar^2$ and Y are as defined above, is treated with a phosphorus ylide (also called a phosphorane) of the general formula G, $T_3—P{=}CH—CO—Ar^1.X$ G in which T can be aliphatic, alicyclic or aromatic, to give the chalcone structure of the general formula (I). The Wittig reaction is known as an exceedingly useful method for the synthesis of alkenes.

The aldehyde may be aliphatic, alicyclic or aromatic; it may contain double or triple bonds; it may contain various functional groups, such as OH, OR, $NR_2$, aromatic nitro or halo, acetal or even ester groups. Double or triple bonds conjugated with the carbonyl also do not interfere; the attack is directed towards the carbonyl carbon atom.

The reaction is suitably carried out in aprotic organic solvents such as ethers (e.g. tetrahydrofuran, dioxan, or diethyl ether) or DMSO or mixtures of these.

The reaction is normally carried out at temperatures in the range of 0–25° C., but can also be carried out at even lower temperatures.

Phosphoranes of the general formula $Me_nPH_{(3-n)}P{=}CHCOPh$ (Ph=phenyl or substituted phenyl, n=0,1,2,3) are reported to react with benzaldehyde to give chalcone in good yield (70–90%). According to DE 1.256.642 (1967), the Wittig reaction is used for the preparation of chalcone in 84% yield (Bestmann, H. J., and Kratzer, O.).

Another route for the preparation of compounds of the general formula I is by reacting benzaldehyde with N-α-styrylmorpholine (Birkofer, L., Kim, S. M., and Engels, H. D., Chem. Ber., 95, 1495 (1962)).

A styrene compound of the general formula H $X—Ar^1—CV═CH_2$ H in which V represents a secondary amino group, is reacted with an aldehyde of the general formula J $Y—Ar^2—CHO$ J to form an intermediate which after hydrolysis and elimination of the secondary amino group gives a compound of the structure K

K

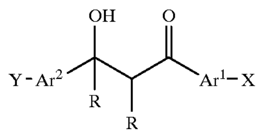

wherein X, Y, $Ar^1$, $Ar^2$ and R are as defined above. In the compound K, the hydroxy group may, if desired, be substituted with another leaving group such as alkoxy, tosyloxy, trifluoromethanesulfonoxy or acyloxy in a manner known per se. After elimination of HOH or HOTt, wherein Tt is such other leaving group, the chalcone structure of the general structure (I) is obtained.

The usefulness of enamines as intermediates lies in the fact that the β-carbon of the double bond of the enamine has nucleophilic character. This will make the reaction between the enamine and the aldehyde possible.

Another route for the synthesis of compounds of the general formula I is by reacting derivatives of cinnamic acid which is based on the fact that cinnamic acid can react with aromatic compounds (e.g. phenols and benzene).

Cinnamic acids of the general formula L $Y—Ar^2—H═CH—COQ$ L in which Q is either a hydroxy group, a carboxylate or a halogen, are condensed with aromates of the general formula M $X—Ar^1$ M to give α,β-unsaturated ketones of the general formula (I).

The reaction is best carried out in the presence of $BF_3$ (Starkov, S. P., Starkova, S. P., and Goncharenko, G. A., Izv. Vyssh. Ucheb. Zaved., Khim. Khim. Tekhnol., 20, 1149 (1977); Chem. Abstr., 88, 22272j (1978)) or polyphosphoric acid (Reichel, L., and Proksch, G., Justus Liebigs Ann. Chem., 745, 59 (1971)). With the former agent, a high preference for para-acylation is observed.

The reaction is preferably carried out in the presence of $AlCl_3$ as a catalyst (Rasschaert, A., Janssens, W., and Slootmaekers, P. J., Bull. Soc. Chim. Belges., 75, 449 (1966); Chem. Abstr., 66,2305e (1967)).

The two latter methods are examples of the Friedel-Craft acylation. Among the reagents (compounds L) used are not only acyl halides or the acids, but also anhydrides.

The reaction can be carried out with only very small amounts of catalyst, often just a trace and sometimes without any catalyst at all. Ferric chloride, iodine, zinc chloride, and iron are the most common catalysts used. Proton acids can be used as catalyst when the reagent (compound L) is in its acid form.

In order to prevent acylation of the solvent used, the reaction is often carried out in a non-aromatic fully saturated solvent or in an aromatic solvent with deactivating groups, which prevents acylation, such as, for example, nitrobenzene.

The reaction is carried out at wide varying temperatures depending on the nature of the reacting compounds.

The prodrugs of the general formula I can be made directly by processes as described below, the desired prodrug groups being in place in the relevant reagents in question, or free AZ groups in which Z is hydrogen, in particular hydroxy groups, can be converted to the corresponding groups in which Z is one of the groups (A) to (E) as defined above.

(Acyloxy)alkyl-α-ethers such as those of the general formulas (IIDa, IIEa, IIEb, I'Db, I'Eb, IIIDa, IIIEa) can be prepared by reacting the corresponding phenols of the general formulas (IIa, IIb, IIIa) with the appropriate (acyloxy)alkyl-α-halide. slettes?

The reaction is most often carried out using acetone or butanone as solvents.

A weak base like potassium carbonate may be added as an acid scavenger.

In the case of pivaloyloxymethyl-α-halides, the halogen should be iodine in order to avoid formation of pivalic esters of phenol (Sloan, K. B., and Koch, S. A. M., J. Org. Chem. 48 (1983) 3777–3783.)

Carboxylic esters of the phenols of the general formula I (I'Ab, IIAa, IIIAa) may be prepared by reacting the corresponding phenols (e.g. IIa, IIb, IIIa) with an activated ester (including the α-halomethylesters), an anhydride or, preferably, an acid halogenide, in particular the acid chloride.

The reaction is performed in an aprotic organic solvent such as lower aliphatic ketones like acetone, butanone, aliphatic ethers like tetrahydrofuran, diethylether, or dioxane or a liquid amine like pyridine.

The reaction is carried out in the presence of an acid scavenger such as potassium or sodium carbonate, an tertiary aliphatic amine such as triethylamine, or pyridine.

An especially spectacular modification of the method involves the reaction of the phenol with the appropriate anhydride using 4-dimethylaminopyridine or 4-(1-pyrrolidino)pyridine as catalyst. With these reaction conditions, the reaction gives a very high yield.

N,N-Dimethylcarbamic esters of the phenols of the general formula I (I'Bb, IIIBa) may be prepared by reacting the corresponding phenols of the general formula I (IIa, IIb) with an activated derivative of N,N-dimethylcarbamic acid such as an activated ester or, preferably, an acid halide, in particular the acid chloride.

The reaction is carried out in an aprotic organic solvent such as lower aliphatic ketones like acetone, butanone, aliphatic ethers such as tetrahydrofuran, diethylether, or dioxane, or a liquid amine such as pyridine, or a liquid nitrile such as acetonitrile.

In general, the reaction is carried out in the presence of an acid scavenger such as potassium or sodium carbonate, a tertiary aliphatic amine such as triethylamine or pyridine Alternatively, the N,N-dimethylcarbamoyl esters may be prepared by condensing the carbamoylated phenolic benzaldehydes or phenolic acetophenones with the appropriate acetophenones or benzaldehydes, respectively.

The alkoxymethoxy ethers of the general formula I (I'Cb, IICa, IICb, IIICa) are most conveniently prepared by condensing the appropriate ethers of the phenolic benzaldehydes or the phenolic acetophenones with the appropriate acetophenones or benzaldehydes, respectively.

They may, however, be prepared by reacting the phenolic chalcones with the appropriate alkyl-α-alkylhalomethyl halide.

The reaction may be carried out in an aprotic organic solvent like a lower aliphatic ketone, such as acetone or butanone, or an ether, such as tetrahydrofuran, dioxane or dioxolane or a liquid nitrile such as acetonitrile.

The reaction may be performrned in the presence of a acid scavenger such as an inorganic or organic base. The base may be potassium or sodium or quaternary ammonium carbonate, or hydroxide.

LEGENDS TO THE FIGURES

Figure 6:
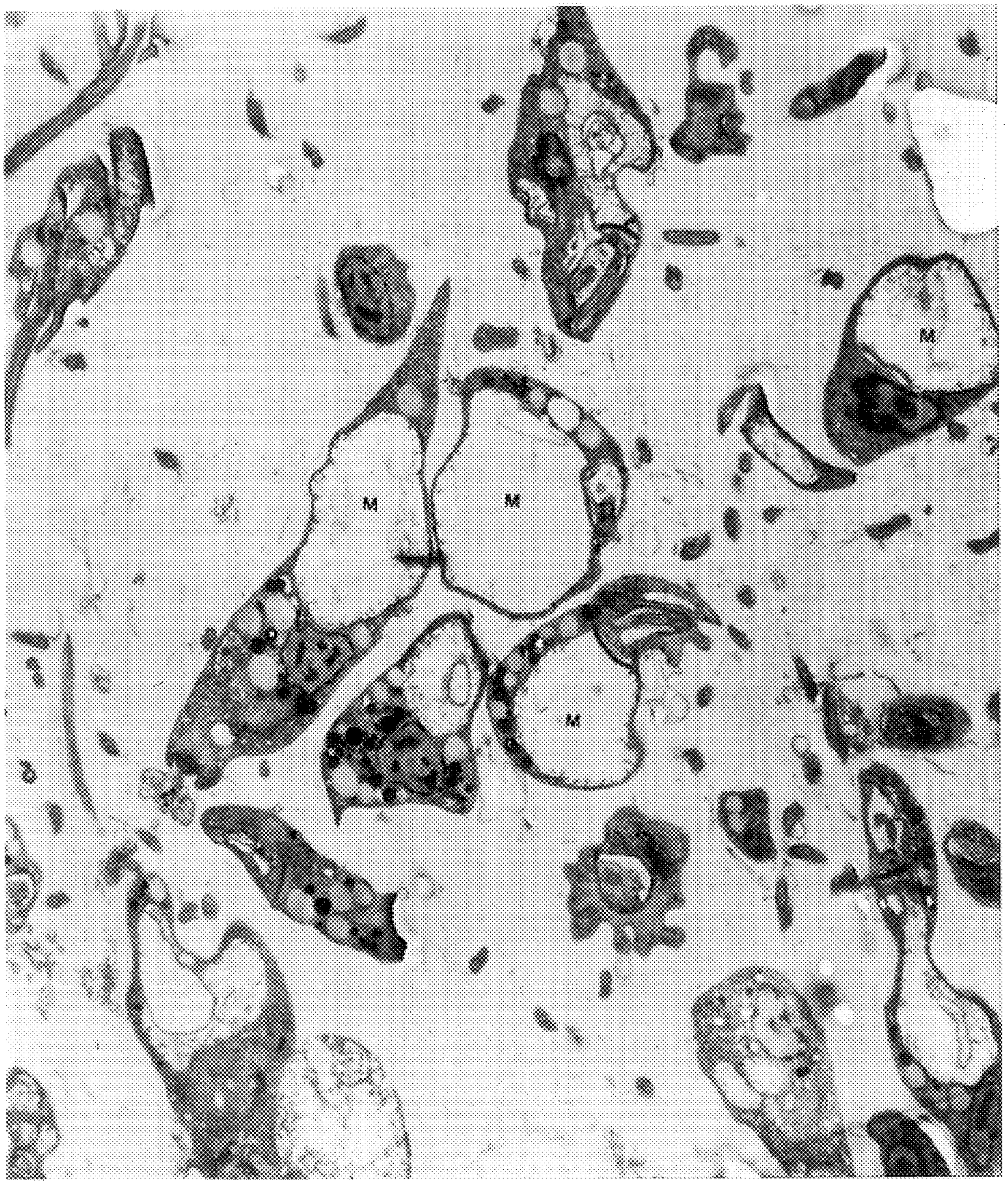

FIG. 6 is an electron rnicroscopic photo (magnification 10,000×9 showing *Leishmania major* promastigotes after incubation with 10 μg/ml of licochalcone A. From the photo it is seen that the mitochondria are swollen to an extent that made it difficult to recognize the structures as mitochondria, if not the characteristic cristae had been preserved. Mitochondria denoted "M".

Figure 7:
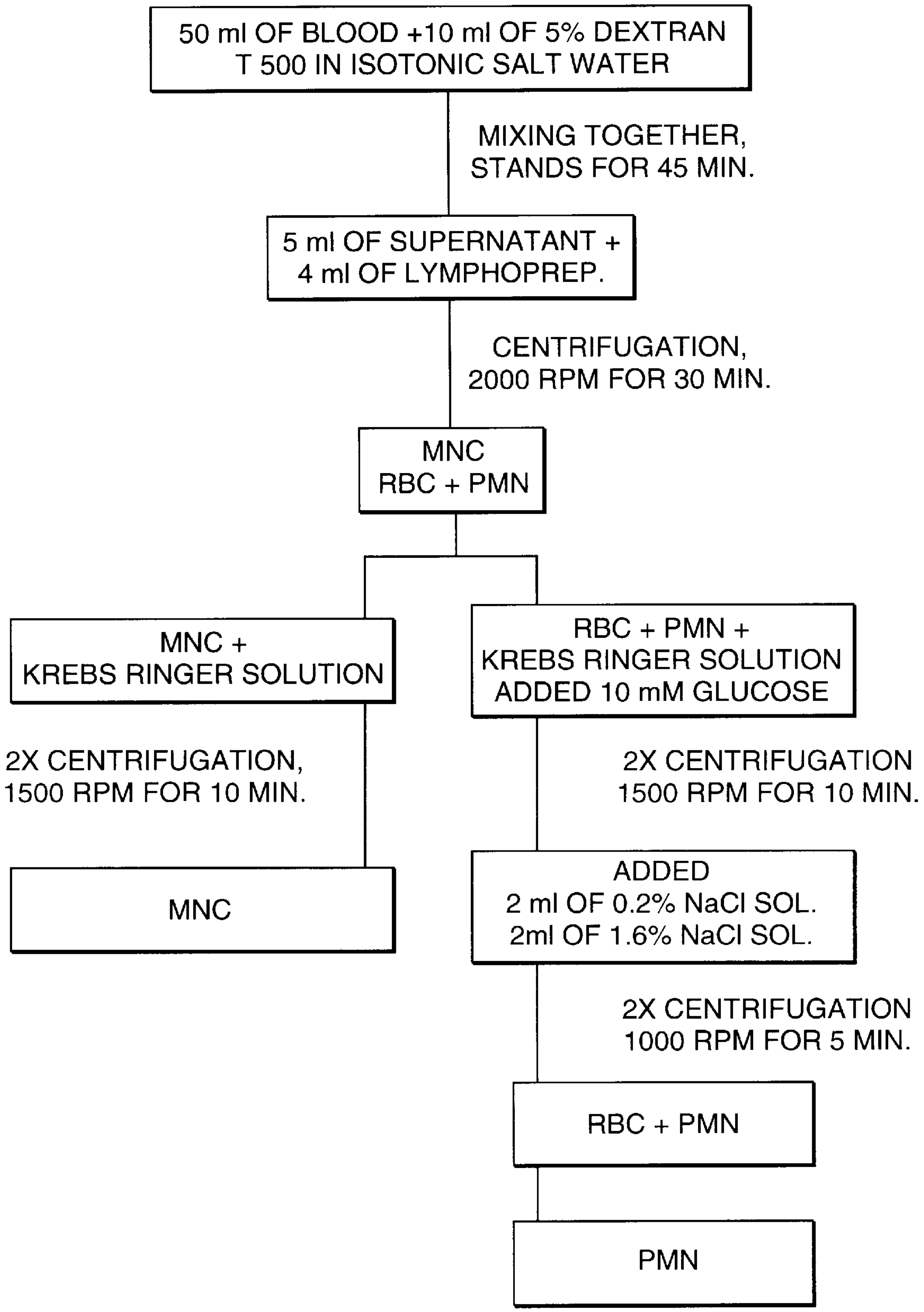

FIG. 7 is a flow sheet illustrating the isolation of various cell types from peripheral blood.

Figure 8:
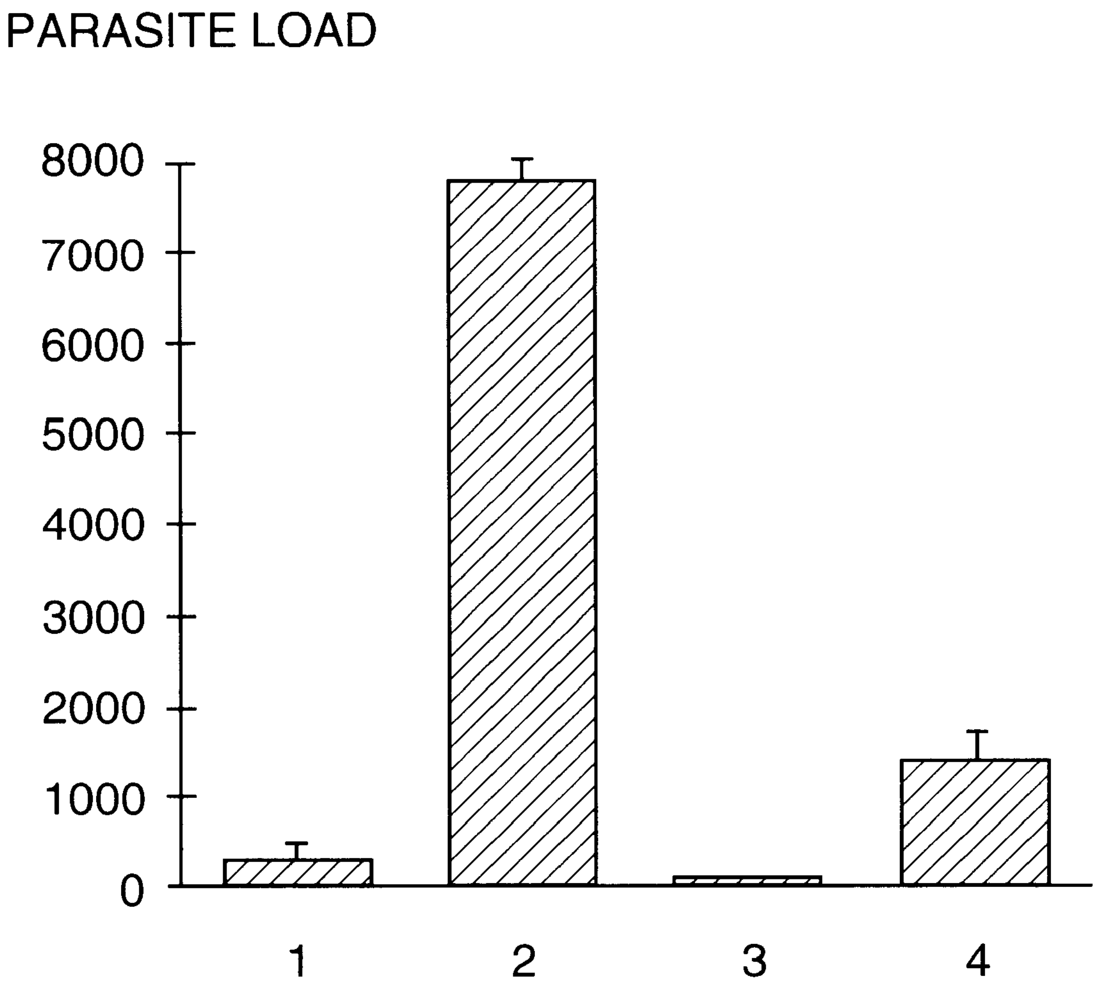

FIG. 8. Five Syrian golden male hamsters weighing 50–70 g which were infected with *L. donovani* by intracardial injection of $2\times10^7$ stationary phase promastigotes. One day later the animals were injected intraperitoneally with 10 mg/kg body weight licochalcone A (100 μl in saline) for 6 days. The animals were sacrificed on day 8 and parasite load in the spleen and liver was determined by determining the growth of promastigotes from the spleen and the liver using $^3$H-thymidine uptake by promastimes.

Figure 9A:
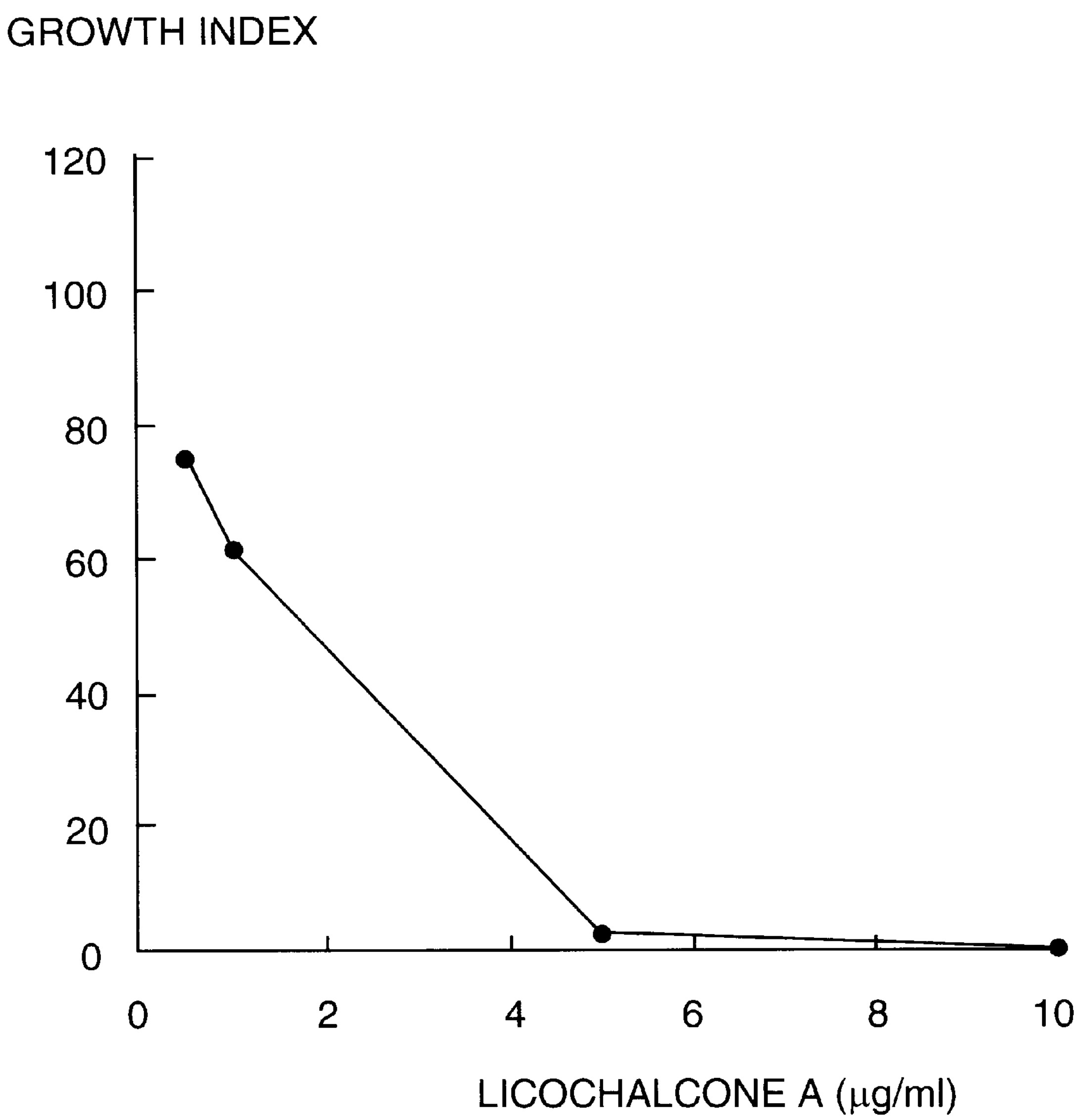
Figure 9B:
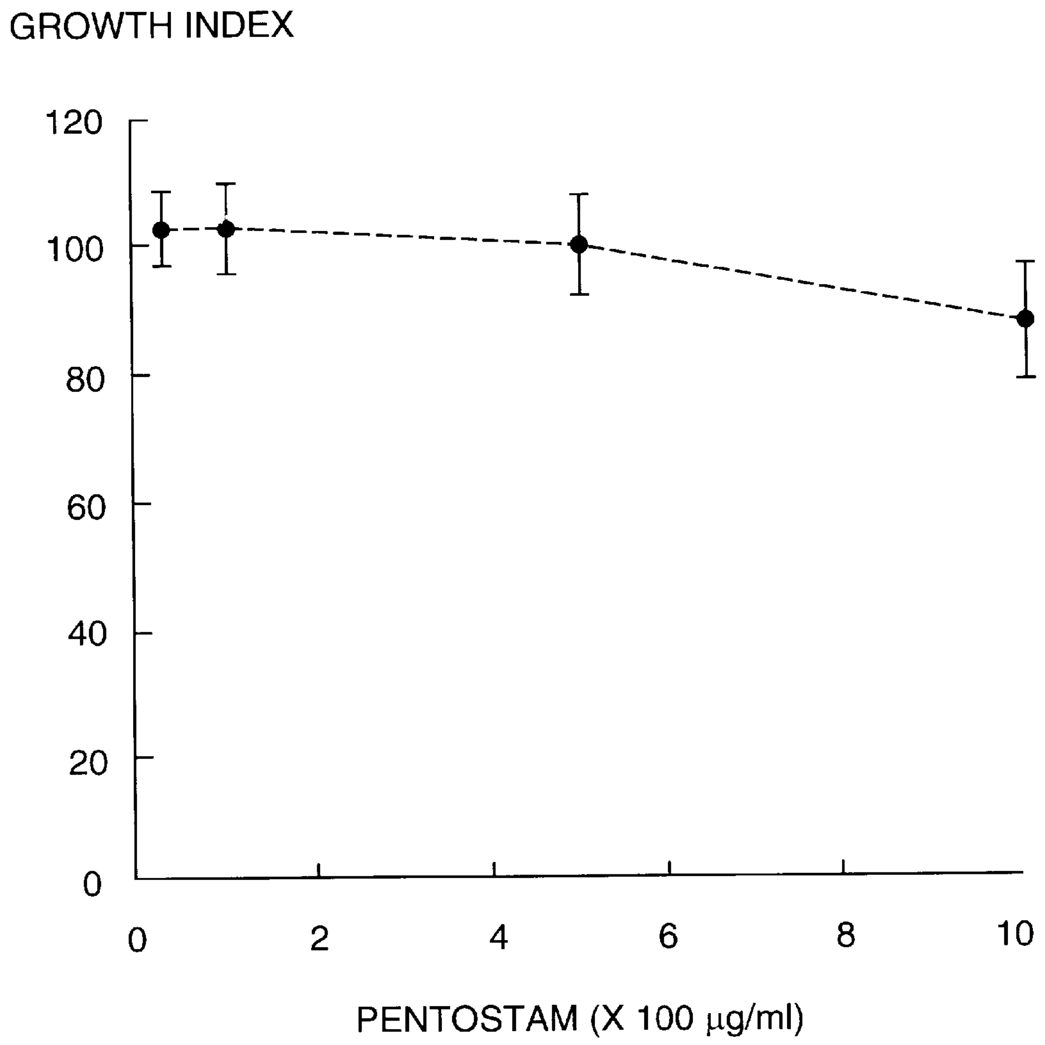
Figure 9C:
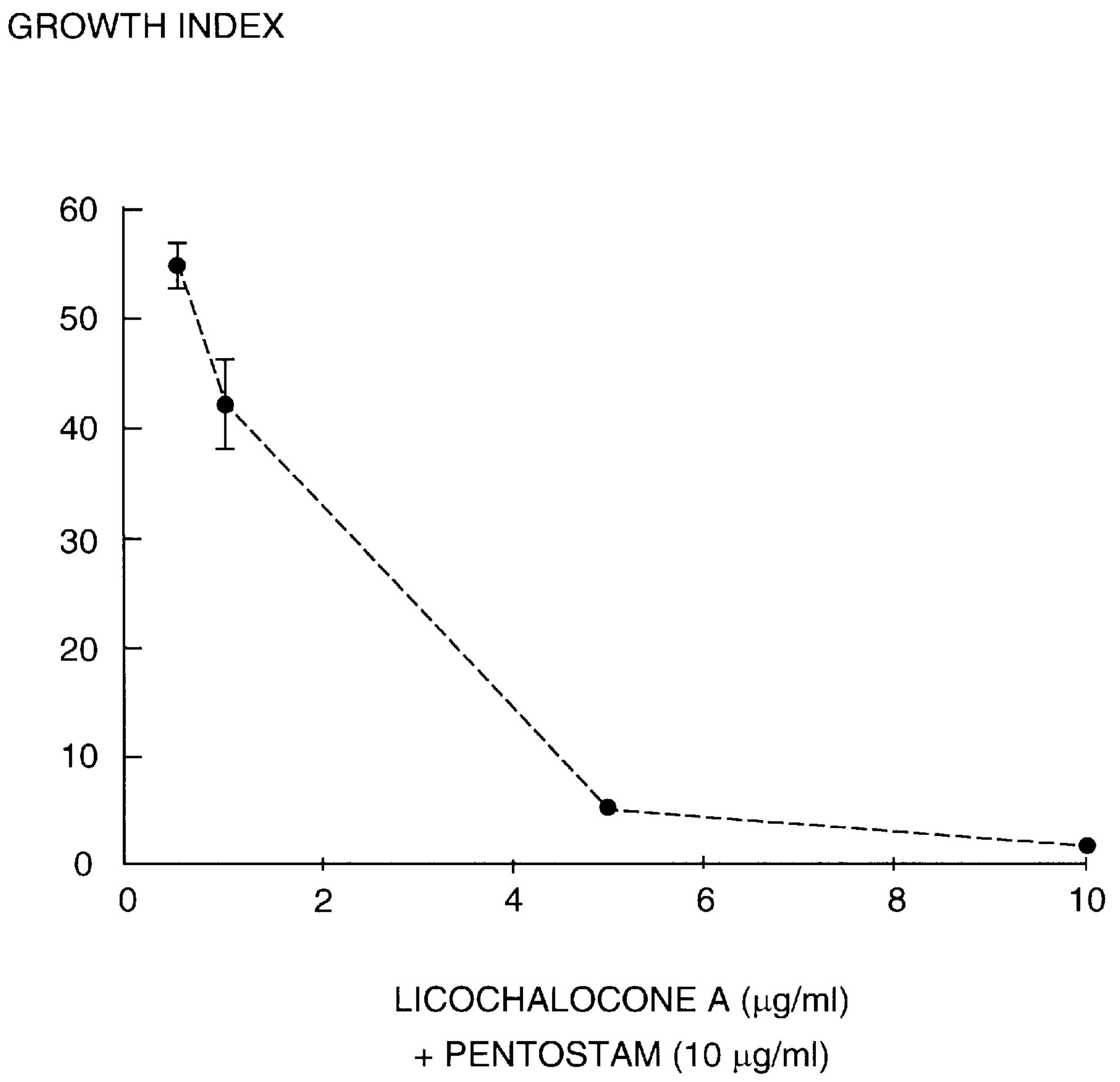

FIG. 9A–C show the effect of licochalcone A on the in Vitro growth of *L. major* WHO pentostam resistant strain promastigotes. $3\times10^6$ promastigotes were incubated in the presence of licochalcone A (μg/ml, FIG. 9A), pentostam (×100 μg/ml, FIG. 9B) and licochalcone A (μg/ml) plus pentostam (10 μg/ml) (FIG. 9C for 2 h followed by 18 h uptake of $^3$H-thymidine. The results are based on 5 experiments and are given as growth index (mean±SEM) as measured by $^3$H-thymidine uptake by promastigotes.

Figure 10A:
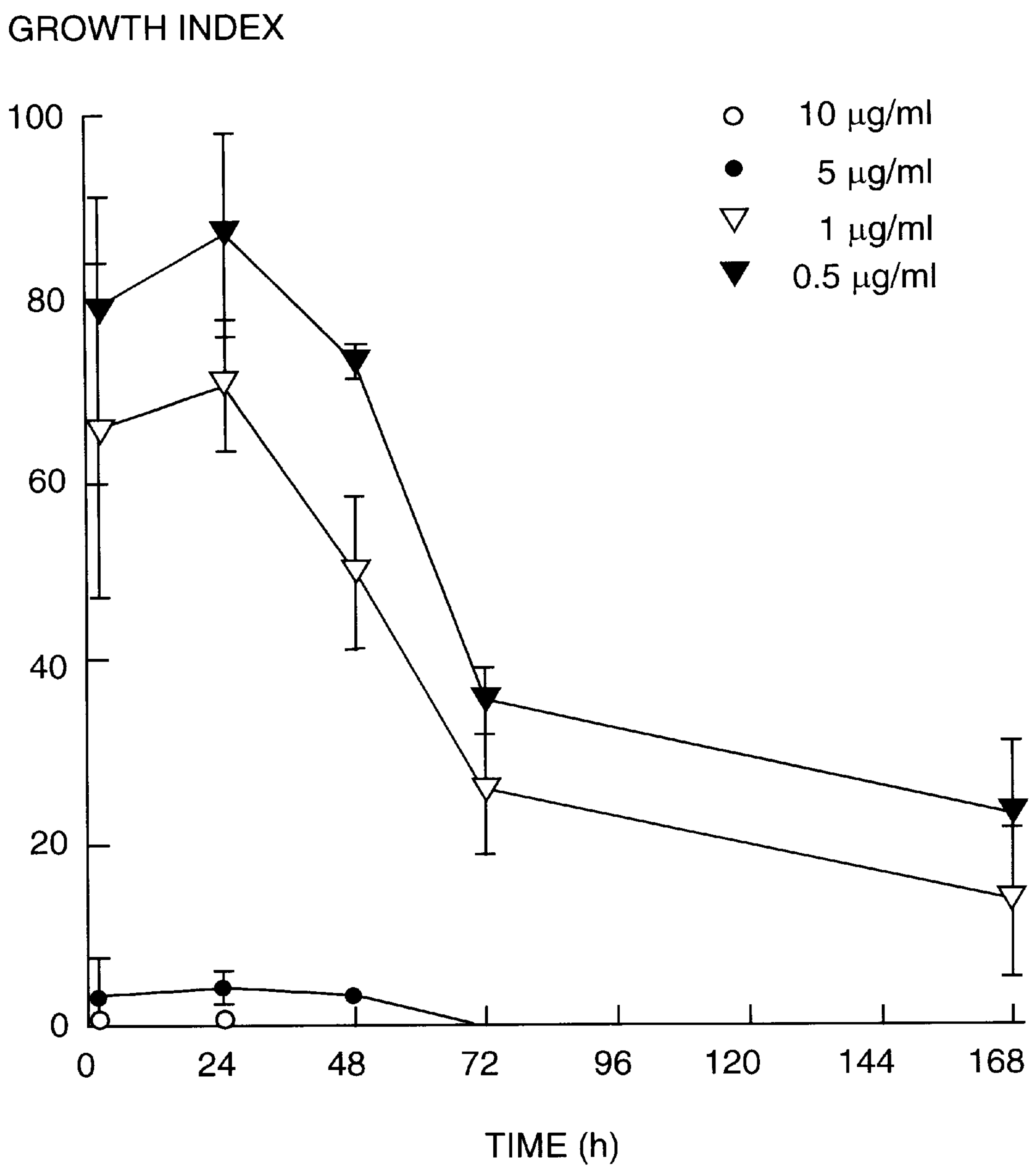
Figure 10B:
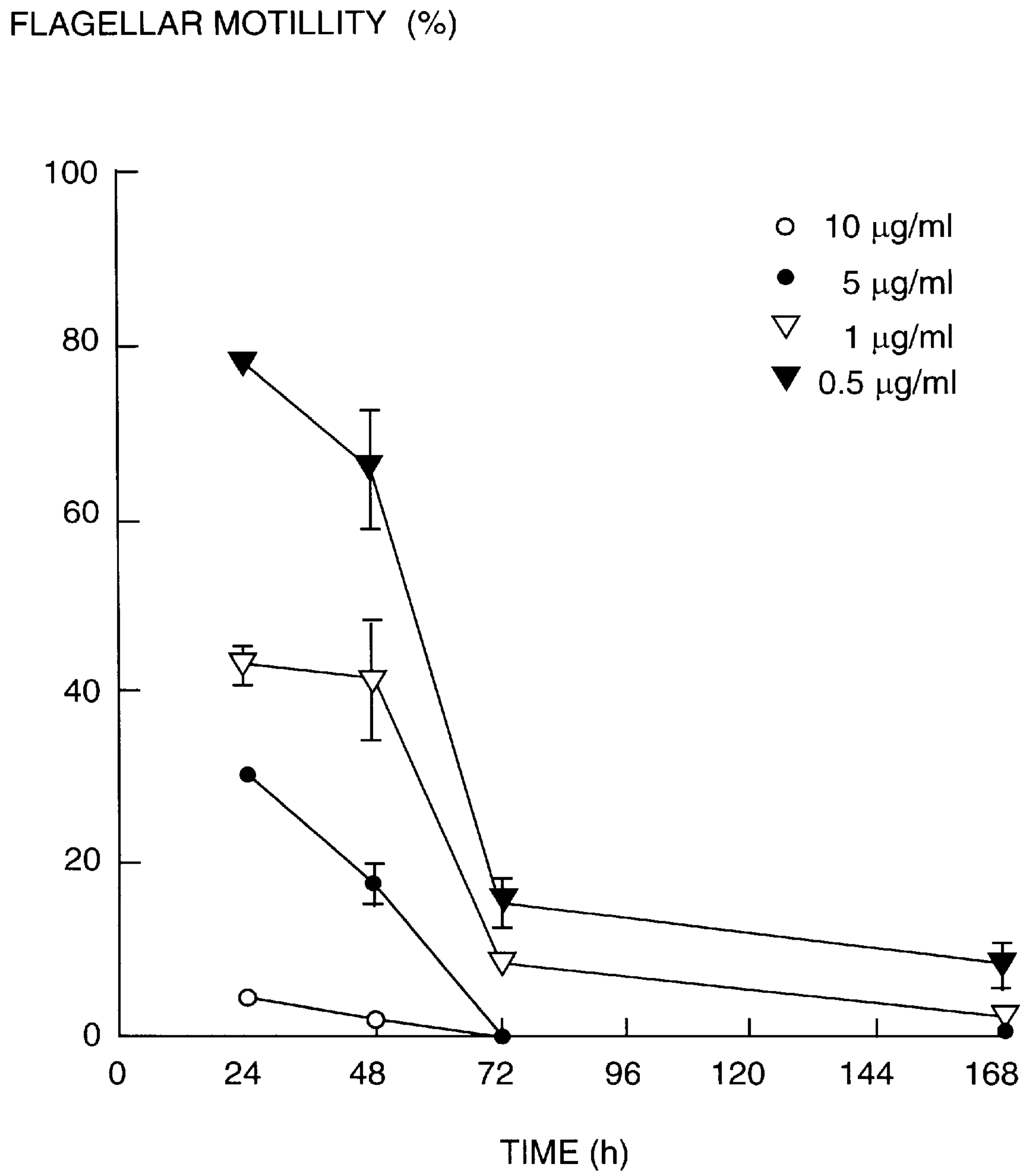

FIG. 10A–B show the effect of licochalcone A on the in vitro growth of *L. major* promastigotes from 4days cultures. The results are based on 5 experiments and are given as growth index (mean±SEM, FIG. 10A) as measured by $^3$H-thymidine uptake and flagellar motility (mean±SEM, FIG. 10B) of parasites as determined microscopically by counting 500 promastigotes.

Figure 11A:
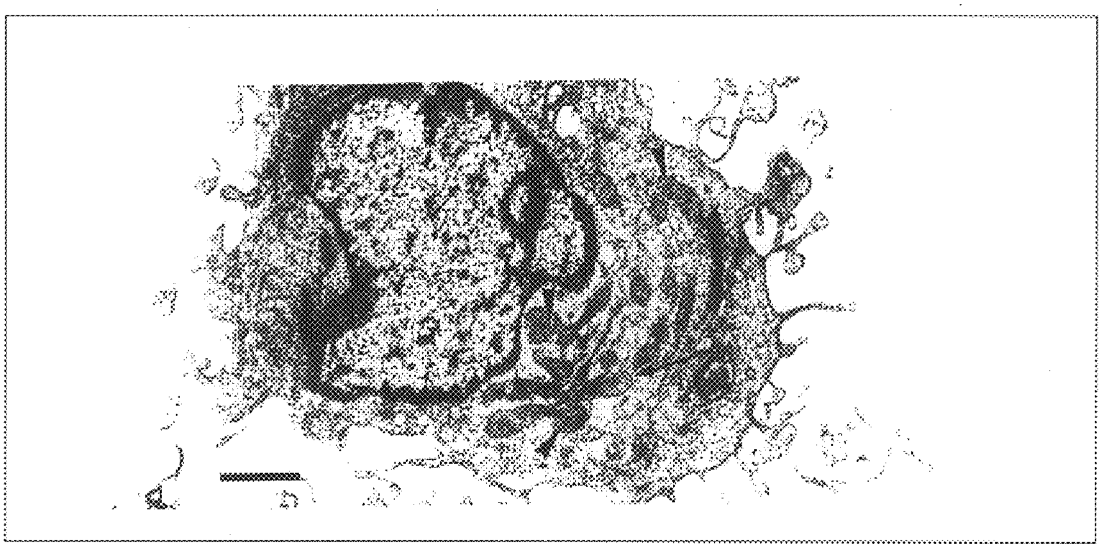
Figure 11B:
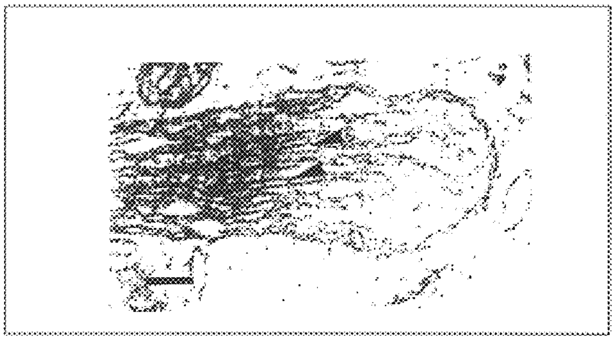
Figure 11C:
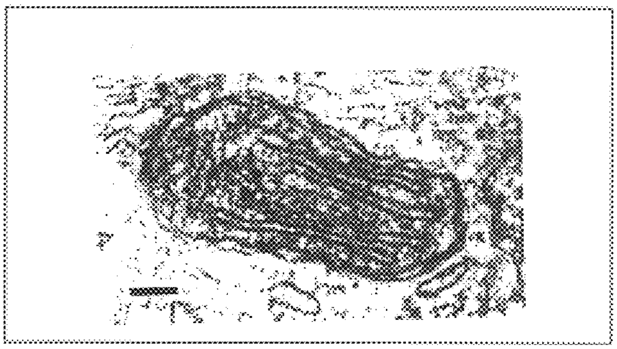

FIG. 11A–C show an electron micrograph of a human macrophage showing a macrophage incubated in the presence of 10 μg/ml licochalcone A for 24 h. The figure shows several mnitochondria (small arrows, A) and a higher magnification of one of the mitochondria (B). The ultrastructure of this mitochondrion shows longitudinally arranged cristae (small arrowheads) and general appearance similar to the mitochondrion from a macrophage grown in the presence of medium alone (C).

EXAMPLE 1

Isolation of bis-aromatic α,β-unsaturated ketone from Chinese licorice root of Glycyrrhiza species rich in licochalcone A (a batch of *G. uralensis* or *G. inflata*)by bioassay-guided fractionation 1) Isolation of licochalcone A

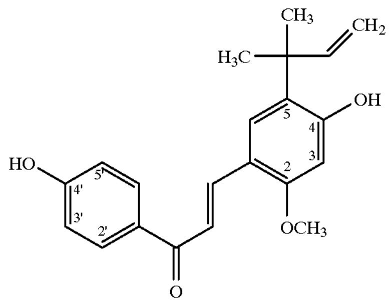

The test for parasitic activity referred to in this example was performed as the in vitro *L. major* growth test described in Example 4.

Comminuted dried roots of chinese licorice roots rich in licochalcone A (a batch of *G. uralensis* or *G. inflat*) (674 g) were extracted with ethanol (2 l) for 24 hours. The mixture was filtered and the filtrate concentrated in vacuo to give 64 g of a gum. The gum was partitioned between 0.5 l of water and 0.5 l of methylene chloride-methanol (1:1), and the two phases concentrated in vacuo. Only the residue from the organic phase showed a major activity against the parasite.

The residue from the organic phase was concentrated in vacuo and partitioned between methanol-water (9:1) (150 ml) and hexane (150 ml) and the two phases concentrated in vacuo. Only the residue from the methanolic phase showed a major activity against the parasite.

The residue from the methanolic phase was partitioned between methanol-water (3:2) (400 ml) and methylene chloride (400 ml) and the two phases concentrated in vacuo. The residues from both phases (a total of 27 g) showed activity against the parasite and were combined.

A sample of the residue from the methylene chloride phase (4 g) was chromatographed over silica gel 60 (Merck 0.063–0.200 mm, 400 g) using toluene-ethyl acetate (9:1, 300 ml), (4:1, 100 ml), (3:2, 100 ml), (1:4, 100 ml), and ethyl acetate to which increasing amounts of methanol were added as eluents.

The residue (1.5 g after concentration in vacuo) of the fractions which eluted while pure ethyl acetate was added as eluent showed the major activity. The residue was chromatographed over silica gel (150 g) using methylene chloride-ethyl acetate (14:1, 100 ml), (9:1, 100 ml), (4:1, 100 ml), (3:2, 100 ml), and (2:3, 100 ml) as eluents.

The residue (0.6 g of a gum after concentration in vacuo) of the fractions which eluted while methylene chloride-ethyl acetate (4:1) was added showed the major activity against the parasite. Licochalcone A (0.3 g) was obtained by crystallization of the residue from methanol-water, m.p. 101–102° C. (T. Saitoh, and S. Shibata in *Tetrahedron Lett.* 50 (1975), 4461: m.p. 101–102° C.).

Recrystallisation afforded a product, m.p. 136–138° C. (polymorphic) (X. Rhen-Seng, W. Kung-Ling, J. Shifa, W.

Chang-gen, J. Fu-Xiang, X. Xu-yan, and G. Yi-Sheng, in *Acta Chem. Sinica* 37 (1979), 289–297 ref. X. R. Sheng: m.p. 136–138° C.). The $^1$H NMR data agreed with those published for licochalcone A by T. Saitoh, and S. Shibata.

2) Isolation of 4,2',4'-trihydroxy-3,3'-di-(3-methylbut-2-enlchalcone

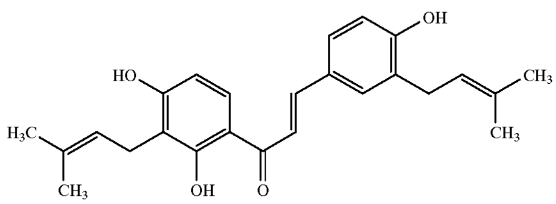

Comminuted dried roots of a sample of chinese licorice roots (1 kg) possessing only a low amount of licochalcone A (*G. uralensis*) were extracted with ethanol (5 l) for 19 h. The mixture was filtered and the filtrate concentrated in vacuo to give 76.5 g of a gum. The gum was partitioned between 500 ml of water and 250 ml of ether. The aqueous phase was extracted with an additional 450 ml of ether and the combined organic phases concentrated in vacuao to give 54 g of a gum. Only the residue from the organic phase showed a major activity against the parasite.

The residue from the organic phase was chromatographed over silica gel 60 (Merck 0.063–0.200 mm, 800 g) using tolueneethyl acetate (9:1, 0.25 1), (8:2, 1 l), (7:3, 1 l), (6:4, 1 l), (1:1, 1 l) and finally pure ethyl acetate (1 l) as eluents.

The residue (1.82 g of a yellow gum after concentration in vacuo) of the fractions which eluted while toluene-ethyl acetate (8:2) was added showed the major activity. The gum was chromatographed over silica gel 60 (Merck 0.063–0.200 mm, 200 g) using methylene chloride (1.5 l), methylene chloride-ethyl acetate (9:1, 1 l) and (8:2, 0.5 l) as eluents.

The residue (0.25 g of a yellow gum after concentration in vacuo) of the fractions which eluted while methylene chloride-ethyl acetate (9:1) was added showed the major activity. The gum was chromatographed over silica gel 60 (Merck 0.063–0.200 mm, 25 g) using petroleum ether-ethyl acetate (8:2, 250 ml), (7:3, 200 ml), and (1:1, 100 ml) as eluents.

The residue (42.4 mg of a yellow gum after concentration in vacuo) of the fractions which eluted while petroleum ether-ethyl acetate (1:1) was added showed the major activity. The gum was chromatographed by high performance liquid chromatography over LiChrosorp RP 18 (Knauer 16×250 mm, 10 $\mu$m) using acetonitrile-water (8:2, flow rate 9.9 ml/min) as an eluent. Two amorphous yellow compounds were obtained, in which no impurities could be observed by $^1$H NMR spectroscopy (200 MHz). The first compound was by $^1$H and $^{13}$C NMR, by UV spectroscopy, and by mass spectroscopy shown to be the not previously characterized (E)-1-(2,4-dihydroxy-3-(3-methyl-2-butenyl) phenyl-3-(2,2-dimethyl-8-hydroxy-2H-benzopyran-1-yl)-2-propen-1-one (A) and the second was by $^1$H and $^{13}$C NMR, by UV spectroscopy, and by mass spectroscopy shown to be identical with the 4,2',4'-trihydroxy-3,3'-di-(3-methylbut-2-enyl)chalcone described by K. Kyogoku, K. Matavama, S. Yokomori, R. Saziki, S. Nakame, N. Sasajima, J Sawada, M. Ohzeki and I. Tanaka in *Chem. Pharm. Bull.* 27 (1979), 2943. Only the latter compound showed major antiparasitic effects.

EXAMPLE 2

Synthesis of intermediates for use in the preparation of bis-aromatic α,β-unsaturated ketones 1) Preparation of 4-((3-methyl)but-2-enyloxy)-2-hydroxybenzaldehyde A solution of 6 g (0.11 mol) of potassium hydroxide, 22.7 g (0.1 mol) of benzyltriethylammonium chloride, and 14 g (0.1 mol) of 2,4-dihydroxybenzaldehyde was concentrated in vacuo. The residue was suspended in 100 ml of ethyl acetate and 11.7 ml (0.1 mol) of dimethylallyl bromide was slowlv added to the solution. The mixture was extracted with 100 ml of water, and the organic phase was dried and concentrated in vacuo to give 3.568 g of a residue, from which 4.738 g (20%) of 4-(3-methyl)-but-2-enyloxy-2-hydroxybenzaldehyde identical to that previously described by S. Khan, and M. Krishnamurti in *Indian J. Chem.* 22B (1983), 276 was purified by column chromatography over silica gel 60 (Merck 0.063–0.200 mm, 200 g) using petroleum ether-ethyl acetate (9:1) as an eluent.

2) Preparation of 4((3-methyl)but-2-enyloxy)-2-methoxybenzaldehyde 4 g (2 mmol) of 4-((3-methyl)but-2-enyloxy)-2-hydroxybenzaldehyde was added to a suspension of 11.4 g of potassium carbonate in 46 ml of acetone and the suspension was refluxed for 6 h. The suspension was filtered and the filtrate concentrated to give 4.701 g of an oil, from which 2.53 g (60%) of 4-((3-methyl)but-2-enyloxy)-2-methoxybenzaldehyde identical to that previously described by S. A. Khan, and M. Krishnamurti in *Indian J. Chem.* 22B (1983), 276–277 was isolated by column chromatography over silica gel 60 (Merck 0.063–0.200 mm, 100 g) using petroleum ether-ethyl acetate (9:1) as an eluent.

3) Preparation of 4-(N,N-dimethylcarbamoyloxy) acetophenone 1.35 ml (15 mmol) of dimethylcarbamoyl chloride and 1.36 g (10 mnnol) 4hydroxyacetophenone were added to a suspension of 5 g of potassium carbonate in 50 ml of acetone. The mixture was left for 2 h under stirring and filtered, and the filtrate was concentrated in vacuo to give a residue, from which 1.13 g (60%) of 4-(N,N-dimethylcarbamoyloxy)acetophenone was obtained by crystallization from methanol.

$^1$H NMR (200 MHz, $CD_3CN$, δ) 7.98 (AA'-part of an AA'MM'-system, H-2 and H-6), 7.21 (MM'-part of an AA'MM'-system, H-3 and H-5), 3.07 and 2.92 ($CH_3$—N), 2.56 ($CH_3$—C).

4) Preparation of 3-(2,4-dimethoxyphenyl)-1-(4-hydroxyhenyl)propan-1-on

A solution of 568 mg (2 mmol) of 2,4dimethoxy-4'-hydroxychalcone in ethanol (20 ml) was added 50 mg of platinum on charcoal (10%) and hydrogenated at 20 atm for 18 h. The colourless solution was filtered and concentrated in vacuo to give 606 mg, from which 143.7 mg (24%) of 3-(2,4-dimethoxyphenyl)-1-(4-hydroxyphenyl)propan-1-on was isolated by column chromatography over silica gel 60 (Merck 0.063–0.200 mm, 60 g) using petroleum ether-ethyl acetate (4:1, 500 ml, 3:1, 500 ml) as eluents, m.p. 126.4–127.4° C.

$^1$H NMR data (200 MHz, $CDCl_3$, δ) 7.91 (AA'-part of an AA'MM'-system, H-2' and H-6'), 7.07 (d, J 8 Hz, H-6), 6.88 (MM'-part of an AA'MM'-system, H-3' and H-5'), 6.43 (d, J 3 Hz, H-3), 6.40 (dd, J 8 and 3 Hz, H-5) 3.83 and 3.78 (s, $CH_3O$), 3.17 (perturbed t, H-2). 2.96 (perturbed t, H-3). Calc. for $C_{17}H_{18}O_4$: C 71.31, H 6.34. Found: C 71.55, H 6.35.

5) Preparation of 2,4diprop-2-enyloxybenzaldehyde

To a solution of 6.9 g (50 mmol) of 2,4dihydroxybenzaldehyde in 100 ml of acetone was added 12 ml (120 mmol) of 3-bromopropene and 40 g of potassium carbonate and the mixture was refluxed for 3 h under stirring. The mixture was filtered and the filtrate concentrated in vacuo to give 10.2 g (93%) of 2,4diprop-2-enyloxybenzaldehyde as slightly reddish crystals.

$^{1}H$ NMR data (200 MHz, $CDCl_3$, δ) 10.35 (s, CHO), 7.80 (d, J 10 Hz, H-6), 6.57 (dd, J 3 and 10 Hz, H-5), 6.47 (d, J 3 Hz, H-3), 6.2–5.9 (m, 2 CH= groups), 5.6–5.2 (2 $CH_2$= groups), 4.63 (2 $CH_2O$ groups).

$^{13}C$ NMR data (50 MHz, δ, $CDCl_3$) 187.5, 12.9, 159.2, 156.5, 142.5, 130.7.

6) Preparation of 2,4-dihydroxy-5-alkylbenzaldehydes or 2,4-dihydroxy-3,5-dialkylbenzaldehydes Many of these compounds are already known and can generally be prepared by reacting the corresponding 1,3-dihydroxy-4-alkylbenzene or the corresponding 1,3dihydroxy-3,5-dialkylbenzaldehyde with hydrogen cyanide or zinc cyanide in an ether solution in the presence of hydrogen chloride followed by hydrolysis of the formed product. Alternatively, the products may be formed through a Vilsmeier-Haack reaction (see J. March, "Advanced Organic Chemistry", 4th Ed., John Wiley & Sons, New York, 1992, 542–543).

7) Preparation of 2-hydroxy-4-alk-2-enyloxy-5-alkylbenzaldehydes or 2-hydroxy-3,5dialkyl4alk-2-enyloxybenzaldhydes The appropriate 3,5-dialkyl-2,4-dihydroxybenzaldehyde or 5-alkyl-2,4-dihydroxybenzaldehyde is selectively alkylated at the 4-hydroxy group with an alk-2-enyl bromide according to the procedure described for the synthesis of 4((3-methyl)but-2enyloxy)-2-hydroxybenzaldehyde (see Example 2.1).

8) Preparation of 2-methoxy-4-alk-2-enyloxy-5-alkylbenzaldehydes or 2-methoxy-3,5-dialkyl-4-alk-2-enloxbenzaldehydes The appropriate 4-alk-2-enyloxy-2-hydroxybenzaldehyde is alkylated with dimethyl sulfate according to the procedure described for the synthesis of 4-((3-methyl)but-2enyloxy)-2-hydroxybenzaldehyde (see Example 2.1).

9) Preparation of 2-methoxy-5-alkyl-4-hydroxybenzaldehydes or 2-methoxy-3,5-dialkyl-4-hydroxybenzaldehydes An acidic methanolic solution of the appropriate 2-methoxy4-alk-2-enyloxy-5-alkylbenzaldehyde or 2-methoxy-3,5-dialkyl-4-alk-2-enyloxybenzaldehyde to which has been added a small amount of water is heated in the presence of palladium on carbon to give the title compound as described in Example 2.22.

10) Preparation of 3,5-dialky-2,6dihydroxybenzaldehydes

A general procedure for the preparation of 3,5-dialkyl-2,6-dihydroxybenzaldehyde comprises reacting the appropriate 1,3-dihydroxy4,6dialkylbenzene with hydrogen cyanide or zinc cyanide in an ether solution in the presence of hydrogen chloride followed by hydrolysis of the resulting product. Alternatively, the products may be prepared through a Vilsmeier-Haack reaction (see J. March, "Advanced Organic Chemistry", 4th Ed., John Wiley & Sons, New York, 1992, 542–543).

11) Preparation of 3,5-dialkyl-2-methoxy-6-hydroxybenzaldehydes

An acetone solution of the appropriate 3,5-dialkyl-2,6-dihydroxybenzaldehyde is treated with an equimolar amount of methyl iodide or dimethyl sulfate in the presence of potassium carbonate (cf. the synthesis described in Example 2.1).

12) Preparation of 2-methoxy-4-hydroxy-5-alk-2-enylbenzaldehydes

A Claisen rearrangement of the appropriate 2-methoxy-4-alk-2-enyloxybenzaldehyde is performed as described for the synthesis of 2-methoxy4-hydroxy-5-(1,1-dimethylprop2-enyl)benzaldehyde (see Example 2.16).

13) Preparation of 2-alk-2-enyloxy-6-hydroxybenzaldehydes

An acetone solution of 2,6-dihydroxybenzaldehyde is treated with an equimolar amount of an alky-2-enyl bromide in the presence of potassium carbonate to give the title compound (cf. Example 2.1).

14) Preparation of 2-alk-2-enyloxy-6-methoxybenzaldehxdes

An acetone solution of the appropriate 2-alk-2-enyloxy-6-hydroxybenzaldehyde is treated with dimethyl sulfate in the presence of potassium carbonate as described in the synthesis of 2-methoxy4-(3-methylbut-2-enyloxy) benzaldehyde (Example 2.16).

15) Preparation of 2-methoxy-5-alk-2-enyl-6-hydroxybenzaldehydes

The appropriate 2-alk-2-enyloxy-6-methoxybenzaldehyde is Claisen rearranged as described for the synthesis of 2-methoxy-4hydroxy-5-(1,1-dimethylprop-2enyl)benzaldehyde (Example 2.16).

Synthesis of bis-aromatic α,β-unsaturated ketones

16) Synthesis of licochalcone A

Two methods for the preparation of licochalcone A are described, one by S. A. Khan, and M. Krishnamurti in *Indian J. Chem.* 22B (1983), 276–277, and one by X. Ren-Sheng, W. Kung-Ling, J. Shifa, W. Chang-gen, J. Fu-Xiang, X. Xu-yan, and G. Yi-Sheng in *Acta Chem. Sinica* 37 (1979), 289–297. The key steps in the Indian method are a Claisen condensation between 4-methoxymethoxybenzaldehyde and 2-methoxy-4-(3-methylbut-2-enyloxy)chalcone followed by a Claisen rearrangement to give 4'-O-methoxymethyllicochalcone A. In the Chinese approach the key step is an acid catalyzed Claisen condensation of 4-hydroxybenzaldehyde with 2-methoxy4-hydroxy-5-(1,1dimethylprop-2-enyl)benzaldehyde to give licochalcone A. The possibility for a contamination of the methoxy-methyl chloride, used for preparation of methoxymethyl ethers with the highly carcinogenic dichloromethyl ether, made the Chinese method preferable. The starting material, 2-hydroxy-hydroxy-5-(1,1-dimethylprop-2enyl) benzaldehyde, was prepared as described below:

34.5 g (250 mmol) of 2,4-dihydroxybenzaldehyde and 14 g (250 mmol) of potassium hydroxide were dissolved in 500 ml of ethanol. To the solution was added 57 g (250 mmol) of benzyltriethylammonium chloride, and the solution was concentrated in vacuo. The residue was dissolved in 500 ml of ethyl acetate and to the solution was over 30 min added a solution of 3-methylbut-2-enyl bromide dissolved in 100 ml of ethyl acetate. The mixture was refluxed for 1 hour and filtered, and the filtrate admixed with 500 ml of ether. The mixture was extracted with 500 ml of water, the organic phase was concentrated in vacuo to give 46 g of an yellow oil, from which 10.6 g of 2hydroxy-4-(3methylbut-2-enyloxy)benzaldehyde was isolated by column chromatography over silica gel 60 (Merck 0.063–0.200 mm, 1000 g) using petroleum ether-ethyl acetate (14:1, 1200 ml), (9:1, 1000 ml), (7:1, 1000 ml), (5:1, 300 ml) as eluents.

2-Methoxy-4-(3-methylbut-2-enyloxy)benzaldehyde was prepared as described below:

10.6 g (206 mmol) of 2-hydroxy4-(3-methylbut-2-enyloxy)benzaldehyde and 5.4 ml of dimethyl sulfate were dissolved in 102 ml of distilled acetone, the solution was added 25.5 g of potassium carbonate, and the resulting mixture was refluxed for 5 hours. The mixture was filtered and the filtrate concentrated in vacuo to give 8.3 g of an yellow oil from which 5.4 g of 2-methoxy4-(3-methylbut-2enyloxy)benzaldehyde was isolated by column chromatography over silica gel 60 (Merck 0.063–0.200 mm, 400 g) using petroleum ether-ethyl acetate (9:1, 1000 ml), (4:1, 500 ml) as eluents.

The Claisen rearrangement of 2-methoxy-4-(3-methylbut-2-enyloxy)benzaldehyde and the Claisen condensation of the resulting 2-methoxy-4hydroxy-5-(1,1-dimethyl-prop2-enyl)benzaldehyde with 4-hydroxybenzaldehyde to give licochalcone A was performed according to the Chinese procedure:

0.8 g (3.6 mmol) of 2-methoxy-4-(3-methylbut-2-enyl) benzaldehyde and 8.8 ml of propionic anhydride were dissolved in 17 ml of freshly distilled N,N-dimethylaniline and the solution was left under argon atmosphere in a sealed glass vessel for 2.5 hours at 200° C. 20 ml was removed from the reaction mixture by Kugelrohr distillation (oven 100° C., 1 mmHg), and to the residue was added 15 ml of water and sulfuric acid until pH 4. The mixture was extracted with two 40 ml portions of ether and the extract was concentrated in vacuo to give 1.1 g of an oil from which 0.398 g of 2-methoxy-4hydroxy-5-(1,1-dimethylprop-2-enyl)benzaldehyde was isolated by column chromatography over silica gel 60 (Merck 0.063–0.200 mm, 80 g) using petroleum etherethyl acetate (9:1, 1000 ml) as an eluent.

A solution of 150 mg (1.1 mmol) of 4-hydroxyacetophenone and 220 mg (1.0 mmol) of 2-methoxy4-hydroxy-5-(1,1-dimethylprop-2-enyl) benzaldehyde in 3 ml of ethanol was left on an ice bath, and 1.1 ml of ethanol saturated with dry hydrogen chloride was added. The solution was left for 2 hours and poured into 10 ml of water. The mixture was concentrated in vacuo and extracted with two 10 ml portions of ethyl acetate, and the extract was dried and concentrated in vacuo to give 281 mg of an oil from which 119 mg of licochalcone A was isolated by column chromatography over silica gel 60 (Merck 0.063–0.200 mm, 23 g) using petroleum ether-ethyl acetate (1:1, 1000 ml) as an eluent.

17) Preparation of 2,4-dimethoxy-4'-(N,N-dimethylcarbamoyloxy)chalcone

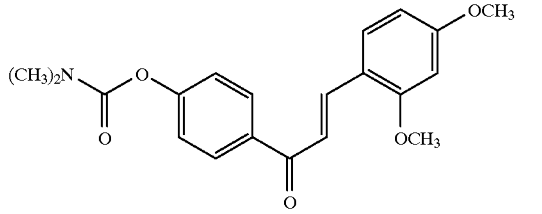

and 2,4-dimethoxy-4'-hydroxychalcone

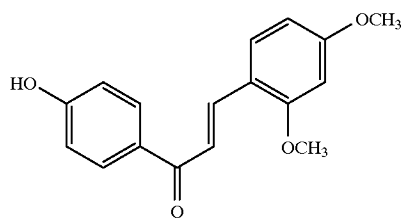

414 mg (2 mmol) 4N,N-dimethylcarbamoyloxyacetophenone and 166 mg (1 mmol) 2,4-dimethoxybenzaldehyde were added to a solution of 1 g of potassium hydroxide in ethanol and the mixture was left for 1 h. The mixture was filtered and the residue poured into 20 ml of 2M hydrochloric acid. The solution was extracted twice with 20 ml of ethyl acetate. The organic phase was dried and concentrated in vacuo to give 0.906 g of an yellow oil, from which 0.157 g of 2,4-dimethoxy-4'-hydroxychalcone and 47 mg of 2,4-dimethoxy4'(N,N-dimethylcarbamoyloxy)chalcone were isolated by column chromatography over silica gel 60 (Merck 0.063–0.200 mm, 50 g) using petroleum ether-ethyl acetate (2:1) as an eluent.

$^1$H NMR data for 2,4-dimethoxy4'-(N,N-dimethylcarbamoyloxy)chalcone (200 MHz, δ, $CD_3CN$): 8.06 (AA'-part of an AA'MM'-system, H-2' and H-6'), 8.00 (d, J 15 Hz, H-β), 7.71 (d, J 7 Hz, H-6), 7.63 (d, J 15 Hz, H-α), 7.24 (MM'-part of an AA'MM'-system, H-3' and H-5'), 6.59 (dd, J 7 and 2 Hz, H-3), 6.57 (d, J 2 Hz, H-5), 3.91 and 3.94 (s, $CH_3$—O), 3.05 and 2.95 (s, $CH_3$—N).

For the identification of 2,2-dimethoxy4'-hydroxy, see Example 2.22.

18) Preparation of 2,4-dimethoxy-4'-methoxymethoxychalcone

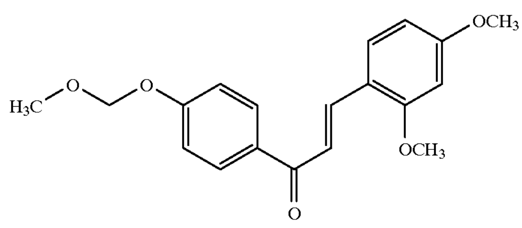

0.9 g (5 mmol) of 4methoxymethoxyacetophenone and 1.66 g (10 mmol) of 2,4-dimethoxybenzaldehyde were added to a solution of 5 g of potassium hydroxide in ethanol and the solution was left for 2.5 h. The reaction mixture was poured into a mixture of 20 ml of a saturated sodium bicarbonate solution and 20 ml of water. The mixture was extracted twice with ether and the combined organic phases were dried and concentrated in vacuao to give 4.621 g of an oil from which 1.60 g (90%) of 2,4-dimethoxy4'-methoxymethoxychalcone was isolated by column chromatography over silica gel 60 (Merck 0.063–0.200 mm, 100 g) using petroleum ether-ethyl acetate (4:1, 1l) and (2:1, 1 l) as eluents.

$^1$H NMR data (200 MHz $CD_3CN$, δ): 8.03 (AA'-part of an AA'MM'-system, H-2' and H6'), 7.96 (d, J 15 Hz, H-β), 7.70 (d, J 9.3 Hz, H6), 7.63 (d, J 15 Hz, H-α), 7.11 (MM'-part of an AA'MM'-system, H3' and H-5'), 6.58 (dd, J 9.3 and 2.6 Hz, H-5), 6.56 (d, J 2.6 Hz, H-3), 5.26 (s, $CH_2$), 3.90 and 3.83 (s, $CH_3O$—Ph), 3.44 ($CH_3$—O—$CH_2$).

19) Preparation of 4'-hydroxychalcone

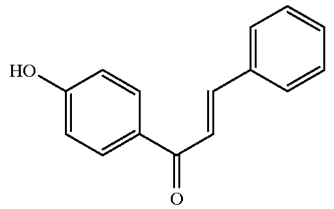

2.7 g (20 mmol) of 4hydroxyacetophenone and 2.1 g (20 mmol) of benzaldehyde were added to a solution of 12 g of sodium hydroxide in 10 ml of water and 50 ml of ethanol, and the solution was refluxed for 3 h. After addition of 50 mnl of water, the solution was acidified with 90 ml of 4M hydrochloric acid and extracted with 100 ml of ether. The organic phase was dried ($MgSO_4$) and concentrated in vacuo to give 4.82 g of a gum, from which 0.124 g of 4'-hydroxychalcone identical with that previously decribed by R, L. Shriner and T. Kurosawa in *J. Am. Chen. Soc.* 52 (1930), 2538–2540 was obtained by column chromatography over silica gel 60 (Merck 0.063–0.200, 300 g) using methylene chloride-ethyl acetate (9:1) as an eluent.

20) Preparation of 4-hydroxychalcone

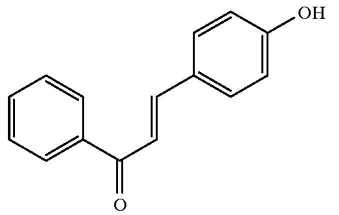

2.2 g (18 mmol) of acetophenone and 1.8 g (15 mmol) of 4-hydroxybenzaldehyde were added to a solution of 12 g of sodium hydroxide in 10 ml of water and 5 ml of ethanol. The solution was refluxed for 1 h and left at room temperature for 3 days. The reaction mixture was acidified with 70 ml of 4M hydrochloric acid and filtered to give 3.78 g of yellow crystals which were recrystallized from ethanol to give 1.85 g of 4hydroxychalcone identical to that described by R. L. Shriner and T. Kurosawa in *J. Am. Chem. Soc.* 52 (1930), 2538–2540.

21) Preparation of 2,4dimethoxy4'-prop-2-enyloxychalcone

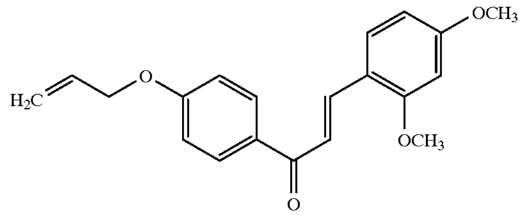

0.88 g of 4-allyloxyacetophenone and 0.42 g of 2,4-dimethoxybenzaldehyde were dissolved in 3.5 ml of ethanol, and to the solution was added ethanol saturated with 3.5 ml of hydrogen chloride. The mixture was left at room temperature for 30 min during which time it turned heavily red. The solution was concentrated in vacuo and the residue chromatographed (column chromatography over silica gel 60 (Merck 0.0630–0.200 mm, 100 g), eluent toluene and toluene to which increasing amounts of ethyl acetate were added) to give 500 mg of 4-methoxyacetophenone and 471 mg of 2,4-dimethoxy-4'-prop-2-enyloxychone. The chalcone was recrystallized from petroleum ether-ethyl acetate to give 370 mg of slightly yellow crystals. For data, see Example 2.24.

23) Preparation of 2,4-dimethoxy-4'-hydroxychalcone

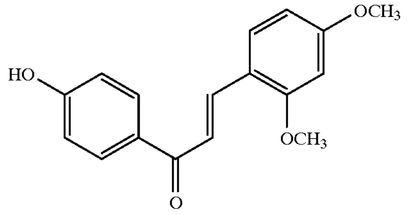

326 mg of 2,4-dimethoxy-4'-allyloxychalcone was dissolved in 5 ml of methanol, 1 ml of added water, palladium on charcoal (10%, 100 mg), and 100 mg of p-toluene-sulfonic acid, and the mixture was refluxed for 24 h. The reaction mixture was filtered and poured into a mixture of 5 ml of a 10% aqueous solution of sodium bicarbonate and 5 ml of a saturated aqueous sodium chloride solution. The solution was extracted with 10 ml of ethyl acetate and concentrated to give 380 mg which were chromatographed over silica gel 60 (Merck 0.063–0.200 mm, 25 g, eluent petroleum ether-ethyl acetate 9:1) to give 130 mg of yellow crystals which were recrystallized from methanol to give 70 mg of 2,4-dimethoxy4'-hydroxychalcone, m.p. 165–166° C.

$^1$H NMR data (200 MHz, $CD_3CN$-DMSO-$d_6$, δ): 7.98 (AA-part of an AA'MM'-system, H-2' and H-6'), 7.96 (d, J 15 Hz, H-β), 7.72 (d, J 7 Hz, H-6), 7.65 (d, J 15 Hz, H-α), 6.91 (MM'-part of an AA'MM'-system, H-3' and H-5'), 6.59 (dd, J 7 and 2 Hz, H-5), 6.57 (d, J 2 Hz, H-3), 3.90 and 3.83 ($CH_3$—O).

$^{13}$C NMR data (50 MHz, $CD_3CN$-DMSO-$d_6$, δ) 187.5, 138.8, 157.8, 117.5, 161.1, 99.2, 162.9, 106.8, 13.0, 131.7, 116.2, 164.0, 116.2, 131.7, 56.4, 56.2.

Calc. for $C_{17}H_{16}O_4$ C 71.82, H 5.67. Found: C 71.48, H 5.82.

23) Preparation of 4'-(2-methoxyethoxymethoxy)-4-(3-methylbut-2-enyloxy)2-methoxy-chalcone

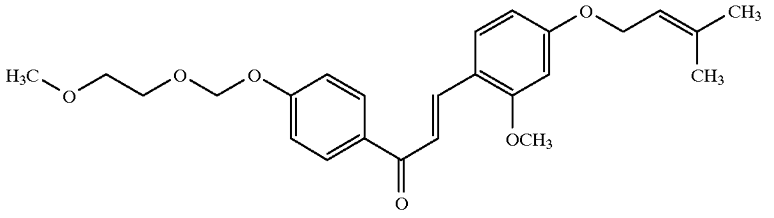

0.9 g (4.1 mmol) of 4-(2-methoxyethoxymethoxy) acetophenone, 1.77 g (7.9 mmol) of 4(3-methyl)but-2-enyloxy-2-methoxybenzaldehyde, and 4 g of potassium hydroxide were dissolved in 16 ml of ethanol, and the solution was left for 24 h. The solution was poured into 20 ml of 4M hydrochloric acid and extracted twice with 10 ml of ether. The ether phase was concentrated in vacuo to give 2.7 g of a yellow oil which was purified by column chromatography (silica gel 60 (Merck 0.063–0.200 mm, 250 g), eluent toluene-ethyl acetate 9:1, to which increasing amounts of ethyl acetate were added). 4'-(2-Methoxyethoxymethoxy)4-(3-methylbut-2-enyloxy)-2-methoxychalcone was obtained as an oil (860 mg, 49%).

$^1$H NMR data (200 MHz, $CD_3CN$, δ) 8.05 (AA'-part of an AA'MM'-system, H-2' and H-6'), 7.98 (d, J 15 Hz, H-β), 7.68 (d, J 8 Hz, H-6), 7.60 (d, J 15 Hz, H-α), 7.12 (MM'-part of an AA'MM'-system, H-3' and H-5'), 6.55 (dd, J 3 and 8 Hz, H4), 6.53 (d, J 3 Hz, H-3), 5.45 (m,=CH—), 5.32 (O—$CH_2$—O), 4.61 (d, $CH_2$—C=J 7 Hz), 3.90 (s, $CH_3$O—Ar), 3.80 (AA'-part of an AA'MM'-system, $CH_2$—O—Ar), 3.55 (MM'-part of an AA'MM'-system, C—O—$CH_2$—), 3.26 (s, $CH_3$—O—C—C), 1.78 and 1.73 (s, $CH_3$—C).

24) Preparation of 2,4-dimethoxy-4'-prop-2-enyloxychalcone

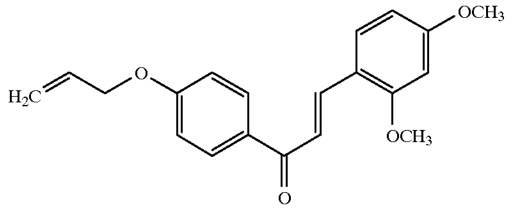

17.6 g (0.1 mol) of 4-allyloxyacetophenone and 16.6 g (0.1 mol) of 2,4-dimethoxybenzaldehyde were under an inert dry atmosphere (argon) dissolved in 100 ml of dry ethanol (freshly distilled from sodium under argon atmosphere). The solution was added 1 g of sodium hydroxide and left under stirring for 18 h. The reaction mixture was filtered to give 29.9 g (97%) of 2,4-dimethoxy-4'-prop-2enyloxychalcone identical to that obtained in Example 2.22, m.p. 74.5–75° C.

$^1$H NMR data (200 MHz, $CDCl_3$, δ) 8.08 (d, J 16 Hz, H-β), 8.03 (AA'-part of an AA'MM'-system, H-2' and H6'), 7.56 (d, J 16 Hz, H-α), 7.56 (d, J 8 Hz, H-6), 6.98 (MM'-part of an AA'MM'-system, H-3' and H-5'), 6.51 (dd, J 3 and 8 Hz, H-5), 6.45 (d, J 3 Hz, H-3), 6.03 (ddt, J 15, 10 and 4 Hz, —CH=), 5.41 (d, J 15 Hz, =CHH), 5.28 (d, J 10 Hz, =CHH), 4.59 (d, J 4 Hz, —$CH_2$—), 3.89 and 3.85 (s, $CH_3$O).

$^{13}$C NMR data (50 MHz, $CDCl_3$, δ) 189.3, 162.9, 162.0, 160.3, 139.6, 132.6, 131.7, 130.8, 130.6, 120.0, 118.0, 117.2, 114.4, 105.4, 98.4, 68.8, 55.5, 55.4.

Calc. for $C_{20}H_{20}O_4$: C 74.06, H 6.21. Found: C 74.12, H 6.30

25) Preparation of 3,4dimethoxy-4'-prop-2-enyloxychalcone

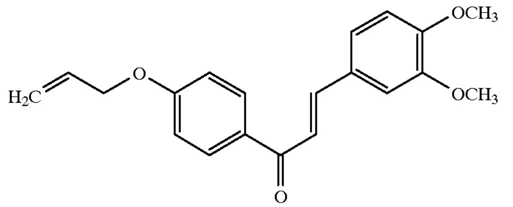

1.76 g (10 mmol) of 4-allyloxyacetophenone and 1.66 g (10 mnol) of 3,4-dimethoxybenzaldehyde were under a dry inert atmosphere (argon) dissolved in 10 ml dry ethanol and the solution was stirred for 18 h. The solution was filtered to give 3.0 g (99%) of 3,4-dimethoxy-4'-prop-2enyloxychalcone which was recrystallized from ethanol, mp. 74.5–75° C.

$^1$H NMR data (200 MHz, $CD_3CN$, δ) 8.06 (AA'-part of an AA'MM'-system, H-2' and H-6'), 7.70 (d, J 15 Hz, H-β), 7.58 (d, J 15 Hz, H-α), 7.33 (d, J 2 Hz, H-2), 7.25 (dd, J 2 and 8 Hz, H-6), 7.00 (MM'-part of an AA'MM'-system, H-3' and H-5'), 6.91 (d, J 8 Hz, H-5), 6.04 (m, =CH—), 5.42 (m, =CHH), 5.28 (m, =CHH), 4.60 (m, —$CH_2$—), 3.87 and 3.83 (s, $CH_3$), $^{13}$C NMR data (50 MHz, $CD_3CN$, δ) 188.3, 161.8, 151.0, 148.9, 142.9, 132.7, 130.8, 130.1, 127.4, 122.8, 119.1, 116.8, 113.9, 110.9, 109.9, 68.1, 54.9, 54.8.

Calc. for $C_{20}H_{20}O_4$: C 74.06, H 6.21. Found: C 74.10, H 6.24.

26) Preparation of 3,4-dimethoxy4'-hydroxychalcone

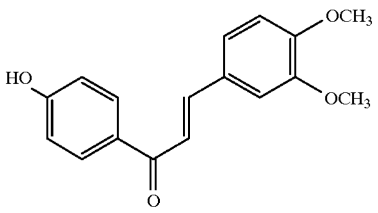

486 mg (1.5 mmol) of 3,4dimethoxy-4'-allyloxychalcone was dissolved in a mixture of 7.5 ml of methanol and 1.5 ml of water. To the solution were added 150 mg of p-toluenesulfonic acid and 150 mg of palladium on carbon (10%) and the solution was heated to 80° C. for 2 h in a sealed flask. The reaction mixture was filtered and poured into a mixture of 10 ml of an aqueous 10% solution of sodium bicarbonate and 10 ml of a saturated aqueous solution of sodium chloride. The mixture was extracted with 15 ml of ethyl acetate and concentrated in vacuo. The residue was recrystallized from methanol to give 0.125 g (25%) of 3,4nethoxy-4'-hydroxychalcone (m.p. 193–198° C.) identical to that described by A. v. n Wacek, and E. David, Ber. 70 (1937),190 (m.p. 208° C.).

27) Preparation of 3,5-dimethoxy-4'-prop-2-enyloxychalcone

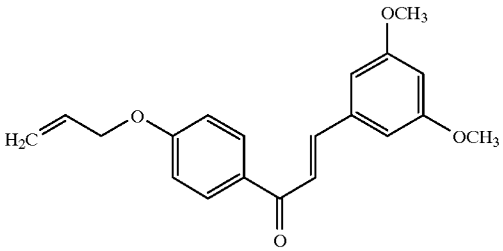

1.76 g (10 nmmol) of 4-allyloxyacetophenone and 1.66 g (10 mmol) of 3,5-dimethoxybenzaldehyde were dissolved in 10 ml of dry freshly distilled ethanol under an inert atmosphere (argon), and the solution was admixed with 100 mg of sodium hydroxide and left under stirring for 18 h. The reaction mixture was filtered to give 2.96 g (99%) of 3,5-dimethoxy-4'-prop-2-enyloxychalcone which was recrystallized from methanol, m.p. 88.5–90° C.

$^1$H NMR data (200 MHz, $CD_3CN$, δ) 8.06 (AA'-part of an AA'MM'-system, H-2' and H-6'), 7.68 (d, J 15 Hz, H-β), 7.62 (d, J 15 Hz, H-α), 7.01 (MM'-part of an AA'MM'-system, H-3' and H-5') 6.88 (d, J 2 Hz, H-2 and H-6) 6.53 (t, J 2 Hz, H-4), 6.10 (m, =CH—), 5.39 (m, =CHH), 5.28 (m, =CHH), 4.61 (m, —$CH_2$—), 3.80 (s, $CH_3$O).

$^{13}C$ NMR data (50 MHz, $CD_3CN$, δ): 187.4, 161.9, 160.6, 142.6, 136.6, 132.6, 130.5, 130.3, 122.0, 116.8, 113.9, 116.8, 113.9, 105.8, 101.9, 68.2, 54.7.

Calc. for $C_{20}H_{20}O_4$: C 74.06, H 6.21. Found: C 74.02, H 6.24

28) Preparation of 2,6-dimethoxy4'-prop-2-enyloxychalcone

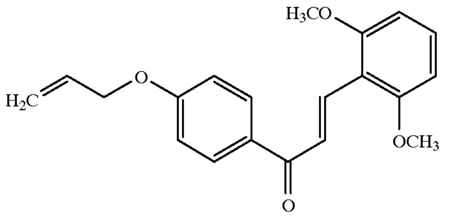

0.59 g (3.3 mmol) of 4-allyloxyacetophenone and 0.56 g (3.3 mmol) of 2,6-dimethoxybenzaldehyde were under an inert atmosphere (argon) dissolved in 3.3 ml of dry freshly distilled ethanol and 100 mg of sodium hydroxide was added to the solution. The mixture was left with stirring for 4.5 h, poured into 10 ml of M hydrochloric acid and extracted with 10 ml of ethyl acetate. The organic phase was dried over $MgSO_4$ and concentrated in vacuo to give 0.89 g of a yellow gum, from which 2,6-dimethoxy4'-prop-2-enyloxychalcone (0.70 g, 70%) was isolated by column chromatography over silica gel 60 (Merck 0.063–0.200 mm, 80 g) using petroleum ether-ethyl acetate (2:1, 800 ml) with 0.5% added glacial acetic acid as an eluent. Crystallization from methanol afforded 0.56 g of 2,6-dimethoxy-4'-prop-2enyloxychalcone, m.p. 102–103° C.

$^1H$ NMR data (200 MHz, $CDCl_3$, δ) 8.26 (d, J 15 Hz, H-β), 8.03 (AA'-part of an AA'MM'-system, H-2' and H-6'), 7.99 (d, J 15 Hz, H-α), 7.27 (t, J 7 Hz, H-4), 6.98 (MM'-part of an AA'MM'-system, H-3' and H-5'), 6.57 (d, J 7 Hz, H-3 and H-5), 6.05 (m, =CH—), 5.42 (m, =CH$\underline{H}$), 5.32 (m, =C$\underline{H}$H), 4.60 (m, —$CH_2$—), 3.90 (s, $CH_3$—O).

$^{13}C$ NMR data (50 MHz, $CDCl_3$, δ): 190.0, 161.6, 159.9, 134.6, 132.3, 131.7, 130.9, 130.4, 124.4, 117.7, 114.0, 112.7, 103.4, 68.5, 55.5.

Calc. for $C_{20}H_{20}O_4$: C 74.06, H 6.21. Found: C 73.79, H 6.34

29) Preparation of 2,6-dimethoxy-4'-hydroxychalcone

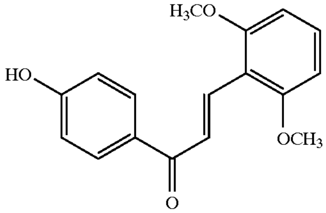

0.32 g (1 mmol) of 2,6-dimethoxy-4'-prop-2-enyloxychalcone was dissolved in 5 ml of methanol, and to the solution was added 1 ml of water, 0.6 g of 10% of palladium on carbon, and 0.1 g of paratoluenesulfonic acid. The mixture was refluxed for 2 h and filtered, and the filtrate was poured into 5 ml of water. The solution was concentrated in vacuo to half the volume and poured into 12 ml of ethyl acetate. The organic phase was washed with 10 ml of a saturated aqueous solution of sodium hydrogen carbonate and subsequently with 10 ml of a saturated aqueous solution of sodium chloride and concentrated in vacuo to give 65.1 mg of a yellow gum. The gum was chromatographed over silica gel 60 (Merck 0.063–0.200 mm, 10 g) using petroleum ether-ethyl acetate (2:1) added 0.5% of acetic acid as an eluent to give 2,6-dimethoxy-4'-hydroxychalcone, which was crystallized from methanol to give 23 mg (7%) of yellow crystals, m.p. 172–176° C.

$^1H$ NMR data (200 MHz, $CDCl_3$, δ) 8.21 (d, J 15 Hz, H-β), 7.92 (d, J 15 Hz, H-α), 7.92 (AA'-part of an AA'MM'-system, H-2' and H-6'), 7.30 (t, J 7 Hz, H-4), 6.91 (MM'-part of an AA'MM'-system, H-3' and H-5'), 6.58 (d, J 7 Hz, H-3 and H-5), 3.90 (s, $CH_3$—O).

Calc. for $C_{17}H_{16}O_4$: C 71.82, H 6.57. Found: C 71.98, H 5.81.

30) Preparation of 2,5-dimethoxy-4'-prop-2-enyloxychalcone

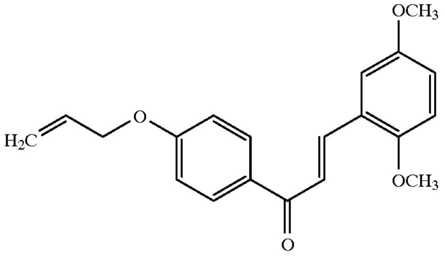

1.76 g (10 mmol) of 4-allyloxyacetophenone and 1.66 g (10 mmol) of 2,5-dimethoxybenzaldehyde were under an inert atmosphere (argon) dissolved in 10 ml of dry freshly distilled ethanol, and 100 mg of sodium hydroxide was added to the solution. The mixture was left under stirring for 2.5 h and filtered. The precipitate was recrystallized from methanol to give 2.50 g (83%) of 2,5-dimethoxy-4'-prop-2-enyloxy-chalcone, m.p. 86–87° C.

$^1H$ NMR data (200 MHz, $CDCl_3$, δ) 8.06 (d, J 15 Hz, H-β), 8.02 (AA'-part of an AA'MM'-system, H-2' and H-6'), 7.59 (d, J 15 Hz, H-α), 7.16 (d, J 2 Hz, H-6), 6.97 (MM'-part of an AA'MM'-system, H-3' and H-5'), 6.93 (dd, J 2 and 7 Hz, H-4), 6.84 (d, J 7 Hz, H-3), 6.05 (m, =CH—), 5.42 (m, =CH$\underline{H}$), 5.32 (m, =C$\underline{H}$H), 4.60 (m, —$CH_2$—), 3.84 (s, $CH_3$—O), 3.80 (s, $CH_3$—O).

$^{13}C$ NMR data (50 MHz, $CDCl_3$, δ) 189.1, 162.3, 153.5, 153.2, 129.3, 132.6, 131.4, 130.8, 124.7, 122.8, 118.2, 116.9, 114.5, 113.8, 112.4, 88.9, 56.1, 55.8.

Calc. for $C_{20}H_{20}O_4$: C 74.06, H 6.21. Found: C 73.81, H 6.18.

31) Preparation of 2,3-dimethoxy-4'-prop-2-enyloxychalcone

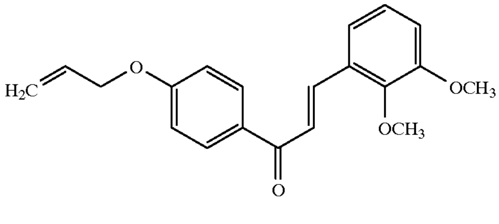

1.76 g (10 mmol) of 4allyloxyacetophenone and 1.66 g (10 imnol) of 2,3dimethoxybenzaldehyde were under an inert atmosphere (argon) dissolved in 10 ml of dry freshly distilled ethanol, and 100 mg of sodium hydroxide was added to the solution. The mixture was left under stirring for 23 h and concentrated in vacuo. The crystalline residue was recrystallized from methanol-water to give 2.92 g (90%) of 2,3-dimethoxy-4'-prop-2-enyloxychalcone, m.p. 98–99° C.

$^1H$ NMR data (200 MHz, $CDCl_3$, δ) 8.09 (d, J 15 Hz, H-β), 8.03 (AA'-part of an AA'MM'-system, H-2' and H-6'), 7.59 (d, J 15 Hz, H-α), 7.27 (d, J 2 Hz, H-6), 7.09 (t, J 7 Hz, H-5), 6.96 (MM'-part of an AA'MM'-system, H-3' and H-5'), 6.95 (dd, J 2 and 7 Hz, H-4), 6.05 (m, =CH—), 5.42 (m, =CH<u>H</u>), 5.32 (m, =C<u>H</u>H), 4.60 (m, —$CH_2$—), 3.88 (s, $CH_3$—O), 3.46 (s, $CH_3$—O).

$^{13}C$ NMR data (50 MHz, $CDCl_3$, δ) 189.1, 162.4, 153.2, 148.8, 138.9, 132.5, 131.2, 130.8, 129.2, 124.2, 123.4, 119.6, 118.2, 114.6, 114.4, 69.0, 61.3, 55.9.

Calc. for $C_{20}H_{20}0_4$ C 74.06, H 6.21. Found: C 73.99, H 6.24

32) Preparation of 2,4-dimethoxy-2'-(3-methylbut-2-nyloxyvchalcone and 2.4-dimethoxy-2'-hydroxychalcone

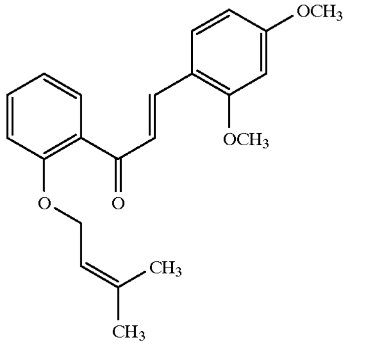

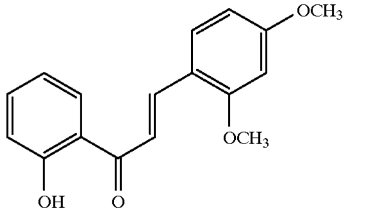

1.76 g (10 mnmol) of 2-(3-methylbut-2-enyloxy) acetophenone and 1.66 g (10 mmol) of 2,4dimethoxybenzaldehyde were under an inert atmosphere (argon) dissolved in 10 ml of dry freshly distilled ethanol, and to the solution was added 100 mg of sodium hydroxide. The mixture was left under stirring for 4.5 h, poured into 10 m 1 of 1M hydrochloric acid and extracted with 10 ml of ethyl acetate. The organic phase was dried over $MgSO_4$, and concentrated in vacuo to give 3.2 g of a yellow gum, from which 2,4-dimethoxy-2'-hydroxychalcone (0.85 g, 27%) and 2,4-dimethoxy-2'-(3-methylbut-2-enyloxy)chalcone (1.24 g, 40%) was isolated by column chromatography over silica gel 60 (Merck 0.063–0.200 mm, 325 g) using toluene-ethyl acetate (19:1, 1000 ml) with 0.5% added glacial acetic acid and toluene-ethyl acetate (14:1, 1000 ml) with 0.5% added glacial acetic acid as eluents. Crystallization of 2,4dimethoxy-2'-hydroxychalcone from methanol afforded 0.42 g of 2,4-dimethoxy-2'-(3-methylbut-2-enyloxy) chalcone.

2,4-Dimethoxy-2'-hydroxychalcone has previously been reported used for studies on oxidation of chalcones with lead tetraacetate, see K. Kurosawa, and J. Higuchi in *J. Bull. Soc. Japan* 45 (1972), 1132–1136, and K. Kurosawa in *J. Bull. Chem. Soc. Japan* 42 (1969), 1456.

$^1H$ NMR data of 2,4-dimethoxy-2'-hydroxychalcone (200 MHz, $CDCl_3$, δ) 8.15 (d, J 15 Hz, H-β) 7.89 (dd, J 2 and 8 Hz, H-6') 7.66 (d, J 15 Hz, H-α) 7.56 (d, J 7 Hz, H-6), 7.46 (dt, J 2 and 7 Hz, H-4'), 6.99 (dd, J 2 and 7 Hz, H-3'), 6.88 (dt, J 2 and 7 Hz, H-5'), 6.53 (dd, J 2 and 7 Hz, H-5) 6.46 (d, J 2 Hz, H-3), 3.90 (s, $CH_3$—O), 3.89 (s, $CH_3$—O).

$^{13}C$ NMR data of 2,4-dimethoxy-2'-hydroxychalcone (50 MHz, $CDCl_3$, δ) 194.2, 163.5, 163.4, 160.7, 141.3, 135.8, 131.5, 129.9, 120.3, 118.6, 118.4, 118.0, 116.2, 105.6, 98.4, 55.6, 55.5.

$^1H$ NMR data of 2,4-dimethoxy-2'-(3-methylbut-2-enyloxy)chalcone (200 MHz, $CDCl_3$, δ) 7.92 (d, J 15 Hz, H-β), 7.64 (dd, J 2 and 8 Hz, H-6'), 7.51 (d, J 7 Hz, H-6), 7.42 (d, J 15 Hz, H-α) 7.39 (dt, J 2 and 7 Hz, H-4'), 7.00 (dt, J 2 and 7 Hz, H-5'), 6.97 (dd, J 2 and 7 Hz, H-3'), 6.49 (dd, J 2 and 7 Hz, H-5) 6.44 (d, J 2 Hz, H-3), 5.48 (m, =CH—) 4.60 (d, J 6 Hz, $CH_2$), 3.84 (s, $CH_3$—O), 3.83 (s, $CH_3$—O), 1.74 (s, $CH_3$—C), 1.70 (s, $CH_3$—C).

$^{13}C$ NMR data of 2,4-dimethoxy-2'-(3-methylbut-2-enyloxy)chalcone (50 MHz, $CDCl_3$, δ) 193.3, 162.7, 160.1, 157.5, 138.3, 132.4, 130.5, 130.0, 125.4, 120.7, 119.7, 113.1, 105.4, 98.3, 65.7, 55.5, 25.7, 18.3.

33) Preparation of 2,4-dimethoxychalcone

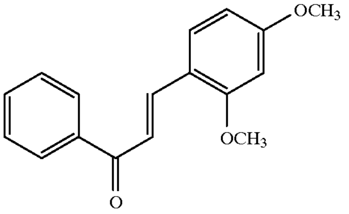

1.20 g (10 mmol) of acetophenone and 1.66 g (10 mmol) of 2,4-dimethoxybenzaldehyde were dissolved in 10 ml of dry freshly distilled ethanol under an inert atmosphere (nitrogen or argon), and 100 mg of sodium hydroxide was added to the solution. The mixture was left under stirring for 23 h, poured into 10 ml of 1M hydrochloric acid and extracted with 10 ml of ethyl acetate. The organic phase was dried over $MgSO_4$ and concentrated in vacuo to give 2.5 g of a yellow gum, from which 2.25 g of 2,4-dimethoxychalcone was isolated by column chromatography over silica gel 60 (Merck 0.063–0.200 mm, 250 g) using petroleum ether-ethyl acetate (14:1, 1700 ml) with 0.5% added glacial acetic acid and petroleum ether-ethyl acetate (9:1, 900 ml) with 0.5% added glacial acetic acid as eluents. Crystallization from methanol-water afforded 0.73 g (25%) of 2,4-dimethoxychalcone, m.p. 49–50° C.

2,4-Dimethoxychalcone has previously been used for chemical studies, see V. F. Laurushin, N. D. Trusevich, and V. N. Tolmachev in *Zh. Obshch Khim.* 39 (1969), 42–45, *Chem. Abstr.* 70 (1969), 105822t, and A. M. Volovick, V. N. Tolmachev, and V. F. Laurushin in *Visn Kharkiv Univ. Khim.* 73 (1971), 85–88, *Chem. Abstr.* 78 (1973), 57241u.

$^1H$ NMR data (200 MHz, $CDCl_3$, δ) 8.06 (d, J 15 Hz, H-β), 8.02–7.95 (m, H-2' and H-6'), 7.53 (d, J 15 Hz, H-α), 7.6–7.4 (m, H-6 and H-3'-5'), 6.51 (dd, J-2 and 8 Hz, H-5), 6.45 (d, J 2 Hz, H-3), 3.87 (s, $CH_3$—O), 3.82 (s, $CH_3$—O).

$^{13}C$ NMR data (50 MHz, $CDCl_3$, δ) 191.1, 163.0, 160.4, 140.5, 132.3, 130.9, 128.4, 128.4, 120.3, 117.1, 105.4, 98.4, 555, 55.4.

Calc. for $C_{17}H_{16}0_3$: C 76.10, H. 6.01. Found: C 76.17, H 6.09.

34) Preparation of 1-(furan-2-yl)-3-(2.4-dimethoxyphenyl) prop-2-en-1-on

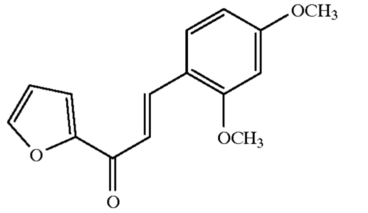

1.09 g (10 mmol) of 2-acetylfurane and 1.66 g (10 mmol) 2,4-dimethoxybenzaldehyde were under an inert atmosphere (argon) dissolved in 10 ml of dry freshly distilled ethanol, and 100 mg of sodium hydroxide was added to the solution. The mixture was left under stirring for 2.5 h, poured into 45 ml of 1M hydrochloric acid and extracted with 45 ml of ethyl acetate. The organic phase was dried over $MgSO_4$, and concentrated in vacuo to give 2.5 g of a yellow gum, from which 2.0 g (80%) of 1-(furan-2-yl)-3(2,4-dimethoxyphenyl)prop-2-en-1-on was isolated as a yellow oil by column chromatography over silica gel 60 (Merck 0.063–0.200 mm, 240 g) using petroleum ether-ethyl acetate (8:2, 2500 ml) with 0.5% added glacial acetic acid as an eluent. The compound crystallized upon standing, m.p. 57–59° C. ($MeOH-H_2O$).

$^1H$ NMR data (200 MHz, $CDCl_3$, δ) 8.12 (d, J 15 Hz, H-β), 7.62 (dd, J 1 and 2 Hz, H-5'), 7.55 (d, J 7Hz, H-6), 7.53 (d, T 15 Hz, H-α), 7.29 (dd, J 1 and 3 Hz, H-3'), 6.55 (dd, J 2 and 3 Hz, H4'), 6.51 (dd, J 2 and 7 Hz, H-5), 6.44 (d, J 2 Hz, H-3), 3.86 (s, $CH_3O$), 3.81 (s, $CH_3$—O).

$^{13}C$ NMR data (50 MHz, $CDCl_3$, δ) 178.8, 163.2, 160.5, 154.0, 146.3, 139.7, 130.9, 119.2, 117.1, 116.8, 112.4, 105.6, 98.3, 55.5, 55.4.

Calc. for $C_{15}H_{14}O_4$: C 69.76, H 5.46. Found: C 69.88, H 5.61.

35) Preparation of 2,4-dimethoxy-4'-pivaloyloxymethoxychalcone

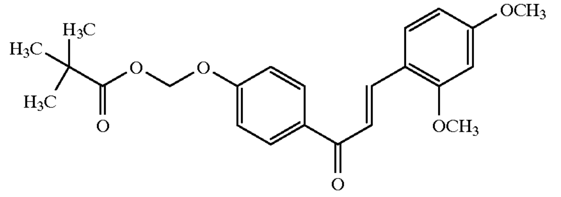

An acetonic solution of iodomethyl pivalate was prepared by allowing 0.29 g (2.1 mmol) of chloromethylpivalate to react for 30 min with 0.15 g (5.7 mmol) of sodium iodide dissolved in 10 ml of dry acetone. The acetonic solution was decanted from the precipitated sodium chloride and added to a suspension of 0.57 g (2 mmol) of 2,4-dimethoxy-4'-hydroxychalcone and 0.5 g (3.7 mmol) of potassium carbonate, which had previously been stirred under argon atmosphere for 30 min. The combined mixtures were left for 2 days at 40° C. in a sealed flask, filtered, and concentrated in vacuo to give a yellow gum, from which 0.48 g (60%) of 2,4-dimethoxy4'-pivaloyloxy-methoxychalcone was isolated as a yellow oil by column chromatography over silica gel 60 (Merck 0.063–0.200 mm, 80 g) using petroleum ether-ethyl acetate (9:1, 1500 ml) as an eluent. The compound crystallized upon standing, m.p. 98–99° C. (methanol).

$^1H$ NMR data (200 MHz, $CDCl_3$, δ) 8.09 (d, J 15 Hz, H-β), 8.05 (AA'-part of an AA'MM'system, H-2' and H-6'), 7.57 (d, J 7 Hz, H-6), 7.54 (d, J 15 Hz, H-α), 7.10 (MM'-part of an AA'MM'-system, H-3' and H-5'), 6.53 (dd, J 2 and 7 Hz, H-15), 6.47 (d, J 2 Hz, H-3), 5.82 (s, $CH_2$), 3.86 (s, $CH_3$—O), 3.85 (s, $CH_3$—O), 1.21 (s, $CH_3$—C).

Calc. for $C_{23}H_{26}O_6$ C 69.33, H 6.58. Found: C 69.29, H 6.56

36) Preparation of chalcone epoxide

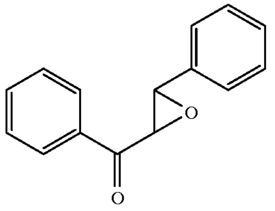

1.040 g (5 mmol) of chalcone was dissolved in 15 ml of ethanol and to the solution was added 2 ml of 25% hydrogen peroxide and 2 ml of an aqueous solution of 1M sodium carbonate. The precipitate which was formed after stirring for 3 h was isolated and recrystallized from DMSO-water to give 250 mg (22%) of chalcone epoxide.

$^1H$ NMR data (200 MHz, DMSO-$d_6$, δ) 8.04 (d, J 8 Hz, H-2' and H-6'), 7.9–7.3 (complex pattern, H-2-6 and H-3'-5'), 4.85 (broad s, H-α), 4.18 (H-β.

$^{13}C$ NMR data (50 MHz, DMSO-d6, δ) 192.7, 156.8, 143.9, 133.7, 128.7, 128.6, 128.2, 127.9, 126.1, 59.6, 58.2.

Calc. for $C15H_{12}O_2$: C 80.34, H 5.39. Found: C 80.25, H 5.37.

37) Preparation of 2-methoxy-5-alkyl-4,4'-dihydroxychalcones or 2-methoxy-3.5dialkyl-4.4'-dihydroxychalcones

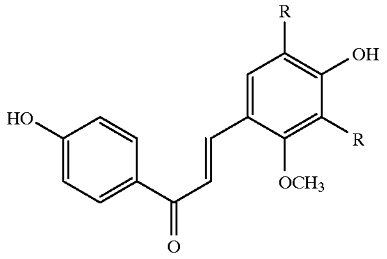

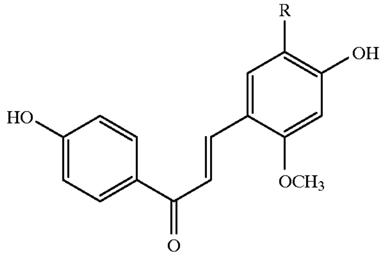

2-Methoxy-4-alk-2-enyloxybenzaldehyde is condensed with an 4-alk-2-enyloxyacetophenone as described in the synthesis of the chalcone allyl ethers (see e.g. Example 2.24). The protecting alkenyl groups are removed by heating an acidic methanolic solution to which is added a small amount of water with palladium on carbon as described in combination with the synthesis of 4'-hydroxychalcone (Example 2.19).

38) Preparation of 2-methoxy-5alkyl-4,4'-dihydroxychalcones or 2-methoxy-3,5-dialkyl-4,4'-dihydroxychalcones

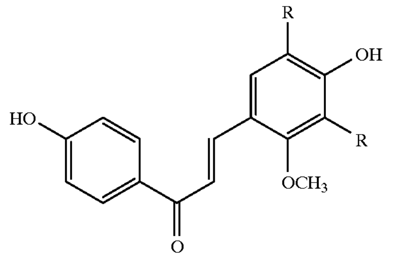

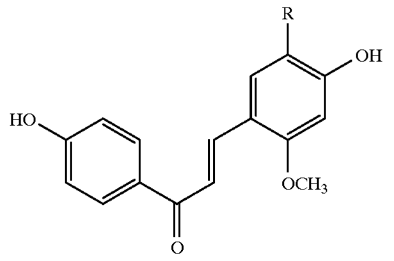

The appropriate 2-methoxy-5-alkyl-4-hydroxyenzaldehyde or 2-mnethoxy-3,5-dialkyl-4-hydroxybenzaldehyde is condensed with 4-hydroxyacetophenone in acidic ethanol as described in combination with the synthesis of licochalcone A (Example 2.16).

39) Preparation of 2-methoxy-3,5-dialkyl-6,4'-dihydroxychalcones

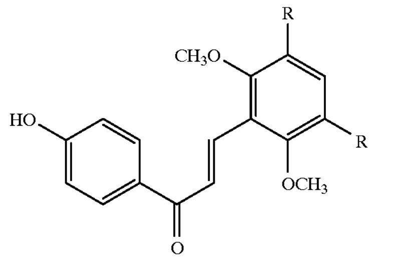

The appropriate 2-methoxy-3,5-dialkyl-6-hydroxybenzaldehyde is condensed with 4-hydroxyacetophenone in alkaline aqueous ethanol as described by T. A. Geissman and R. O. Clinton in *J. Am. Chim. Soc.* 68 (1946), 697–700.

40) Preparation of 2-mnethoxy-5-alk-2-enyl-4,4'-dihydroxychalcones

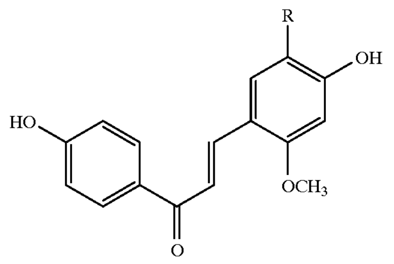

The appoprate 2-methoxy-5-alk-2-enyl-4-hydroxybenzaldehyde is condensed with 4-hydroxyacetophenone as described in the synthesis of licochalcone A (Example 2.16).

41) Preparation of 2-methoxy-5-alk-2-enyl-6,4'-dihydroxychalcones

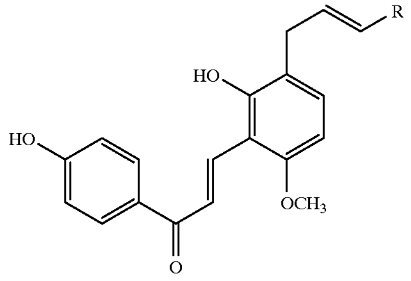

The appropriate 2-methoxy-5-alk-2-enyl-6-hydroxybenzaldehyde is condensed with 4-hydroxyacetophenone as described by T. A. Geissman and R. O. Clinton in *J. Am. Chem. Soc.* 68 (1946), 697–700.

42) Preparation of 2-methoxy-5-propyl-6,4'-dihydroxychalcone, 2-methoxy-5-(α-alkylpropyl)-6,4'-dihydroxychalcones, 2-methoxy-5-(α,α-dialkylprolpyl)-6,4-dihydroxychalcones or 2-methoxy-(α,α,β-dialkylpropyl)-6,4'-dihydroxychalcones

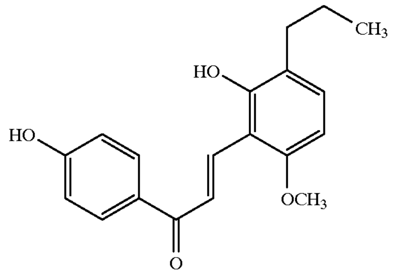

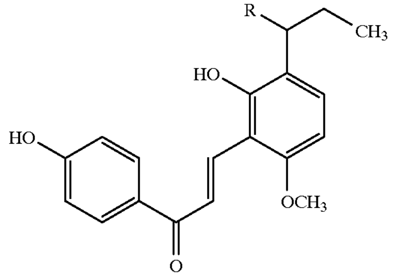

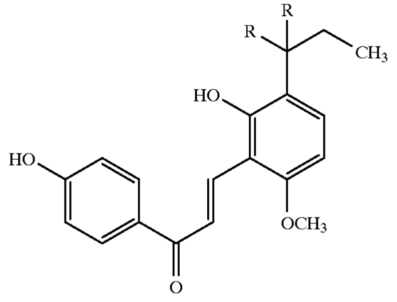

-continued

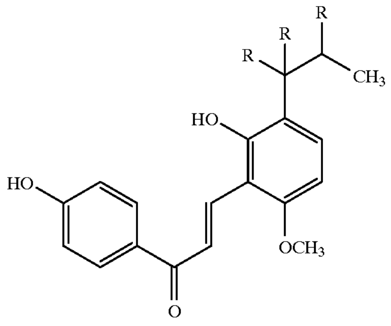

A solution of the appropriate 2-methoxy-5-alk-2-enyl-4,4'-dihydroxychalcone (e.g. licochalcone A) in an aprotic solvent is hydrogenated using dyrdidocarbonyltris (triphenylphosphine)rhodium(I) as a catalyst. This catalyst selectively catalyses the reduction of terminal double bonds.

43) Preparation of 2-methoxy-5-propyl-4,4'-dihydroxychalcone, 2-methoxy-5-(α-alkylropyl)-4,4'-dihydroxychalcone, 2-methoxy-5(α,α-dialkylpropyl)-4,4'-dihydroachalcone or 2-methoxy-(α,α,β-dialkylpropyl)-4,4'-dihydroxychalcones

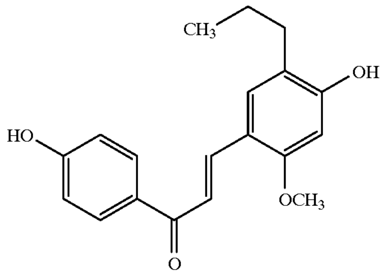

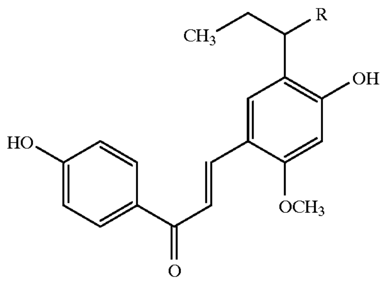

-continued

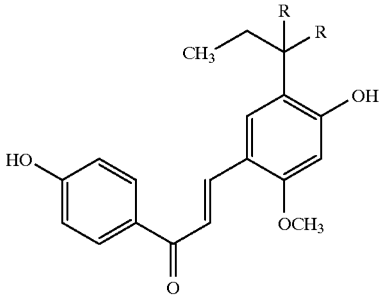

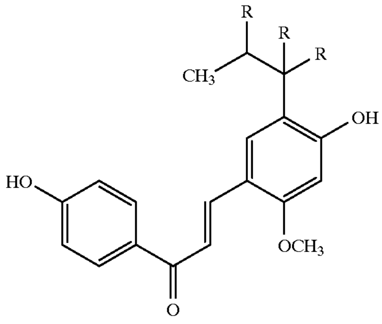

A solution of the appropriate 2-methoxy-5-alk-2-enyl-4,4'-dihydroxychalcone (e.g. licochalcone A) in an aprotic solvent is hydrogenated using hydridocarbonyltris (triphenylphosphine)rhodium(I) as a catalyst which selectively catalyses the reduction of terminal double bonds.

EXAMPLE 3

Formulations of pharmaceutical compositions

Tablets

An appropriate amount of α,β-unsaturated bis-aromatic ketone is added to a mixture of potato starch and lactose (7:3) and a granule is prepared by moistening with a 4% solution of gelatin in water, sifting and drying. Tablets are compressed after addition of glidants and lubricants such as magnesium stearate and talc.

Thus, tablets containing 500 mg of α,β-unsaturated bis-aromatic ketone are prepared by mixing 500 g of the ground chalcone with 36 g of lactose and 84 g of potato starch. The mixture is moistened with a 4% aqueous solution of gelatin and converted into a granulate by sifting or spraying. The granulate is compressed into 1000 tablets with an average weight of 650 mg and a diameter of 13.5 mm after addition of 30 g of a mixture of talc and magnesium stearate (9:1).

Suppositories

The appropriate amount of α,β-unsaturated bis-aromatic ketone is suspended into 2 g of melted hard fat and poured into a matrix.

Capsules

The appropriate amount of α,β-unsaturated bis-aromatic ketone, if convenient mixed with a diluent like potato starch, lactose or both, is filled into a prefabricated cylindrical capsule, and the capsule is closed.

Liquids for oral administration

The α,β-unsaturated bis-aromatic ketone is dissolved in a mixture of water and ethanol. Flavouring substances such as a licorice extract and a sugar solution may be added to the solution.

EXAMPLE 4

Effect of licochalcone A on the in vitro growth of *L. major* and *L. donovani* promastigotes Materials and methods Parasite cultures. The WHO reference vaccine strain of *L. major* originally isolated from a patient in Iran kindly provided by R. Behin, WHO Immunology Research and Training Centre, Lausanne, Switzerland and a Kenyan strain of *L. donovani* (MHOM(/KE/85/NLB 274) kindly provided by Kenya Medical Research Institute, Nairobi, Kenya. Promastigotes were cultured in medium 199 containing 0.02 mg/ml gentamycin, 25 mM Hepes, 4 mM L-glutamine, and 20% heat inactivated fetal calf serum (56° C., 30 min). Incubation was carried out at 26° C. Promastigotes were harvested on day 3 and 6 of the culture and used for the parasiticidal assay.

Drugs. Licochalcone A was purified from Chinese licorice roots as described in Example 1.1 mg of licochalcone A was dissolved in 20 μl of 99% (v/v) ethanol, and then added to 980 μl of medium 199, stored at −20° C.

Effect on promastigotes. The effect of licochalcone A on promastigotes was assessed by a method similar to the one described by Pearson et al., by incubating promastigotes ($3\times10^6$/ml) at 26° C. for 2 hrs in the presence of licochalcone A or the medium alone in 96 wells flat bottom microtiter plates. Following incubation, 100 μCi of [$^3$H] thymidine was added to each well and further incubated for 18 hrs. Promastigotes were then harvested on filter paper by means of a cell harvester (Skatron, Lierbyen, Norway), extensively washed with distilled water and counted in a scintillation counter (Minaxi Ti-Carb 4000, United Technologies, Packard, USA). The promastigotes were also counted microscopically and their flagellar motility was assessed.

Results

The antileishzmanial activity of licochalcone A was tested on promastigotes of *L. major* and *L. donovani* at both logarithmic and stationary stages of growth. The 3-day culture was taken as the logarithmic and the 6-day culture as the stationary stage promastigotes. Licochalcone A inhibited the growth of promastigotes of both *L. major* and *L. donovani* in a concentration-dependent manner (Table 4.1). A significant reduction of growth of promastigotes of *L. donovani* at 3-day and 6-day cultures was observed at 5 μg/ml. The licochalcone A exhibited a stronger inhibitory effect on the 6-day culture as compared to the 3-day culture of the parasite. The 50% inhibition of the log phase promastigotes was reached at a concentration of licochalcone A between 2 μg/ml and 5 μg/ml whereas the 50% inhibition of the stationary phase promastigotes was reached at a concentration of licochalcone A around 2 μg/ml. At 20 μg/ml of Licochalcone A there was total inhibition of promastigotes growth at both stages. More than 90% inhibition of promastigote growth was observed with 10 μg/ml on the growth of *L. major* 3-day cultures and 6-day cultures and the growth of *L. donovani* 6-days cultures.

The stationary phase (6-day culture) which is known to be the infective form of the parasite was more sensitive than the log phase (3-day culture).

Table 4.1. Comparison of the effect of licochalcone A on *L. major* and *L. donovani* promastigotes from 3-days and 6-days cultures. The results are from 5 experiments and are given as mean ±SEM percentage inhibition of $^3$H-thymidine uptake in control promastigotes grown in medium alone.

TABLE 4.1

Comparison of the effect of licochalcone A on *L. major* and *L. donovani* promastigotes from 3-days and 6-days cultures. The results are from 5 experiments and are given as mean ± SEM percentage inhibition of $^3$H-thymidine uptake in control promastigotes grown in medium alone.

| Licochalcone A (μg/ml) | *L. major* 3-day | *L. major* 6-day | *L. donovani* 3-day | *L. donovani* 6-day |
|---|---|---|---|---|
| 20 | 96.0 ± 7.5 | 99.4 ± 1.1 | 96.7 ± 0.08 | 98.3 ± 0.8 |
| 10 | 91.9 ± 8.4 | 96.4 ± 1.2 | 81.5 ± 8.0 | 91.9 ± 3.1 |
| 5 | 63.9 ± 13.0 | 80.7 ± 6.4 | 53.7 ± 14.0 | 70.1 ± 12.4 |
| 2 | 14.8 ± 21.5 | 42.6 ± 19.7 | 23.5 ± 16.4 | 42.2 ± 16.6 |
| 1 | 3.6 ± 11.5 | 15.8 ± 16.5 | 15.2 ± 14.5 | 30.4 ± 23.8 |

Conclusion

The major importance of this finding was that licochalcone A at non-toxic concentrations inhibited the growth of the extracellular promastigote stage of both *L. major* and *L. donovani*. The lethal effect of licochalcone A on *L. donovani*, the causative agent of the fatal visceral leishmaniasis, is important especially in the light of resistance development against antimonials, the only antileishmanial drugs in use.

Licochalcone A was lethal to both the infective and the non-infective promastigote forms of the parasite, and therefore has the potential of preventing macrophage infection in a prophylactic manner.

EXAMPLE 5

Effect of seven bis-aromatic α,β-unsaturated ketones on the in vitro growth of *L. major* promastigotes Materials and methods Parasite cultures. The same parasite culture as described in Example 4. Promastigotes were harvested on day 4 of the culture and used for the parasiticidal assay.

Drugs. Seven bis-aromatic α,β-unsaturated ketones prepared as described in Example 2.

Effect on promastigotes. The effect of seven α,β-unsaturated bis-aromatic ketones was assessed by a method similar to the one described by Pearson et al. (1984) by incubating promastigotes ($3\times10^6$/ml) at 26° C. for 2 hrs in the presence of drugs or the medium alone in 96 wells flat bottom microtiter plates. Following incubation, 100 μC of $^3$H-thymidine was added to each well and further incubated for 18 hrs. Promastigotes were then harvested on filter paper by means of a cell harvester (Skatron, Lierbyen, Norway), extensively washed with distilled water and counted in a scintillation counter (Minaxi Ti-Carb 4000, United Technologies, Packard, USA).

Results

Table 5.1. Comparison of the effect of seven bis-aromatic α,β-unsaturated ketones on *L. major* promastigotes from 4-days cultures. The results are given as mean±SEM percentage inhibition of $^3$H-thymidine uptake in control promastigotes grown in medium alone.

TABLE 5.1
Comparison of the effect of seven bis-aromatic α,β-unsaturated ketones on *L. major* promastigotes from 4-days cultures. The results are given as mean ± SEM percentage inhibition of $^{3}$H-thymidine uptake in control promastigotes grown in medium alone.
| drug (μg/ml) | | n | mean ± SEM |
|---|---|---|---|
| 20 | 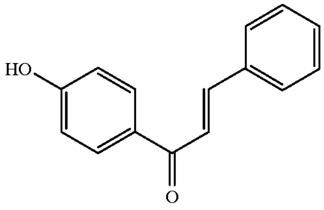 | 7 | 91.9 ± 2.1 |
| 10 | | 7 | 82.8 ± 4.1 |
| 5 | | 7 | 70.8 ± 4.6 |
| 1 | | 7 | 35.9 ± 3.2 |
| 20 | 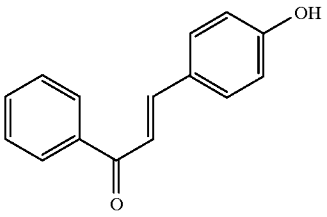 | 7 | 94.3 ± 1.6 |
| 10 | | 7 | 84.5 ± 2.8 |
| 5 | | 7 | 70.1 ± 5.0 |
| 1 | | 7 | 39.1 ± 7.8 |
| 10 | 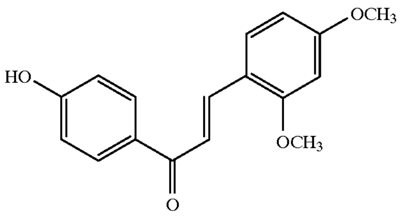 | 3 | 19.9 ± 4.6 |
| 5 | | 3 | 61.8 ± 6.8 |
| 1 | | 3 | 27.3 ± 7.6 |
| 0.5 | | 3 | 19.4 ± 5.6 |
| 10 | 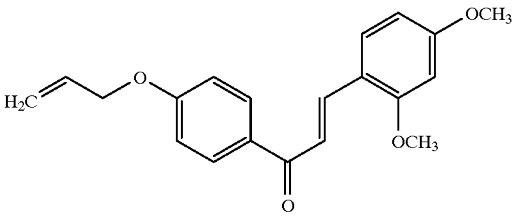 | 3 | 84.3 ± 3.5 |
| 5 | | 3 | 64.5 ± 4.6 |
| 1 | | 3 | 17.5 ± 5.8 |
| 0.5 | | 3 | 7.5 ± 6.9 |
| 10 | 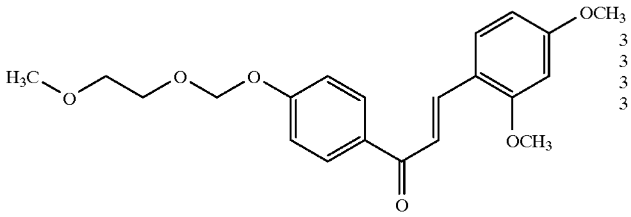 | 3 | 60.5 ± 5.6 |
| 5 | | 3 | 31.0 ± 6.7 |
| 1 | | 3 | 14.0 ± 4.5 |
| 0.5 | | 3 | 20.0 ± 7.5 |

TABLE 5.1-continued

Comparison of the effect of seven bis-aromatic α,β-unsaturated ketones on *L. major* promastigotes from 4-days cultures. The results are given as mean ± SEM percentage inhibition of $^3$H-thymidine uptake in control promastigotes grown in medium alone.

| drug (μg/ml) | | n | mean ± SEM |
|---|---|---|---|
| 10 | 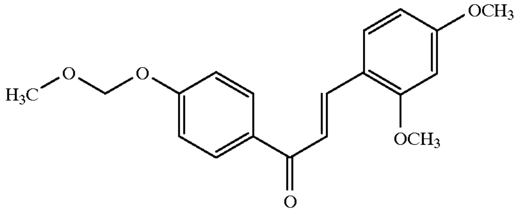 | 2 | 65.0 ± 5.9 |
| 5 | | 2 | 56.3 ± 7.6 |
| 1 | | 2 | 18.1 ± 7.8 |
| 0.5 | | 2 | 8.5 ± 5.6 |
| 10 | 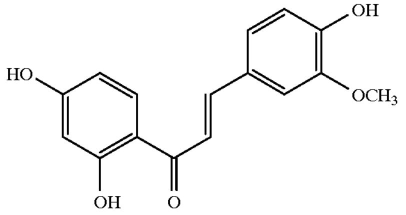 | 2 | 83.3 ± 4.6 |
| 5 | | 2 | 66.7 ± 5.5 |
| 1 | | 2 | 14.3 ± 6.4 |
| 0.5 | | 2 | 7.8 ± 6.7 |

EXAMPLE 6

Effect of licochalcone A on the in vitro growth of *L. major* and *L. donovani* amastigotes Materials and Methods Macrophage culture. The method used in this studv was a modification of the one described by Berman et al. (1979). Human peripheral blood monocytes were obtained by Ficoll-Hypaque fractionation of blood from the Blood Bank, Rigshospitalet, Copenhagen, Denmark. Washed cells were suspended in medium RPMI-199 containing penicillin (50 U/ml), and streptomycin (50 μg/ml), 25 mM Hepes, 4 mM L-glutamine, and 10% heat inactivated fetal calf serum (56° C., 30 min). One milliliter of suspension containing $1\times10^6$ mononuclear cells was added to each well (16 mm in diameter, with one piece of cover glass in 12 mm diameter) of 24 wells of plastic culture trays (Nunc, Denmark). After 4 h and again after 3 days of incubation at 37° C. in 5% $CO_2$-95% air, old medium was removed and washed with warm fresh medium three times, and then replaced with warm fresh medium.

Infection of macrophages with *L. major* promastigotes. After 6 days incubation the old medium was removed, and one milliliter of $1\times10^7$ 4 days culture of *L. major* promastigotes (same promastigotes culture as in Example 4) was added to each well. After 24 h infection, rnacrophage cultures were washed three times with warm fresh medium and replenished with warm fresh medium with different concentrations of licochalcone A or medium alone. The medium was changed every 3 days. After infection, day 3 and day 6 a certain number of macrophage cultures were fixed with absolute methanol, stained with 5% Giemsa stain for 10 min, and examined by light microscopy (x1,000). The percentage of macrophages that contained amastigotes and the number of amastigotes present per infected macrophage were determnined in replicate cultures by counting 200 cells per well.

Results

As shown in Table 6.1 the number of amastigotes/infected macrophage/100 macrophages was reduced from 299/63/100 in controls to 11/5/100 in the presence of 5 μg/ml of licochalcone A.

Table 6.1. Effect of licochalcone A on *L. major* amastigotes. Human macrophages were infected with promastigotes. After 24 hrs the free promastigotes were removed. The infected macrophages were then incubated with licochalcone A for 3 days and 6 days. The results are presented as the number of amastigotes/number of infected nxmacrophages/100 macrophages.

TABLE 6.1

Effect of licochalcone A on *L. major* amastigotes. Human macrophages were infected with promastigotes. After 24 hrs the free promastigotes were removed. The infected macrophages were then incubated with licochalcone A for 3 days and 6 days. The results are presented as the number of amastigotes/number of infected macrophages/100 macrophages.

| Licochalcone A (μg/ml) | 0-day | 3-day | 6-day |
|---|---|---|---|
| 10 | 237/51/100 | 10/5/100 | 6/4/100 |
| 5 | " | 18/7/100 | 11/5/100 |
| 1 | " | 54/43/100 | 45/45/100 |
| 0 | " | 252/52/100 | 299/63/100 |

Conclusion

The amastigote phase of the parasite is the phase to which the parasite converts to in the macrophages of the host. From both tables it is seen that not only the total amount of parasites was reduced, but also the amount of cells infected was reduced when treated with licochalcone A.

EXAMPLE 7

Effect of licochalcone A on the in vitro multiplication of *Leishmania major* amastigotes in human macrophages and U937 cells Materials and methods:

Drugs. Licgchalcone A was purified from Chinese licorice roots as described in Example 1.

Human PBM-derived (Peripheral Blood Mononuclear cells) macrophage culture. The methods which were used in this study are a modification of the methods described by Berman et al. Human peripheral blood monocytes, obtained by Ficoll-Hypaque fractionation, and washed cells were suspended in medium RPMI-199 containing 550 U/ml of penicillin and 50 U/ml of streptomycin, 25 mM Hepes, 4 mM L-glutamine, and 10% heat inactivated fetal calf serum at 56° C. for 30 min. One ml of suspension containing $5\times10^6$ mononuclear cells was added to each well (16 mm in diameter, with one piece of cover glasses in 12 mm diameter) of 24 wells of plastic culture trays (Nunc, Denmark). 200 μl of $5\times10^6$ mononuclear cells were added to each well in flat-bottom microtiter plates (Nunc, Denmark). After 4 h and again after 3 days of incubation at 37° C. in 5% $CO_2$-95% air, old medium was removed and washed with warm fresh medium three times and then replaced with warm fresh medium.

U937 cell culture. U937 cells were maintained at 37° C. as suspension cultures in the same medium as the one used for macrophages culture. Two days before infection, U937 cells were treated with 10 ng/ml of phorbol myristate acetate (PMA, L.C. Services, Woburn, Mass.) in the culture medium. This caused the cells to differentiate into a non-dividing adherent monolayer.

Promastigotes culture. The *L. major* (WHO vaccine strain) promastigotes were obtained from footpad tissue of BALB/c mice infected 1 to 2 months previously by subcutaneous inoculation with $1\times10^7$ stationary phase promastigotes. The promastigotes were passaged in culture two times before use. The culture was the same as the one used in Example 6.

Infection of macrophages with *L. major* promastigotes. After 6 days incubation the old medium was removed, and one ml or 200 μl of $1\times10^7$/ml 6 days culture of *L. major* promastigotes as described in Example 6 was added to each well, and the cultures were carried out at 34° C. After 24 h infection, macrophages were washed three times with warm fresh medium and replenished with warm fresh medium with different concentrations of licochalcone A or medium alone.

Infection of U937 cells with *L. major* promastigotes. Differentiated U937 cells were infected with *L. major* promastigotes as described above for macrophages.

Measurement of intracellular parasite killing

Killing was quantified by a modification of a technique described by Berman et al. Briefly, 3 days after infection, microtiter well cultures were rinsed once with medium, exposed to 100 μl of prewarmed (37° C.) 0.01% sodium dodecyl-sulfate (SDS) in medium RPMI 1640, and returned to 34° C. for 15 min. By this procedure, macrophages were lysed, according to microscopic observation, and amastigotes were released. 100 μl of medium RPMI 1640 with 20% HFCS were added to each well without removal of the lysing solution. The plates were then transferred to a 26° C. incubator, and amastigotes were left to transform to promastigotes. After 48 h, parasite growth was recorded by adding 1 μCi of $^3$H-thymidine (New England Nuclear Corp., Boston, Mass.) to each well. The parasites were harvested 24 h later on glass fiber filters with a harvesting machine (Skatron, Lierbyen, Norway), and $^3$H-thymidine incorporation was measured in a liquid scintillation counter (Tricarb; Packard Instrument Co., Inc., Rockville, Md.). The parasite survival index (PSI) was determined. This index is the mean $^3$H-thymidine incorporation (cpm) in treated infected cells as compared with the untreated infected cells.

$$PSI = \frac{\text{cpm of treated infected cells}}{\text{cpm of untreated infected cells}} \times 100$$

3 days and 6 days after infection, macrophage cultures on cover glasses were fixed with absolute methanol, stained with 5% Giemsa stain for 10 min and examined by light microscopy (×1,000). The percentage of macrophages that contained amastigotes and the number of amastigotes and promastigotes present per infected macrophage were determined in replicate by counting 200 cells per well in microscope.

Results

Figure 1:
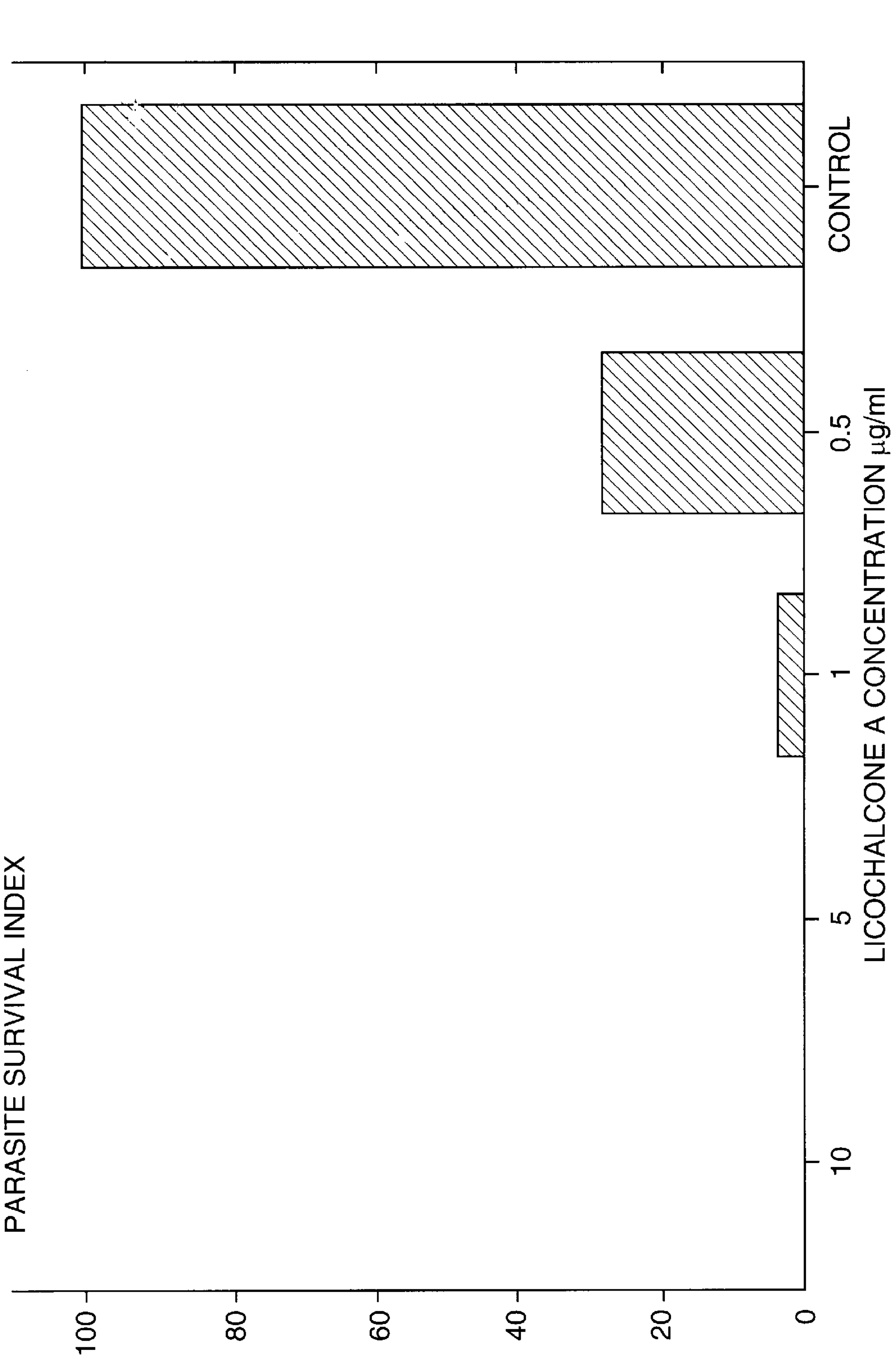
FIG. 1 shows the effect of licochalcone A on intracellular survival of *Leishmania major* vaccine strain in U937 cells measured by the parasite survival index (PSI).
Figure 2:
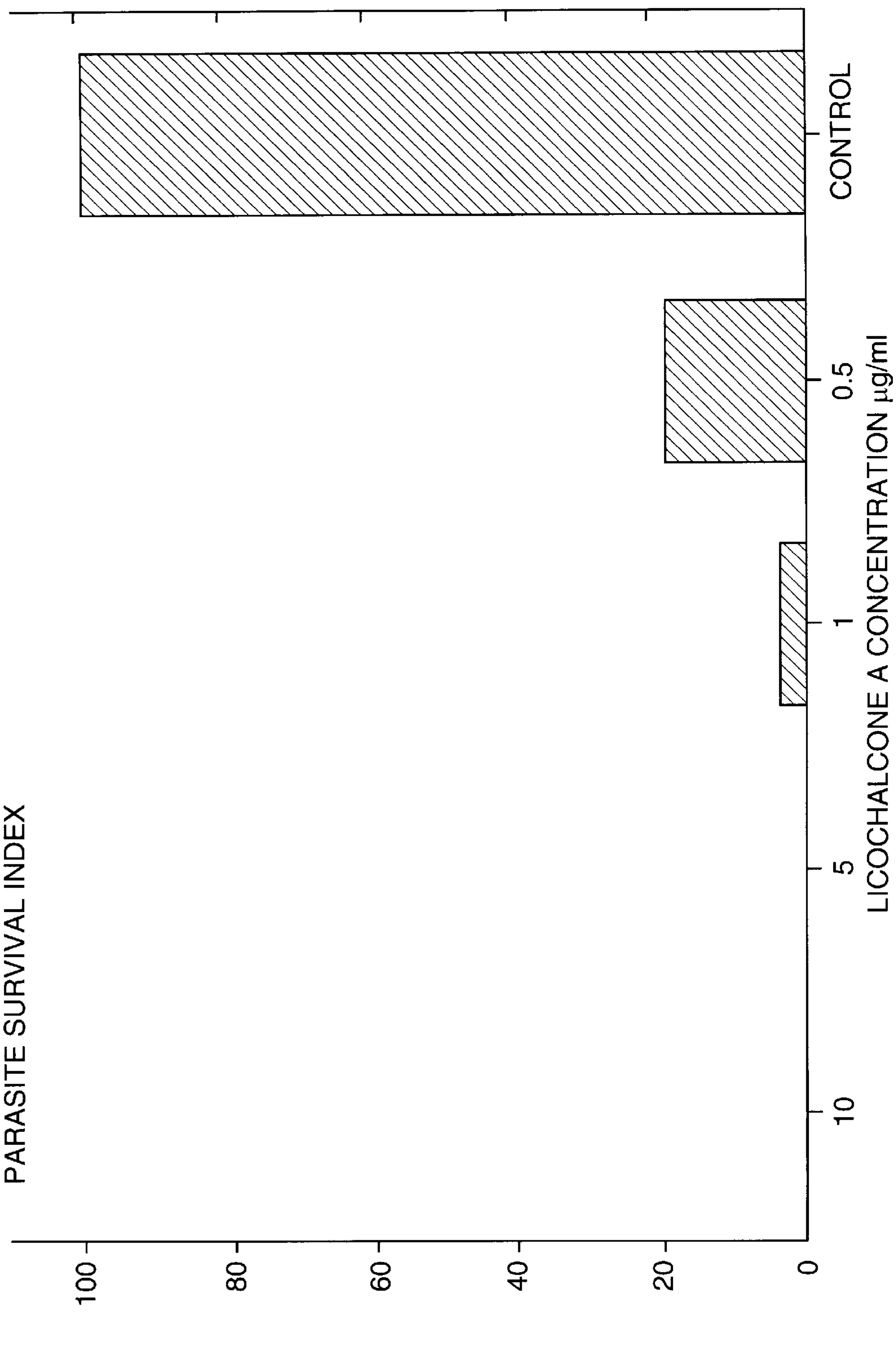
FIG. 2 shows the effect of licochalcone A on intracellular survival of *Leishmania major* vaccine strain in human peripheral blood monocytes derived macrophages measured by the parasite survival index (PSI).

The PSI-index was plotted against the concentration of licochalcone A. The plots are shown in FIG. 1 and FIG. 2.

Table 7.1. Effect of licochalcone A on *L. major* amastigotes in U937 cells (macrophage cell line). The data is given as mean percentage of 3 experiments. Microscopic counting.

TABLE 7.1

Effect of licochalcone A on *L. major* amastigotes in U937 cells (macrophage cell line). The data is given as mean percentage of 3 experiments. Microscopic counting.

| Licoch. A (μg/ml) | % of infec. cells | amast. per cell | proma. per cell | % of amast. | total amast. ($\times10^6$) | total proma. ($\times10^6$) |
|---|---|---|---|---|---|---|
| | | | 0 days after infection | | | |
| | 40.7 | 2.9 | 0.4 | 86.9 | 117 | 17.7 |
| | | | 3 days after infection | | | |
| 10 | 0 | | | | | |
| 5 | 0 | | | | | |
| 1 | 19.0 | 2.0 | 0.2 | 91.2 | 38.3 | 3.7 |
| 0.5 | 28.0 | 2.3 | 0.1 | 96.6 | 65.0 | 2.3 |
| control | 43.3 | 5.7 | 0.2 | 97.2 | 258.3 | 7.0 |
| | | | 6 days after infection | | | |
| 10 | 0 | | | | | |
| 5 | 0 | | | | | |
| 1 | 3.0 | 1.8 | 0 | 100 | 5.3 | 0 |
| 0.5 | 13.7 | 3.1 | 0 | 100 | 42.0 | 0 |
| control | 47.3 | 6.3 | 0.02 | 99.9 | 298.3 | 2.0 |

Table 7.2. fct of licochalcone A on *L. major* in human PBM-derived macrophages The data is given as mean percentage of 3 experiments. Microscopic counting.

TABLE 7.2

Effect of licochalcone A on *L. major* in human PBM-derived macrophages. The data is given as mean percentage of 3 experiments. Microscopic counting.

| Licoch. A (μg/ml) | % of infec. cells | amast. per cell | proma. per cell | % of amast. | total amast. ($\times10^6$) | total proma. ($\times10^6$) |
|---|---|---|---|---|---|---|
| | | | 0 days after infection | | | |
| | 36.3 | 2.1 | 0.2 | 91.4 | 76.7 | 7.3 |

TABLE 7.2-continued

Effect of licochalcone A on *L. major* in human PBM-derived macrophages. The data is given as mean percentage of 3 experiments. Microscopic counting.

| Licoch. A (μg/ml) | % of infec. cells | amast. per cell | proma. per cell | % of amast. | total amast. ($\times10^6$) | total proma. ($\times10^6$) |
|---|---|---|---|---|---|---|
| 3 days after infection | | | | | | |
| 10 | 0 | | | | | |
| 5 | 0 | | | | | |
| 1 | 10.7 | 1.7 | 0.2 | 88.2 | 17.7 | 2.0 |
| 0.5 | 14.0 | 1.7 | 0.1 | 91.6 | 23.3 | 2.0 |
| control | 44.0 | 3.6 | 0.1 | 98.0 | 157.7 | 3.3 |
| 6 days after infection | | | | | | |
| 10 | 0 | | | | | |
| 5 | 0 | | | | | |
| 1 | 7.3 | 22 | 0 | 100 | 16 | 0 |
| 0.5 | 8.0 | 1.7 | 0 | 100 | 14 | 0 |
| control | 44.0 | 4.4 | 0.1 | 100 | 99.6 | 0 |

Discussion

The major importance of this finding is that licochalcone A at non-toxic concentrations inhibited the growth of both the extracellular promastigote stage and the intracellular amastigote stage of *L. major*. By comparing the results shown in Table 7.1 and Table 7.2 with the results shown in FIG. 1 and FIG. 2 it is seen, e.g. for infected U937 cells treated with licochalcone A in a concentration of 1 μg/ml, that although 2.0 amastigotes per cell were seen in the microscope in the treated group compared to 5.7 amastigotes in the control group, the PSI index for the same concentration of licochalcone A was only about 5%. This means that many of the parasites seen in the microscope were killed and therefore not able to take up $^3$H-thymidine. Therefore, the best method to measure the intracellular killing of the parasites is the PSI-index. Inhibition of growth and multiplication of the amastigote form of the parasite is crucial, since Leishmania parasites exist solely inside macrophages during established infection.

EXAMPLE 8

Effect of licochalcone A on the in vivo growth of *L. major*

Materials and Methods

Mice. BALB/c female mice aged eight weeks old were used throughout.

Parasite. The maintenance, cultivation, and isolation of the promastigote-stage of the parasite *L. major* (WHO reference vaccine strain) have been described in detail in Example 4. For animal infection, 6 groups of 10 mice each received s.c. injections (in 0.05 ml of PBS) in the left hind footpad with $1\times10^7$ stationary phase promastigotes.

The lesions that developed in the footpad were measured with a dial-calliper and expressed as footpad thickness increase (in mm). The footpad thickness of mice was measured before infection and every 3 days after 7 days of infection. From 7 days of infection, mice received licochalcone A injections i.p. or intralesionally once a day. After 42 days of licochalcone A injection, some of the mice were killed and the footpads, spleens and livers removed. The parasite loads in the footpads and livers were estimated by a modification of the method described by Liew et al. 1990. Briefly, the tissues were cut and minced into very small pieces, and supernatants containing the released parasites were cultured in 15 ml of medium RPMI 199 containing 0.02 mg/ml gentamycin, 25 mM Hepes, 4 mM L-glutamine, and 20% heat inactivated fetal calf serum (56° C., 30 min) in 25 cm$^2$, 50 ml culture flask (Nunc, Roskilde, Denmark). Incubation was carried out at 28° C. for 3 days and then pulsed with 1 μCi of $^3$H-thymidine. Cultures were harvested 18 h later on filter paper by a cell harvester (Skatron, Lierbyen, Norway), extensively washed with distilled water and counted in a scintillation counter (Minaxi Ti-Carb 4000, United Technologies, Packard, USA). The results were expressed as cpm. The footpads, spleens and livers impression was also estimated.

Drugs. One mg of licochalcone A was dissolved in 20 μl of 99% (v/v) ethanol, and then 980 μl of medium 199 was added an the resulting mixture was stored at −20° C. before use.

Results

TABLE 8.1

Effect of licochalcone A on the parasitic load of the footpad of the mice infected with *L. major*. The results are from 2 mice from each group and are given as mean $\times10^3$ cpm of $^3$H-thymidine uptake.

| Group | mean |
|---|---|
| 1) 100 μg i.p. | 89.0 |
| 2) 50 μg i.p. | 58.0 |
| 3) 50 μg intralesional | 282.6 |
| 4) 20 μg intralesional | 243.5 |
| 5) Buffer i.p. | 357.6 |
| 6) Buffer intralesional | 485.4 |

TABLE 8.2

Effect of licochalcone A on the parasitic load of the liver of the mice infected with *L. major*. The results are from 2 experiments and are given as mean $\times10^3$ cpm of $^3$H-thymidine uptake.

| Group | mean |
|---|---|
| 1) 100 μg i.p. | 12.8 |
| 2) 50 μg i.p. | 11.7 |
| 3) 50 μg intralesional | 20.8 |
| 4) 20 μg intralesional | 10.8 |
| 5) Buffer i.p. | 184.0 |
| 6) Buffer intralesional | 90.8 |

TABLE 8.3

Effect of licochalcone A on *L. major* parasite in the footpad, spleen and liver of the mice infected with *L. major*. The results are given as amastigotes findings on the impression smear.

| Group | Footpad | Spleen | Liver |
|---|---|---|---|
| 1) 100 μg i.p. | + | − | − |
| 2) 50 μg i.p. | + | − | − |
| 3) 50 μg intralesional | + | + | + |
| 4) 20 μg intralesional | + | + | + |
| 5) Buffer i.p. | +++ | ++ | ++ |
| 6) Buffer intralesional | +++ | ++ | ++ |

− no parasite amastigotes detected in 5 fields of microscopical vision
+: parasite amastigotes from 5 fields of microscopical vision < 100
++: parasite amastigotes from 5 fields of microscopical vision = 100–500
+++: parasite amastigotes from 5 fields of microscopical vision = 500–1000

Figure 3:
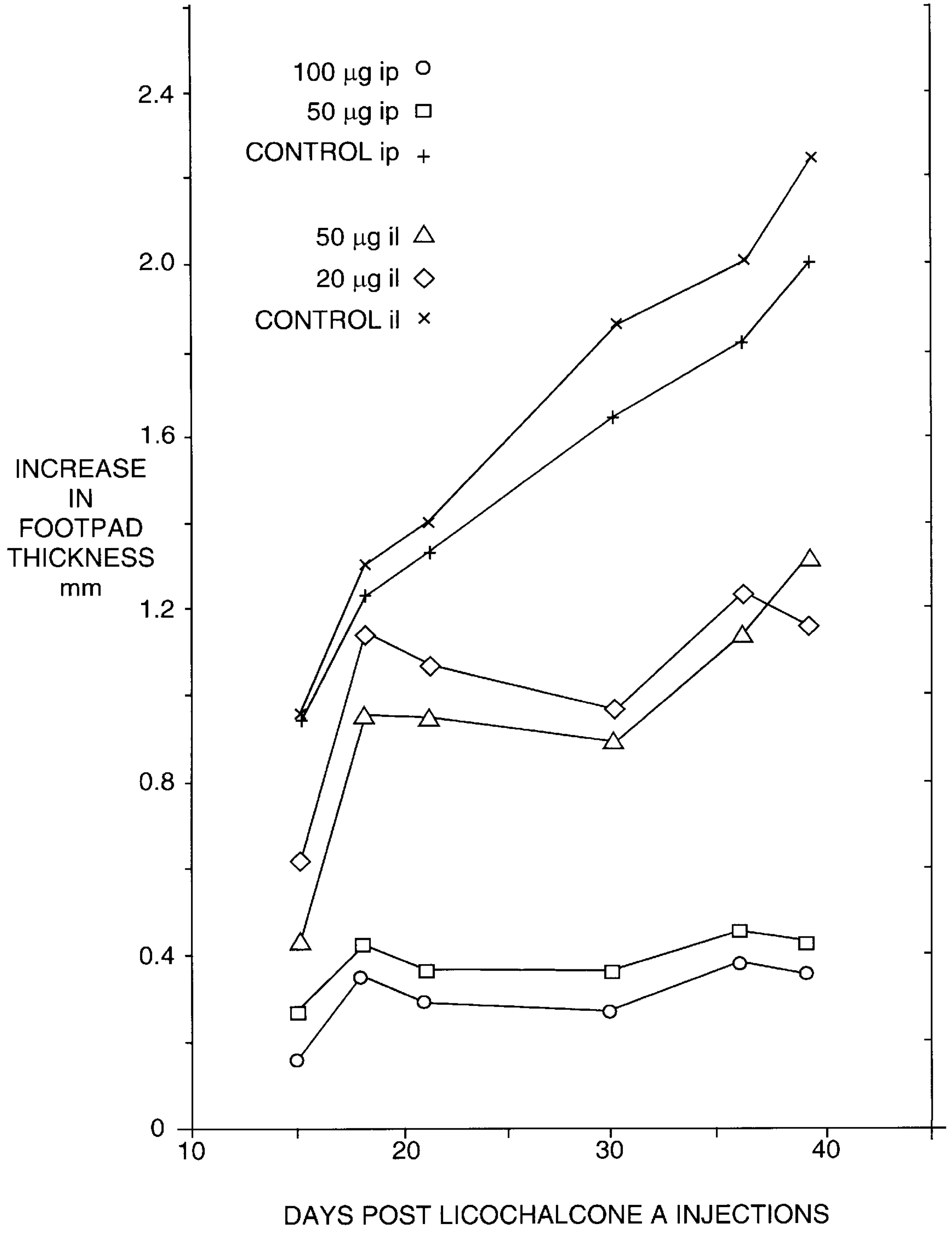
FIG. 3 shows the effect of licochalcone A on the parasitic load of the footpad of the mice infected with *Leishmania major* as described in example 8.

FIG. 3 shows the effect of licochalcone A on footpad thickness increase (swelling) in BALB/c mice infected with *L. major*, expressed in mm.

Conclusion

It appears that intraperitoneal administration of licochalcone A gives a better effect than intralesional administration. This could be due to leaking of the administered drug from the lesions. However, the latter administration form is also effective compared to the results from the group treated with buffer.

From FIG. 3 the same picture is seen, in that the increase in the footpad thickness is less in the group treated intraperitoneally compared to the group treated intralesionally. The footpad thickness is an expression of the degree of disease, in that the more the infected footpad is swollen the more disease has developed.

These data clearly demonstrate that both intraperitoneal and intralesional administration of licochalcone A prevents lesion development in mice caused by Leishmania infection.

EXAMPLE 9

Effect of licochalcone A on *L. donovani* infection in hamsters

Animals. Male Syrian golden hamsters (Mesocricetus auratus), 50–70 g body weight, were used throughout.

Parasite. *L. donovani* (MHOM/KE/85/NLB 439) promastigotes were cultured in medium 199 containing 0.02 mg/ml gentamycin, 25 mM Hepes, 4 mM L-glutamine, and 10% heat inactivated fetal calf serum (56° C., 30 min).

Drugs. Licochalcone A was dissolved in 20 $\mu$l of 99% (v/v) ethanol, and the 980 $\mu$l of medium 199 was added, and the resulting mixture was stored at −20° C.

Animals were intracardially inoculated with $2\times10^7$ *L. donovani* promastigotes in 0.1 ml medium 199 (Day 0). One hour later, one of the animals was killed. The liver and the spleen were weighed. The liver and the spleen impression smears were made. After air-drying, the impression smears were fixed with water-free methanol and stained with Giemsa. Five of the animals were treated (i.p.) with licochalcone A (10 mg/kg body weight two times per day) from Day+1 to Day+7. Another five animals were treated with 0.85% NaCl. The animals were killed on Day+8. The liver and spleen were weighed, and the liver and the spleen impression smears were made. The number of the parasite in the liver and the spleen were counted under microscope. The spleen of the animals were cut into very small pieces, cultured in 15 ml of the culture medium at 26° C. overnight. The spleen cultures were centrifuged at 1,000 rpm for 10 min and then, the supernatant were removed and the residue was recultured in the same medium for five days at 26° C. 200 $\mu$l of the spleen culture was added into one well of 96 wells flat bottom microtiter plates (triplicate). 100 $\mu$C of $^3$H-thynidine were added to each well and the incubation was continued for 18 h. Promastigotes were then harvested on filter pater by means of a cell harvester (Skatron, Lierbyen, Norway), extensively washed with distilled water and counted in a scintillation counter (Minaxi TiCarb 4000, United Technologies, Packard, USA).

Results and conclusions

As shown in FIG. 8, the parasite load both in the liver and the spleen of animals receiving intraperitoneal injections of 10 mg per kg body weight licochalcone A two times per day for 7 days was reduced to almost undetectable levels.

The in vivo inhibitory effect of licochalcone A on *L. donovani*, the causative agent of the fatal visceral leishmaniasis, is quite promising especially in the light of resistance development against antimonials, the only antileishmanial drug in use.

EXAMPLE 10

Effect of Licochalcone A on pentostam resistant *L. major* promastigotes

The experiment was performed the same way as described in Example 4.

Results and conclusions

The results are shown in FIGS. 9A, 9B and 9C. As it can be seen from the figures, licochalcone A at concentrations of 5 $\mu$g/ml (FIG. 9A) completely inhibited the growth of pentostam resistant Leishmania parasites. Combination of licochalcone A with 10 $\mu$g/ml pentostam resulted in an increased inhibitory effect by licochalcone A on pentostam resistant Leishmania parasites (FIG. 9C).

EXAMPLE 11

Effect of different concentrations of licochalcone A on the ultrastructure of *Leishmania major*

Electron microscopic studies. In order to examine the effect of licochalcone A on the ultrastructure of the parasite, electron microscopy studies were carried out on promastigotes and amastigotes incubated with different concentrations of licochalcone A.

Materials and Methods

Drugs. Licochalcone A was dissolved in 20 $\mu$l of 99% (v/v) ethanol, and then 980 $\mu$l of medium 199 was added and stored at −20° C.

Effect on promastigotes. The effect of licochalcone A on promastigotes was assessed by incubating promastigotes ($3\times10^6$/ml, 5 ml) at 26° C. for 20 hrs in the presence of licochalcone A or the medium alone in plastic tubes. Cultures were centrifuged at 1.500 rpm for 10 min, supernatants were removed, and the pellets were resuspended in 2 ml of 3% glutaraldehyde in 0.1M cacodylate buffer pH 7.3.

Macrophage culture. Human peripheral blood monocytes were obtained by Ficoll-Hypaque fractionation of blood from the Blood Bank, Rigshospitalet. Washed cells were suspended in medium RPMI-199 containing penicillin (50 U/ml), and streptomycin (50 $\mu$g/ml), 25 mM Hepes, 4 mM L-glutamine, and 10% heat inactivated fetal calf serum (56° C., 30 min). 15 ml of suspension containing $1\times10^6$ mononudear cells per ml was added to each flask (25 $cm^2$, 50 ml, Nunc, Roskilde, Denmark). After 4 h and again after 3 days of incubation at 37° C. in 5% $CO_2$-95% air, old medium was removed and washed with warm fresh medium three times, and then replaced with warm fresh medium.

Infection of macrophages with *L. major* promastigotes. After 6 days incubation the old medium was removed, and 15 ml of $1\times10^7$/ml 4 days culture of *L. major* promastigotes was added to each flask. After 24 h infection, macrophage cultures were washed three times with warm fresh medium and replenished with warm fresh medium with different concentrations of licochalcone A or medium alone. The medium was changed every 3 days. After 6 days, the medium was removed and 4 ml of a suspension of Versene (EDTA) and Trypsin (prepared by adding 3 ml of 0.2% Trypsin to 50 ml of Versene) was added, and shaken a few times. After 5–10 min (the adherent cell layer should loosen in 5–10 min), 4 ml of 6% glutaraldehyde in 0.1M cacodylate buffer pH 7.3 was added to the flasks and the cells were fixed for 20 min at room temperature.

Promastigotes of *L. major* grown in media for 24 hours at 26° C. with different concentrations of licochalcone A. The number of organisms was $3\times10^6$/ml.

Sample A: *L. major* grown in media alone (control)

Sample B: *L. major* grown in media with 1 $\mu$g/ml licochalcone A

Sample C: *L. major* grown in media with 5 $\mu$g/ml licochalcone A

Sample D: *L. major* grown in media with 10 μg/ml

After 24 hours of incubation, 5 ml of each sample was centrifuged (1500 rpm), and the pellets were resuspended in 1 ml of media. Then the organisms were fixed by adding 1 ml of 6% glutaraldehyde in 0.1M cacodylate buffer containing 0.01M $CaCl_2$ pH 7.3.

After 2 hours of fixation at room temperature, the specimens were centrifuged (Eppendorf 8000 rpm) for 2 min, and the pellets were enrobed in 45° C. melted 1.5% Noble Agar (Difko) in 0.1M cacodylate buffer containing 0.01M $CaCl_2$ pH 7.3, followed by en block staining in 2% uranylacetate in barbiturate buffer pH 7.2 for another hour.

The agar blocks with cells were then dehydrated in alcohol and propylene oxide and finally embedded in Vestopal-W. After hardening of the blocks, sections were obtained on the LKB-ultratome III microtome. The sections were post-stained for 15 min with magnesium uranyl acetate and afterwards for 2 min with lead citrate diluted 1:10 with redistilled water.

Electron microscopy was carmed out with a Philips EM 201 C electron microscope. Exposures were made on Eastman Kodak Fine Grain Release Positive Film Type 5302 at primary magnifications of 1500 and 9000× and suitable fields were enlarged photographically ten times.

Results

Figure 5:
FIG. 5 is an electron microscopic photo (magnification 10,000×) showing *Leishmania major* promastigotes as a control. *Leishmania major* promastigotes are shown with normal mitochondria. Mitochondria denoted "M".

The ultrastructure of *L. major* in the control sample showed a uniform population of cells, all with flagella and rounded uncondensed nuclei, see FIG. 5.

The cytoplasm contained very few profiles of rough endoplasmic reticulum, whereas well developed golgi complexes were found in several cells together with electron-dense and electron-lucent granules.

The kinetoplast and its associated mitochondrion were slender and contained a few cristae. Long slender mitochondria were also found surrounding the nuclei and the golgi complex.

After 1 μg/ml of licochalcone A no morphological changes could be found, compared to the control culture.

After 5 μg/ml of licochalcone A a higher percentage of *L. major* showed cytoplasmic granules than the control culture (70% versus 50%). However, the most spectacular changes were seen in the ultrastructure of the mitochondria. These were swollen to an extent that made it difficult to recognize the structures as mitochondria, if the characteristic cristae had not been preserved.

10 μg/ml of licochalcone A increased the above mentioned ultrastructural change (see FIG. 6).

TABLE 11.1

Shows the measurements of the diameters of mitochondria, measured on prints at a magnification of 15000 ×.

| | n | Maximum (mean) (nm) | n | Minimum (mean) (nm) |
|---|---|---|---|---|
| A Control | 20 | 170 | 4 | 70 |
| B 1 μg/ml | 10 | 203 | 4 | 104 |
| C 5 μg/ml | 28 | 548 | 7 | 165 |
| D 10 μg/ml | 20 | 1043 | 5 | 294 |

EXAMPLE 12

Effect of different concentrations of licochalcone A on the ultrastructure of human monocytes/macrophages with and without ingested *L. major* with special reference to the ultrastructure of the mitochondria in *L. major* and in the human mononuclear cells Materials and methods:

Human mononuclear cells isolated from the same donor were cultivated in 200 ml Nunc flasks, each containing 30 ml of $5\times10^6$/ml cells. They were grown for 6 days, whereby the macrophage cells will adhere to the bottom. Media were changed after 3 days. After 6 days the *L. major* promastigotes were added in a concentration of $1\times10^7$ to four of the specimens, and incubated together for 24 hours. Then the media were exchanged with media containing Licochalcone A in different concentrations. The cultures were then grown for 6 days.

After the media were sucked off, the adhering cells were loosened by adding 8 ml of a mixture of EDTA and Trypsin (3 ml of 0.2% trypsin to 50 ml of EDTA). After 5 min the cells loosened, and the cells were fixed by adding 4 ml of 6% glutaraldehyde in cacodylate buffer. After 20 min of fixation, the cells were transferred to polypropylene tubes, and the further preparation and treatment took place as described in Example 10.

Results

A) Macrophage+*L. major*+0 μg/ml licochalcone A Control culture. Cells with up to 20 amastigotes were seen. The ultrastructure of the mitochondria was well preserved in both the human cells and in *L. major.*

B) Macrophage+*L. major*30 1 μg/ml licochalcone A. The ultrastructure of the cells in this experiment did not deviate from A.

C) Macrophage+*L. major*+5 μg/ml licochalcone A. The amastigotes found in the cytoplasm of the mononuclear cells showed distended mitochondria, whereas no ultrastructural changes could be seen in mitochondria of the human mononuclear cells.

D) Macrophage+*L. major*+10 μg/ml licochalcone A. Most of the intracellular amastigotes were now killed by licochalcone A and degraded by the macrophages, so it was often difficult to recognize the structure of an amastigote. Some were however found with the characteristic distension of the mitochondria. Again no ultrastructural changes were seen in the mitochondria of the macrophage.

E) Macrophage grown alone control culture. Well preserved ultrastructure and mitochondria.

F) Macrophage+5 μg/ml licochalcone A. No changes compared to the control culture.

G) Macrophage+10 μg/ml licochalcone A. No changes compared to the control culture (see FIG. 11).

Conclusion

These results show that the mitochondria and the other organelles of the cell are not in any way deteriorated by the licochalcone A in concentrations necessary to kill the parasites.

EXAMPLE 13

Effect of licochalcone A on the function of human lymphocytes, polymorphonuclear leucocytes, and monocytes Materials and methods Lymphocyte proliferation. Human blood mononuclear cells (BMNC) from heparinized blood were isolated by metrizoate sodium-Ficoll (Lymphoprep, Nyegaard, Oslo, Norway) density gradient centrifugation, washed 3 times in RPMI 1640 medium (Gibco) supplemented with 5% fetal calf serum (FCS) and with 400 IU of penicillin plus 400 μg/ml streptomycin.

BMNC were resuspended in the medium and cultured in triplicate, $0.63\times10^5$/ml and 160 μl per vial, in round-bottom microtiter plates (Nunc, Roskilde, Denmark) with 20 μl of various concentrations of licochalcone A. Immediately prior to incubation, optimum concentrations of the mitogen phytohaemagglutinin (PHA) and the antigen purified protein derivative of tuberculin (PPD) were added to the cultures in a volume of 20 μl. Unstimulated control cultures were always included.

Cultures were incubated for 3 or 7 days. The degree of lymphocyte proliferation was estimated by $^3$H-thymidine (1 μCi per well; New England Nudear Corp., Boston, Mass.) addition 24 h before the cells were harvested on glass fiber filters by means of a harvesting machine (Skatron, Lierbyen, Norway), and $^3$H-thymidine incorporation was measured in a liquid scintillation counter (Tricarb; Packard Instrument Co., Inc., Rockville, Md.). For each set of triplicate values, the median was recorded. Unstimulated cultures were always included as controls.

Chemiluminescence. Monocytes were prepared from heparinized blood by metrizoate sodium-Ficoll (the same as lymphocyte proliferation). Polymorphonudear leucocytes (PMN) were prepared from heparinized blood by dextran sedimentation and metrizoate sodium-Ficoll separation. Remaining erythrocytes were removed by hypotonic lysis. A zymosan-enhanced chemiluminescence assay was used. The assay was performed in a total volume of 5.5 ml at ambient temperature in glass scintillation vials. A Beckman L 8000 scintillation counter (placed under air-conditioned, thermostat controlled, 21±1° C. conditions) was used in the out-of-coincidence mode. A 1.1 ml portion of PMN or monocyte suspension ($1\times10^6$ cells per ml) was pre-incubated with 1.1 ml of various concentrations of licochalcone A for 30 min at 37° C. in a rotor at 20 rpm. Luminol (5-amino-2,3-dihydro-1,4-phatalazinedione) obtained from Sigma Chemical Co., St. Louis, Mo., U.S.A., was maintained as a stock solution of 10 mg/ml in NaOH (0.1N) and diluted in Krebs-Ringer solution immediately before use. Each vial contained $5\times10^5$ pre-incubated PMN or monocyte, 4 mg of opsonized zymosan (Sigma), 50 μl of luminol solution, and 4.45 ml of Krebs-Ringer solution containing 5 mM glucose. The final concentration of luminol in the assay mixture was $5\times10^{-8}$M.

Trypan blue dye exclusion method. This is a standard method used to determine cell viability. The assay is performed by incubating a given cell suspension with trypan blue for various periods of time after which the cells are examined under microscope. Dead cells will take up the dye and therefore show a blue colour. Percent viability is determined by counting at least a total of 200 cells.

Drug. Licochalcone A was purified from a batch Chinese licorice roots as described in Example 1.1 mg of licochalcone A was dissolved in 20 μl of 99% (v/v) ethanol, and then added in 980 μl of medium 199, stored at −20° C.

Results

Licochalcone A in a concentration of 20 μg/ml had no toxic effect on human lymphocytes, neutrophils, and monocytes as measured by the trypan blue dye exclusion method.

Table 13.1 shows that licochalcone A decreased the human lymphocyte proliferation response to PHA and PPD in concentrations of 20 μg to 10 μg/ml. Table 13.2 shows that licochalcone A caused a marked decrease in chemiluminescence response of human PMN and monocyte to opsonized zymosan in concentrations of licochalcone A of 20 μg/nml to 10 μg/ml.

TABLE 13.1

Effect of licochalcone A on human lymphocyte proliferation response to PHA and PPD as measured by $^3$H-thymidine incorporation. Results are given as percentage inhibition of control cells response ±SEM in the absence of licochalcone A (7 experiments).

| Licochalone A (μg/ml) | PHA | PPD |
|---|---|---|
| 20 | 65.3 ± 7.0* | 64.4 ± 12.0* |
| 10 | 39.7 ± 5.4* | 58.3 ± 14.2* |
| 5 | 20.8 ± 4.8* | 16.3 ± 7.3 |
| 2 | 7.8 ± 5.7 | 7.2 ± 7.2 |
| 1 | 4.7 ± 5.6 | 11.3 ± 5.3 |

*P < 0.05.

TABLE 13.2

Effect of licochalcone A on chemiluminescence response of human PMN and monocytes to opsonized zymosan. Results are given as mean ± SEM percentage inhibition of control cells response in the absence of licochalcone A (7 experiments).

| Licochalcone A (μg/ml) | PMN | Monocytes |
|---|---|---|
| 20 | 47.0 ± 4.3* | 56.5 ± 3.8* |
| 10 | 29.7 ± 4.8* | 37.9 ± 3.1* |
| 5 | 18.9 ± 3.7* | 24.8 ± 5.3* |
| 2 | 10.3 ± 3.3* | 7.8 ± 6.5 |
| 1 | 2.1 ± 3.3 | 8.2 ± 3.3 |

*P < 0.05.

EXAMPLE 14

Effect of a number of bis-aromatic α,β-unsaturated ketones on *L. major* promastigotes from 4-days cultures on *Plasmodium falciparum* growth in vitro and on human lymphocyte proliferation response to PHA Materials and methods Drugs. Licochalcone A and a large number of analogues, some prodrugs, and a few compounds with modified chalcone structure.

Lymphocytes. Lymphocytes were prepared and analyzed as described in Example 13.

*L. major* promastigotes. The *L. major* promastigotes were prepared as described in Example 4 and harvested after 4 days. The results are given as mean±SEM percentage inhibition of $^3$H-thymridine uptake compared to control promastigotes grown in medium alone.

The *P. falciparum* experimental setup was as described in Example 15.

The compounds in Table 14.1 marked with an asterisk are comparison compounds which clearly do not show sufficient potency or selectivity to be useful for the purpose of the invention, whereas the other compounds illustrate the invention.

TABLE 14.1

The effect of chalcones on *L. major* promastigotes from 4-days cultures, on *P. falciparum* growth in vitro, and on human lymphocyte proliferation response to PHA. The upper figures are percentage inhibition of human promastigotes, the middle figures (italic) are inhibition of malaria parasites, the lower figures (bold) are inhibition of lymphocytes. When standard deviation is given, more than five experiments have been performed.

| Formula | 10 $\mu$g/ml | 5 $\mu$g/ml | 1 $\mu$g/ml | 0.5 $\mu$g/ml |
|---|---|---|---|---|
| Hydroxychalcones, and Chalcone | | | | |
| 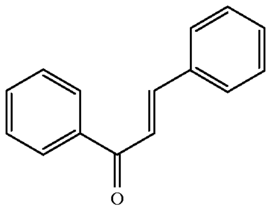 | 97.3<br>**100** | 91.9<br>**91** | 34.8<br>**7.3** | 21.6<br>**2** |
| 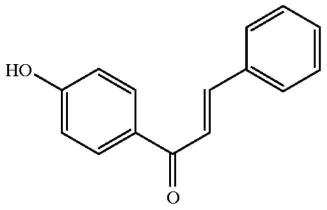 | 90.1 ± 6.5<br>*95.6 ± 1*<br>**17.0 ± 18.3** | 73.4 ± 15.3<br>*64.3 ± 8.5*<br>**10.2 ± 13.0** | 37.3 ± 13.6<br>*40.5 ± 11.0*<br>**3.6 ± 6.0** | 26.4 ± 6.5<br>*29.9 ± 10.7* |
| 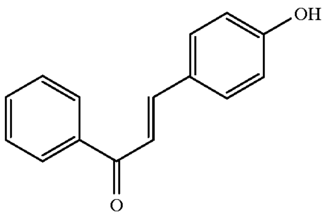 | 91.0 ± 5.4<br>*88.2 ± 5.3*<br>**14.2 ± 16.7** | 80.1 ± 12.6<br>*61.3 ± 10.6*<br>**7.73 ± 7.1** | 49.1 ± 16.8<br>*29.2 ± 7.7*<br>**2.24 ± 3.3** | 7.0<br>*20.5 ± 11.0* |
| 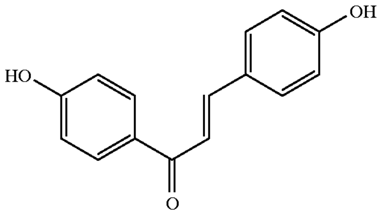 | 53.1 ± 7.9<br>**94.8 ± 5.0** | 34.6 ± 10.5<br>**96.3 ± 4.2** | 26.6 ± 7.6<br>**0 ± 31.7** | 22.5 ± 10.0<br>**0 ± 22.7** |
| 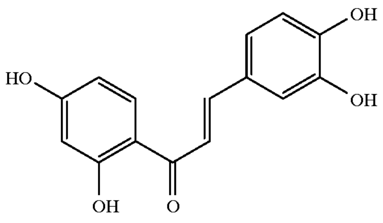 | 10.6<br>**51** | 4.2<br>**12** | 8<br>**1** | 7<br>**0** |

TABLE 14.1-continued

The effect of chalcones on *L. major* promastigotes from 4-days cultures, on *P. falciparum* growth in vitro, and on human lymphocyte proliferation response to PHA. The upper figures are percentage inhibition of human promastigotes, the middle figures (italic) are inhibition of malaria parasites, the lower figures (bold) are inhibition of lymphocytes. When standard deviation is given, more than five experiments have been performed.

| Formula | 10 μg/ml | 5 μg/ml | 1 μg/ml | 0.5 μg/ml |
|---|---|---|---|---|
| 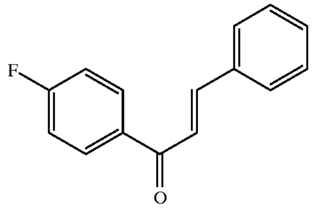 | 99 | 88 | | |
| Methoxychalcones, and Methoxyhydroxychalcones | | | | |
| 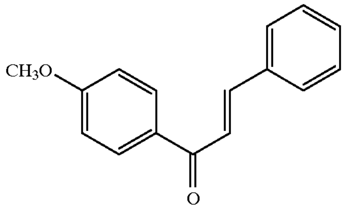 | 85.8<br>**100** | 68.1<br>**91** | 26.3<br>**7.5** | 20.6<br>**2** |
| 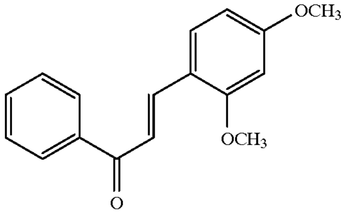 | 95.5 ± 3.8<br>*81.8*<br>**3.1 ± 15.4** | 77.8 ± 11.3<br>*35.6*<br>**2.0 ± 13.2** | 27.0 ± 13.7<br>*14.7*<br>**9.2 ± 10.8** | 14.5 ± 11.6<br>*0*<br>**9.1 ± 14.0** |
| 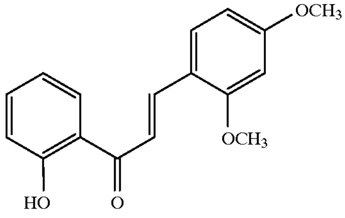 | 98.3 ± 1.0<br>*67.9*<br>**0 ± 7.0** | 89.4 ± 13.8<br>*23.4*<br>**2.6 ± 10.3** | 37.6 ± 18.3<br>*0.8*<br>**5.5 ± 12.3** | 19.2 ± 18.1<br>*0*<br>**3.0 ± 10.3** |
| 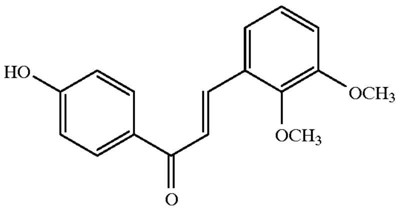 | 97.1 ± 3.5<br>**99.8 ± 0.1** | 95.2 ± 4.7<br>**89.3 ± 16.2** | 43.0<br>**7.5 ± 16.5** | 32.0<br>**2.0 ± 11.0** |

TABLE 14.1-continued

The effect of chalcones on *L. major* promastigotes from 4-days cultures, on *P. falciparum* growth in vitro, and on human lymphocyte proliferation response to PHA. The upper figures are percentage inhibition of human promastigotes, the middle figures (italic) are inhibition of malaria parasites, the lower figures (bold) are inhibition of lymphocytes. When standard deviation is given, more than five experiments have been performed.

| Formula | 10 μg/ml | 5 μg/ml | 1 μg/ml | 0.5 μg/ml |
|---|---|---|---|---|
| 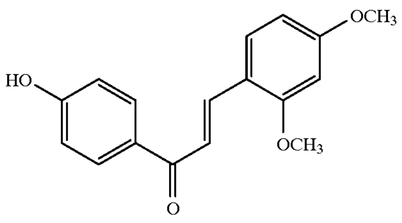 | 90.9 ± 7.4<br>*64.2*<br>**4.0 ± 15.1** | 66.9 ± 15.9<br>*31.6*<br>**2.4 ± 11.1** | 29.0 ± 22.2<br>*14.8*<br>**6.3 ± 14.9** | 20.0 ± 20.6<br>*2.2*<br>**1.5 ± 11.6** |
| 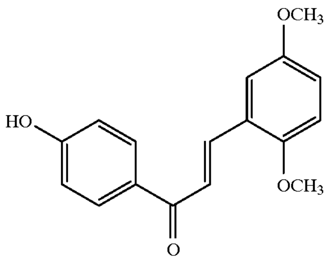 | 99.1<br>*93.1*<br>**98.2 ± 2.9** | 96.2<br>*71*<br>**78.8 ± 23.0** | 61.9<br>*23.1*<br>**6.9 ± 12.7** | 34.3<br>*15.2*<br>**3.2 ± 12.5** |
| 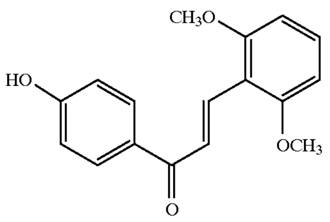 | 93.1 ± 4.6<br>*90.6*<br>**4.4 ± 27.9** | 77.5 ± 4.3<br>*71*<br>**2.3 ± 18.4** | 21.5 ± 10.6<br>*16.6*<br>**3.3 ± 12.2** | 11.4 ± 9.2<br>*0*<br>**0 ± 11.5** |
| 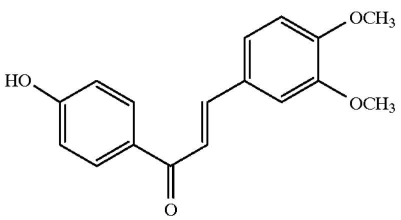 | 80<br>*73.4*<br>**27.4 ± 26.8** | 65.6<br>*39.9*<br>**5.2 ± 9.9** | 34.3<br>*35.1*<br>**0.1 ± 8.71** | 17.8<br>*21.0*<br>**0 ± 6.62** |
| 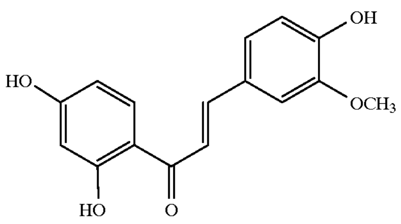 | 83.3<br>**38.3** | 56.7<br>**9.5** | 14.3<br>**6** | 7.8<br>**2** |

TABLE 14.1-continued

The effect of chalcones on *L. major* promastigotes from 4-days cultures, on *P. falciparum* growth in vitro, and on human lymphocyte proliferation response to PHA. The upper figures are percentage inhibition of human promastigotes, the middle figures (italic) are inhibition of malaria parasites, the lower figures (bold) are inhibition of lymphocytes. When standard deviation is given, more than five experiments have been performed.

| Formula | 10 µg/ml | 5 µg/ml | 1 µg/ml | 0.5 µg/ml |
|---|---|---|---|---|
| 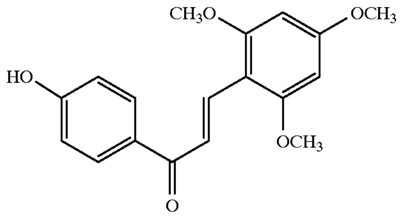 | 25.1 ± 17.3<br>**63.6 ± 15.7** | 23.6 ± 10.9<br>**48 ± 13.3** | 25.6 ± 10.9<br>**0 ± 23.4** | 25 ± 9.5<br>**0 ± 20.5** |
| 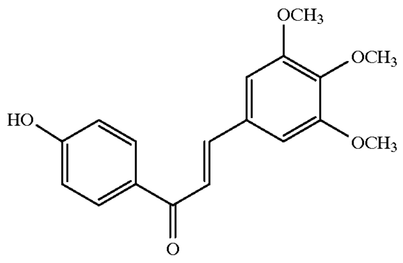 | 24.9 ± 13.1<br>**1.1 ± 17.2** | 26.7 ± 9.6<br>**0 ± 21.1** | 30.5 ± 16.3<br>0 ± 19.1 | 27.6 ± 8.6<br>0 ± 22.7 |
| 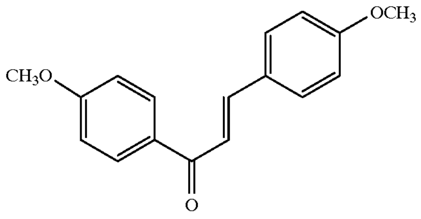 | 51.8 ± 15.8<br>**0 ± 12.8** | 35.6 ± 23.4<br>**0 ± 22.8** | 8.3 ± 4.6<br>0 ± 19.2 | 11.7 ± 9.2<br>**0 ± 19.9** |
| Methoxyallyloxychalcones | | | | |
| 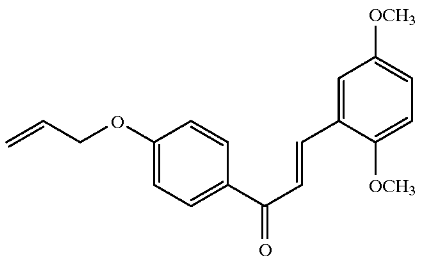 | 89.4 ± 10.2<br>*80*<br>**2.3 ± 12.7** | 63.0 ± 15.1<br>*35*<br>**4.3 ± 14.8** | 15.6 ± 15.1<br>*0*<br>**12.6 ± 16.6** | 10.0 ± 9.7<br>*0*<br>**5.7 ± 13.0** |
| 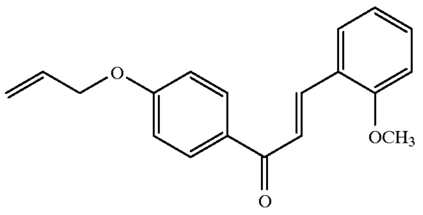 | 76.6 ± 22.4<br>**80.1 ± 8.8** | 52.8 ± 19.1<br>**1.1 ± 27.8** | 25.8 ± 15.3<br>**0 ± 21.8** | 20.9 ± 7.7<br>**0 ± 22.5** |

TABLE 14.1-continued

The effect of chalcones on *L. major* promastigotes from 4-days cultures, on *P. falciparum* growth in vitro, and on human lymphocyte proliferation response to PHA. The upper figures are percentage inhibition of human promastigotes, the middle figures (italic) are inhibition of malaria parasites, the lower figures (bold) are inhibition of lymphocytes. When standard deviation is given, more than five experiments have been performed.

| Formula | 10 μg/ml | 5 μg/ml | 1 μg/ml | 0.5 μg/ml |
|---|---|---|---|---|
| 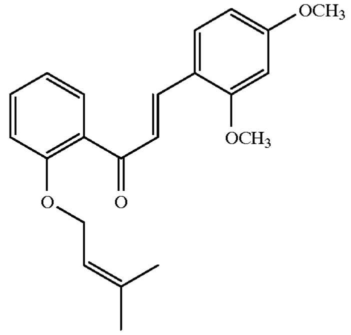 | 83.2<br>**35.9** | 49.0<br>**8.7** | 1.8<br>**6.6** | 4.3<br>**7.1** |
| 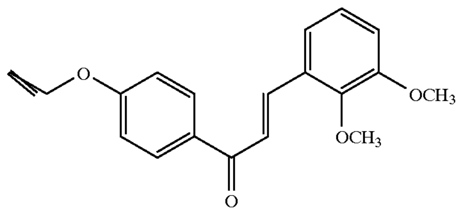 | 98.1 ± 1.0<br>*73.1*<br>**13.8 ± 14.6** | 82.1 ± 13.6<br>*68.2*<br>**8.8 ± 20.1** | 20.7 ± 17.1<br>*17.2*<br>**14.2 ± 20.5** | 13.9 ± 12.9<br>*0*<br>**10.8 ± 19.3** |
| 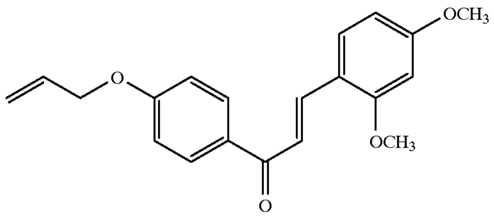 | 85.4<br>*97.3*<br>**5.5 ± 18.8** | 71.4<br>*74.4*<br>**5.9 ± 9.9** | 62.8<br>*36.5*<br>**1.7 ± 11.5** | 35.4<br>*31.1*<br>**0 ± 9.8** |
| 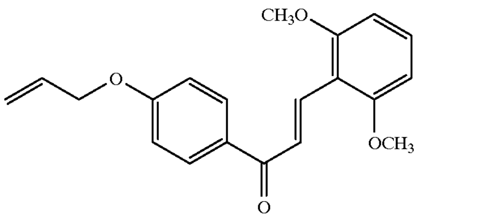 | 91.1 ± 4.1<br>*65.7*<br>**0 ± 11.6** | 63.7 ± 24.2<br>*39.7*<br>**0 ± 10.2** | 16.3 ± 12.4<br>*27.4*<br>**1.3 ± 10.2** | 11.3 ± 9.8<br>*0*<br>**1.0 ± 11.4** |
| 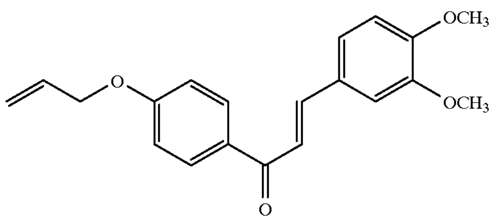 | 90.8 ± 9.7<br>*68*<br>**15.6 ± 25.0** | 70.4 ± 15.2<br>*22.8*<br>**0 ± 8.7** | 30.4 ± 23.2<br>*11.4*<br>**0 ± 9.3** | 15.2 ± 11.3<br>*2.9*<br>**0 ± 10.6** |

TABLE 14.1-continued

The effect of chalcones on *L. major* promastigotes from 4-days cultures, on *P. falciparum* growth in vitro, and on human lymphocyte proliferation response to PHA. The upper figures are percentage inhibition of human promastigotes, the middle figures (italic) are inhibition of malaria parasites, the lower figures (bold) are inhibition of lymphocytes. When standard deviation is given, more than five experiments have been performed.

| Formula | 10 µg/ml | 5 µg/ml | 1 µg/ml | 0.5 µg/ml |
|---|---|---|---|---|
| 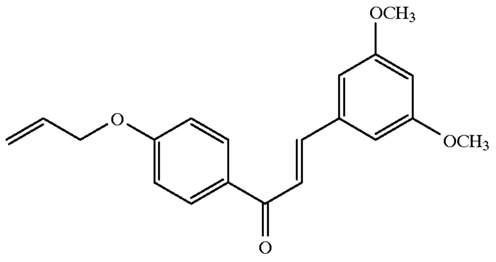 | 98.3 ± 0.9<br>*98.6*<br>*25.4 ± 16.3* | 82.8 ± 10.0<br>*74.3*<br>**4.6 ± 8.4** | 27.6 ± 23.3<br>*15.3*<br>**0 ± 7.8** | 10.6 ± 10.7<br>*13.8*<br>**0 ± 5.9** |
| 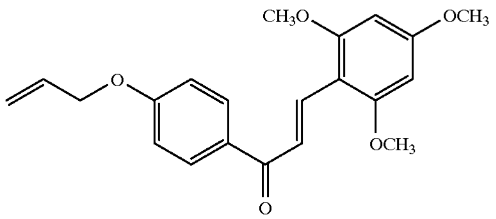 | 22–49<br>**48** | 14–50<br>**24** | 15–46<br>**12** | 25–44<br>**8** |
| 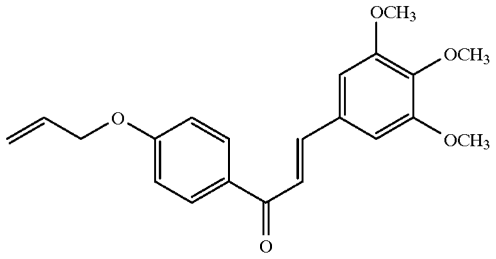 | 91–86<br>**98** | 44–60<br>**38** | 16–47<br>**4** | 11–45<br>**4** |
| 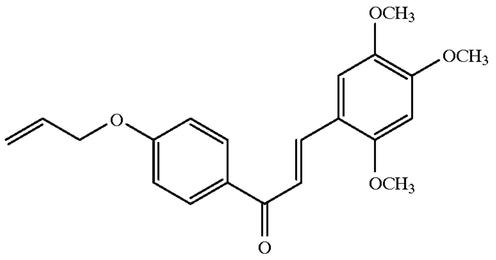 | 28.8 ± 16<br>**27.6 ± 11** | 23.2 ± 12.8<br>**0 ± 22.7** | 23.8 ± 12.5<br>**0 ± 26.1** | 24.0 ± 12<br>**0 ± 23.4** |
| Potential Prodrugs | | | | |
| 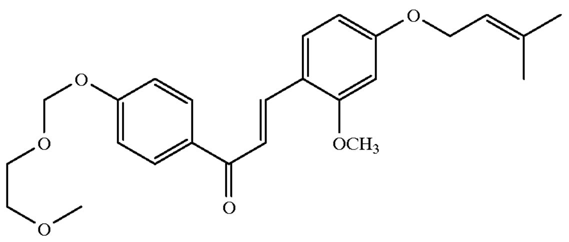 | 61.5<br>**28.3 ± 11.5** | 33.1<br>**14.1 ± 7.8** | 14<br>**8.1 ± 11.2** | 11.5<br>**0 ± 11.0** |

TABLE 14.1-continued

The effect of chalcones on *L. major* promastigotes from 4-days cultures, on *P. falciparum* growth in vitro, and on human lymphocyte proliferation response to PHA. The upper figures are percentage inhibition of human promastigotes, the middle figures (italic) are inhibition of malaria parasites, the lower figures (bold) are inhibition of lymphocytes. When standard deviation is given, more than five experiments have been performed.

| Formula | 10 μg/ml | 5 μg/ml | 1 μg/ml | 0.5 μg/ml |
|---|---|---|---|---|
| 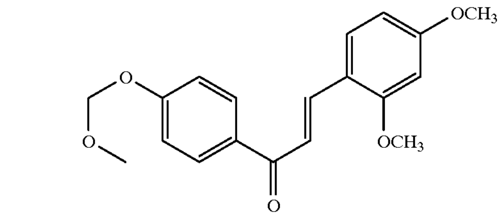 | 65.4 ± 16.1<br>**15.4 ± 18.7** | 50.2 ± 13.0<br>**11.2 ± 15.4** | 27.6 ± 10.9<br>**5.1 ± 11.9** | 22.8 ± 9.7<br>**0 ± 4.5** |
| 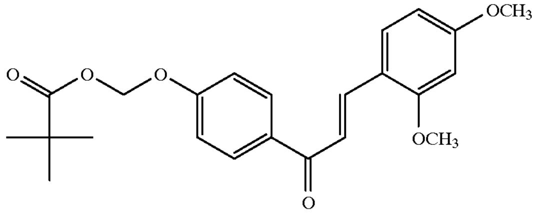 | 28.6<br>**32.7** | 7.9<br>**9.0** | 0<br>**8.2** | 3.9<br>**7.1** |
| Drugs with a modified chalcone skeleton | | | | |
| 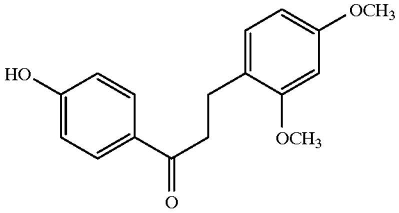 | 31.3 ± 16.0<br>**1.5 ± 6.2** | 22.5 ± 9.7<br>**3.0 ± 7.0** | 5.6 ± 5.4<br>**0 ± 7.9** | 8.5 ± 1.8<br>**0 ± 8.4** |
| 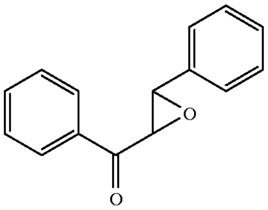 | 88 ± 7.5<br>**85.4 ± 11** | 73.2 ± 17.8<br>**2 ± 32.2** | 33.4 ± 15.4<br>**0 ± 24.5** | 28.4 ± 13<br>**0 ± 28.3** |
| Heterocyclic chalcones | | | | |
| 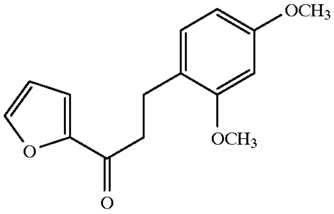 | 89.6<br>**41.9** | 55.1<br>**33.6** | 9.4<br>**11.7** | 9.5<br>**3.6** |

TABLE 14.1-continued

The effect of chalcones on *L. major* promastigotes from 4-days cultures, on *P. falciparum* growth in vitro, and on human lymphocyte proliferation response to PHA. The upper figures are percentage inhibition of human promastigotes, the middle figures (italic) are inhibition of malaria parasites, the lower figures (bold) are inhibition of lymphocytes. When standard deviation is given, more than five experiments have been performed.

| Formula | 10 µg/ml | 5 µg/ml | 1 µg/ml | 0.5 µg/ml |
|---|---|---|---|---|
| 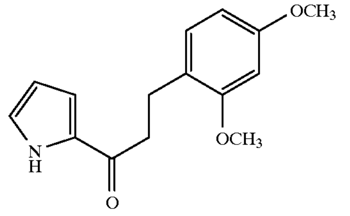 | 40.6<br>**41.9** | 18.5<br>**20** | 9.4<br>**2** | 0.6<br>**10** |
| Chalcones isolated from Licorice Roots and Derivatives thereof | | | | |
| 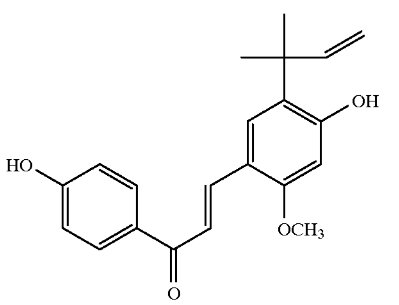 | 92<br>*98.0 ± 0.0*<br>**39.7 ± 5.4** | 64<br>*98.0 ± 0.0*<br>**20.8 ± 4.8** | 25<br>*69.0 ± 4.0*<br>**7.7 ± 5.7** | 12<br>*39.0*<br>**4.7 ± 5.6** |
| 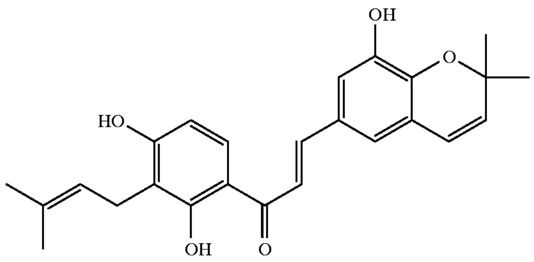 | 18 | | | |
| 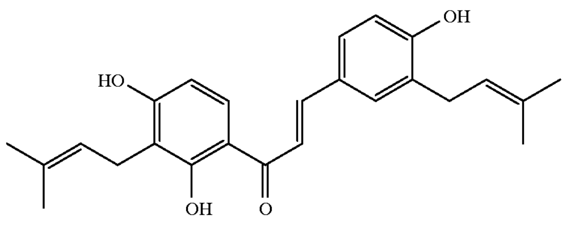 | 91 | 28 | 12 | |

Conclusion

The data in table 14.1 indicate the importance of oxygenation in the 2- or the 4-position or in the 2- and 4-positions for obtaining compounds which preferentially inhibit thymidine uptake into the parasites (with a single exception which is 2,5-dimethoxy-4'-allyloxychalcone; the high selectivity of 2,5-dimethoxy-4'-allyloxychalcone is interesting in view of the poor selectivity of 2,5-dimethoxy-4'-hydroxychalcone).

The in vitro results reported above confirm the hypothesis that the unsaturated α,β-position is of importance for the activity, c.f. the very low activity shown by 1-(4-hydroxyphenyl)-3-(2,4dimethoxy)phenyl-2-propan-1-one. The pattern shown by the results indicates that one of the mechanisms of action might be an alkylation of the target biomolecule by the α,β-unsaturated ketones. This is substantiated by the reaction illustrated in Example 27, between licochalcone A and a thiol-containing peptide, where a nucleophilic thiol group is added to the α,β-double bond. The principle is well known from the anti-cancer activity of α-methylene sesquiterpene lactones. One such α-methylene sesquiterpene lactone has been tested in the in vitro model and has been found to be extremely active against Leishmania parasites in vitro, but at the same time also to show extreme toxicity on human lymphocytes. Thus, the substituents in the chalone skeleton contribute to the selectivity of these compounds. The effect of the substituents can also be seen from the fact that chalcone in itself also has a very high activity against Leish mania parasites but is also extremely high toxicity against human lymphocytes, whereas, as is evident from the above data, e.g. 2,4- or 2- or 4-oxygen substituted chalcones show considerable selectivity for a number of chalcones. This selectivity seems to be hampered by the presence of a 5- or 3-substituent which, however, does not applv to the above-mentioned 2,5-dimethoxy-4'-allyloxychalcone.

EXAMPLE 15

Effect of Licorice extract and licochalcone A on *Plasmodium falciparum*

Material and methods:

Drugs. Licorice extract was obtained by extracting the comminuted licorice roots rich in licochalcone A with ethanol for 24 h, filtering the extract and concentrating the extract in vacuo, cf. Example 1.1.

*Plasmodium falciparum* continuous cultures. *Plasmodium falciparum* was kept in continuous culture by a modification of the method originally described by Trager and Jensen (1976). Peripheral blood was drawn into 10 ml vaccutainers containing citrate-phosphateafxtrose, and stored at 4° C. for 2–4 weeks before use. At the day of use, the cells were washed twice in RPMI medium (RPMI 1640 supplemented with 5% A Rh pos serum, Hepes 5.94 g/1000 ml medium, and sodium bicarbonate 7.5% (31 ml/1000 ml medium)), and after each wash the supernatant and the buffy coat containing leukocytes were removed. The parasites were cultured in Nunc culture flasks (Nunc, Roskilde, Denmark) containing 200 μl of packed erythrocytes in 5 ml of RPMI medium. The supernatants of the cultures were changed every 24 hours and the pack erythrocytes were supplied twice weekly. The parasitemia in the cultures was kept below 2%. The parasite cultures were grown at 37° C. in an atmosphere of 2% oxygen, 5% carbon dioxide and 93% nitrogen. Two different parasite strains were kept in continuous culture: 1) The 3D7A chloroquine sensitive strain and 2) the chloroquine resistant DD2 strain. Both strains were kindly provided by Professor D. Walliker (Edinburgh, Scotland).

Testing of the effect of drugs and serum on the in vitro growth of the parasites. The experiments in which compounds were tested for their ability to inhibit parasite growth were performed by a modification of the method originally described by Jensen et al. (1982). Fifty μl of parasitized erythrocytes (parasitemia approximately 1%) in a concentration of $5\times10^8$/ml and 50 μl of RPMI medium containing different concentrations of the test compound was added to each well of a 96 well flat-bottomed microtiter plate (Nunc). The cultures were then incubated for 48 hours, 24 hours before termination of the culture adding 20 μl of 3-H-hypoxanthine (40 uCi/ml) (New England Nuclear, Boston, Mass., USA) was added to each well. The cultures were then harvested onto glass fiber filters using a Skatron cell harvester (Skatron, Lierbyen, Norway), and the incorporation of 3-H-hypoxanthine into the DNA of dividing parasites was determined by liquid scintillation spectrometry.

Control cultures with uninfected erythrocytes and infected erythrocytes in RPMI medium without test compounds were always performed in parallel to the test cultures.

In some experiments thin smears of parasite cultures were stained by Giemsa and examined under microscope (×1000).

The test compounds described above, were diluted in RPMI medium immediatelv before use. In the experiments, chloroquine phosphate (Rigshospitalets Apotek, Copenhagen, Denmark) was used as a positive control as a drug known to inhibit parasite growth.

Results

The effect of licorice extract and licochalcone A on the uptake of 3-H-hypoxantine by dividing malaria parasites was tested by the addition of these compounds to *P. falciparum* cultures. Chloroquine was tested as a positive control.

Table 15.1 shows the effect of the compounds on a chloroquine sensitive parasite strain. It is apparent that both the extract and licochalcone A were able to inhibit the parasite growth. The concentration in which growth was retarded by 50% was between 0.5–1 μg/ml and 38–75 ng/ml for licochalcone A and chloroquine, respectively.

Table 15.2 shows the effect of the same compounds on a chloroquine resistant parasite strain. The compounds also inhibited the growth of this parasite strain. The concentration in which parasite growth was retarded by 50% was between 0.5–1 μg/ml and 75–150 ng/ml for licochalcone A and chloroquine, respectively. When comparing the effects of the compounds on the two parasite strains, it was clear that the effect of licochalcone A on the strains was comparable, whereas higher dosages of chloroquine were needed to inhibit the DD2 strain than the dosage needed to inhibit the 3D7A strain of the parasite.

Figure 4A:
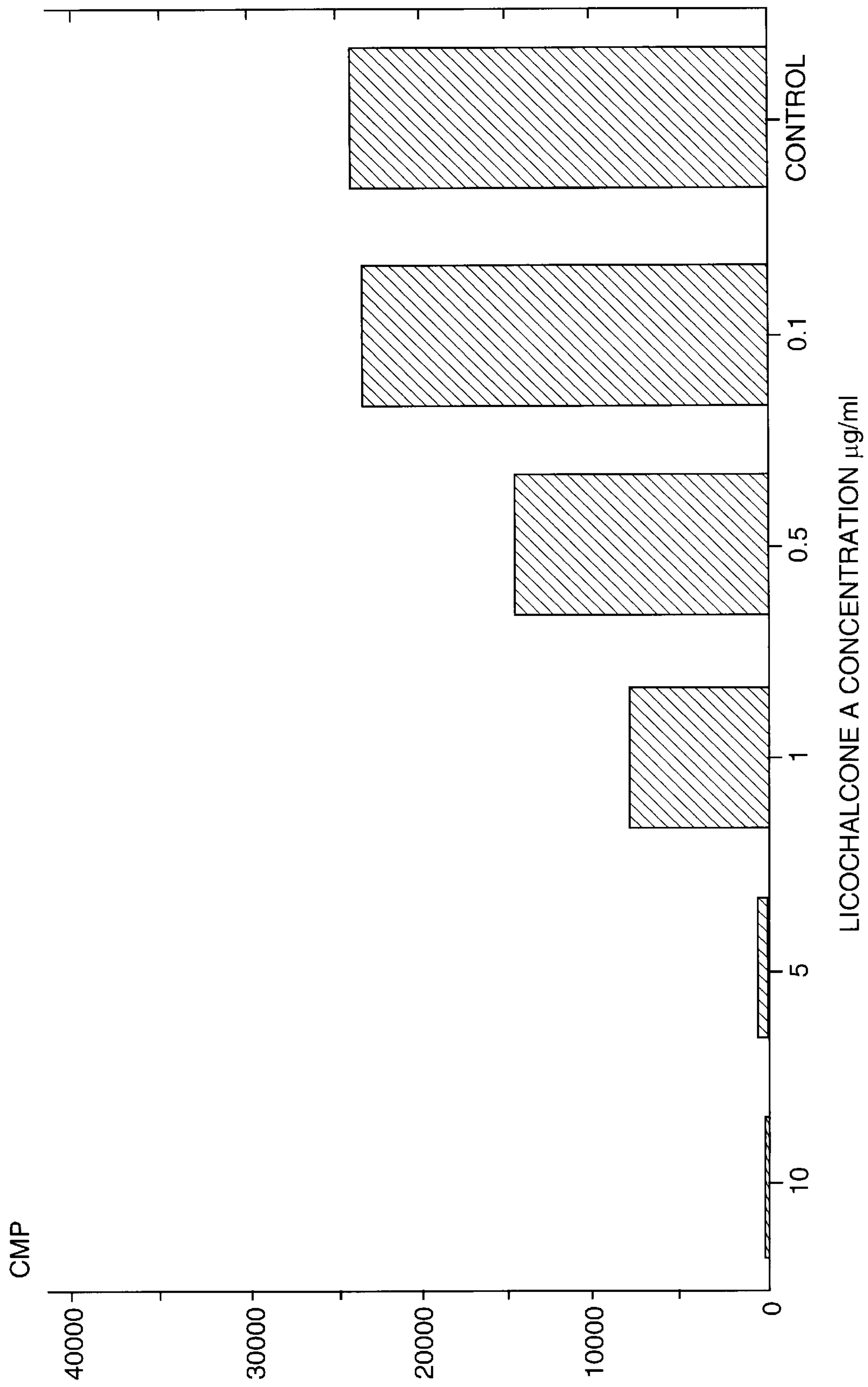
FIG. 4A and 4B show the effect of licochalcone A on the in vitro growth of chloroquine-resistant *Plasmodium falciparum* and chloroquine-sensitive *Plasmodium falciparum*, respectively as described in example 14.
Figure 4B:
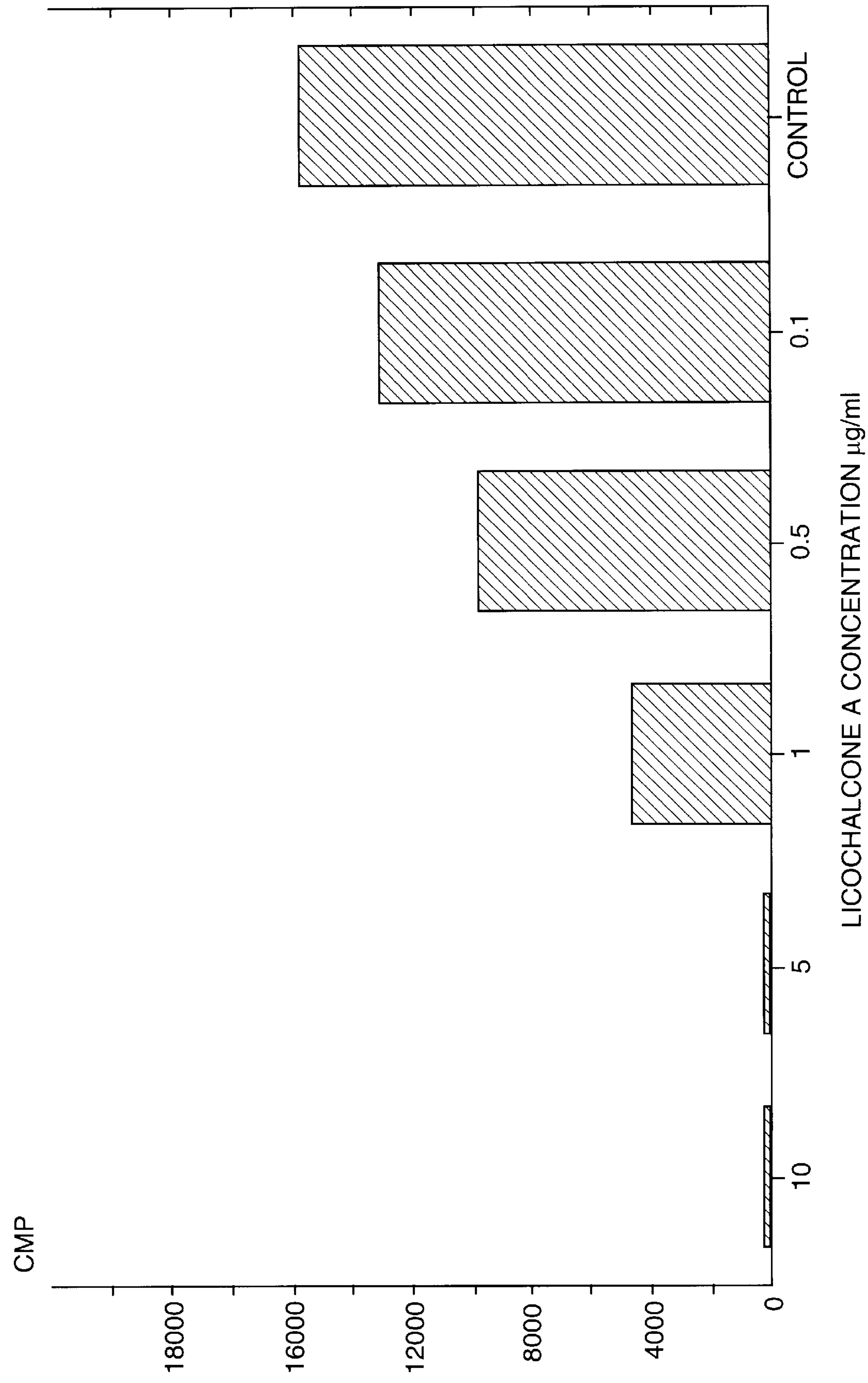

These data are also shown in FIG. 4A and FIG. 4B.

Table 15.3 shows the effect of 4'-hydroxychalcone and 4hydroxychalcone on the growth of the 3D7A strain of the parasite. The results indicate that these compounds were also able to inhibit parasite multiplication in vitro. The concentration in which growth was retarded by 50% was between 1–5 μg/mnl for both compounds.

Table 15.4, 15.5, and 15.6 show the effect of 14 different licochalcone A analogues on the in vitro growth of *P. falciparum* (DD2 stain, chloroquine resistant strain). The analogues all inhibited the cultures in a dose dependant manner. The concentration in which the growth was inhibited by 50% was approximately between 1–10 μg/ml.

In some experiments the morphology of parasites cultured in the presence of licochalcone A was examined. In the cultures that had been incubated with licochalcone A in a concentration of 5 μg/ml, vent few parasites could be detected inside the erythrocytes. The parasites that were found were pvknotic and without structure. In cultures incubated with licochalcone A at a concentration of 10 μg/ml, no parasites could be detected (data not shown).

TABLE 15.1

Effect of Licorice extract, licochalcone A and chloroquine on the in vitro growth of chloroquine-sensitive *P. falciparum* 3D7A strain. Data are given as percentage inhibition of the uptake of $^3$H-hypoxanthine in cultures incubated with the test compound compared to the uptake in control cultures incubated with medium (mean ± SEM).

| Drug | Number of experiments | Growth in % of control (mean ± SEM) |
|---|---|---|
| Licorice extract | | |
| 1:100 | 4 | 99.0 ± 0.0001 |
| 1:200 | 4 | 96.0 ± 2.0 |
| 1:400 | 4 | 63.0 ± 6.0 |
| 1:800 | 4 | 32.0 ± 5.0 |
| Licochalcone A | | |
| 10 μg/ml | 6 | 98.0 ± 0.0001 |
| 5 μg/ml | 6 | 98.0 ± 0.001 |

TABLE 15.1-continued

Effect of Licorice extract, licochalcone A and chloroquine on the in vitro growth of chloroquine-sensitive *P. falciparum* 3D7A strain. Data are given as percentage inhibition of the uptake of $^3$H-hypoxanthine in cultures incubated with the test compound compared to the uptake in control cultures incubated with medium (mean ± SEM).

| Drug | Number of experiments | Growth in % of control (mean ± SEM) |
|---|---|---|
| 1 μg/ml | 6 | 69.0 ± 4.0 |
| 0.5 μg/ml | 6 | 39.0 ± 6.0 |
| 0.1 μg/ml | 6 | 15.0 ± 3.0 |
| Chloroquine | | |
| 300 ng/ml | 6 | 98.8 ± 0.3 |
| 150 ng/ml | 6 | 97.1 ± 1.0 |
| 75 ng/ml | 6 | 80.2 ± 3.7 |
| 38 ng/ml | 6 | 34.0 ± 6.1 |

TABLE 15.2

Effect of Licorice extract, licochalcone A and chloroquine on the in vitro growth of chloroquine-resistant i P. falciparum DD2 strain. Data are given as percentage inhibition of the uptake of $^3$H-hypoxanthine in cultures incubated with the test compound compared to the uptake in control cultures incubated with medium (mean ± SEM).

| Drug | Number of experiments | Growth in % of control (mean ± SEM) |
|---|---|---|
| Licorice extract | | |
| 1:100 | 4 | 98.0 ± 2.0 |
| 1:200 | 4 | 87.0 ± 9.0 |
| 1:400 | 4 | 65.0 ± 14.0 |
| 1:800 | 6 | 26.0 ± 4.0 |
| Licochalcone A | | |
| 10 μg/ml | 6 | 99.0 ± 0.0001 |
| 5 μg/ml | 6 | 98.0 ± 1.0 |
| 1 μg/ml | 6 | 66.0 ± 3.0 |
| 0.5 μg/ml | 6 | 41.0 ± 4.0 |
| 0.1 μg/ml | 6 | 5.0 ± 2.0 |
| Chloroquine | | |
| 300 ng/ml | 4 | 94.8 ± 3.0 |
| 150 ng/ml | 4 | 80.3 ± 4.1 |
| 75 ng/ml | 4 | 43.9 ± 3.1 |
| 28 ng/ml | 4 | 11.3 ± 4.2 |

TABLE 15.3

Effect of 4'-hydroxychalcone and 4-hydroxychalcone on the in vitro growth of chloroquine-sensitive *P. falciparum* 3D7A strain. Data are given as percentage inhibition of the uptake of $^3$H-hypoxanthine in cultures incubated with the test compound compared to the uptake in control cultures incubated with medium (mean ± SEM).

| Drug | Number of experiments | Growth in % of control (mean ± SEM) |
|---|---|---|
| 4'-Hydroxychalcone | | |
| 10 μg/ml | 3 | 95.5 ± 1.1 |
| 5 μg/ml | 3 | 64.2 ± 8.5 |
| 1 μg/ml | 3 | 40.5 ± 11.1 |
| 0.5 μg/ml | 3 | 29.9 ± 10.7 |
| 4-Hydroxychalcone | | |
| 10 μg/ml | 3 | 88.2 ± 5.3 |
| 5 μg/ml | 3 | 61.3 ± 10.6 |

TABLE 15.3-continued

Effect of 4'-hydroxychalcone and 4-hydroxychalcone on the in vitro growth of chloroquine-sensitive *P. falciparum* 3D7A strain. Data are given as percentage inhibition of the uptake of $^3$H-hypoxanthine in cultures incubated with the test compound compared to the uptake in control cultures incubated with medium (mean ± SEM).

| Drug | Number of experiments | Growth in % of control (mean ± SEM) |
|---|---|---|
| 1 μg/ml | 3 | 29.2 ± 7.7 |
| 0.5 μg/ml | 3 | 20.5 ± 10.9 |

TABLE 15.4

Effects of analogues of licochalcone A on the in vitro growth of *P. falciparum* (DD2, chloroquine resistant strain). Data are given as percentage inhibition of the uptake of $^3$H-hypoxanthine in cultures incubated with the test compound compared to the uptake in control cultures incubated with medium (mean ± SEM).

| Drug | Number of experiments | Growth in % of control (mean ± SEM) |
|---|---|---|
| 2,4-Dimethoxy-4'-allyloxychalcone | | |
| 10 μg/ml | 9 | 75.2 ± 7.8 |
| 5 μg/ml | 9 | 44.3 ± 10.5 |
| 1 μg/ml | 9 | 23.6 ± 11.2 |
| 0.5 μg/ml | 9 | 29.1 ± 10.8 |
| 2,4-Dimethoxy-4'-hydroxychalcone | | |
| 10 μg/ml | 10 | 68.0 ± 4.7 |
| 5 μg/ml | 10 | 46.8 ± 6.6 |
| 1 μg/ml | 10 | 21.8 ± 7.3 |
| 0.5 μg/ml | 10 | 18.6 ± 7.2 |
| 2,4-Dimethoxy-4'-methoxymethoxychalcone | | |
| 10 μg/ml | 4 | 40.8 ± 9.3 |
| 5 μg/ml | 4 | 0 ± 10.2 |
| 1 μg/ml | 4 | 0 ± 10.9 |
| 0.5 μg/ml | 4 | 14.0 ± 6.8 |
| 3,4-Dimethoxy-4'-hydroxychalcone | | |
| 10 μg/ml | 7 | 82.6 ± 4.7 |
| 5 μg/ml | 7 | 48.5 ± 8.4 |
| 1 μg/ml | 7 | 7.1 ± 8.1 |
| 0.5 μg/ml | 7 | 9.3 ± 9.2 |

TABLE 15.5

Effects of analogues of licochalcone A on the in vitro growth of *P. falciparum* (DD2, chloroquine resistant strain). Data are given as percentage inhibition of the uptake of $^3$H-hypoxanthine in cultures incubated with the test compound compared to the uptake in control cultures incubated with medium (mean ± SEM).

| Drug | Number of experiments | Growth in % of control (mean ± SEM) |
|---|---|---|
| 3,4-Dimethoxy-4'-allyloxychalcone | | |
| 10 μg/ml | 5 | 52.8 ± 4.7 |
| 5 μg/ml | 5 | 16.2 ± 5.5 |
| 1 μg/ml | 5 | 9.4 ± 15.8 |
| 0.5 μg/ml | 0 ± 11.3 | |
| 3,5-Dimethoxy-4'-allylchalcone | | |
| 10 μg/ml | 5 | 79.1 ± 10.5 |
| 5 μg/ml | 5 | 44 ± 8.1 |
| 1 μg/ml | 5 | 3.4 ± 4.7 |
| 0.5 μg/ml | 5 | 9.1 ± 5.2 |

TABLE 15.5-continued

Effects of analogues of licochalcone A on the in vitro growth of *P. falciparum* (DD2, chloroquine resistant strain). Data are given as percentage inhibition of the uptake of $^3$H-hypoxanthine in cultures incubated with the test compound compared to the uptake in control cultures incubated with medium (mean ± SEM).

| Drug | Number of experiments | Growth in % of control (mean ± SEM) |
|---|---|---|
| 2,5-Dimethoxy-4'-allyloxychalcone | | |
| 10 μg/ml | 8 | 74.4 ± 4.4 |
| 5 μg/ml | 8 | 45.3 ± 7.2 |
| 1 μg/ml | 8 | 12.1 ± 13.7 |
| 0.5 μg/ml | 8 | 15.8 ± 13.2 |
| 2,4-Dimethoxychalcone | | |
| 10 μg/ml | 9 | 58.8 ± 6.4 |
| 5 μg/ml | 9 | 27.1 ± 5.3 |
| 1 μg/ml | 9 | 5.5 ± 5.1 |
| 0.5 μg/ml | 9 | 11 ± 7.7 |

TABLE 15.6

Effects of analogues of licochalcone A on the in vitro growth of *P. falciparum* (DD2, chloroquine resistant strain). Data are given as percentage inhibition of the uptake of $^3$H-hypoxanthine in cultures incubated with the test compound compared to the uptake in control cultures incubated with medium (mean ± SEM).

| Drug | Number of experiments | Growth in % of control (mean ± SEM) |
|---|---|---|
| 2,3-Dimethoxy-4'-allyloxychalcone | | |
| 10 μg/ml | 9 | 49.9 ± 9.1 |
| 5 μg/ml | 9 | 22.2 ± 10.1 |
| 1 μg/ml | 9 | 29.6 ± 10.9 |
| 0.5 μg/ml | 9 | 28.5 ± 9.6 |
| 2,3-Dimethoxy-4'-hydroxychalcone | | |
| 10 μg/ml | 3 | 67.6 ± 12.4 |
| 5 μg/ml | 3 | 53.5 ± 20.1 |
| 1 μg/ml | 3 | 54.4 ± 22.2 |
| 0.5 μg/ml | 3 | 46 ± 22 |
| 2,5-Dimethoxy-4'-hydroxychalcone | | |
| 10 μg/ml | 8 | 92.5 ± 2.4 |
| 5 μg/ml | 8 | 68.4 ± 6.8 |
| 1 μg/ml | 8 | 21.2 ± 11.1 |
| 0.5 μg/ml | 8 | 14 ± 7.5 |
| 2,6-Dimethoxy-4'-allyloxychalcone | | |
| 10 μg/ml | 9 | 56.7 ± 8.9 |
| 5 μg/ml | 9 | 40.2 ± 8.7 |
| 1 μg/ml | 9 | 24.3 ± 9.5 |
| 0.5 μg/ml | 9 | 23.3 ± 10.9 |

TABLE 15.7

Effects of analogues of licochalcone A on the in vitro growth of *P. falciparum* (DD2, chloroquine resistant strain). Data are given as percentage inhibition of the uptake of $^3$H-hypoxanthine in cultures incubated with the test compound compared to the uptake in control cultures incubated with medium (mean ± SEM).

| Drug | Number of experiments | Growth in % of control (mean ± SEM) |
|---|---|---|
| 2,4-Dimethoxy-2'-hydroxychalcone | | |
| 10 μg/ml | 11 | 55.3 ± 7.4 |
| 5 μg/ml | 10 | 33.7 ± 8.2 |
| 1 μg/ml | 10 | 20.8 ± 8.8 |

TABLE 15.7-continued

Effects of analogues of licochalcone A on the in vitro growth of *P. falciparum* (DD2, chloroquine resistant strain). Data are given as percentage inhibition of the uptake of $^3$H-hypoxanthine in cultures incubated with the test compound compared to the uptake in control cultures incubated with medium (mean ± SEM).

| Drug | Number of experiments | Growth in % of control (mean ± SEM) |
|---|---|---|
| 0.5 μg/ml | 10 | 23.1 ± 8.3 |
| 2,6-Dimethoxy-4'-hydroxychalcone | | |
| 10 μg/ml | 10 | 86.8 ± 7.3 |
| 5 μg/ml | 10 | 54.2 ± 10.2 |
| 1 μg/ml | 10 | 9 ± 7 |
| 0.5 μg/ml | 10 | 14.5 ± 7.2 |

Conclusion

The results show that a certain licorice extract, licochalcone A and some other bis-aromatic α,β-unsaturated ketones are powerful inhibitors of nucleic acid biosynthesis in *Plasmodium falciparum* and are able to kill the parasite. There was no difference in the effect of licochalcone A on a chloroquine resistant and a chloroquine sensitive parasite strain and it must therefore be concluded that the compounds are as effective on chloroquine sensitive strains as they are on chloroquine resistant strains.

EXAMPLE 16

Effects of licochalcone A and some oxygenated chalcones on the in vivo growth of malaria parasites Materials and Methods Mice. BALB/c female mice aged eight weeks were used throughout.

Parasites. The Plasmodium sp. causing malaria in humans can only infect certain primates. Therefore it has not been possible to determine whether licochalcone A inhibits parasite multiplication of human malaria parasites in vivo. However, there are several Plasmodium sp. that infect rodents. These systems have earlier been used to test the ability of drugs to inhibit malaria infections in vivo. In the experiments described below mice were infected with either *P. yoelii* (strain not characterized, Table 15.1) or *P. yoelii* YM strain (Table 16.2–16.12) and were compared to the outcome of infection in untreated control animals and in animals treated with licochalcone A. The parasites were maintained by passage through BALB/c mice, and the animals were infected by injection of infected erythrocytes obtained from mice with a parasitemia of approximately 40%. The animals were injected intraperitoneally with either $2\times10^5$ (Table 16.1) or $1\times10^6$ (Tables 16.2–16.12) parasitized erythrocytes diluted in 0.9% NaCl and in a final volume of 0.2 ml. The day of infection was termed day 0.

Assessment of effect. The outcome of infection was assessed microscopically by examination of Giemsa stained blood films. The load of infection (the parasitemia) was calculated as the percentage of infected erythrocytes of the total number of erythrocytes.

Drug. Licochalcone A was prepared and stored as described in Example 8. Licochalone A was administered intraperitoneally in a total volume of 0.2 ml at the indicated dosages. In parallel to the licochalcone A injections in the treated animals, control mice received injections of 0.2 ml 0.9% NaCl.

TABLE 16.1

Effect of licochalcone A in BALB/c mice infected with *P. yoelii* (strain not characterized). Parasitemia in 3 control mice (animal no. 1, 2, and 3 respectively, and mean) and in 3 mice treated with licochalcone A. The licochalcone A treatment was initiated 24 hours after infection with $2 \times 10^5$ parasites/mouse, and the mice treated with licochalcone A received 5 mg per kg body weight twice daily for 8 days.

| | Control | | | | Licochalcone A | | | |
|---|---|---|---|---|---|---|---|---|
| Day | No. 1 | No. 2 | No. 3 | mean | No. 1 | No. 2 | No. 3 | mean |
| D + 1 | 0.01 | 0.02 | 0.02 | 0.02 | 0.05 | 0.03 | 0.02 | 0.03 |
| D + 2 | 1.0 | 2.0 | 1.6 | 1.5 | 0.5 | 0.05 | 0.01 | 0.2 |
| D + 3 | 6.0 | 3.0 | 2.5 | 3.8 | 2.0 | 0.5 | 0.5 | 1.0 |
| D + 4 | 11.0 | 8.0 | 6.0 | 8.3 | 4.0 | 1.5 | 2.0 | 2.5 |
| D + 5 | 15.0 | 12.0 | 13.0 | 13.3 | 4.0 | 1.5 | 2.0 | 2.5 |
| D + 6 | 22.0 | 18.0 | 17.0 | 19.0 | 4.5 | 2.0 | 1.0 | 2.3 |
| D + 7 | 25.0 | 27.0 | 22.0 | 25.0 | 4.0 | 1.5 | 1.0 | 2.2 |
| D + 8 | 37.0 | 33.0 | 30.0 | 33.3 | 4.0 | 1.5 | 1.5 | 2.3 |
| D + 9 | 45.0 | 40.0 | 44.0 | 43.0 | 4.0 | 1.0 | 1.5 | 2.2 |
| D + 11 | 59.0 | 55.0 | 52.0 | 55.3 | 2.0 | 1.0 | 2.0 | 1.7 |
| D + 12 | died | 59.0 | 64.0 | 61.5 | 2.0 | 1.0 | 2.0 | 1.7 |
| D + 14 | | 61.0 | 61.0 | 61.0 | 1.0 | 0.0 | 1.0 | 0.7 |
| D + 16 | | died | 61.0 | | 0.0 | 0.0 | 0.1 | 0.03 |
| D + 18 | | | 40.0 | | 0.0 | 0.0 | 0.0 | 0.0 |
| D + 20 | | | 45.0 | | 0.0 | 0.0 | 0.0 | 0.0 |
| D + 21 | | | died | | 0.0 | 0.0 | 0.0 | 0.0 |

TABLE 16.2

Effect of licochalcone A in BALB/c mice infected with *P. yoelii* strain YM. Parasitemia in 3 control mice (animal no 1, 2 and 3 respectively, and mean) and in mice treated with licochalcone A. The mice treated with licochalcone A received 10 mg per kg body weight twice daily from days +1 to +4.

| | Control | | | | Licochalcone A | | | |
|---|---|---|---|---|---|---|---|---|
| Day | No. 1 | No. 2 | No. 3 | mean | No. 1 | No. 2 | No. 3 | mean |
| D + 2 | 0.1 | 0.1 | 2.0 | 0.73 | 0.1 | 0.1 | 0.01 | 0.1 |
| D + 3 | 1.0 | 1.5 | 2.0 | 1.5 | 0.00 | 0.5 | 0.01 | 0.2 |
| D + 4 | 9.0 | 14.5 | 18.0 | 13.8 | 0.00 | 1.2 | 0.00 | 0.4 |
| D + 5 | 45.0 | 61.0 | 62.0 | 56.0 | 0.1 | 1.5 | 0.00 | 0.7 |
| D + 6 | 90.0 | 91.0 | 81.0 | 87.3 | 1.0 | 4.0 | 1.5 | 2.2 |
| D + 7 | 91.0 | died | died | | 2.0 | 4.0 | 3.0 | 3.0 |
| D + 8 | died | | | | 4.0 | 8.0 | 8.0 | 6.7 |
| D + 9 | | | | | 20.0 | 18.0 | 31.0 | 23.0 |
| D + 10 | | | | | 27.0 | 24.0 | died | 25.5 |
| D + 11 | | | | | 33.0 | 41.0 | | 37.0 |
| D + 12 | | | | | 80.0 | 68.0 | | 74.0 |
| D + 13 | | | | | 80.0 | 20.0 | | 50.0 |
| D + 14 | | | | | 65.0 | 5.0 | | 35.0 |
| D + 15 | | | | | 2.0 | 2.0 | | 2.0 |
| D + 16 | | | | | 0.5 | 0.1 | | 0.3 |
| D + 17 | | | | | 0.0 | 0.0 | | 0.0 |

TABLE 16.3

Effect of chloroquine on the parasitemia of mice infected with *P. yoelii* strain YM ($10^6$ parasites/mouse). Mice were 8 weeks old, female, BALB /c mice. Each group consisted of 5 mice. Chloroquine were given i.p.. The dosage, dosage interval and the days the animals were treated are indicated. Data are given as % parasitemia (mean ± SEM)and were measured by microscopic counting of Giemsa stained blood smears, and mortality (no. of dead mice/total no. of tested mice). The treatment was initiated 3 h after infection.

| Day | Control | Chloroquine 5 mg/kg/day once daily D0 − D + 3 | Chloroquine 2.5 mg/kg/day once daily D0 − D + 3 | Chloroquine 0.5 mg/kg/day once daily D0 − D + 3 |
|---|---|---|---|---|
| D + 4 | 15.8 ± 2.8 | 0.02 ± 0.04 | 0.2 ± 0.2 | 0.9 ± 0.5 |
| D + 6 | 55.2 ± 7.2 | 0 | 2.4 ± 2.2 | 24 ± 8.6 |

TABLE 16.3-continued

Effect of chloroquine on the parasitemia of mice infected with *P. yoelii* strain YM ($10^6$ parasites/mouse). Mice were 8 weeks old, female, BALB /c mice. Each group consisted of 5 mice. Chloroquine were given i.p.. The dosage, dosage interval and the days the animals were treated are indicated. Data are given as % parasitemia (mean ± SEM)and were measured by microscopic counting of Giemsa stained blood smears, and mortality (no. of dead mice/total no. of tested mice). The treatment was initiated 3 h after infection.

| Day | Control | Chloroquine 5 mg/kg/day once daily D0 − D + 3 | Chloroquine 2.5 mg/kg/day once daily D0 − D + 3 | Chloroquine 0.5 mg/kg/day once daily D0 − D + 3 |
|---|---|---|---|---|
| D + 8 | 85.6 ± 3.5 (5/5) | 0.1 ± 0.17 | 28.3 ± 16.2 | 57.4 ± 4.2 |
| D + 10 | | 2.8 ± 2.7 | 33.7 ± 19.8 | 66.3 ± 6.6 (2/5) |
| D + 12 | | 13 ± 4.4 | 40.2 ± 21 | 49.7 ± 17.6 (2/5) |
| D + 14 | | 22.4 ± 6.1 | 37.4 ± 19.8 | 35.3 ± 4.7 (2/5) |
| D + 16 | | 62.2 ± 24.5 | 4.7 ± 4.6 (2/5) | 18.5 ± 19.1 (3/5) |
| D + 18 | | 75.2 ± 3.3 | 0 (2/5) | 9 (4/5) |
| D + 20 | | 50 ± 16.4 (1/5) | 0 (2/5) | 0 (4/5) |

TABLE 16.4

Effect of licochalcone A in BALB/c mice infected with *P. yoelii* strain YM. Parasitemia in 2 control mice (animal no. 1 and 2) and in groups of 2 mice treated with licochalcone A at a dosage of 40 mg per kg body weight, 20 mg per kg body weight or 10 mg per kg body weight per day, respectively. The licochalcone A treatment was initiated 24 hours after infection, and the daily dosage was divided into 2 injections given of 12 hours interval. The drug was administered from days +1 +6.

| | Control | | 40 mg/kg/day | | 20 mg/kg/day | | 10 mg/kg/day | |
|---|---|---|---|---|---|---|---|---|
| Day | No. 1 | No. 2 | No. 1 | No. 2 | No. 1 | No. 2 | No. 1 | No. 2 |
| D + 4 | 45.0 | 26.0 | 0.1 | 0.5 | 0.01 | 0.0 | 1.5 | 4.0 |
| D + 5 | 89.0 | 68.0 | 0.5 | 1.0 | 0.0 | 0.0 | 1.5 | 3.0 |
| D + 6 | died | 90.0 died | 1.0 | 1.5 | 0.0 | 0.0 | 2.0 | 2.5 |
| D + 7 | | | 4.5 | 5.8 | 0.01 | 0.05 | 8.0 | 10.0 |
| D + 8 | | | 12.0 | 15.0 | 1.0 | 1.5 | 18.0 | 20.0 |
| D + 10 | | | 32.0 | 38.0 | 5.0 | 8.0 | 39.0 | 42.0 |
| D + 11 | | | 51.0 | 50.0 | 15.0 | 19.2 | 67.0 | 71.0 |
| D + 12 | | | 76.0 | 81.0 | 23.0 | 26.0 | 85.0 | 89.0 |
| D + 13 | | | 89.0 | 88.0 | 12.0 | 15.0 | 90.0 | 90.0 |
| D + 14 | | | died | died | 5.0 | 8.0 | died | died |
| D + 16 | | | | | 0.1 | 0.5 | | |
| D + 18 | | | | | 0.0 | 0.0 | | |

TABLE 16.5

Effect of licochalcone A on the parasitemia of mice infected with *P. yoellii* strain YM ($10^6$ parasites/mouse). Mice were 8 weeks old female BALB/c mice. Each group consisted of 5 mice. Licochalcone A was given i.p. 3 h after infection and from D+1 to D+3. Data are given as % parasitemia (mean ± SEM) and were measured by microscopic counting of Giemsa stained blood smears, and as mortality (no. of dead mice/total no of tesred mice).

| Day | Control | 15 mg/kg/day twice daily | 10 mg/kg/day twice daily | 5 mg/kg/day twice daily |
|---|---|---|---|---|
| D + 4 | 32.2 ± 2.2 | 2.0 ± 2.0 | 1.1 ± 1.0 | 1.6 ± 0.6 |
| D + 6 | 86.4 ± 2.8 (1/5) | 10.4 ± 7.4 | 14.2 ± 4.6 | 13.8 ± 4.4 |
| D + 8 | (5/5) | 22 ± 11.6 | 30.2 ± 6.4 | 36.6 ± 5.7 |
| D + 10 | | 22 ± 11.6 (1/5) | 48 ± 5.4 (1/5) | 64 ± 5.0 (2/5) |
| D + 12 | | 4.8 ± 3.2 (1/5) | 82 (4/5) | (5/5) |
| D + 14 | | 0 (1/5) | (5/5) | |

TABLE 16.6

Effect of licochalcone A on the parasitemia of mice infected with *P. yoelii* strain YM ($10^6$ parasites/mouse). Mice were 8 weeks old female BALB/c mice. Each group consisted of 5 mice. The dosage, dosage interval and the number of days the animals were treated are indicated. Data are given as % parasitemia (mean ± SEM) and were measured by microscopic counting of Giemsa stained blood smears, and as mortality (no. of dead mice/total no. of tested mice).

| | | Licochalcone A 3 h after infection From D + 1 to D + 5 | |
|---|---|---|---|
| Day | Control | 15 mg/kg/day twice daily | 10 mg/kg/day twice daily |
| D + 6 | 70 ± 4.5 | 0 | 0.1 ± 0.1 |
| D + 8 | 80 (4/5) | 0 | 0.7 ± 0.4 |
| D + 10 | (5/5 | 0 | 6.0 ± 3.8 |
| D + 12 | | 0 | 14.4 ± 8.9 |
| D + 14 | | 0 | 17 ± 17 (1/5) |
| D + 16 | | 0 | 0 (2/5) |
| D + 18 | | 0 | 0 (2/5) |

TABLE 16.7

Effect of licochalcone A in BALB/c mice infected with *P. yoelii* strain YM. Parasitemia in 2 control mice (animal no. 1 and 2) and in 2 groups of 2 mice treated with licochalcone A. Group 1 received one injection of licochalcone A (10 mg per kg body weight) 3 hours before infection. Group 2 received one injection of 10 mg per kg body weight 1 hour after infection, and 2 injections of 10 mg per kg body weight on days +1 and +2, respectively.

| | Control | | 10 mg/kg[a] | | 10 mg/kg[b] | |
|---|---|---|---|---|---|---|
| Day | No. 1 | No. 2 | No. 1 | No. 2 | No. 1 | No. 2 |
| D + 4 | 25.0 | 20.0 | 1.0 | 2.0 | 0.1 | 0.1 |
| D + 5 | 73.0 | 61.0 | 5.0 | 6.0 | 0.1 | 0.5 |
| D + 6 | died | 58.0 died | 22.0 | 21.0 | 0.5 | 0.5 |
| D + 7 | | | 55.0 | 45.0 | 1.5 | 0.8 |
| D + 8 | | | 65.0 | 15.0 | 0.1 | 0.1 |
| D + 9 | | | 85.0 | 82.0 | 0.1 | 0.1 |
| D + 10 | | | died | 90.0 | 0.00 | 0.00 |

[a]Intraperipetoneally 3 hours before infection
[b]Intraperipetoneally 1 hour after infection; two times per day on D + 1 and D + 2.

TABLE 16.8

Effect of licochalcone A in mice infected with *P. yoelii* strain YM. Mice were 8 weeks old female BALB/c mice. Each group consisted of 5 mice. Licochalcone A was given i.p.. The dosage interval and the number of days the animals were treated are indicated. Data are given as % parasitemia (mean ± SEM) and were measured by microscopic counting of Giemsa stained blood smear, and as mortality (no. of dead mice/total no. of tested mice).

| Day | Control | Licochalcone A 10 mg/kg twice daily D − 1, D0 | Licochalcone A 10 mg/kg four times daily D + 4 to D + 7 |
|---|---|---|---|
| D + 4 | 15.8 ± 2.8 | 1.2 ± 1.1 | 14.2 ± 3.8 |
| D + 6 | 55.2 ± 7.2 | 9.7 ± 0.7 | 6.6 ± 1.5 |
| D + 8 | 85.6 ± 3.5 (5/5) | 27.8 ± 16.1 | 17 ± 6.2 |
| D + 10 | | 47.4 ± 27.7 | 27.6 ± 12.1 |
| D + 12 | | 55.7 ± 48.4 (2/5) | 50.4 ± 15.6 |
| D + 14 | | 0 (4/5) | 58.6 ± 9.0 |
| D + 16 | | 0 (4/5) | 75.8 ± 6.6 (1/5) |
| D + 18 | | 0 (4/5) | 53 ± 25 (2/5) |
| D + 20 | | 0 (4/5) | 19 ± 9.7 (3/5) |

TABLE 16.9

Effect of licochalcone A on the parasitemia of mice infected with *P. yoelii* strain YM. Mice were 8 weeks old, 20 g body weight, female BALB/c mice. Licochalcone A was given by intraperitoneal implantation of 1007D Micro-Osmotic Pump (6 mg/100 μl/mouse) 3 h after infection. The pump releases 0.5 μl of drug solution per hour. The drug was released during a period of 7 days. Data are given as % parasitemia and were measured by microscopic counting of Giemsa stained blood smears.

| | | DMSO | | Licochalcone A | |
|---|---|---|---|---|---|
| Day | unoperated | mouse 1 | mouse 2 | mouse 1 | mouse 2 |
| D + 7 | 30 | 26 | 15 | 0.5 | 0 |
| D + 9 | 78 (died D + 10) | 72 | 59 | 6 | 0 |

TABLE 16.10

Effect of licochalcone A on the parasitemia of mice infected with *P. yoelii* strain YM. ($10^6$ parasites/mouse). Mice were 8 weeks old, 20 g body weight, female BALB/c mice. Licochalcone A was given orally (100 mg/kg/dose) 3 and 24 h after infection. Data are given as % parasitemia (mean ± SEM) and were measured by microscopic counting of Giemsa stained blood smears.

| | Control | | | | Licochalcone A | | | |
|---|---|---|---|---|---|---|---|---|
| Day | No. 1 | No. 2 | No. 3 | mean | No. 1 | No. 2 | No. 3 | mean |
| D + 4 | 17 | 20 | 22 | 19.7 | 0.5 | 1.0 | 1.5 | 1.0 |
| D + 7 | died | died | died | | 4.0 | 10.0 | 15.0 | 9.7 |
| D + 10 | | | | | 31.0 | 55.0 | died | 43 |
| D + 13 | | | | | 5.0 | 8.0 | | 6.5 |
| D + 16 | | | | | 0 | 0 | | 0 |

TABLE 16.11

Effect of 2,4-dimethoxy-4'-hydroxychalcone (2,4m4'hc) and 2,4-dimethoxy −4'-allyloxychalcone (2,4m4'ac) on the parasitemia of mice infected with *P. yoelii* strain YM ($10^6$ parasites/mouse). Mice were 8 weeks old female BALB /c mice. The analogues were given i.p.. The dosage, dosage interval and the number of days the animals were treated are indicated. Data are given as % parasitemia (mean ± SEM) and were measured by microscopic counting of Giemsa stained blood smears and as mortality (no. of dead mice/total no. of tested mice).

| | | 3 h after infection twice daily From D + 1 to D + 5 | | |
|---|---|---|---|---|
| Day | Control | 40 mg/kg | 30 mg/kg | 20 mg/kg |
| | | 2,4m4'hc | | |
| D + 6 | 70 ± 4.5 | (5/5) | 46.4 ± 2.1 | 4.8 ± 1.5 |
| D + 8 | (5/5) | | 70.8 ± 3.5 (1/5) | 12.4 ± 2.4 |
| D + 10 | | | (5/5) | 58.6 ± 14 |
| D + 12 | | | | 25 (3/5) |
| D + 14 | | | | 6 (3/5) |
| D + 16 | | | | 0 (3/5) |
| | | 2,4m4'ac | | |
| D + 6 | 70 ± 4.5 | 55.8 ± 1.5 | 37.4 ± 0.9 | 0.4 ± 0.2 |
| D + 8 | (5/5) | 83 ± 2.1 (2/5) | 67.2 ± 0.9 | 0.8 ± 0.2 |
| D + 10 | | (5/5) | (5/5) | 14.3 ± 4.0 |
| D + 12 | | | | 32.4 ± 4.0 |
| D + 14 | | | | 7 (3/5) |
| D + 16 | | | | 0 (3/5) |

TABLE 16.12

Effect of 2.4-dimethoxychalcone (2,4mc) and 2,5-dimethoxy-4'-allyloxy-chalcone (2,5m4'ac) on the parasitemia of mice infected with *P. yoelii* strain YM ($10^6$ parasites/mouse). Mice were 8 weeks old female BALB/c mice. The analogue were given i.p.. The dosage, dosage interval and the number of days the animals were treated are indicated. Data are given as % parasitemia (mean ± SEM)and were measured by microscopic counting of Giemsa stained blood smears and as mortality (no. of dead mice/total no. of tested mice).

| | | twice daily | | | |
|---|---|---|---|---|---|
| Days | Control | 40 mg/kg | 30 mg/kg | 20 mg/kg | 10 mg/kg |
| | | 2,4mc | | | |
| D ± 5 | 80 ± 11 | 78 (4/5) | | | |
| D + 6 | 89 (4/5) | (5/5) | 29 (3/5) | 85 (4/5) | (5/5) |
| D + 8 | (5/5) | | 15 (4/5) | (5/5) | |
| D + 10 | | | 65 (4/5) | | |
| D + 12 | | | (5/5) | | |
| | | 2,5m4'ac | | | |
| D ± 5 | 80 ± 11 | | | | |
| D + 6 | 89 (4/5) | (5/5) | 62 (3/5) | 79 (4/5) | (5/5) |
| D + 8 | (5/5) | | 78 (4/5) | (5/5) | |
| D + 10 | | | (5/5) | | |
| D + 12 | | | | | |

Results and discussion

*P. yoelii* is a very virulent parasite in mice. The parasitemia increased rapidly and the animals die if treatment is not initiated. The control animals of the experiment presented in Table 16.1 reached a parasitemia of approximately 50% at day 11, and the animals died between day 12 and 21. The control animals of the experiments presented in Table 16.2–16.12 had an even more rapid disease development, these animals reached a parasitemia of 60–70% on day 5, and the animals died on day 6, 7 or 8. The experiment reported in Table 16.1 was performed with another strain of parasites than the following experiments, this is probably the reason for the slight difference in the disease development between this experiment and the rest of the experiments.

Table 16.1 and 16.2 show that licochalcone A given two times dailv in a dosage of 3–10 mg per kg body weight maintained the parasitemia at a low level for as long as the treatment was given. After the treatment was withdrawn, the parasitemia increased, but the delay of parasitemia caused by the licochalcone treatment enabled most animals to control the infection and clear the parasites.

The results presented in Table 16.3 show the effect of chloroquine treatment in mice infected with the virulent *P. yoelii* YM infection.The data show that treatment with chloroquine in this model is unable to protect the animals from parasitemia, and underlines the difficulty of drug treatment in this model. When interpreting the efficiency of the test compounds this fact should be taken into consideration.

The results presented in Table 16.4 confirm the results presented in Table 16.1 and 16.2. Furthermore thev show that a dosage of 20 mg per kg body weight per day was more effective than a dosages of 10 mg per kg body weight per day or 40 mg per kg body weight per day, when the drug was administered twice daily. This indicates that to increase the efficacv of the drug it should be attempted to decrease the intervals between the injection of the drug rather than increasing the amount of drug per injection.

Table 16.5 shows the results of an experiment in which licochalcone A treatment was maintained for the same period as chloroquine in the experiments reported in Table 16.3. The results indicate that the efficiency of licochalcone A was comparable to that of chloroquine. The experiments reported in Table 16.6 were essentially performed as the experiments reported in Table 16.3, the only difference was that the treatment was continued for five days instead of three days. The results (Table 16.6) indicate that the efficiency of licochalcone A was markedlv enhanced by extending the treatment period.

The results presented in Table 16.7 show that one injection of 10 mg per kg body weight 3 hours before infection causes a considerable delay in the increase of parasitemia (group 1). This is interesting since the pharmaco-kinetic studies indicated that the half-life of the drug in the plasma was about 20 min. Hence, the results indicate that the drug was concentrated within the erythrocytes or that metabolites of the drug could affect the parasites. Table 16.7 also showed that the efficienccy of the drug was higher if the drug was given shortly after infection, since mice in which licochalcone A treatment was initiated 1 hour after infection controlled the infection even when the treatment was given for 2 days only (group 2). When the drug was given the day before infection and the day of infection at a dosage of 10 mg two times daily (Table 16.8), the efficiency of the drug was comparable to that found in Table 16.7 (group 1). The experiment reported in Table 16.8 was performed to test the efficiency of the compound in animals in which the infection was established and the parasiternia was high at the initiation of treatment. The results show that licochalcone A was able to reduce the parasitemia as long as the treatment was maintained. However, when the treatment was stopped, the parasitemia increased.

Table 16.9 shows the results of an experiment in which licochalcone A was injected into a pump from which the drug was slowly released over a period of 7 days. Administered this way 6 mg of licochalcone A seems to have considerable efficiency.

Table 16.10 shows the results of experiments where licochalcone A was given orally. Due to difficulties in administering the drug via a mouth catheter, the drug was only administered twice. The results show that licochalcone A administered orally has the same efficiency as when administered by i.p. injections.

Tables 16.11 and 16.12 show the results of studies in which 4 licochalcone A analogues were tested in the in vivo mouse model. The analogues presented in Table 16.12 did not have any effect. The analogues presented in Table 16.11 inhibited the parasitemia when given at a dosage of 60 mg/day or 40 mg/day, respectively. When administered at a dosage of 80 mg/day, no effect was seen. At a dosage of 40 mg/day, the analogues were able to prevent the death of 2 out of 5 animals.

Conclusion

One strain of *P. yoelii* with a parasitemia up to 61% are able to kill the control mice within 12–20 days following infection. Using a more virulent strain of *P. yoelii* malaria called YM, the control mice died within 6–7 days following infection with a parasitemia of up to 90%.

The in vivo experiments using *P. yoelii* infection in mice indicate that administration of licochalcone A at concentrations of 15 mg per kg body weight twice a day (30 mg per kg body weight per day) over a period of 5 days was able to completely clear the parasite from the infected mice and completely protect the mice from death induced by the parasite as compared to the control mice.

If the treatment with licochalcone A was initiated one hour before the animals were infected two days of treatment with 20 mg licochalcone A per-day were sufficient to control the parasitemia and prevent death of the animals (Table 16.7, group 2).

The data shown in Table 16.4 using the same strain of *P. yoelii* YM show that the ranges of concentrations of licochalcone A used for the treatment of these animals were fairly narrow, indicating that concentration of 10 mg per kg body weight (20 mg per kg body weight per day) given twice a day was able to completely protect the mice as shown in the previous experiment. On the other hand, the third group of animals receiving a concentration of 5 mg per kg body weight (10 mg per kg body weight per day) given twice a day over a period of 6 days were not able to survive the infection.

In the experiments reported in Tables 16.3 and 16.5, chloroquine (a widely used antimalarial drug) and licochalcone A were administered at different dosages but with the same regimen with regard to administration route, dosage intervals and length of the treatment. The results indicate that the efficiency of the two compounds was comparable.

The experiment shown in Table 16.7 (group 1) using the same malaria parasite showed that when licochalcone A was given three hours before the infection and only once in a dose of 10 mg per kg body weight, the parasitermia was lower in the treated group in the first week of infection than in the controls. However, the treatment did not prevent the death of the animals.

The experiment reported in Table 16.8 was performed to test the efficiency of the compound in animals in which infection was established and in which the parasitemia was high when the treatment was initiated. The results show that licochalcone A was able to reduce the parasitemia as long as the treatment was maintained. However, when the treatment was stopped, the parasitemia increased.

Table 16.9 shows the results of an experiment in which licochalcone A was injected into a pump from which the drug was slowly released over a period of 7 days. Administered this way 6 mg of licochalcone A seems to have considerable efficiency. This is an interesting observation since it indicates that the efficiency of licochalcone A is not dependent on the high concentration of the compound which may be assumed to follow i.p. injections.

Table 16.10 shows the effect of licochalcone A when administered orally. Although the results are preliminary, they indicate that the efficiency of licochalcone A administered orally is at the level of the efficiency when administered by i.p. injections. Four licochalcone A analogues were tested in the in vivo mouse model. The analogues presented in Table 16.11 inhibited the parasitemia when given at a dosage of 60 mg/day or 40 mg/day, respectively. When administered at a dosage of 80 mg/day, no effect was observed. At a dosage of 40 mg/day, the analogues were able to prevent the death of 2 out of 5 animals.

Conclusion

Thus, the data presented in the 12 tables indicate that:

1. Licochalcone A is able to completely clear the infection of *P. yoelii* in mice.

2. The dose range protective for the mice is fairly narrow when the drug is administered i.p.

3. When licochalcone A is given one hour after infection of the mice, the compound is able to completely stop or inhibit the multiplication of the parasite and establishment of the infection in these mice, indicating that the compound can be used for prophylactic measures. When the compound is used for the treatment of an established infection, it is able to decrease the parasitemia. This is important because it allows the mice to establish an immune response which then may be able to eventually eliminate the parasites. Because of the short half-life of licochalcone A, it appears advantageous either to administer the compound frequently or to administer the compound in a slow release composition or as a prodrug from which the drug is slowly released.

4. Licochalcone A is effective when administered orally.

5. Analogues of licochalcone A has some effect in the in vivo mouse model, although the efficiency of the tested analogues appears to be less than the efficiency of licochalcone A.

EXAMPLE 17

Effect of licochalcone A on Legionella and some other bacterial species

Materials and methods:

Drug. Licochalcone A was isolated as described in Example 1.

Bacteria. 20 Legionella strains: Five clinical isolates from bronchial secretions and a lung abscess: 2 *Legionella pneumophila* serogroup 1 and 3 *Legionella micdadei* (*L. detroit, L. bari*, L. F 1433). Eight *Legionella pneumophila* serogroups 1–7 and one strain of each of *L. bozemanii, L. dumoffii, L. gormanii, L. micdadei, L. feelei, L. wadsworthii, L. longbeacheae. Staphylococcus aureus* ATCC 25923 was the control strain.

The following respiratory commensals were tested: three Corynebacterium species, two *Branhamella catarrhalis*, one *Streptococcus pneumonia*, one Non-haemblytic streptococci, one *Bacillus subtilis*, one *Sarcina lutea*. All strains were kept frozen at −80° C. until assayed.

The Legionella strains were subcultured on buffered charcoal yeast extract with alfaketoglutarate (BCYE-α), and the rest of the strains were subcultured on 10% horse blood agar for 48 hours and 24 hours, respectively.

Minimal inhibitory concentrations. Macrodilution rows were made with buffered yeast extract with alfa-ketoglutarate (BYE-α) with 2 ml aliquots in vials, the dilution of G.radix extract from 1000 μg/ml to 0.04 μg/ml. Suspensions of Legionella species and the other pathogens and commensals were made in BYE-α. All the dilution rows were inoculated to give a final concentration of $10^5$ CFU//ml. After incubation at 37° C. for 2 and 24 hours, respectively, aliquots of 10 μl were taken from all dilution steps and plated onto BCYE-x agar plates (all Legionella species) and to 10% horse blood agar (all non-Legionella strains). All the BCYE-x plates were incubated for 48 hours in a humid atrmosphere at 37° C. and read. The inoculated 10% horse blood agar plates were incubated in a normal atmosphere at 37° C. for 24 hours and read.

Results

All the clinical *Legionella pneumophilia* isolates were sensitive to licochalcone A, their MIC-values ranging from 1 to 4 μg/ml, whereas *Legionella gormanii* and the 4 *L. micdadei* isolates had MIC-values from 15 to 500 μg/ml.

The Gram positive cocci all had MIC's from 4 to 8 mg/ml. One of the corynebacterium species was very sensitive, having MIC of 0.3 μg/ml.

TABLE 17.1

*Legionella* species susceptibility to licochalcone A in μg/ml.

| | No. of strains | MIC |
|---|---|---|
| *L. pneumophilia* serogr. 1 | 4 | 1–4 |
| *L. pneumophilia* serogr. 2–7 | 6 | 2–4 |
| *L. bozemanii* | 1 | 2 |
| *L. domoffii* | 1 | 2 |
| *L. gormanii* | 1 | 500 |
| *L. micdadei* | 1 | 500 |
| *L. micdadei* (Detroit) | 1 | 15 |
| *L. micdadei* (Bari) | 1 | 60 |

TABLE 17.1-continued

| *Legionella* species susceptibility to licochalcone A in μg/ml. | No. of strains | MIC |
|---|---|---|
| *L. micdadei* (F 1433) | 1 | 60 |
| *L. feelei* | 1 | 4 |
| *L. wadsworthii* | 1 | 2 |
| *L. longbeacheae* | 1 | 1 |

TABLE 17.2

Susceptibility of Gram positive pathogens and commensals to licochal-1/32 cone A in μg/ml.

| | No. of strains | MIC |
|---|---|---|
| *Staphylococcus aureus* ATCC 25923 | 18 | |
| *Sarcina lutea* | 1 | 4 |
| *Non-haemolytic streptococci* | 1 | 4 |
| *Streptococcus pneumonia* | 1 | 4 |
| Corynebacterium species | 3 | 0.3–4 |
| *Bacillus subtilis* | 1 | 4 |

Conclusion

Licochalcone A exhibited a clear anti-legionella activity at MIC values form 1 μg/ml, in most cases from 1 to 4 μg/ml.

The low MIC for *L. pneumophila*, the human pathogen, is promising and therefore licochalcone A can be considered as a potential drug against respiratonr infections.

The reason that the MIC was very high for the inhibition of *Legionella micdadei* could be that the cell wall of *L. micdadei* is different from the cell wall of *L. pneumophila* (Heberret al, 1984) and therefore, that the uptake of licochalcone A in *L. micdadei* is poorer than the uptake in *L. pneumophila.*

Although some of the Gram positive pathogens and commensals were sensitive to licochalcone A, it was surprisingly found that not all bacteria even within the same group of bacteria were sensitive to the licochalcone A in atoxic concentrations. However, the bacteria showing sensitivity towards licochalcone A were the pathogenic bacteria.

EXAMPLE 18

Effect of licochalcone A on *Helicobacter pylori*

Material and methods

Bacteria. 16 recent clinical isolates of *Helicobacter pylori* from patients with duodenal ulcer or chronic gastritis. The medium used both for transportation of the biopsies and the minimal inhibitory concentration (MIC) assavs was: brain heart infusion broth with 0.0002% resazurine, 0.15% L-cystein and 5% horse serum (Helicomedia), pH 6,8.

*Staphylococcus aureus* ATCC 25923 was used as control strain. The *Helicobacter pylori* strains were subcultured on chocolate agar plates with cysteine in a microaerophilic atmosphere at 37° C. for 72 hours and kept frozen at −80° C. until assaved.

MIC determinations. Macrodilution rows were made with Helicomedia with 2 ml in all vials. The dilution of licochalcone A was from 500 μg/ml to 1 μg/ml.

All dilution rows were inoculated to give a final concentration of $10^5$ CFU/ml.

The MIC rows were incubated under microaerophilic conditions for two hours. Hereafter aliquots of 10 μl were taken from all dilution steps and plated on chocolate agar with cysteine and incubated in a microaerophilic atmosphere for 72 hours at 37° C. The control strain *Staphylococcus aureus* was incubated both aerobically and rnicroaerophilicaliy at 37° C. for 24 hours. All plates were read by the Karber method.

Results

TABLE 18

The minimal inhibitory concentration of licochalcone A on *Helicobacter* pylori in μg/ml.

| $MIC_{50}$ | $MIC_{90}$ | Range |
|---|---|---|
| 62 | 125 | 16–125 |

Only one strain had a low MIC: 16 μg/ml.

After 2 hours incubation with licochalcone A, the MIC of *Staphylococcus aureus* was, as expected, 4 μg/ml when incubated in a normal atmosphere, whereas under microerophilic conditions it raised to more than 500 μg/ml.

Conclusion

From the results it is seen that very high concentration of licochalcone are necessary to inhibit bacteria under microaerophilic conditions. However, since the use of licohalcone A and other bis-aromatic α,β-unsaturated ketones against *Helicobacter pylori* could be in the treatment or prophylaxis of gastric ulcer which often is caused or aggravated by Helicobacter, it means that the treatment would be local treatment, such is any suitably targeted controlled release compositions and therefore it is possible to administer high doses.

EXAMPLE 19

Effect of licochalcone A on Mycobacteria species

Materials and methods 63 strains of mycobacteria were used in this study. The bacteria were grown in Dubos broth media before susceptibility testing. Licochalcone A was isolated as described in Example 1. Licochalcone A was dissolved in dimethyl sulfoxide (DMSO) and diluted in distilled water to the desired concentration.

Susceptibility testing was performed radiometrically by using a BECTEC 460-TB apparatus (Becton Dickinson) in a confined atmosphere (5% $CO_2$). Bacterial growth was measured as a function of the ability of the bacteria to catabolize $^{14}C$-labelled palmitic acid in the BECTEC 7H12B TB medium (Becton Dickinson) during growth. which resulted in the release of $^{14}C$-labeiled $CO_2$. The growth was expressed as a numerical value called the growth index (GI) which ranged from 1 to 999. The 7H12 vials were inoculated with 0.1 ml of an appropriately diluted Dubos broth culture to give a final inoculum of about $5\times10^4$ colony-forming units (CFU) per ml together with 0.1 ml of different concentrations of licochalcone A. The final concentrations of licochalcone A tested ranged from 1.25 μg/ml to 80 μg/ml. A vial without licochalcone A, but with an inoculum diluted 1:100, was included as a control. The final inoculum was determinated by culturing 0.1 ml from the control vial onto one Lowenstein-Jensen slant. The vials were incubated under stationary conditions at 35° C. and growth was monitored by daily GI determination for 7 days. At day 7, 0.1 ml from each vial with a GI reading <30 was cultured onto one Lowenstein-Jensen slant. Colony counts were enumerated after incubation at 35° C. for 3 weeks.

Minimal inhibitory concentration (MIC) was defined as the lowest concentration of licochalcone A which could inhibit 99% or more of the mycobacteria population.

Minimal bactericidal concentration (MBC) was defined as the lowest concentration of licochalcone A which killed 99% or more of the mycobacteria population.

Results

TABLE 19.1

Eighteen different species of *Mycobacteria* were screened for susceptibility of 20 μg/ml of licochalcone A.

| Species MIC ≦ 20 μg/ml | MID > 20 μg/ml |
|---|---|
| *M. tuberculosis* | *M. szulgai* |
| *M. bovis* | *M. avium*/intracellular |
| BCG | *M. scrofulaceum* |
| *M. kansasii* | *M. malmoense* |
| *M. xenophii* | *M. terrae/triviale* |
| *M. marinum* | *M. nonchromogenicum* |
| | *M. smegmatis* |
| | *M. flavescens* |
| | *M. fortuitum* |
| | *M. chelonae* |

Determinations of MIC and MBC of licochalcone A against strains belonging to the *M. tuberculosis* complex:

| | |
|---|---|
| *M. tuberculosis* | $mean_{MIC}$ = 7.1 μg/ml |
| | $range_{MIC}$ = 5–10 μg/ml (n = 19) |
| | $mean_{MBC}$ = 40 μg/ml (n = 2) |
| *M. bovis* | $mean_{MIC}$ = 15.7 μg/ml |
| | $range_{MIC}$ = 10–20 μg/ml (n = 8) |
| BCG | $mean_{MIC}$ = 8.6 μg/ml |
| | $range_{MIC}$ = 5–10 μg/ml (n = 3) |
| | $mean_{MBC}$ = 40 μg/ml (n = 3) |

Determinations of MIC of licochalcone A against strains of *M. avium*/intracellular:

*M. avium* (AIDS patients): $mean_{MIC}$>80 μg/ml (n=4)

*M. avium* (non AIDS patients): $mean_{MIC}$>80 μg/ml (n=7)

*M. intracellular*: $mean_{MIC}$=50.0 μg/ml $range_{MIC}$=20–80 μμg/ml (n=9)

TABLE 19.2

2/31 Influence of 10% serum on MIC determination of licochalcone A.

MIC (μg/ml) with and without 10% Human Serum: Strain = H37RV

| | Ethambutol (40% protein binding) | Ofloxacin (5% protein binding) | Fusidic acid (90% protein binding) | Licochalcone A |
|---|---|---|---|---|
| $MIC_{-serum}$ | 1 | 0.5 | 8 | 5 |
| $MIC_{+serum}$ | 2 | 0.5 | 32 | 40 |

Conclusion

With a proposed "cut off" concentration value of 20 μg/ml, most strains belonging to the *M. tuberculosis* complex were susceptible. The bactericidal concentration was 4 to 8 times the inhibitory concentration which in all strain tested was higher than the "cut off" concentration.

All *M. avium*/intracellular strains were on the other hand resistant with MIC >20 μg/ml and most with MIC >80 μg/ml.

From Table 19.2 it is seen that MIC of licochalcone A increases 8-fold when supplemented with 10% of serum which may indicate that licochalcone A is highly protein-bound.

EXAMPLE 20

Licochalcone A absorption studies

The absorption pattern and pharmaco-kinetics of licochalcone A in rats given by oral route were determined compared with pharmacokinetics of licochalcone A in rats given intravenously.

Number of rats: 4 for each group

Groups:

1. receiving licochalcone A
2. receiving buffer

Dose: 1000 mg/kg body weight of licochalcone A.

Route: Oral, administered once.

Samples: 2 ml of blood was drawn 4 times from each rat.

1. 4 hrs after licochalcone A administration
2. 24 hrs after licochalcone A administration
3. 48 hrs after licochalcone A administration
4. one week after licochalcone A administration After one week one rat from each group was sacrificed and the spleen and liver were examined for histology and licochalcone A measurements.

Number of rabbits: 1 rabbit for each group

Groups:

1. receiving licochalcone A
2. receiving buffer

Dose: 20 mg per kg body weight

Route: Intravenously, administered once

Samples: Samples were drawn from each rabbit twice.

1. 1 hour after licochalcone A administration
2. 24 hours after licochalcone A administration Results In the serum samples of rats receiving 1000 mg per kg body weight taken 4 hours after licochalcone A administration, licochalcone A concentrations of 0.14 μg/ml and 0.16 μg/ml were detected. Licochalcone A concentrations in the serum after 24 hours were <0.05 μg/ml (detection limit of the assay). It should be mentioned that licochalcone A absorbs to glassware and perhaps other material during the assay, and therefore the actual serum concentrations may be higher.

In rabbits, concentrations of 0.35 μg/ml licochalcone A were detected in the serum one hour following intravenous administration of 20 mg per kg body weight of licochalcone A. 24 hours after administration the licochalcone A concentration in the serum was <0.05 μg/ml (detection limit of the assay).

Conclusion

From the results it is seen that already after 4 hours, the concentration of licochalcone A in the blood was very small compared to the dose administered orally to the rats. This could be due to an extraordinarily large first pass elimination of licochalcone A in the liver since the concentration found in rabbits 1 hours after intravenous administration was higher even though the dose administered was lower than in the rat study.

EXAMPLE 21

Animal toxicity studies with licochalcone A

Study in mice

Drug. Licochalcone A solution was prepared as follows: 20 mg of licochalcone A was dissolved in 0.2 ml of ethanol. 60 mg of melted polyoxyethylene (23)lauryletherb (Brij 35) was added. 1.7 ml of phosphate buffer was then added while stirring on a warm plate. pH in the licochalcone A solution was adjusted to 7.3.

Mice. NMRI female mice (30–35 gram) in groups of 4 each were used for these studies. For the oral route experiment, the animals were fasted for 16 hrs with access to drinking water. Licochalcone A was suspended in 2% carboxymethylcellulose in water. This suspension was available for the mice in an amount of 0.1 ml per 10 gram body weight. The animals were observed every day for 7 days. For the intravenous injection experiment the animals were not fasted. Licochalcone A in solution (20 mg/ml) prepared as mentioned above was injected intravenously 0.1 ml per 10 gram body weigh over a period of one hour and again 24 hrs later.

Results

TABLE 21.1

8/25 Licochalcone A toxicity studies in mice.

| Licochalcone A dose (mg/kg) | Solution strength | No. dead (after 1 hr) |
|---|---|---|
| Control Brij | 3 | 0 |
| Licochalcone A: | | |
| 100 | 1 | 4 |
| 60 | 0.6 | 4 |
| 50 | 0.5 | 1 |
| 20 | 0.2 | 0 |
| 1000 mg/kg perorally | 10 | 0 (after 7 days) |

Approximate LD50 i.v.=55 mg per kg body weight LD50 peroral >1000 mg per kg body weight Study in rats. To 4 rats was administered one dose of 1000 mg per kg body weight perorally. The rats were observed for one week. None of the animals died.

Results

LD50 peroral in rats >1000 mg per kg.

Conclusion

The results above shows that licochalcone A is atoxic even in high concentrations.

EXAMPLE 22

Animal toxicity studies of 4-hydroxychalcone in mice

Mice. BALB/c female mnice, 8 weeks old, 20 g body weight.

Drug. 4-Hydroxychalcone prepared as in Example 2.

LD50. 80 mg of 4-hydroxychalcone was dissolved in 0.2 ml of 99% (v/v) ethanol, and then mixed with 240 mg of Brij 35 dissolved in 19.8 ml of buffer pH 7.3 ($NaH_2PO_4.H_2O$ 26 mg, $Na_2HPO_4.2H_2O$ 520 mg and distilled water 100 ml), and then sterile filtered through a 0.22 μm Millipore filter. Drug was injected intraperitoneally into mice once.

Results

TABLE 22.1

7/26 4-Hydroxychalcone toxicity study in mice.

| Groups | n | No. died after 24 h |
|---|---|---|
| 50 mg/kg i.p. | 4 | 0 |
| 100 mg/kg i.p. | 4 | 0 |
| 200 mg/kg i.p. | 4 | 1 |
| 400 omg/kg i.p. | 4 | 2 |

Conclusion

From Table 22.1 it is seen that when administering intraperitoneally, LD50 is 400 mg per kg. However, intraperitoneal administration is comparable to intravenous administration and then 400 mg per kg is a very high dose, which means that in therapeutical doses licochalcone A is an atoxic drug.

EXAMPLE 23

Quantification of licochalcone A in serum or plasma

Serum or plasma was diluted with one part of acetonitrile, left for 15 min at 4° C., and centrifugated for 3 min at 10,000 g. An aliquot of the supernatant was chromatographed at 37° C. by HPLC over Spherisorb ODS-2 (5 μm, 120×4.5 mm, Phase Separation LTD, UK) using acetonitrile aqueous acetic acid, 2%, (1:1) as an eluent, flow rate 1.5 ml/min, and UV detection (370 nm and 254 nm).

Detection limit (25% acetonitrile in water, 370 nm): 0.05 μg/mnl.

Detection limit (plasma, 370 nm): 0.1 μg/ml $t_R$ is approximately 3.23 min for licochalcone A (k' 3.51) and 3.93 min for 2,4-dimethylnitrobenzene (k' 8.32) used as an internal standard.

No interfering peaks were observed in serum or plasma from rodents not treated w licochalcone A.

Conclusion

This quantification test will be used in the pharmacokinetic studies of bis-aromatic α,β-unsaturated ketones and derivatives thereof (see Examples 24 and 25).

EXAMPLE 24

Quantification of intracellular concentration of licochalcone A

Material and Methods

UV-detector: Beckmann, model G, 2400 (single-ray apparatus)

Centrifuge: Heraeus, Christ, Labofuge GL.

Methods. A standard curve of licochalcone A solutions in concentrations between μg/ml and 10 μg/ml was prepared. A basic solution of 10 mg licochalcone A in 5 n DMSO was produced. The desired concentrations was obtained by dilution of the b solution with Krebs Ringer solution. The solutions were measured with a UV-sin ray apparatus at 385 nm. The detection wavelength was determined by UV-scanning of licochalcone A dissolved in DMSO and Krebs Ringer solution.

The uptake of licochalcone A in human cells was determined by using granulocvt (PMN) and mononuclear cells (MNC) incubated with 4 different concentrations o: licochalcone A at 37° C. Cells incubated without licochalcone A, as well as licochal( A solutions without cells were used as control measurements.

Isolation of the different cell types from blood was done as described in FIG. 7.

The isolated cells were counted in microscope and diluted with Krebs Ringer solt to $2\times10^4$ cells/ml and $4\times10^4$ cells/ml.

To supernatants of $2\times10^4$ cells/mnl and $4\times10^4$ cells/ml were added aliquots of the licochalcone A solution to give final concentrations of 20, 10, and 5 μg/ml. After incubation for 5 min at 37° C. the cells were spun down at 2000 rpm for 10 min. TI supernatant was collected and the licochalcone A concentration determined spec photometrically.

The pellet was resuspended in distilled water and lysed by freezing and thawing several times. The suspension was centrifugated at 1500 rpm for 10 min and the licochalcone A concentration determined spectrophotometrically.

Results

The amount of licochalcone A taken up by the cells varied between 10% and 25%.

Conclusion

Licochalcone A is taken up by the cells and the effect of licochalcone A on the parasites in vivo may well also be due to intracellular killing of the parasites in the macrophages since it is understood from this example that licochalcone is taken up by the cells.

EXAMPLE 25

Detection of the half live of licochalcone A in mice

Standards. Standards containing 14.68 μg/ml, 4.90 μg/ml, and 0.45 μg/ml plasma were freshly prepared every day. The standards were wrapped in tinfoil to avoid light catalyzed isomerization.

A solution of 2,4-dimethylnitrobenzene (0.20 μl/ml) was used as an internal standard.

Licochalcone A (10 mg/kg mouse 200 μg/mouse) was injected i.p. into mice. The mice were sacrificed and bleeded after 15, 30, 60, 120, 240 and 480 min. The plasma was obtained by centrifugation. 100 μl of plasma was added to 100 μl of the solution of the internal standard and the mixture left for 30 min. The mixture was centrifuged for 5 min at 10,000 g and 20 μl of the clear supernatant was analyzed by HPLC (Example 23).

Results

| Samples | Licochalcone A μg/ml |
|---|---|
| Control | 0 |
| Mouse bleeded after 15 min | 1.33 |
| after 30 min | 0.28 |
| after 60 min | 0.14 |
| after 120 min | below det. limit |
| after 240 min | below det. limit |
| after 480 min | below det. limit |

Beside the peak corresponding to licochalcone A additional peaks were observed. Three peaks were detected by changing the eluent to acetonitrile-2% aqueous acetic acid (43:57), lica-M, k 2.2, lica-$M_2$, k 0.69, and lica-$M_3$ k 1.3, licochalcone A, k 8.3. Cleavage of the two fast moving peaks was catalyzed by a 5-glucoronidase (Helix pomatia, Sigma), which is contaminated with sulfatase. The UV-visible spectra of these compounds were similar to that of licochalcone A. The slow moving metab( had max at much lower wavelength than licochalcone A.

Conclusion

A half live of approximately 18 min is calculated assuming that licochalcone A is metabolized according to a 1-compartment model and eliminated by a first order mechanism. Three metabolites have been detected. The two fast moving metaboli are either glucoronides, sulfates or glucoronides and sulfates. The low wavelength which Amax of the slow moving metabolite was located indicated that the double b of the a, O-ketone has been changed or that the aromaticity of the A-ring was lost.

EXAMPLE 26

Reaction between licochalcone A and thiol-containing peptides Formation of N-acetyl-L-cysteine conjugates of licochalcone A. A solution of 1.5 rr licochalone A and 100 mg of N-acetyl-L-cysteine in acetonitrile-0.13M aqueous pi sium phosphate buffer solution pH 7.5 (1:3) was left for 7 days at ambient tempera protected from light. Analysis of the solution by HPLC (Example 23) using acetoni 2% aqueous acetic acid (45:55) as an eluent showed decreased amounts of licochalc A and appearance of two new peaks probably the two conjugates of licochalcone A and N-acetyl-L-cysteine of the below formulae A and B.

A

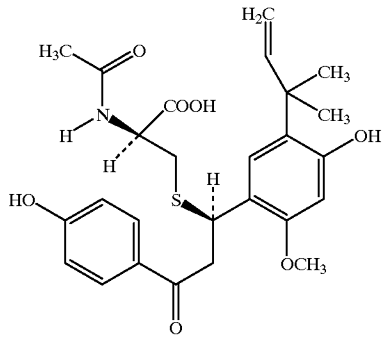

B

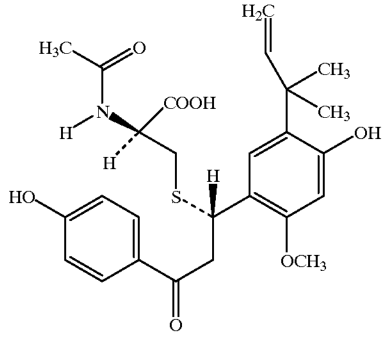

No similar decrease of the concentration of licochalcone A was seen when the chalcone was dissolved in the buffer and left for 7 days without addition of N-acetyl-L-cysteine.

The same two conjugated were formed by reacting licochalcone A with N-acetyl-L-cysteine in a preparative scale:

22 mg (70 μmole) of licochalcone A and 1.4 g (8.5 mmol) of N-acetyl-L-cysteine were dissolved in methanol-water-0.2M potassium phosphate buffer, pH 8.5 (2:9:9) and the solution was left for 4 days at room temperature. The solution was concentrated in vacuo to half volume and the two conjugates were isolated by HPLC over PLRP-S (3 μm) using acetonitrile-methanol-0.1M ammonium acetate buffer, pH 4.0 (2:9:9) as an eluent. The appropriate fractions were concentrated in vacuo to half the volume and the remaining solvent removed by freeze drving. The procedure of dissolving the residue was dissolved in water and freeze drying was repeated several times in order to remove remaining amounts of ammonium acetate. The two conjugates were isolated in yields of 20 (57%) and 10 mg (28%), respectively.

$^1H$ NMR data for conjugate I (400 MHz, $CD_3OD$, δ) 7.79 (AA'-part of an AA'MM'-system, H-2' and H-6'), 7.17 (s, H-2), 6.80 (MM'-part of an AA'MM'-system, H-3 and H-5'), 6.30 (s, H-5), 6.17 (dd, J 18 and 10 Hz, CH═), 4.88 (signal partly hidden by $CD_3OH$ signal, $CH_2$═), 4.82 (dd, J 8.4 and 6.8 Hz, H-β), 4.40 (dd, J 7.6 and 4.3 Hz, H-α(cysteine)), 3.71 (s, $CH_3O$), 3.5–3.3 (signal partly hidden by $CHD_2O$, AB-part of an ABX-system, 2H-α), 2.96 (dd, J 13.2 and 4.3 Hz, H-β(cysteine)), 2.82 (dd, J 13.2 and 7.6 Hz, H-β (cysteine)), 1.92 (s, $CH_3CO$), 1.38 (s, $(CH_3)_2C$═).

$^{13}C$ NMR data for conjugate I (50 MHz, $CD_3OD$, δ) 196.0, 176.6, 172.6, 163.8, 157.4, 156.9, 149.5, 132.1., 130.2, 127.9, 127.3, 120.5, 116.2, 110.4, 101.1, 56.1, 55.8, 45.5, 41.2, 41.1, 35.4, 27.6, 22.8.

$^1H$ NMR data for conjugate II (400 MHz, $CD_3OD$, δ) 7.82 (AA'-part of an AA'MM'-system, H-2' and H-6'), 7.21 (s, H-2), 6.80(MM'-part of an AA'MM'-system, H-3 and H5'), 6.30 (s, H-5), 6.18 (dd, J 18 and 10 Hz, CH=), 4.9 (signal partly hidden by $CD_3OH$ signal, $CH_2$=), 4.9 (signal partly hidden by $CHD_2O$, AB-part of an ABX-system, 2H-β), 4.48 (t, J 5.7 Hz, H-α(cysteine)), 3.69 (s, $CH_3O$), 3.5–3.3 (signal partly hidden by $CHD_2O$, AB-part on an ABX-system, 2H-α), 2.81 (d, J 5.8 Hz, H-β(cysteine)), 2.00 (s, $CH_3CO$), 1.39 (s, $(CH_3)_2C$=).

$^{13}C$ NMR data for conjugate II (50 MHz, $CD_3OD$, δ) 197.3, 174.7, 170.7, 161.8, 155.6, 154.9, 147.6, 130.2, 128.3, 126.3, 125.3, 118.7, 114.5, 108.4, 99.0, 54.0, 53.6, 43.7, 39.2, 39.0, 33.1, 25.7, 20.9.

Formation of glutathione conjugates of licochalcone A. A solution of 1.5 mg of licochalone A and 100 mg of glutathione in acetonitrile-0.13M aqueous potassium phosphate buffer solution pH 7.5 (1:3) was left for 7 days at ambient temperature protected from light. Analysis of the solution by HPLC (Example 23) using acetonitrile-2% aqueous acetic acid (45:55) as an eluent showed decreased amounts of licochalcone A and appearance of two new peaks probably the two conjugates of licochalcone A and glutathione of the below formulae C and D.

-continued

D

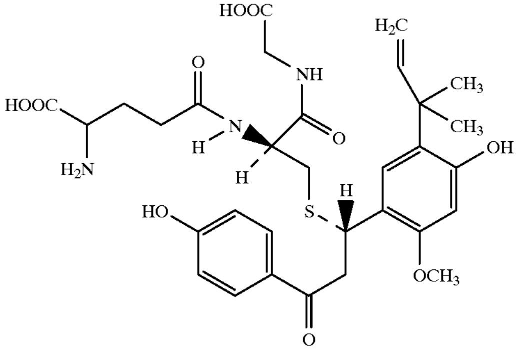

No similar decrease was seen when only licochalcone A was dissolved in the buffer and left for 7 days.

EXAMPLE 27

Estimation of the rate of the reaction between N-acetyl-L-cysteine and chalcones

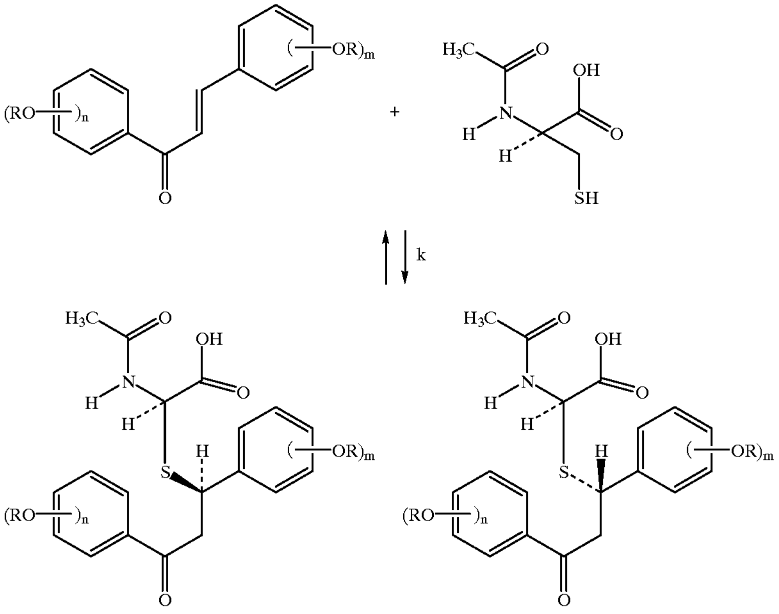

C

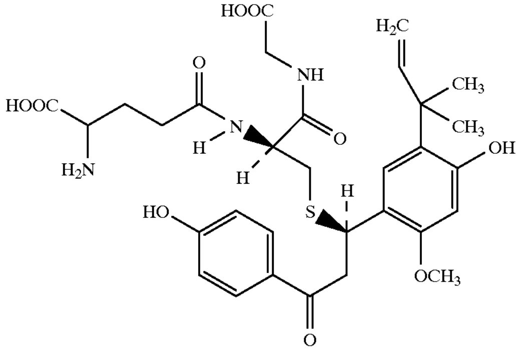

150 µg of the chalcone in question and 10 mg (0.06 mmol) of N-acetyl-L-cysteine were dissolved in 2.5 ml of methanol-water-potassium phosphate buffer (40:10:50 v/v, pH 7.5), and the solution was left at 30° C.

The decline of the chalcone concentration was followed by HPLC. The following experimental setups were used:

1. Column Spherisorb ODS-2 (120×4.6 m, 5 µm), eluent acetonitrile-aqueous acetic acid (2%) in ratios 43:57 or 50:50, flow rate 1.5 ml/rnin, detection at 254 and 360 nm.

The polaeluent was used for the following chalcones: licochalcone A, chalcone, 2,4-dimetoxychalcone and 4,4'-dihydroxychalcone. The apolar eluent was used for the following chalcones: 3,4,5-trimethoxy-4'-(3-methylbut-2-enyloxy)chalcone, 2,4-dimethoxy-4'-(3-methylbut-2-enyloxy)chalcone and 2,4,6-trimethoxy-4'-(3-methylbut-2-enyloxy)chalcone.

2. Column Polygosil Si 60 (120×4.6 mm, 5 µm), eluent methanol-water-0.2M potassium phosphate buffer (65:30:5, pH 7.5) added cetyltrimethylammonium bromide to a final concentration of 2.5 mM, column temperature 45° C., flow rate 1.0 ml/min, detection at 254 nm. This system was used i the case of 4'-methoxychalcone.

Results

The rate of decline of the chalcone concentration was followed by HPLC. The rate constant was estimated using Grafit and assuming that the reaction followed first order kinetic; i.e.:

$$[c]=[c_0]\exp(-kt)$$

where [c] is the concentration of the chalcone in question at time t, $[c_0]$ is the concentration of the chalcone in question at time zero, k is the rate constant, and t the time.

In all cases, very good fits between the observed concentrations and the concentrations calculated using the estimated rate constants were obtained.

TABLE 27.1

Estimated rate constants.

| Formula | Number of oxygens | k ($min^{-1}$) |
|---|---|---|
| 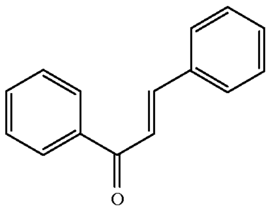 | 0 | 0.034 |
| 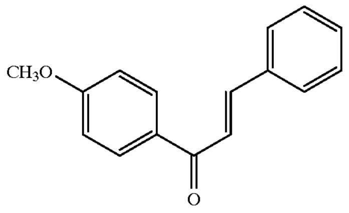 | 1 | 0.016 |
| 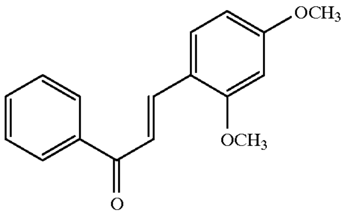 | 2 | 0.0033 |
| 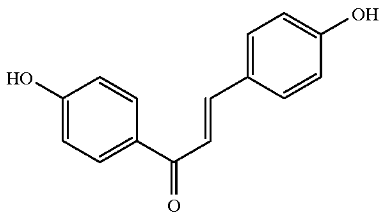 | 2 | 0.0020 |
| 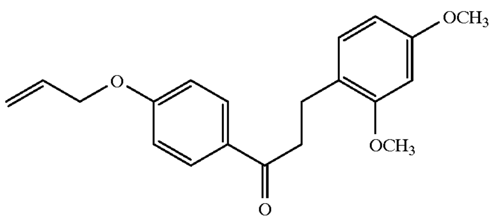 | 3 | 0.0011 |

TABLE 27.1-continued

Estimated rate constants.

| Formula | Number of oxygens | k ($min^{-1}$) |
|---|---|---|
| 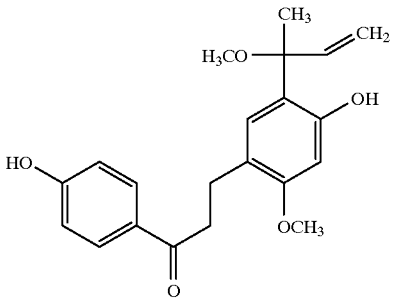 | 3 | 0.00058 |
| 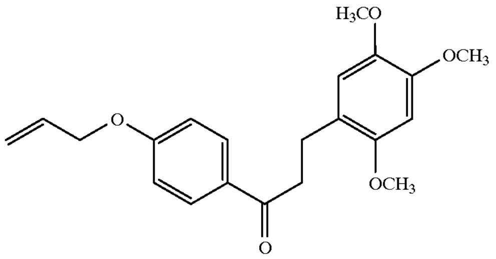 | 4 | 0.0175 |
| 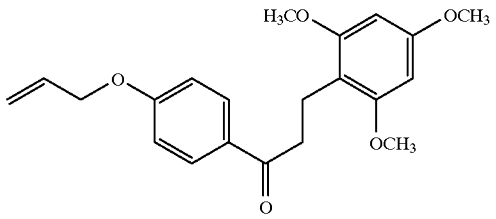 | 4 | 0.0006 |

Conclusion

Introduction of oxygen functions in the 2-position, the 4-position or the 2- and the 4-positions, or in the 4'-position appears to decrease the reaction rate. In contrast, comparison of the rate constants of 3,4,5-trimethoxy-4'-(3-methylbut-2-enyloxy)chalcone and 2,4,6-trimethoxy-4'-(3-methylbut-2-enyloxy)chalcone indicates that introduction of oxygen functions in the 3- and 5-position increases the electron density at the double bond and consequently reduces the reactivity toward nucleophilic reagents, whereas the inductive effects of oxygen in the 3- or 5-position will decrease the electron density at the double bond. Analogously, the Hammet $\sigma_P$ constant for methoxy is −0.27 but $\sigma_m$ is 0.12.

EXAMPLE 28

Anticdetidial activity of licochalcone A, 2,5-dimethoxy-4'-allyloxychalcone and 2,4-dimethoxychalcone in chickens The experiment was carried out in collaboration with Korn og Foderstof Kompagniel (KFK) at KFK's Experimental Station (Forsogsgard, Sdr. Forumvej 18, DK-6715 Esbjerg, Denmark).

Test compounds.

1) Licochalcone A 2) 2,5-Dimethoxy4'-allyloxychalcone (2,5m4'ac)

3) 2,4Dimethoxychalcone (2,4mc).

The three compounds were mixed manually with chicken feed one week before use. 2.6 g licochalcone A, 20.6 g 2,4-dimethoxyy-4'-chalcone and 20.1 g 2,4-dimethoxychalcone were each mixed separately with 1 kg rye flour. Each of the 1 kg mixtures was then mixed with ten kg chicken feed. Appropriate concentrations of each compound were obtained by adding more chicken feed. The prepared feed as well as a standard feed used, containing 70 ppm salinomvcin which is a known coccidiostatic agent, were stored at a temperature between 10° C. and 15° C. prior to use.

Parasite strain. *Eimeria tenella* sporulated oocysts were obtained from the Agricultural and Food Council Institute for Animal Health, Compton Laboratory, Compton Nr. Newbury, Berkshire RG 16 ONN, England. Permission to import Coccidia into Denmark from England has been obtained from the Danish Veterinary authorities, Ministry of Agriculture (Veterinaerdirektoratet, Landbrugsministeriet). The oocysts were washed and resuspended in 30 ml saline to give a concentration of $15\times10^6$/30 ml. A volume of 0.1 ml (50,000 oocysts) was given to each chicken by a Tuberculin syringe in the crop.

Anticoccidial testing. The experimental set-up consisted of 6 groups of 14-days old chickens. During the first 14 days of life, all the chickens received chicken feed containing no coccidiostatic agents. The first 5 groups were given 50,000 *E. tenella* oocysts per chicken by oral administration on day 14. Feeding the chickens with the feed preparations described above started one day before infection with the parasite (day 13). The treatment continued for 14 days according to the set-up shown in Table 28.1.

TABLE 28.1

Experimental set-up for testing anticoccidial activity of licochalcone A and two of its analogues.

| Groups | Number | Infection with *E. tenella* | Treatment |
|---|---|---|---|
| 1 | 35 | Yes | Standard KFK feed containing salinomycin |
| 2 | 35 | Yes | Compound 2,5m4'ac (30 mg/kg chicken body weight/day) |
| 3 | 35 | Yes | Compound 2,4mc (30 mg/kg chicken body weight/day) |
| 4 | 20 | Yes | Licochalcone A (10 mg/kg chicken body weight/day) |
| 5 | 35 | Yes | None |
| 6 | 35 | Yes | None |

The following parameters were examined and the samples were obtained:

1. Before infection with oocysts approximately 5 ml of pooled blood sample were taken from 2–5 chickens. Serum from these samples was prepared and stored at a temperature of −20° C.

2. All the chickens were weighed once a week as a standard procedure.

3. Mortality of the chickens was observed and recorded on a daily basis.

4. At the end of the experiment (14 days treatment, 28 days old chickens), the chickens were slaughtered and a necropsy was performed for identification of gross pathologic. Histopathohology was registered in standard HE sections of 10–15 mm of one cecal sac, one transverse and one longitudinal. The sections from each chicken were examined. The pathology was registered according to J. Johnson and W. M. Reid, Anticoccidial drugs: Lesion scoring techniques in battery and floor pen experiments with chickens. Experimental Parasitology 28 (1970), 30–36.

5. Parasite load in the intestne or number per smear may be deterrrined at the end of the experiment. The number of oocysts in 10 viewfields may be counted at 100× enlargement and the average of 10 fields were used. Oocysts index may calculated as:

$$\frac{\text{Oocysts in infected animal/field} \times 100}{\text{Oocysts in control animal/field}}$$

and may be recorded as follows:

0=no oocysts

+=1 oocysts/field

++=1–10 oocysts/field

+++=>10 oocysts/field

6. Blood samples for measurement of concentrations of these compounds were obtained from groups 2, 3, and 4 as follows:

1. Prior to treatment with the compounds.
2. Seven days after initiation of treatment.
3. At the end of the experiment before slaughtering the chickens.

TABLE 28.2

Effect of licochalcone A and two of its analogues on weight gain of chickens. The groups are as shown in Table 28.1. The weights are given in grams per chicken.

| | Weight | Before treatment | After initiation of treatment | |
|---|---|---|---|---|
| Group | 7 days old | Weight gain in 7 days | Weight gain in 7 days | Weight gain in 14 days |
| 1 | 148 | 215 | 425 | 900[a] |
| 2 | 138 | 207 | 366 | 804 |
| 3 | 138 | 200 | 380 | 803 |
| 4 | 135 | 201 | 414 | 864[b] |
| 5 | 138 | 200 | 367 | 803 |
| 6 | 130 | 204 | 404 | 866 |

[a]Difference between groups 1 (standard feed) and 5 (control infected) after treatment for 14 days is 12%.
[b]Difference between groups 4 (licochalcone A) and 5 (control infected) after treatment for 14 days is 7.6%.

Normal variation in such experiments is ±2%.

TABLE 28.3

Effect of licochalcone A and two of its analogues on feed consumption and mortality of chickens. The groups are as shown in Table 28.1.

| | Before treatment | After initiation of treament | | |
|---|---|---|---|---|
| Group | after 14 days | after 7 days | after 14 days | Mortality |
| 1 | 1.10 | 1.30 | 1.44 | 0 |
| 2 | 1.12 | 1.31 | 1.54 | 2 |
| 3 | 1.13 | 1.30 | 1.48 | 1 |
| 4 | 1.13 | 1.26 | 1.31 | 0 |
| 5 | 1.15 | 1.36 | 1.48 | 1 |
| 6 | 1.11 | 1.32 | 1.46 | 0 |

TABLE 28.4

Effect of licochalcone A and two of its analogues on gross lesions induced by *E. tenella* infection. The pathological scores are according to Johnson and Reid and are given as number of chickens with + to ++++ gross pathology/total number in each group. Total percentages with pathological changes are given in the last column.

| | Pathological scores | | | |
|---|---|---|---|---|
| Group | Total | Score | Numbers | % chicken |
| 1 | 0/20 | 0 | 20 | 0% |
| | | + | 0 | |
| | | ++ | 0 | |
| | | +++ | 0 | |
| 2 | 13/20 | 0 | 7 | 65% |
| | | + | 8 | |
| | | ++ | 0 | |
| | | +++ | 2 | |
| | | ++++ | 3 | |
| 3 | 17/20 | 0 | 3 | 85% |
| | | + | 12 | |
| | | ++ | 2 | |
| | | +++ | 2 | |
| | | ++++ | 1 | |
| 4 | 7/20 | 0 | 13 | 35% |
| | | + | 6 | |
| | | ++ | 0 | |
| | | +++ | 1 | |
| | | ++++ | 0 | |
| 5 | 35/40 | 0 | 5 | 87.5% |
| | | + | 24 | |
| | | ++ | 5 | |
| | | +++ | 4 | |
| | | ++++ | 2 | |
| 6 | 0/40 | 0 | 40 | 0% |

TABLE 28.4-continued

Effect of licochalcone A and two of its analogues on gross lesions induced by *E. tenella* infection. The pathological scores are according to Johnson and Reid and are given as number of chickens with + to ++++ gross pathology/total number in each group. Total percentages with pathological changes are given in the last column.

| | | Pathological scores | | |
|---|---|---|---|---|
| Group | Total | Score | Numbers | % chicken |
| | | + | 0 | |
| | | ++ | 0 | |
| | | +++ | 0 | |
| | | ++++ | 0 | |

0 = normal
+ = few hemorrhages (punctuate)
++ = blood in lumen, mucosal lesions, thickened walls
+++ = blood in lumen (coagulated, clumps), detached epithelium
++++ = diffuse bleeding, obstructed cecum, big masses mixed with lots of oocysts Conclusions The results from this experiment dearly indicate that licochalcone A is able to control *E. tenella* infection in chickens. This is documented by the following:

1. No mortality was observed in the group receiving licochalcone A (Table 28.3).

2. A 7.6% increase in weight gain in chickens receiving licochalcone A as compared to the infected group not receiving any cocciostatic treatment (Table 28.2). The normal variation in such experiments is +2%.

3. Feed consumption, measured as the amount of feed consumed per kg chicken weight gain in the group receiving licochalcone A was the lowest among all the 6 groups both on 7 days of treatment and on 14 days of treatment (Table 28.3). The feed consumption of the group receiving licochalcone A was even lower than the group receiving standard chicken feed containing salinomvcin which is a know coccidiostatic agent. This indicates that licochalcone A might have a growth promoting effect or another form of nutritional value.

4. The percentages of chickens showing pathological signs were much lower in the group receiving licochalcone A than in the infected control group (Table 28.4).

The chickens receiving licochalcone A did not perform the same way as those receiving standard chicken feed containing salinomycin. However, when comparing the licochalcone A group with the group receiving standard feed, it should be noted that this group received standard feed which besides a coccidiostatic agent also contains larger amounts of nutrients, vitamin, and growth promoting factors.

In the above experiment, licochalcone A did not show a complete protection against *E. tenella* infection. This is probably due to the dosage of licochalcone A used in the experiment. It should also be mentioned that the experimental infection is a much stronger form of infection than the infection which will normally be encountered in practice.

REFERENCES

Ann (WHO), Wkly Epidem Rec. 1990, vol. 65, 189–196

Ashford, R. W.: "The Leishmaniases", Clinics in Tropical Medicine and Communicable Diseases, eds. H. M. Gilles, vol. 1, No. 3, W. B. Saunders Comp. Ltd., London, 1986 513–533.

Berenguer, E., Moreno S., Cercenado E., Quiros JCLBd, Fuente AGdl, Bouza E.: "Visceral leishmaniasis in patients infected with human immunodeficiency virus (HIV)", Ann. Intern. Med. 1989, vol. 111, 129–132.

Berman, J. D., Dwyer, D. M., and Wyler, D. J.: "Multiplication of Leishmania in human macrophages in vitro", Infect. Imnuun., vol. 26, 1979, 375–379.

Bowden, K., Duah, C. K., and Ranson, R. J.: *J. Chem. Soc. Perkin Trans.* 2 (1990), 109.

Davis, and Armstrong: *J. Am. Chem. Soc.* 57 (1935), 1583.

Flegg P J, Brettle R P: "Visceral Leishmaniasis in HIV-Infected Patients", AIDS 4(4), 1990, 366–367.

Geissman, T. A., Clinton, R. O.: *J. Am. Chem. Soc.* 68 (1946), 697–700.

Hatano, T., Kagawa, H., Yasuhara, T., and Okuda, T.: "Two new flavonoids and other constituents in licorice root. Their relative astringency and radical scavenging effects", *Chem. Pharm. Bull.* 36(6) (1988),2090–2097.

Hébert, G. Ann, Callaway, Carey S., and Ewing, Edwin P.: "Comparison of Legionella pneumophila, L. micdadei, L. bozemanii and L. dumoffii by Transmission Electron Microscopy", *J. Clin. Microbial* 19 (1984), 116–121.

Inoue, B. Inaba, K., Mori, T., Izushi, F., Eto, K., Sakai, R., Ogata, M. and Utsumi, K. *J. Toxicol. Sci.* 7 (1982), 245–254.

Jensen J B, Boland M T, Haves M., *Exp. Parasitol.* 54 (1982), 416–424.

Johnson, J. and Reid, W. M.,Experzmental Parasitology 28 (1970), 28–30.

Kenzo Okada, Yukivoshi Tamura, Masaji Yamamoto, Yoshimoto Inoue, Ryoji Takagaki, Kunio Takahashi, Sachio Dernizu, Kiichiro Kajivama, Yukio Hiraga and Takeshi Kinoshita: "Identification of Antimicrobial and Antioxidant constituents from Licorice of Russian and Xinjingang Origin", *Chem. Pharm. Bull.* 37 (1989), 2528–2530.

Khan, S. A., and Krishnamurti, M.: *Indian J. Chem.* 22B (1983), 276.

Kimura, Y., Okuda, H., Okuda, T., and Arichi, S.: "Effects of chalcones isolated from licorice roots on leukotriene biosvnthesis in human polymorphonuclear neutrophils", *Phytotherapy Research* 2(3) (1988), 140–145.

Kurosawa, K., annd Higuchi, *J.: Bull. Chem. Soc. Japan* 45 (1972), 1132–1136.

Kurosawa, K.: *Bull. Chem. Soc. Japan* 42 (1969), 1456.

Kyogoku, K., Hatamava, K., Yokomori, S., Saziki, R., Nakane, S., Sasajima, M., Sawada, M., Ohzeki, M., Tanaka, I.: *Chem. Pharm. Bull.* 27 (1979), 2943.

Lambros C., Vanderberg J. P.: "Synchronization of Plasmodium faiciparum erythrocvtic stages in culture", *J. Parasitol.* 65 (1979), 418–420.

Laurushin, V. F., Trusevich, N. D., and Tolmachev, V. N.: Zh. *Obshch Khim.* 39 (1969), 42–45*, Chem. Abstr.* 70 (1969), 105822t.

Liew F. Y., Millott, S., Parkinson, C., Palmer, R. M. J., and Moncada, S.: "Macrophage killing of Leishmania parasite in vivo is medicated by nitric oxide from L-arcinine", *J. Immun.* 144 (1990),4794–4797.

Manson-Bahr, C. E. P. and Bell, R. D.: "Manson's Tropical Diseases", Baillière Tindall, 19 Ed., 1987 B.

Nielsen, A. T. and Houlihahn, W.: *J. Org. React.* 16 (1968), 1.

Pearson, R., A. A. Manian, D. Hall, J. L. Harcus, and E. L. Hewlett: "Antileishmanial activity of chlorpromazine", *Antimicrob. Agents Chemother.* 25 (11984), 571–574.

Ren Jun, Wang Zhengang: "Pharmacological research on the effect of licorice": *J. Trad. Chinese Med.* 3 (1988), 307–309.

Rhen-Seng, X., Kung-Ling, W., Shifa J., Chang-gen, W., Fu-Xiang, J., Xu-van, X., and Yi—Sheng, C.: *Acta Chem. Sinica* 37 (1979), 289–297.

Ristroph, Joseph D., Hedlund, Kenneth W., and Allen, Richard G.: "Liquid medium for growth of Legionella pneumophila": *J. Clin. Microb.* 11 (1980), 19–21.

Sachio Demizu, Kiichiro Kajiyama, Kunio Takahashi, Yukio Hiraga, Susumu Yamamoto, Yukiyoshi Tamura, Kenzo Okada and Takeshi Kinoshita: *Chem. Pharm. Bull.* 36 (1988), 3474–3479.

Saitoh, T., and Shibata, S.: *Tetrahedron Lett.* 50 (1975), 4441.

Sallai, J., Gabor, M., and Kallay, F.: *Acta Farm. Hung.* 46 (1976), 49–56.

Salmon D., Deloron P., Gaudin C., Malhotra K., Lebras J., Pocidalo JJ.: "Activities of peploxacin and ciprofloxacin against experimental malaria in mice", *Antimicrob. Agents Chemother.* 34 (1990), 2327–2330.

Sheng, L. H.: "Traditional Chinese medicine and immunity", Guangdong Scientific Publishing House, Guangzhou, People's Republic of China, 4149, 1982

Shriner, R. L., Kurosawa, T.: *J. Am. Chem. Soc.* 52 (1930), 2538.

Swarbrick, J. and Boylan, J. C.: "EWmcyclopedia of Pharmaceutical Technology", Marcel Dekker, Inc., New York, 1988.

Swarbrick, J. and Boylan, J. C.: "Remington's Pharmaceutical Sciences", Marcel Dekker, Inc., New York, 1988.

Teelucksingh, S. et al.: "Liquorice", *The Lancet* 37 (1991), 1549.

Thoda, Y, Sonogashihare, K., and Haghara, N.: *Synthesis* (1977), 777.

Trager, W., Jensen J B.: "Human malaria in continuous cultures", *Science* 193 (1976), 673–675.

UNDP/World Bank/WHO Special Programme for research and Training in Tropical Diseases (TDR), Ninth Programme Report, Tropical Diseases: Progress in international research, 1987–1988, "The leishmaniases", 85–92, WHO, Geneva 1989.

UNDP/World Bank/WHO: "Antimonial: Large-scale failure in leishmaniasis "alarming"", TDR News, vol. 34, December 1990, 1, 7.

Volovich, A. M., Tolmachev, V. N., and Larushin, V. F.: *Visn, Kharkiv Univ. Khim.* 73 (1971), 85–88, Chem. Abstr. 78 (1973), 57241u.

Walton, C. B.: "Leishmaniasis", Tropical Medicine and Parasitology, eds. R. Goldsmith & D. Heyneman, Printece-Hall Int. Editions, 1989, 276–302.

Wattanasin, S. and Murphy, S.: Synthesis (1980), 647.

WHO: "Global Estimates for Health Situation Assessment and projections—1990", WHO/HST/90.2, 1990, 18–33, A.

We claim:

1. A method for treatment or prophylaxis of a disease caused by a microorganism or a parasite in an animal, the microorganism or parasite being selected from Leishmania, Tryvanosoma, Toxo lasma, Plasmodium, Cryptospoidium, Pneumocystis, Babesia and Theilenia; intestinal protozoan flagellates; and intestinal protozoan Coccidia;

which method comprises selecting an animal in need of treatment for said disease or an animal from a population that is at risk from contracting said disease and administering to said animal an effective amount of an aromatic compound, or a prodrug thereof, wherein the aromatic compound is a bis-aromatic α,β-unsaturated ketone of the general formula I $$X_m\text{—}Ar^1\text{—}CO\text{—}W\text{—}Ar^2\text{—}Y_n \qquad I$$

wherein

W is either —CR═CR— or —C≡C—, wherein each R independently of the other R designates hydrogen, $C_{13}$ alkyl, or halogen, $Ar^1$ and $Ar^2$ are the same or different and each designate an aromatic group selected from phenyl and 5- or 6-membered unsaturated heterocyclic rings containing one, two or three heteroatoms selected from oxygen, sulfur, and nitrogen, which aromatic group may be substituted with one or more substituents selected from halogen; nitro; nitroso; and $C_{1-12}$, straight or branched aliphatic hydrocarbyl which may be saturated or may contain one or more unsaturated bonds selected from double bonds and triple bonds, which hydrocarbyl may be substituted with one or more substituents selected from hydroxy, halogen, amino, and amino which is optionally alkylated with one or two $C_{1-6}$ alkyl groups;

Y and X are the same or different and each designate a group $AR_H$ or a group AZ, wherein A is —O—, —S—, —NH—, or —N($C_{1-6}$ alkyl)—, $R_H$ designates $C_{1-6}$ straight or branched aliphatic hydrocarbyl which may be saturated or may contain one or more unsaturated bonds selected from double bonds and triple bonds, and Z designates H or (when the compound is a prodrug) a masking group which is readily decomposed under conditions prevailing in the animal body to liberate a group AH, in which A is as defmed above; m designates 0, 1 or 2, and n designates 0, 1, 2 or 3, whereby, when m is 2, when the two groups X are the same or different, and when n is 2 or 3, then the two or three groups Y are the same or different, with the proviso that n and m are not both 0.

2. The method according to claim 1, wherein the aromatic compound, in a concentration in which it causes less than 50% reduction of the thymidine uptake by human lymphocytes in the Lymphocyte Proliferation Assay using phytohemagglutinin (PHA), meets at least one of the following criteria:

a) the aromatic compound is capable of inhibiting in vitro the growth or multiplication of *Leisnmania major* promastizotes by at least 80%, as determined by uptake of tritiated thymide, b) the aromatic compound is capable of inhibiting in vitro the growth or multiplication of *Plasmodium falciparum* by at least 80%, as determined by uptake of tritiated hypoxanthine, c) the aromatic compound is capable of inhibiting in vitro the growth or multiplication of *Eimeria tenelia* in chicken fibroblast cell cultures by at least 70%, as determined by counting the parasites, d) the aromatic compound is capable of inhibiting in vitro the growth or multiplication of *Mycobacterium tuberculosis* or *Legionelia pneumophila* by at least 50%, as determined by colony counts.

3. The method according to claim 2, wherein the aromatic compound meets all of the criteria a) to d).

4. The method according to claim 2, wherein the aromatic compound, in a concentration in which it causes less than 40% reduction of the thymidine uptake by human lymphocytes in the Lymphocyte Proliferation Assay using PHA, meets at least one of the criteria a) to d).

5. The method according to claim 2, wherein the aromatic compound, in a concentration in which it causes less than 20% reduction of the thymidine uptake by human lymphocytes in the Lymphocyte Proliferation Assay using PHA, meets at least one of the criteria a) to d).

6. The method according to claim 1, for the treatment or prophylaxis of diseases caused by Leishmania in humans or dogs, wherein the aromatic compound is capable of inhibiting in vitro the growth of *Leishmania major* promastigotes by at least 80%, as determined by uptake of tritiated thymidine, in a concentration of the compound in which it causes less than 50% reduction of the thymidine uptake by human lymphocytes in the Lymphocyte Proliferation Assay using PHA.

7. The method according to claim 6, wherein the aromatic compound is capable of inhibiting in vitro the growth of *Leishmania major* promastigotes by at least 80%, as determined by uptake of tritiated thymidine, in a concentration of the compound in which it causes less than 40% reduction, preferably less than 20% reduction, of the thymidine uptake by human lymphocytes in the Lymphocyte Proliferation Assay using PHA.

8. The method according to claim 1, for the treatment or prophylaxis of diseases caused by Leishmania in humans or dogs, wherein the aromatic compound, or the prodrug, when administered intraperitoneally in the in vivo test described in Example 8 herein in a dose of up to 20 mg per kg body weight once daily for 40 days to female BALB/c mice which have been infected with *L. major* ($10^7$/mouse), the administration being initiated one week after infection, is capable of preventing increase in lesion size by at least about 60%.

9. The method according to claim 1, wherein the aromatic compound, or the prodrug, when administered intraperitoneally in the in vivo test described in Example 8 herein in a dose of up to 10 mg per kg body weight once daily for 40 days to female BALB/c mice which have been infected with *L. major* ($10^7$/mouse), the administration being initiated one week after infection, is capable of preventing increase in lesion size by at least about 60%.

10. The method according to claim 1, for the treatment or prophylaxis of diseases caused by Leishmania in humans or dogs, wherein the aromatic compound, or the prodrug, when administered intraperitoneally in the in vivo test described in Example 9 herein in a dose of up to 20 mg per kg body weight two times daily for 7 days to male Syrian golden hamsters which have been infected with *L. donovani* promastigotes ($2\times10^7$/hamster), the administration being initiated one day after infection, is capable of reducing the parasite load in the liver of the hamsters by at least about 60%.

11. The method according to claim 1, wherein the aromactic compound when administered intraperitoneally in the in vivo test described in Example 9 herein in a dose of up to 10 mg per kg body weight twice daily for 7 days to male Syrian golden hamsters which have been infected with *L. donovani* promastigotes ($2\times10^7$/hamster), the administ ration being initiated one day after infection, is capable of reducing the parasite load in the liver of the hamsters by at least about 60%.

12. The method according to claim 1, for the treatment or prophylaxis of malaria caused by Plasmodiumn spp. in humans, wherein the aromatic compound is capable of inhibiting in vitro the growth of *Plasmodium falciparumn* by at least 80%, as measured by uptake of tritiated hypoxanthine, in a concentration of the compound in which it causes less than 50% reduction of the thymidine uptake by human lymphocytes, as measured by the Lymphocyte Proliferation Assay using PHA.

13. The method according to claim 1, wherein the aromatic compound is capable of inhibiting in vitro the growth of *Plasmodium falciparum* by at least 80% in a concentration of the compound in which it causes less than 40% reduction of the thymidine uptake by human lymphocytes, as measured by the Lymphocyte Proliferation Assay using PHA.

14. The method according to claim 1, for the treatment or prophylaxis of diseases caused by Plasmodium spp. in humans, wherein the aromatic compound, when administered intraperitoneally in the in vivo test described in Example 16 herein in a dose of up to 20 mg per kg body weight two times daily for 6 days to female BALB/c mice which have been infected with malaria *P. yoelii* ($2\times10^5$/mouse), the administration being initiated one day after infection, is able to prevent increase in the parasitemia during the administration period.

15. The method according to claim 1, wherein the aromatic compound, or the prodrug, when administered intraperitoneally in the in vivo test described in Example 16 herein in a dose of up to 20 mg per kg body weight two times daily for 10 days to 8 weeks old female BALB/c mice which have been infected with malaria *P. yoelii* ($2\times10^5$/mouse), the administration being initiated one day after infection, is capable of clearing the parasite from the mice within at the most 23 days.

16. The method according to claim 1, wherein the aromatic compound, or the prodrug, when administered intraperitoneally in the in vivo test described in Example 16 herein in a dose of up to 20 mg per kg body weight two times daily for 8 days to 8 weeks old female BALB/c mice which have been infected with malaria *P. yoelii* strain YM ($1\times10^6$/mouse), the administration being initiated one day after infection, is capable of clearing the parasite from the mice within at the most 21 days.

17. The method according to claim 1, wherein the aromatic compound, or the prodrug, when administered intraperitoneally in the in vivo test described in Example 16 herein in a dose of 5 mg per kg body weight two times daily for 10 days to 8 weeks old female BALB/c mice which have been infected with malaria *P. yoelii* ($2\times10^5$/mouse), the administration being initiated one day after infection, is capable of clearing the parasite from the mice within at the most 23 days.

18. The method according to claim 1, wherein the aromatic compound, or the prodrug, when administered intraperitoneally in the in vivo test described in Example 16 herein in a dose of up to 5 mg per kg body weight two times daily for 8 days to 8 weeks old female BALBic mice which have been infected with malaria *P. yoelii* strain YM ($1\times10^6$/mouse), the administration being initiated one day after infection, is capable of clearing the parasite from the mice within at the most 21 days.

19. The method according to claim 1, for the treatment or prophylaxis of diseases caused by Coccidia in poultry such as chickens or turkeys, wherein the aromatic compound, or the prodrug, is capable of alkylating the thiol group in N-acetyl-L-cysteine at physiological pH, and wherein the aromatic compound, or the prodrug, when administered to chickens with the feed in a concentration of up to 400 ppm for at most 28 days in the in vivo test described in Example 28 herein, is capable of controlling infection by *Eimeria tenella* in at least 60% of the chickens and preventing pathological alterations in at least 50% of the chickens.

20. The method according to claim 1, wherein the aromatic compound, when administered to chickens with the feed in a concentration of up to 120 ppm for at most 28 days in the in viva test described in Example 28 herein, is capable of controlling infection by *Eimeria tenella* in at least 60% of the chickens and preventing pathological alterations in at least 65% of the chickens.

21. The method according to claim 1, wherein Z, when designating a masking group, is selected from the below groups (A)–(E)

—CO—R' (A)

—CON($CH_3$)$_2$ (B)

—CR*R**—O—R" (C)

—CR*R**—O—CO—R"' (D)

(E)

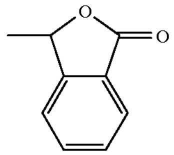

wherein R* and R** each independently designate hydrogen or $C_{1-3}$ alkyl, and R', R" and R"' each independently designate $C_{1-6}$ alkyl or is an aromatic group $Ar^1$ or $Ar^2$ which are the same or different and designate an aromatic group selected from phenyl and 5- or 6-membered unsaturated heterocyclic rings containing one, two or three heteroatoms selected from oxygen, sulfur, and nitrogen, which aromatic group may be substituted with one or more substituents selected from halogen; nitro; nitroso; and $C_{1-12}$, straight or branched aliphatic hydrocarbyl which may be saturated or may contain one or more unsaturated bonds selected from double bonds and triple bonds, which hydrocarbyl may be substituted with one or more substituents selected from hydroxy, halogen, amino, and amino which is optionally alkylated with one or two $C_{1-6}$ alkyl groups.

22. The method according to claim 1, wherein $Ar^1$ or $Ar^2$ or both independently are phenyl or an aromatic 5- or 6-membered heterocyclic ring containing one, two or three heteroatoms selected from oxygen, sulphur and nitrogen, n is 0, 1, 2, or 3, m is 0, 1 or 2, at least one of the groups X is in a position in $Ar^1$ most remote relative to and/or next to the position through which $Ar^2$ is bound to the carbonyl group, and at least one of the groups Y is in a position in $Ar^2$ most remote relative to and/or next to the position through which $Ar^2$ is bound to W.

23. The method according to claim 1, in which A is O.

24. The method according to claim 1, in which Z is pivaloyl, pivaloyloxymethyl or N,N-dimethylcarbamoyl.

25. The method according to claim 1, in which the compound of formula I is a compound of formula II $$X_m\text{—Ph—C(O)—CH=CH—Ph—}Y_n \qquad \text{II}$$

wherein Ph designates phenyl, and $X_m$ and $Y_n$ are as defined in claim 32, and each phenyl group may be substituted with one or more substituents selected from halogen; nitro; nitroso; and $C_{1-12}$ straight or branched aliphatic hydrocarbyl which may be saturated or may contain one or more unsaturated bonds selected from double bonds and triple bonds, which hydrocarbyl may be substituted with one or more substituents selected from hydroxy, halogen, amino, and amino which is optionally alkylated with one or two $C_{1-6}$ alkyl groups.

26. The method according to claim 25, in which X and/or Y is OH or a group $OR_H$, in which $R_H$ is as defined in claim 1, or OZ*, in which Z* is a masking group which is readily decomposed under conditions prevailing in the animal body to liberate the group OH, in particular one of the groups (A)–(E) as defined in claim 21, preferably pivaloyl, pivaloyloxymethyl or N,N-dimethylcarbonyl.

27. The method according to claim 25, wherein the substituent or substituents on the phenyl groups is/are $C_{1-12}$, preferably $C_{1-6}$, straight or branched aliphatic hydrocarbyl which may be saturated or may contain one or more unsaturated bonds selected from double bonds and triple bonds, which hydrocarbyl may be substituted with one or more substituents selected from hydroxy, halogen, amino, and amino which is optionally alkylated with one or two $C_{1-6}$ alkyl groups.

28. The method according to claim 27, wherein the substituent or substituents on the phenyl groups is/are methyl, ethyl, propyl, isopropyl, tert.-butyl, prop-2-enyl, 1,1-dimethylpropyl, 1,1-diethylprop-2-enyl, 3-methylbutyl, or 3-methylbut-2-enyl.

29. The method according to claim 25, wherein the bis-aromatic α,β-unsaturated ketone has the general formula III

III

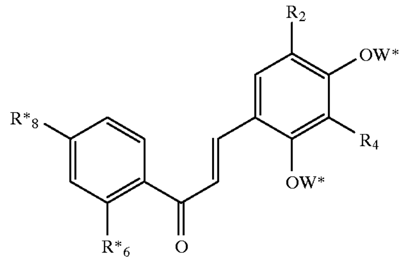

wherein $R_2$ and $R_4$ each independently designate $R_H$ wherein $R_H$ designates $C_{1-6}$ straight or branched aliphatic hydrocarbyl which may be saturated or may contain one or more unsaturated bonds selected from double bonds and triple bonds, or $R_H$ is H, one of $R*_6$ and $R*_8$ designate OW* and the other is H, or both $R*_6$ and $R*_8$ designate H, and W* designates H, $R_H$ or a group (A)–(E)

—CO—R' (A)

—CON($CH_3$)$_2$ (B)

—CR*R**—O—R" (C)

—CR*R**—O—CO—R"' (D)

(E)

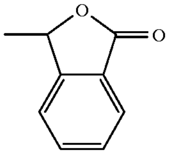

wherein both R* and R** designate hydrogen, and R', R" and R"' each independently designate $C_{1-6}$ alkyl or an aromatic group selected from phenyl and 5- or 6-membered unsaturated heterocyclic rings containing one, two or three heteroatoms selected from oxygen, sulfur, and nitrogen, which aromatic group may be substituted with one or more substituents selected from halogen; nitro; nitroso; and $C_{1-12}$, straight or branched aliphatic hydrocarbyl which may be saturated or may contain one or more unsaturated bonds selected from double bonds and triple bonds, which hydrocarbyl may be substituted with one or more substituents selected from hydroxy, halogen, amino, and amino which is optionally alkylated with one or two $C_{1-6}$ alkyl groups.

30. The method according to claim 25, wherein the bis-aromatic α,β-unsaturated ketone has the general formula IV

IV

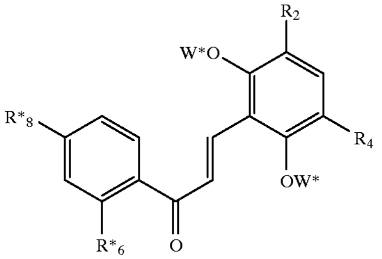

wherein $R_2$ and $R_4$ each independently designates $R_H$ wherein $R_H$ designates $C_{1-6}$ straight or branched aliphatic hydrocarbyl which may be saturated or may contain one or more unsaturated bonds selected from double bonds and triple bonds, or H, one of $R^*_6$ and $R^*_8$ OW* and the other H designates or both $R^*_6$ and $R^*_8$ designate H, and W* designates H, $R_H$ or a group (A)–(E)

—CO—R' (A)

—CON(CH$_3$)$_2$ (B)

—CR*R**—O—R" (C)

—CR*R**—O—CO—R"' (D)

(E)

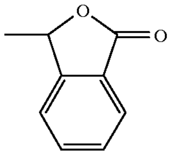

wherein both R* and R** designate hydrogen, and R', R" and R"' each independently designate $C_{1-6}$ alkyl or an aromatic group selected from phenyl and 5- or 6-membered unsaturated heterocyclic rings containing one, two or three heteroatoms selected from oxygen, sulfur, and nitrogen, which aromatic group may be substituted with one or more substituents selected from halogen; nitro; nitroso; and $C_{1-12}$, straight or branched aliphatic hydrocarbyl which may be saturated or may contain one or more unsaturated bonds selected from double bonds and triple bonds, which hydrocarbyl may be substituted with one or more substituents selected from hydroxy, halogen, amino, and amino which is optionally alkylated with one or two $C_{1-6}$ alkyl groups.

31. The method according to claim 25, in which the bis-aromatic α,β-unsaturated ketone has the general formula V

V

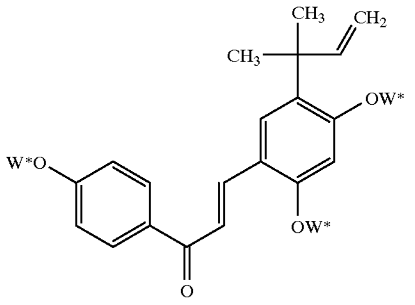

wherein W* designates H, $R_H$, wherein $R_H$ designates $C_{1-6}$ straight or branched aliphatic hydrocarbyl which may be saturated or may contain one or more unsaturated bonds selected from double bonds and triple bonds, or a group (A)–(E)

—CO—R' (A)

—CON(CH$_3$)$_2$ (B)

—CR*R**—O—R" (C)

—CR*R**—O—CO—R"' (D)

(E)

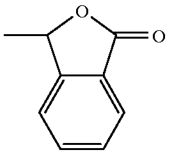

wherein both R* and R** designate hydrogen, and R', R" and R"' each independently designate $C_{1-6}$ alkyl or an aromatic group selected from phenyl and 5- or 6-membered unsaturated heterocyclic rings containing one, two or three heteroatoms selected from oxygen, sulfur, and nitrogen, which aromatic group may be substituted with one or more substituents selected from halogen; nitro; nitroso; and $C_{1-12}$, straiaht or branched aliphatic hydrocarbyl which may be saturated or may contain one or more unsaturated bonds selected from double bonds and triple bonds, which hydrocarbyl may be substituted with one or more substituents selected from hydroxy, halogen, amino, and amino which is optionally alkylated with one or two C1-6 alkyl groups.

32. The method according to claim 25, in which the bis-aromatic α,β-unsaturated ketone has the general formula VI

VI

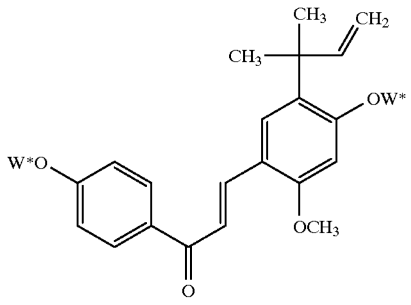

wherein W* designates H, $R_H$, wherein $R_H$, designates $C_{1-6}$ straight or branched aliphatic hydrocarbyl which may be saturated or may contain one or more unsaturated bonds selected from double bonds and triple bonds, or a group (A)–(E)

(A)

—CO—R'

(B)

—$CON(CH_3)_2$ (C)

—CR*R**—O—R"

(D)

—CR*R**—O—CO—R'"

(E)

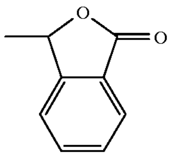

wherein R* and R** both designate hydrogen, and R', R"and R'" each independently designate $C_{1-6}$ alkyl or aromatic group selected from phenyl and 5- or 6-membered unsaturated heterocyclic rings containing one, two or three heteroatoms selected from oxygen, sulfur, and nitrogen, which aromatic group may be substituted with one or more substituents selected from halogen; nitro; nitroso, and $C_{1-12}$, straight or branched aliphatic hydrocarbyl which may be saturated or may contain one or more unsaturated bonds selected from double bonds and triple bonds, which hydrocarbyl may be substituted with one or more substituents selected from hydroxy, halogen, amino, and amino which is optionally alkylated with one or two $C_{1-6}$ alkyl groups.

33. The method according to claim 25 in which the bis-aromatic α,β-unsaturated ketone has the general formula VII

VII

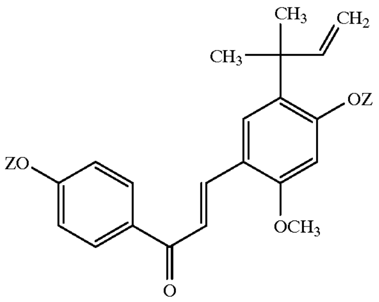

wherein Z when designating a masking group is selected from the below groups (A)–(E)

(A)

—CO—R'

(B)

—$CON(CH_3)_2$ (C)

—CR*R**—O—R"

(D)

—CR*R**—O—CO—R'"

(E)

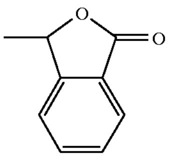

wherein both R* and R** designate hydrogen, and R', R" and R'" each independently designate $C_{1-6}$ alkyl or an aromatic group selected from Phenyl and 5- or 6-membered unsaturated heterocyclic rings containing one, two or three heteroatoms selected from oxygen, sulfur, and nitrogen, which aromatic group may be substituted with one or more substituents selected from halogen; nitro; nitroso; and $C_{1-6}$, straight or branched aliphatic hydrocarbyl which may be saturated or may contain one or more unsaturated bonds selected from double bonds and triple bonds, which hydrocarbyl may be substituted with one or more substituents selected from hydroxy, halogen, amino, and amino which is optionally alkylated with one or two $C_{1-6}$ alkyl groups.

34. The method according to claim 33, wherein Z designates pivaloyl, pivaloyloxymethyl or N,N-dimethylcarbonyl.

35. The method according to claim 25 in which the bis-aromatic α,β-unsaturated ketone has the general formula VIII

VIII

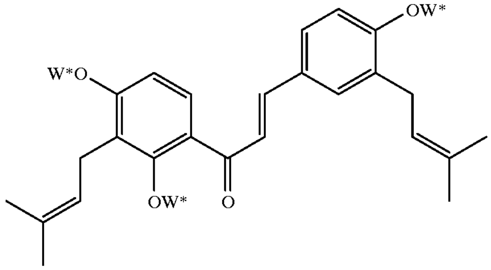

wherein W* designates H, $R_H$, wherein $R_H$ designates $C_{1-6}$ straight or branched aliphatic hydrocarbyl which may be saturated or may contain one or more unsaturated bonds selected from double bonds and triple bonds, or a group (A)–(E)

(A)

—CO—R'

(B)

—CON($CH_3$)$_2$ (C)

—CR*R**—O—R"

(D)

—CR*R**—O—CO—R'"

(E)

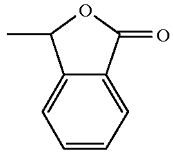

wherein both R* and R** designate hydrogen, and R', R" and R'" each independently designate $C_{1-6}$ alkyl or an aromatic group selected from phenyl and 5- or 6-membered unsaturated heterocyclic rings containing one, two or three heteroatoms selected from oxygen, sulfur, and nitrogen, which aromatic group may be substituted with one or more substituents selected from halogen; nitro; nitroso; and $C_{1-12}$, straiaht or branched aliphatic hydrocarbyl which may be saturated or may contain one or more unsaturated bonds selected from double bonds and triple bonds, which hydrocarbyl may be substituted with one or more substituents selected from hydroxy, halogen, amino, and amino which is optionally alkylated with one or two $C_{1-6}$ alkyl groups.

36. A method according to claim 1, in which the aromatic compound or the prodrug is administered in an amount of about 0.1–80 mg per kg body weight per day, preferably in an amount of about 0.5–20 mg per kg body weight per day.

37. A method according to claim 1, in which the aromatic compound or the prodrug is administered rectally in the form of suppositories.

38. A method according to claim 1, in which the aromatic compound or prodrug is added to animal feed and/or drinking water such as poultry feed and/or drinking water.

39. A method according to claim 1, wherein the aromatic compound or the prodrug is administered in combination with another antiparasitic, antimycotic, antibiotic or antibabesial drug or anticoccidial agent or another drug against fish parasites.

40. A method according to claim 39, wherein the other antiparasitic drug is an antileishmanial drug selected from a pentavalent antimonv-sodium gluconate, and allopurinol, or an anitmalarial drug selected from chloroquine and derivatives thereof, quinine, proguanil, cydoguanil, mefloquine, pyrimethamine, and artemisinin.

41. A method according to claim 39, wherein the other antibabesial drug is selected from quinuronium sulfate, pentamidine isethionate, imidocarb or diminazene, or the other anticoccidial drug is selected from sulfonamnides, amprocid and coccidiostatic agents selected from ionomycins, such as monensin and salinomycin, or the other drug used against fish parasites is selected from benzimidazol and formaldehyde, or the additional antibiotic drug is an antituberculous drug selected from isoniazide, ethambutol, pyrazinamid, and rifampicin or the additional antimvcotic drug is selected from amphothericin B, muconarcidol, griseofluyin, and miconazol.

42. A method for controlling transmission of parasitic diseases caused by parasites which have part of their life cycle in a vector, said method comprising applying an aromatic compounds, or a prodrug thereof, which aromatic compound contains an alkylating site and is capable of alkylating the thiol group in N-acetyl-L-cysteine at physiological PH, preferably a compound as defined in claim 21, to a locus which is a habitat of the vector so as to eradicate the parasites.

43. The method according to claim 42, wherein the application is performed by spraying a sprayable composition containing the aromatic compound.

44. A compound of the general formula I as defined in claim 21 with the proviso that W is a group —C≡C—.

45. The method of claim 1 wherein the animal is a vertebrate.

46. The method of claim 1 wherein the animal is a human.

47. The method of claim 1 wherein the compound is 3,5-dimethoxy-4'-prop-2-enyloxychalcone.

* * * * *

UNITED STATES PATENT AND TRADEMARK OFFICE

CERTIFICATE OF CORRECTION

PATENT NO. : 5,985,935

DATED : November 16, 1999

INVENTOR(S) : A. Kharazmi, S. B. Christensen, C. Ming, and T. G. Theander

It is certified that error appears in the above-indentified patent and that said Letters Patent is hereby corrected as shown below:

Column 153, line 54, please change "Tryvanosoma, Toxo lasma" to --Trypanosoma, Toxoplasma--;
Column 153, line 55, please change "Cryptospoidium" to --Cryptosporidium--;
Column 154, line 2, please change "$C_{13}$" to --$C_{1-3}$--;
Column 154, line 28, please change "when" to --then--;
Column 154, lines 38-39, please change "promastizotes" to --promastigotes--;
Column 156, line 42, please change "BALBic" to --BALB/c--;
Column 156, line 61, please change "viva" to --vivo--;
Column 157, line 52, please change "32" to --1--;
Column 160, line 56, please change "straiaht" to --straight--;
Column 161, line 55, please insert --an-- between "or" and "aromatic";
Column 162, line 50, please change "$C_{1-6}$" to --$C_{1-12}$--;
Column 164, line 29, please change "antimvcotic" to --antimycotic--;
Column 164, line 38, please change "PH" to --pH--; and
Column 164, line 38, please change "21" to --1--.

Signed and Sealed this

Third Day of April, 2001

Attest:

NICHOLAS P. GODICI

*Attesting Officer*

*Acting Director of the United States Patent and Trademark Office*

UNITED STATES PATENT AND TRADEMARK OFFICE

CERTIFICATE OF CORRECTION

PATENT NO. : 5,985,935 
DATED : November 16, 1999
INVENTOR(S) : A. Kharazmi et al.

It is certified that error appears in the above-identified patent and that said Letters Patent is hereby corrected as shown below:

Column 153,
Line 54, please change "Tryvanosoma, Toxo lasma" to -- Trypanosoma, Toxoplasma --;
Line 55, please change "Cryptospoidium" to -- Cryptosporidium --;

Column 154,
Line 2, please change "$C_{13}$" to -- $C_{1-3}$ --;
Line 28, please change "when" to -- then --;
Lines 38-39, please change "promastizotes" to -- promastigotes --;

Column 156,
Line 42, please change "BALBic" to -- BALB/c --;
Line 61, please change "viva" to -- vivo --;

Column 160,
Line 56, please change "straiaht" to -- straight --;

Column 161,
Line 55, please insert -- an -- between "or" and "aromatic";

Column 162,
Line 50, please change "$C_{1-6}$" to -- $C_{1-12}$ --;

Column 164,
Line 29, please change "antimvcotic" to -- antimycotic --; and
Line 38, please change "PH" to -- pH --.

Signed and Sealed this

Ninth Day of November, 2004

JON W. DUDAS
*Director of the United States Patent and Trademark Office*